United States Patent
Mujacic et al.

(10) Patent No.: US 12,215,348 B2
(45) Date of Patent: Feb. 4, 2025

(54) METHODS FOR PRODUCING GENETICALLY ENGINEERED CELL COMPOSITIONS AND RELATED COMPOSITIONS

(71) Applicant: Juno Therapeutics, Inc., Seattle, WA (US)

(72) Inventors: Mirna Mujacic, Seattle, WA (US); Ayu Rahardjo, Kirkland, WA (US)

(73) Assignee: Juno Therapeutics, Inc., Seattle, WA (US)

(*) Notice: Subject to any disclaimer, the term of this patent is extended or adjusted under 35 U.S.C. 154(b) by 0 days.

(21) Appl. No.: 18/506,851

(22) Filed: Nov. 10, 2023

(65) Prior Publication Data

US 2024/0076617 A1 Mar. 7, 2024

Related U.S. Application Data

(63) Continuation of application No. 16/637,709, filed as application No. PCT/US2018/046149 on Aug. 9, 2018, now Pat. No. 11,851,678.

(60) Provisional application No. 62/596,770, filed on Dec. 8, 2017, provisional application No. 62/543,363, filed on Aug. 9, 2017.

(51) Int. Cl.
| | | |
|---|---|---|
| A61K 35/17 | (2015.01) | |
| A61K 38/19 | (2006.01) | |
| A61K 38/20 | (2006.01) | |
| A61K 39/00 | (2006.01) | |
| C12N 5/0783 | (2010.01) | |
| C12N 7/00 | (2006.01) | |
| C12N 15/86 | (2006.01) | |
| G01N 33/569 | (2006.01) | |

(52) U.S. Cl.
CPC ........ *C12N 5/0636* (2013.01); *A61K 39/4611* (2023.05); *A61K 39/4631* (2023.05); *A61K 39/464417* (2023.05); *C12N 7/00* (2013.01); *C12N 15/86* (2013.01); *G01N 33/56972* (2013.01); *A61K 2239/48* (2023.05); *C12N 2502/1114* (2013.01); *C12N 2740/13043* (2013.01); *C12N 2740/15043* (2013.01); *G01N 2333/70514* (2013.01); *G01N 2333/70517* (2013.01)

(58) Field of Classification Search
CPC .............. C12N 5/0636; A61K 39/4611; A61K 39/4631; A61K 39/464402; A61K 39/464417
See application file for complete search history.

(56) References Cited

U.S. PATENT DOCUMENTS

| | | | |
|---|---|---|---|
| 4,452,773 A | 6/1984 | Molday | |
| 4,690,915 A | 9/1987 | Rosenberg | |
| 4,795,698 A | 1/1989 | Owen | |
| 5,168,062 A | 12/1992 | Stinski | |
| 5,200,084 A | 4/1993 | Liberti | |
| 5,219,740 A | 6/1993 | Miller | |
| 5,385,839 A | 1/1995 | Stinski | |
| 5,773,224 A | 6/1998 | Grandics et al. | |
| 5,994,136 A | 11/1999 | Naldini et al. | |
| 6,013,516 A | 1/2000 | Verma et al. | |
| 6,040,177 A | 3/2000 | Riddell et al. | |
| 6,207,453 B1 | 3/2001 | Maass | |
| 6,410,319 B1 | 6/2002 | Raubitschek | |
| 6,451,995 B1 | 9/2002 | Cheung | |
| 7,070,995 B2 | 7/2006 | Jensen | |
| 7,265,209 B2 | 9/2007 | Jensen | |
| 7,354,762 B2 | 4/2008 | Jensen | |
| 7,446,179 B2 | 11/2008 | Jensen | |
| 7,446,190 B2 | 11/2008 | Sadelain | |
| 7,446,191 B2 | 11/2008 | Jensen | |
| 8,324,353 B2 | 12/2012 | Jensen | |
| 8,339,645 B2 | 12/2012 | Nakawaki | |
| 8,389,282 B2 | 3/2013 | Sadelain et al. | |
| 8,479,118 B2 | 7/2013 | Lyndersay et al. | |
| 8,802,374 B2 | 8/2014 | Jensen | |
| 8,911,993 B2 | 12/2014 | June et al. | |
| 11,400,115 B2 | 8/2022 | Ramsborg et al. | |
| 11,851,678 B2 | 12/2023 | Mujacic et al. | |

(Continued)

FOREIGN PATENT DOCUMENTS

| | | |
|---|---|---|
| CN | 103 305 464 | 9/2013 |
| CN | 103 502 438 | 1/2014 |

(Continued)

OTHER PUBLICATIONS

US 8,252,592 B2, 08/2012, Sadelain (withdrawn)
Abate-Daga et al., "CAR models: next-generation CAR modifications for enhanced T cell function," Mol Ther Oncolytics (May 2016) 3:16014.

(Continued)

*Primary Examiner* — Barry A Chestnut
(74) *Attorney, Agent, or Firm* — MORRISON & FOERSTER LLP

(57) ABSTRACT

Provided herein are methods and compositions for generating engineered cells, such as cells expressing a recombinant receptor, including methods involving stimulation and/or engineering of an input composition having a defined ratio of naïve-like CD4+ T cells to naïve-like CD8+ T cells. In particular, the methods can be used to engineer T cells with genetically engineered receptors, such as genetically engineered antigen receptors such as engineered (recombinant) TCRs and chimeric antigen receptors (CARs), or other recombinant chimeric receptors. Features of the methods include producing a more consistent and/or predictable T cell product and/or a product with lower toxicity compared with other methods.

26 Claims, 6 Drawing Sheets

Specification includes a Sequence Listing.

(56) References Cited

U.S. PATENT DOCUMENTS

| | | |
|---|---|---|
| 2002/0131960 A1 | 9/2002 | Sadelain |
| 2002/0150914 A1 | 10/2002 | Anderson et al. |
| 2003/0170238 A1 | 9/2003 | Gruenberg |
| 2003/0223994 A1 | 12/2003 | Hoogenboom et al. |
| 2003/0235908 A1 | 12/2003 | Berenson et al. |
| 2004/0191260 A1 | 9/2004 | Reiter et al. |
| 2006/0034850 A1 | 2/2006 | Weidanz et al. |
| 2006/0074008 A1 | 4/2006 | Senter et al. |
| 2007/0099253 A1 | 5/2007 | Erkhov et al. |
| 2007/0116690 A1 | 5/2007 | Yang et al. |
| 2008/0085532 A1 | 4/2008 | Gorlach et al. |
| 2009/0226474 A1 | 9/2009 | Weidanz et al. |
| 2009/0304679 A1 | 12/2009 | Weidanz |
| 2011/0003380 A1 | 1/2011 | Miltenyi |
| 2011/0070581 A1 | 3/2011 | Gupta |
| 2013/0149337 A1 | 6/2013 | Cooper et al. |
| 2013/0287748 A1 | 10/2013 | June |
| 2014/0255993 A1 | 9/2014 | Follstad et al. |
| 2014/0294841 A1 | 10/2014 | Scheinberg et al. |
| 2015/0283178 A1 | 10/2015 | June et al. |
| 2016/0152723 A1 | 6/2016 | Chen et al. |
| 2016/0362472 A1 | 12/2016 | Bitter et al. |
| 2017/0037369 A1 | 2/2017 | Ramsborg et al. |
| 2017/0051035 A1 | 2/2017 | Payne et al. |
| 2017/0051252 A1 | 2/2017 | Morgan et al. |
| 2017/0209492 A1 | 7/2017 | June et al. |
| 2017/0356902 A1 | 12/2017 | Ukekawa et al. |
| 2018/0296602 A1 | 10/2018 | Riddell et al. |
| 2020/0239910 A1 | 7/2020 | Bonyhadi et al. |
| 2020/0384025 A1 | 12/2020 | Mujacic et al. |
| 2021/0128616 A1 | 5/2021 | Himanshu et al. |
| 2023/0090176 A1 | 3/2023 | Ramsborg et al. |
| 2023/0190814 A1 | 6/2023 | Ramsborg et al. |

FOREIGN PATENT DOCUMENTS

| | | |
|---|---|---|
| EP | 0452342 | 10/1991 |
| EP | 2537416 | 12/2012 |
| JP | 2006-525013 | 11/2006 |
| JP | 2010-75191 | 4/2010 |
| WO | WO 1992/008796 | 5/1992 |
| WO | WO 1994/028143 | 12/1994 |
| WO | WO 1996/013593 | 5/1996 |
| WO | WO 1996/018105 | 6/1996 |
| WO | WO 1999/018129 | 4/1999 |
| WO | WO 1999/060120 | 11/1999 |
| WO | WO 2000/014257 | 3/2000 |
| WO | WO 2000/043551 | 7/2000 |
| WO | WO 2003/020763 | 3/2003 |
| WO | WO 2003/068201 | 8/2003 |
| WO | WO 2004/029221 | 4/2004 |
| WO | WO 2004/033685 | 4/2004 |
| WO | WO 2004/096975 | 11/2004 |
| WO | WO 2006/000830 | 1/2006 |
| WO | WO 2007/117602 | 10/2007 |
| WO | WO 2009/003493 | 1/2009 |
| WO | WO 2009/072003 | 6/2009 |
| WO | WO 2009/072006 | 6/2009 |
| WO | WO 2009/076524 | 6/2009 |
| WO | WO 2010/033140 | 3/2010 |
| WO | WO 2011/044186 | 4/2011 |
| WO | WO 2012/099973 | 7/2012 |
| WO | WO 2012/129514 | 9/2012 |
| WO | WO 2013/011011 | 1/2013 |
| WO | WO 2013/038272 | 3/2013 |
| WO | WO 2013/062365 | 5/2013 |
| WO | WO 2013/071154 | 5/2013 |
| WO | WO 2013/123061 | 8/2013 |
| WO | WO 2013/124474 | 8/2013 |
| WO | WO 2013/126726 | 8/2013 |
| WO | WO 2013/166321 | 11/2013 |
| WO | WO 2014/011996 | 1/2014 |
| WO | WO 2014/031687 | 2/2014 |
| WO | WO 2014/055668 | 4/2014 |
| WO | WO 2014/130657 | 8/2014 |
| WO | WO 2015/157252 | 10/2015 |
| WO | WO 2015/164675 | 10/2015 |
| WO | WO 2015/164745 | 10/2015 |
| WO | WO 2016/019300 | 2/2016 |
| WO | WO 2016/090190 | 6/2016 |
| WO | WO 2016/090312 | 6/2016 |
| WO | WO 2016/090320 | 6/2016 |
| WO | WO 2016/090327 | 6/2016 |
| WO | WO 2016/090329 | 6/2016 |
| WO | WO 2016/164580 | 10/2016 |
| WO | WO 2017/068421 | 4/2017 |
| WO | WO 2017/075389 | 5/2017 |
| WO | WO 2018/157171 | 8/2018 |
| WO | WO 2019/032929 | 2/2019 |
| WO | WO 2019/113557 | 6/2019 |
| WO | WO 2019/113559 | 6/2019 |

OTHER PUBLICATIONS

Ali et al., "T cells expressing an anti-B-cell maturation antigen chimeric antigen receptor cause remissions of multiple myeloma," Blood (Sep. 2016) 128(13):1688-1700.

Alonso-Camino et al., "CARbodies: Human Antibodies Against Cell Surface Tumor Antigens Selected From Repertoires Displayed on T Cell Chimeric Antigen Receptors," Mol Ther Nucl Acids (2013) 2: e93.

Alvarez-Fernandez et al., "A short CD3/CD28 costimulation combined with IL-21 enhance the generation of human memory stem T cells for adoptive immunotherapy," J Transl Med. (Jul. 2016) 14(1):214.

Applikon Biotechnology/BioPharma-Reporter (2016) How automation has changed the way we count cells BioPharma-Reporter.com; 1-4 (Year: 2016).

Barrett et al., "Chimeric Antigen Receptor Therapy for Cancer," Annual Review of Medicine (2014) 65:333-347.

Berdeja et al., "First-in-human multicenter study of bb2121 anti-BCMA CAR T-cell therapy for relapsed/refractory multiple myeloma: Updated results," J Clin Oncol (Jun. 2017) 35(15)-suppl.; 3010.

Bersenev, "Crude versus defined CAR T-cell therapy product," dated May 1, 2016. Retrieved from the Internet: https://stemcellassays.com/2016/05/crude-versus-defined-car-t-cell-therapy-product/.

Berthois et al., "Phenol red in tissue culture media is a weak estrogen: Implications concerning the study of estrogen-responsive cells in culture," Proc. Natl. Acad. Sci (1986) 83: 2496-2500.

Boris-Lawrie et al., "Recent advances in retrovirus vector technology," Cur. Opin. Genet. Develop. (1993) 3:102-109.

Brash et al., "Strontium phosphate transfection of human cells in primary culture: stable expression of the simian virus 40 large-T-antigen gene in primary human bronchial epithelial cells," Mol. Cell Biol. (1987) 7: 2031-2034.

Brentjens et al., "CD19-targeted T cells rapidly induce molecular remissions in adults with chemotherapy-refractory acute lymphoblastic leukemia," Sci Transl Med. (2013) 5(177):177ra38.

Brentjens et al., "Safety and persistence of adoptively transferred autologous CD19-targeted T cells in patients with relapsed or chemotherapy refractory B-cell leukemias," Blood (2011) 118(18):4817-4828.

Brown et al., "Structure-Based Mutagenesis of the Human Immunodeficiency Virus Type 1 DNA Attachment Site: Effects on Integration and cDNA Synthesis," J Viral (1999) 73(11):9011-9020.

Burns et al., "Vesicular stomatitis virus G glycoprotein pseudotyped retroviral vectors: concentration to very high titer and efficient gene transfer into mammalian and nonmammalian cells," Proc. Natl. Acad. Sci. USA (1993) 90:8033-8037.

Carlens et al., "Ex vivo T lymphocyte expansion for retroviral transduction: influence of serum-free media on variations in cell expansion rates and lymphocyte subset distribution," Exp Hematol (2000) 28(10): 1137-1146.

Carrillo et al., "The Multiple Sequence Alignment Problem in Biology," SIAM Journal on Applied Mathematics (1988) 48(5):1073-1082.

Casati et al., "Clinical-scale selection and viral transduction of human naïve and central memory CD8+ T cells for adoptive cell therapy of cancer patients," Cancer Immunology (2013) 62(10): 1563-1573.

(56) References Cited

OTHER PUBLICATIONS

Cavalieri et al., "Human T lymphocytes transduced by lentiviral vectors in the absence of TCR activation maintain an intact immune competence," Blood (2003) 102(2): 497-505.
Cheadle et al., "Chimeric antigen receptors for T-cell based therapy," Methods Mol Biol (2012) 907:645-666.
Chervin et al., "Engineering higher affinity T cell receptors using a T cell display system," J Immunol Methods. (2008) 339(2): 175-84.
Chicaybam et al., "An efficient low cost method for gene transfer to T lymphocytes," PLoS ONE (2013) 8(3): e60298.
Cho et al., "Human mammalian cell sorting using a highly integrated micro-fabricated fluorescence-activated cell sorter (microFACS)," Lab Chip (2010) 10: 1567-1573.
Chothia et al.,. "The outline structure of the T-cell alpha beta receptor," EMBO J. (1988) 7(12): 3745-55.
Church et al., "Tumor-specific CD4+ T cells maintain effector and memory tumor-specific CD8+ T cells," Eur J Immunol (2013) 44(1):69-79.
Clackson et al., "Making antibody fragments using phage display libraries," Nature (1991) 352(6336):624-628.
Clarke and Davies in: Methods in Molecular Medicine, vol. 58: Metastasis Research Protocols, vol. 2: Cell Behavior In Vitro and In Vivo, Edited by: S. A. Brooks and U. Schumacher © Humana Press Inc., Totowa, NJ (2001) pp. 17-25.
Cohen et al., "Recombinant antibodies with MHC-restricted, peptide-specific, T-cell receptor-like specificity: new tools to study antigen presentation and TCR-peptide-MHC interactions," J Mol Recognit. (2003) 16(5): 324-332.
Cooper et al., "T-cell clones can be rendered specific for CD19: toward the selective augmentation of the graft-versus-B-lineage leukemia effect," Blood. (2003) 101:1637-1644.
Dai et al., "Chimeric Antigen Receptors Modified T-Cells for Cancer Therapy." J Natl Cancer Inst. (Jul. 2016) 108(7); djv349.
Davila et al., "CD19 CAR-targeted T cells induce long-term remission and B Cell Aplasia in an immunocompetent mouse model of B cell acute lymphoblastic leukemia," PLoS ONE (2013) 8(4): e61338.
Davis et al., "Assessment of a positive selection technique using an avidin column to isolate human peripheral blood T cell subsets," J Immunol Methods. (1994) 175(2):247-57.
De Felipe et al., "Targeting of proteins derived from self-processing polyproteins containing multiple signal sequences," Trafic (2004) 5(8):616-626.
De Felipe, "Skipping the co-expression problem: the new 2A "CHYSEL" technology," Genetics Vaccines and Therapy (2004) 2:13.
Dirks et al., "Genome-wide epigenomic profiling for biomarker discovery," Clin Epigenetics (Nov. 2016) 8:122.
Dull, T. et al. (Nov. 1998) "A Third-Generation Lentivirus Vector with a Conditional Packaging System," J. Viral. 72:8463-8471.
Eaker et al., "Concise review: guidance in developing commercializable autologous/patient-specific cell therapy manufacturing," Stem Cells Transl Med. (2013) 2(11): 871-83.
Engelman et al., "Multiple effects of mutations in human immunodeficiency virus type 1 integrase on viral replication," J Viral (1995) 69(5):2729-2736.
Fan et al., "Durable remissions with BCMA-specific chimeric antigen receptor (CAR)-modified T cells in patients with refractory/relapsed multiple myeloma," J Clin Oncol (Jun. 2017) 35(18 suppl.):LBA3001.
Fedorov et al., "PD-1- and CTLA-4-Based Inhibitory Chimeric Antigen Receptors (iCARs) Divert Off-Target Immunotherapy Responses," Sci Transl Medicine (2013) 5(215):215ra172.
Fernandes et al., "Kinetics of class II MHC expression on cytotoxic T cells generated by skin allograft," Tissue Antigens. (1990) 36(3):93-9.
Fraietta et al., "Biomarkers of Response to Anti-CD19 Chimeric Antigen Receptor (CAR) T-Cell Therapy in Patients with Chronic Lymphocytic Leukemia," Blood (Dec. 2016) 128(22):57.
Fraietta et al., "Identification of functional determinants of response and resistance to CD19 chimeric antigen receptor (CAR) T-cell therapy if chronic lymphocytic leukemia," Blood (Dec. 2017) 130:3181.
Frayer et al., "Mean Body Weight, Height, Waist Circumference, and Body Mass Index Among Adults: United States, 1999-2000 Through 2015-2016," Natl Health Stat Report. (2018) (122):1-16.
Gantke et al., "AFM26 is a novel, highly potential BCMA/CD16A-directed bispecific antibody for high affinity NK-cell engagement in multiple myeoma," J Clin Oncol (May 2017) 35(15_suppl.); Abstract 8045.
Gardner et al., "Intent to treat leukemia remission by CD19CAR T cells of defined formulation and dose in children and young adults," Blood (Jun. 2017) 129(25):3322-3331.
Gattinoni et al., "T memory stem cells in health and disease," Nat Med. (Jan. 2017) 23(1):18-27.
Ghassemi et al., "203. Shortened T Cell Culture with IL-7 and IL-15 Provides the Most Potent Chimeric Antigen Receptor (CAR)-Modified T Cells for Adoptive Immunotherapy," Molecular Therapy, May 2016, vol. 24, Supplement 1, p. S79.
Godin et al., "Microfluidics and photonics for Bio-System-on-a-Chip: a review of advancements in technology towards a microfluidic flow cytometry chip," J Biophoton. (2008) 1(5):355-376.
Gunzer et al,, "Two-step negative enrichment of CD4+ and CD8+ T cells from murine spleen via nylon wool adherence and an optimized antibody cocktail," J Immunol Methods. (2001) 258(1-2): 55-63.
Harrington et al., "Development of JCARH125: Optimization of a Fully Human Anti-BCMA CAR for Use in the Treatment of Multiple Myeloma," ASH 2017. Abstract. Blood (Dec. 2017) 130:1813.
Harrington et al., "JCARH125: Development of an Optimized Fully Human Anti-BCMA CAR for the Treatment of Multiple Myeloma," ASH 2017. Poster 1813. Presented on Dec. 9-12 . . . .
Henning et al., "Epigenetic control of CD8+ T cell differentiation," Nat Rev Immunol (2018) 18(5): 340-356.
Hermans et al., "The VITAL assay: a versatile fluorometric technique for assessing CTL- and NKT-mediated cytotoxicity against multiple targets in vitro and in vivo," J. Immunological Methods (2004) 285(1): 25-40.
Hinrichs et al., "Human effector CD8+ T cells derived from naïve rather than memory subsets possess superior traits for adoptive immunotherapy," Blood (2011) 117(3): 808-814.
Hirakawa et al., "IL-2, IL-7, IL-15 and IL-6 Induce Differential Activation of Naive and Memory T Cell Subsets," Blood (Dec. 2015) 126(23):3425, 4 pages.
Hoffmann et al., "Differences in expansion Potential of naive chimeric antigen receptor T cells from healthy Donors and Untreated chronic lymphocytic leukemia Patients," Front. Immunol. (2018) 8:1956.
Holler et al., "In vitro evolution of a T cell receptor with high affinity for peptide/MHC," Proc Natl Acad Sci U S A. (2000) 97(10): 5387-5392.
Holler et al., "TCRs with high affinity for foreign pMHC show self-reactivity," Nat Immunol. Jan. 2003;4(1):55-62.
Hou et al., Tutorial on Animal Cell Culture Techniques, Gansu Science and Technology Press, Sep. 2009: p. 105 (Article in Chinese; English translation provided).
Huang et al., "DNA transposons for modification of human primary T lymphocytes," Methods Mol Biol (2009) 506: 115-126.
Hudecek et al., "Receptor affinity and extracellular domain modifications affect tumor recognition by ROR1-specific chimeric antigen receptor T cells," Clin Cancer Res (2013) 19(12):3153-3164.
Hunziker et al., "Exhaustion of cytotoxic T cells during adoptive immunotherapy of virus carrier mice can be prevented by B cells or CD4+ T cells," Eur J Immunol (2002) 32(2):374-382.
Imadome, "The clinical condition and diagnosis of EBV-T/NK-LPD (CAEBV, EBV-HLH etc.)," [Rinsho Ketsueki] Japanese J Clin Hematol (2013) 54(10):1992-98. (Reference in Japanese) English translation provided.
Irving et al., "Engineering Chimeric Antigen Receptor T-Cells for Racing in Solid Tumors: Don't Forget the Fuel," Front Immunol (Apr. 2017) 8:267.

(56) References Cited

OTHER PUBLICATIONS

Janas et al., "Perfusion's role in maintenance of high-density T-cell cultures," BioProcesses International. (2015) pp. 1-12.
Janeway et al., Immunobiology: The Immune System in Health and Disease, 3rd ED., Current Biology Publications (1997), p. 4:33.
Jethwa et al., "Use of gene-modified regulatory T-cells to control autoimmune and alloimmune pathology: is now the right time?," Clin Immunol. (2014) 150(1):51-63.
Joao et al., "Immunologic autograft engineering by manipulation of apheresis machine collection settings," Am. Soc. Transplantation and Cellular Therapy 12(2): Suppl 1, p. 105, Abstract 298, Feb. 2006.
Johnston, et al., "Biolistic transformation: microbes to mice," Nature (1990) 346: 776-777.
Jores et al., "Resolution of hypervariable regions in T-cell receptor beta chains by a modified Wu-Kabat index of amino acid diversity.," PNAS (1990) 87(23):9138-9142.
Kaartinen et al., "Low interleukin-2 concentration favors generation of early memory T cells over effector phenotypes during chimeric antigen receptor T-cell expansion," Cytotherapy. (Jun. 2017) 19(6):689-702.
Kaech et al., "Effector and memory T-cell differentiation: implications for vaccine development," Nat Rev Immunol (2002) 2(4):251-62.
Kahn et al., "Optimization of retroviral vector-mediated gene transfer into endothelial cells in vitro," Circ Res. (1992) 71(6): 1508-17.
Katz et al., "Therapeutic targeting of CD19 in hematological malignancies: past, present, future and beyond." Leuk Lymphoma. (2014) 55(5):999-1006.
Kindt et al., "Antigens and Antibodies," in Chapter 4 of Kuby Immunology, 6th ed., W.H. Freeman and Co., N.Y, (2007) pp. 91, 14 pages.
Klaver et al., "T Cell Maturation Stage Prior to and During GMP Processing Informs on CAR T Cell Expansion in Patients," Front Immunol. (Dec. 2016) 7:648.
Klebanoff et al., "Sorting through subsets: which T-cell populations mediate highly effective adoptive immunotherapy?," J Immunother. (2012) 35(9): 651-660.
Kochenderfer et al., "Construction and preclinical evaluation of an anti-CD19 chimeric antigen receptor," J. Immunotherapy (2009) 32(7): 689-702.
Kochenderfer et al., "Treating B-cell cancer with T cells expressing anti-CD19 chimeric antigen receptors," Nature Reviews Clinical Oncology (2013) 10:267-276.
Koste et al., "T-cell receptor transfer into human T cells with ecotropic retroviral vectors," Gene Therapy (2014) 21: 533-538.
Kotb, "Bacterial pyrogenic exotoxins as superantigens," Clin Microbiol Rev. (1995) 8(3):411-426.
Kueberuwa et al., "CCR7+ selected gene-modified T cells maintain a central memory phenotype and display enhanced persistence in peripheral blood in vivo," J Immunother Cancer. (Feb. 2017) 5: 14.
Kugler, "Analytical Characterization Studies for CAR-T Cell Therapy," presentation presented at Immuno-Oncology Summit Europe, Adoptive T Cell Therapy on Mar. 19, 2018.
Kurucz et al., "A bacterially expressed single-chain Fv construct from the 2B4 T-cell receptor," Proc Natl Acad Sci U S A. (1993) 90(9): 3830-3834.
Lefranc et al., "IMGT unique numbering for immunoglobulin and T cell receptor variable domains and Ig superfamily V-like domains," Dev Comp Immunol (2003) 27(1):55-77.
Levine et al., "Global manufacturing of CAR T cell therapy" Mol. Ther. Methods & Clin. Dev. (Dec. 2016) 4: 92-101.
Levine et al: "Global Manufacturing of CART Cell Therapy", Molecular Therapy—Mthods & Clinical Develop, vol. 4, Mar. 4, 2017 (Mar. 4, 2017), pp. 92-101, XP055510414.
Li et al., "Comparison of inlet geomery in microfluidic cell affinity chromatography," Analytical chemistry (2011) 83(3):774-781.
Li et al., "Directed evolution of human T-cell receptors with picomolar affinities by phage display," Nat Biotechnol. (2005) 23:349-354.
Li et al., "Negative enrichment of target cells by microfluidic affinity chromatography," Analytical Chemistry (2011) 83(20):7863-7869.
Li et al., "Multiparameter cell affinity chromatography: Separation and analysis in a single microfluidic channel," Anal Chem (2012) 84(19):8140-8148.
Life Technologies Corporation (2013) OpTmizer™CTS™ T-cell Expansion SFM Technical information; pp. 1-2 (Year: 2013).
Ling et al., "B-cell and plasma cell antigens: new and previously defined clusters," Leucocyte typing III. (1987) 302-355.
Liu et al., "Inclusion of Strep-tag II in design of antigen receptors for T-cell immunotherapy," Nature Biotechnology (Apr. 2016) 34(4):430-434.
Lu et al., "A Rapid Cell Expansion Process for Production of Engineered Autologous CAR-T Cell Therapies," Human Gene Therapy Methods (Dec. 2016) 27(6):209-218.
Lupton et al., "Dominant positive and negative selection using a hygromycin phosphotransferase-thymidine kinase fusion gene," Mol. and Cell Biol. (1991) 11:6: 3374-3378.
Manuri et al., "piggyBac transposon/transposase system to generate CD19-specific T cells for the treatment of B-lineage malignancies," Hum Gene Ther (2010) 21(4): 427-437.
Matsuki et al., "CD45RA-Foxp3(high) activated/effector regulatory T cells in the CCR7 + CD45RA-CD27 + CD28+central memory subset are decreased in peripheral blood from patients with rheumatoid arthritis," Biochem Biophys Res Commun. (2013) 438(4): 778-83.
Maus et al., "Chimeric antigen receptor T-cell therapy for the community oncologist," Oncologist (May 2016) 21(5):608-617.
Mcwilliams et al., "Mutations in the 5' end of the human immunodeficiency virus type 1 polypurine tract affect RNase H cleavage specificity and virus titer," J Viral (2003) 77(20):11150-11157.
Mei et al., "Rationale of anti-CD19 immunotherapy: an option to target autoreactive plasma cells in autoimmunity," Arthritis Res Ther. (2012) 14 Suppl 5(Suppl 5):S1.
Miller et al., "Improved retroviral vectors for gene transfer and expression," Bio Techniques (1989) 7:980-990.
Miller et al., "Retrovirus packaging cells," Human Gene Therapy (1990) 1:5-14.
Milone et al., "Chimeric Receptors Containing CD137 Signal Transduction Domains Mediate Enhanced Survival of T Cells and Increased Antileukemic Efficacy In Vivo," Mol Ther (2009) 17(8):1453-64.
Miyoshi et al. "Development of a self-inactivating lentivirus vector," J Viral (1998) 72(10):8150-8157.
Mock et al., "Automated manufacturing of chimeric antigen receptor T cells for adoptive immunotherapy using CliniMACS Prodify," Cytotherapy (Aug. 2016) 18(8):1002-1011.
Moeller et al., "Adoptive transfer of gene-engineered CD4+ helper T cells induces potent primary and secondary tumor rejection," Blood (2005) 106(9):2995-3003.
Naldini et al., Efficient transfer, integration, and sustained long-term expression of the transgene in adult rat brains injected with a lentiviral vector, Proc Natl Acad Sci U S A. (1996) 93(21):11382-8.
Naldini et al., "In vivo gene delivery and stable transduction of nondividing cells by a lentiviral vector," Science. Apr. 12, 1996;272(5259):263-7.
Naldini et al., "Lentiviruses as gene transfer agents for delivery to non-dividing cells", Curr Opin Biotechnol., Oct. 9, 1998; 5:457-63.
Nascimbeni et al., "Peripheral CD4+CD8+ T cells are differentiated effector memory cells with antiviral functions," Blood (2004) 104(2):478-86.
Navarro et al., "Estrogen Stimulation Differentially Impacts Human Male and Female Antigen-specific T cell Anti-Tumor Function and Polyfunctionality," Gender and the Genome (Dec. 2017) 1(4); 167-179.
Okern et al., "CTS™ immune cell SR for serum free culture and expansion of human T cells," Journal for Immuno Therapy of Cancer (2015) 3(suppl 2): P1.
Park et al., "Treating cancer with genetically engineered T cells," Trends Biotechnol. (2011) 29(11): 550-557.
Philpott et al., "Use of Nonintegrating Lentiviral Vectors for Gene Therapy," Human Gene Therapy (2007) 18:483.

(56) References Cited

OTHER PUBLICATIONS

Portolano et al., "Lack of promiscuity in autoantigen-specific H and L chain combinations as revealed by human H and L chain "roulette"," J Immunol (1993) 150(3):880-887.
Powell et al., "Sequence and structural determinants required for priming of plus-strand DNA synthesis by the human immunodeficiency virus type 1 polypurine tract," J Viral (1996) 70(8):5288-5296.
Pullagurla et al., "Parallel affinity-based isolation of leukocyte subsets using microfluidics: application for stroke diagnosis," Analytical chemistry (2014) 86(8):4058-4065.
Riddell et al., "Phase I study of cellular adoptive immunotherapy using genetically modified CD8+ HIV-specific T cells for HIV seropositive patients undergoing allogeneic bone marrow transplant," Human Gene Therapy (1992) 3:319-338.
Rosenberg, et al., "Cell transfer immunotherapy for metastatic solid cancer—what clinicians need to know," Nat Rev Clin Oncol. (2011) 8(10):577-85.
Sabatino et al., "Generation of clinical-grade CD19-specific CAR-modified CD8+ memory stem cells for the treatment of human B-cell malignancies," Blood. (Jul. 2016) 128(4): 519-528.
Sadelain et al., "The basic principles of chimeric antigen receptor design," Cancer Discov. (2013) 3(4): 388-398.
Scarpa et al., "Characterization of recombinant helper retroviruses from Moloney-based vectors in ecotropic and amphotropic packaging cell lines," Virology (1991) 180:849-852.
Schlueter et al., "Specificity and binding properties of a single-chain T cell receptor," J Mol Biol. (1996) 256(5): 859-69.
Schuler et al., SYFPEITHI, Database for Searching and T-Cell Epitope Prediction. in Immunoinformatics Methods in Molecular Biology, (2007) 409(1): 75-93.
Sharma et al., "Efficient sleeping beauty DNA transposition from DNA minicircles," Molec Ther Nucl Acids (2013) 2, e74.
Singh et al., "ProPred: prediction of HLA-DR binding sites," Bioinformatics. (2001) 17(12): 1236-1237.
Skea et al., "The selective expansion of functional T cell subsets," J Hematother Stem Cell Res. (1999) 8(5): 525-38.
Smith et al., "Development and evaluation of a human single chain variable fragment (scFv) derived BCMA targeted CAR T cell vector leads to a high objective response rate in patients with advanced MM," Blood (Dec. 2017) 130 (Suppl. 1):742.
Smith, "Development and evaluation of human anti-BCMA CAR T cell therapy from concept to clinic: Outline," Oral presentation presented at ASH Dec. 2017.
Soo Hoo et al., "Characterization of a single-chain T-cell receptor expressed in *Escherichia coli*," Proc Natl Acad Sci U S A. (1992) 89(10): 4759-4763.
Stemberger et al., "Novel Serial Positive Enrichment Technology Enables Clinical Multiparameter Cell Sorting," PLoS One (2012) 7(4): e35798.
Sun et al., "Early transduction produces highly functional chimeric antigen receptor-modified virus-specific T-cells with central memory markers: a Production Assistant for Cell Therapy (PACT) translational application," J Immunother Cancer. (2015) 3:5.
Tang et al., "Third-generation CD28/4-1BB chimeric antigen receptor T cells for chemotherapy relapsed or refractory acute lymphoblastic leukaemia: a non-randomised, open-label phase I trial protocol," BMJ Open. (Nov. 2016) 6(12): e013904, p. 1-7, doi:10.1136/bmjopen-2016-013904.
Terakura et al., "Generation of CD19-chimeric antigen receptor modified CD8+ T cells derived from virus-specific central memory T cells," Blood (2012) 1:72-82.

Themeli et al., "Generation of tumor-targeted human T lymphocytes from induced pluripotent stem cells for cancer therapy," Nat Biotechnol. (2013) 31(10): 928-933.
ThermoFisher Scientific, DynabeadsTM M-450 product description, Catalog No. 14011; https://www.thermofisher.com/order/catalog/product/14011; last visited Oct. 6, 2022.
Tsukahara et al., "CD19 target-engineered T-cells accumulate at tumor lesions in human B-cell lymphoma xenograft mouse models," Biochem Biophys Res Commun (2013) 438(1): 84-89.
Turtle et al., "Anti-CD19 Chimeric Antigen Receptor-Modified T Cell Therapy for B Cell Non-Hodgkin Lyphoma and Chronic Lyphocytic Leukemia: Fludarabine and Cyclophosphamide Lyphodepletion Improves In Vivo Expansion and Persistence of CAR-T Cells and Clinical Outcomes," Blood (2015) 126:184.
Turtle et al., "CD19 CAR-T cells of defined CD4+:CD8+ composition in adult B cell ALL patients," J. Clin. Invest. (Jun. 2016) 126(6):2123-38.
Turtle et al., "Engineered T cells for anti-cancer therapy," Curr. Opin. Immunol. (2012) 24(5): 633-39.
Upparahalli et al., "GPRC5D is a cell surface plasma cell marker whose expression is high in myeloma cells and reduced following coculture with osteoclasts," Blood (2013) 122(21):3099.
Van Tendeloo et al., "High-level transgene expression in primary human T lymphocytes and adult bone marrow CD34+ cells via electroporation-mediated gene delivery," Gene Therapy (2000) 7(16): 1431-1437).
Verhoeyen et al., "Lentiviral vector gene transfer into human T cells," Methods Mol Biol. (2009) 506: 97-114.
Wang et al., "Clinical manufacturing of CAR T cells: foundation of a promising therapy," Molecular Therapy—Oncolytics (Jun. 2016) 3:16015.
Wang et al., "Current advances in T-cell-based cancer immunotherapy," Immunotherapy (2014) 6(12): 1265-1278.
Wang et al., "Phenotypic and functional attributes of lentivirus-modified CD19-specific human CD8+ central memory T cells manufactured at clinical scale," J Immunother. (2012) 35(9):689-701.
Wang et al., "Open-tubular capillary cell affinity chromatography: single and tandem blood cell separation," Anal Chem (2008) 80(6):2118-2124.
Weng et al., "The molecular basis of the memory T cell response: differential gene expression and its epigenetic regulation," Nat Rev Immunology (2012) 12(4): 306-315.
Wu et al., "Adoptive T-cell therapy using autologous tumor-infiltrating lymphocytes for metastatic melanoma: current status and future outlook," Cancer (2012) 18(2): 160-175.
Wulfing et al., "Correctly folded T-cell receptor fragments in the periplasm of *Escherichia coli*. Influence of folding catalysts," J Mol Biol. (1994) 242(5): 655-669.
Xu et al., "Closely related T-memory stem cells correlate with in vivo expansion of CAR.CD19-T cells and are preserved by IL-7 and IL-15," Blood (2014) 123(24):3750-3759.
Xu et al., "Multiparameter comparative analysis reveals differential impacts of various cytokines on CART cell phenotypes and function ex vivo and in vivo," Oncotarget (Dec. 2016) 7(50):82354-82368.
Yarilin, "Immunology principles," M. Medicine (1999) 184-195, 339-347 (English Translation included).
Zufferey et al. "Self-Inactivating Lentivirus Vector for Safe and Efficient In Vivo Gene Delivery," J. Viral (1998) 72(12):9873-9880.
Zufferey et al., "Multiply attenuated lentiviral vector achieves efficient gene delivery in vivo," Nat Biotechnol. Sep. 1997;15(9):871-875.

METHODS FOR PRODUCING GENETICALLY ENGINEERED CELL COMPOSITIONS AND RELATED COMPOSITIONS

CROSS-REFERENCE TO RELATED APPLICATIONS

This application is a continuation of U.S. patent application Ser. No. 16/637,709, filed on Feb. 7, 2020, which is a National Stage application under 35 U.S.C. § 371 of International Application No. PCT/US2018/046149, filed on Aug. 9, 2018, which claims priority from U.S. provisional application No. 62/543,363, filed Aug. 9, 2017, entitled "METHODS FOR PRODUCING GENETICALLY ENGINEERED CELL COMPOSITIONS AND RELATED COMPOSITIONS," and U.S. provisional application No. 62/596,770, filed Dec. 8, 2017, entitled "METHODS FOR PRODUCING GENETICALLY ENGINEERED CELL COMPOSITIONS AND RELATED COMPOSITIONS," the contents of which are hereby incorporated by reference in their entirety.

INCORPORATION BY REFERENCE OF SEQUENCE LISTING

The present application is being filed along with a Sequence Listing in electronic format. The Sequence Listing is provided as a file entitled 735042013101SeqList.xml, created Nov. 10, 2023, which is 74,438 bytes in size. The information in the electronic format of the Sequence Listing is herein incorporated by reference in its entirety.

FIELD

The present disclosure relates to methods and compositions for generating engineered cells, such as cells expressing a recombinant receptor, including methods involving stimulation and/or engineering of an input composition having a defined ratio of naïve-like CD4+ T cells to naïve-like CD8+ T cells. In particular, the methods can be used to engineer T cells with genetically engineered receptors, such as genetically engineered antigen receptors such as engineered (recombinant) TCRs and chimeric antigen receptors (CARs), or other recombinant chimeric receptors. Features of the methods include producing a more consistent and/or predictable T cell product and/or a product with lower toxicity compared with other methods.

BACKGROUND

Various methods are available for preparing cells for therapeutic use and administering the cells. For example, methods are available for preparing cells, including T cells, for engineering and cell therapy, including methods involving depletion of or enrichment for certain sub-populations. Improved methods are needed, for example, to reduce toxicity associated with certain adoptive cell therapy administrations, to improve the manufacturing process, to allow improved administration, and/or to reduce cost or other resources. Provided are methods, cells, compositions, kits, and systems that meet such needs.

SUMMARY

Provided herein is a method for generating a cell composition including combining a first cell composition containing naïve-like CD4+ T cells with a second cell composition containing naïve-like CD8+ T cells to produce an input cell composition in which the ratio of naïve-like CD4+ T cells to naïve-like CD8+ T cells is between or about between 0.8:1 and 2.2:1, inclusive. In some embodiments, the first cell composition is produced by isolating CD4+ T cells from a biological sample obtained from a subject and/or the second cell composition is produced by isolating CD8+ T cells from the biological sample obtained from the subject.

In some embodiments, prior to the combining, the method includes determining the number, number per volume, number per weight, and/or percentage of the naïve-like CD4+ T cells in the first cell composition and/or the number, number per volume, number per weight, and/or percentage of the naïve-like CD8+ T cells in the second composition. In some cases, prior to the combining, the method includes determining the number, number per volume, number per weight, and/or percentage of the naïve-like CD4+ T cells and/or the number, number per volume, number per weight, and/or percentage of naïve-like CD8+ T cells in the biological sample from the subject. In some of any such embodiments, the ratio of the naïve-like CD4+ T cells to naïve-like CD8+ T cells in the input composition is adjusted or altered compared to the ratio of the naïve-like CD4+ T cells to naïve-like CD8+ T cells in the biological sample from the subject.

Provided herein is a method for generating a cell composition, the method including determining the number, number per volume, number per weight, and/or percentage of naïve-like CD4+ T cells and naïve-like CD8+ T cells in a biological sample obtained from a subject or in one or more samples derived therefrom; and producing an input composition containing CD4+ T cells and CD8+ T cells in which the ratio of the naïve-like CD4+ T cells to naive-like CD8+ T cells is between or about between 2.2:1 to 0.8:1, inclusive, wherein said ratio in the input composition is adjusted or altered compared to the ratio of the naïve-like CD4+ T cells to naive-like CD8+ T cells in the biological sample from the subject.

In some embodiments, the method further includes contacting the input composition with an agent containing a nucleic acid molecule encoding a recombinant receptor under conditions to introduce the nucleic acid encoding the recombinant receptor into cells in the input composition.

Provided herein a method of generating a cell composition, the method including contacting an input composition containing naïve-like CD4+ T cells and naïve-like CD8+ T cells from a biological sample from a subject with an agent containing a nucleic acid molecule encoding a recombinant receptor under conditions to introduce the nucleic acid encoding the recombinant receptor into cells in the composition, wherein the ratio of naïve-like CD4+ T cells to naïve-like CD8+ T cells present in the input composition is between or about between 0.8:1 and 2.2:1, inclusive.

In some embodiments, the method further includes stimulating the cells, prior to, during and/or subsequent to said contacting, wherein stimulating includes incubating the cells in the presence of one or more stimulating agents, wherein stimulating results in activation and/or proliferation of the cells.

Provided herein is a method of generating a cell composition, the method including combining a first cell composition containing naïve-like CD4+ T cells with a second cell composition containing naïve-like CD8+ T cells to produce an input cell composition in which the ratio of naïve-like CD4+ T cells to naïve-like CD8+ T cells is between or about between 0.8:1 and 2.2:1, inclusive; contacting the input composition with an agent containing a nucleic acid molecule encoding a recombinant receptor under conditions to introduce the nucleic acid encoding the recombinant receptor into cells in the composition; and stimulating the cells, prior to, during and/or subsequent to said contacting, wherein stimulating includes incubating the cells in the presence of one or more stimulating agents, wherein stimulating results in activation and/or proliferation of the cells.

In some of any such embodiments, the naïve-like CD4+ and/or the naïve-like CD8+ cells are surface positive for a marker selected from the group consisting of CD45RA, CD27, CD28, CD62L, and CCR7; and/or are surface negative for a marker selected from the group consisting of CD25, CD45RO, CD56, KLRG1; and/or have low expression of CD95; and/or are negative for intracellular expression of a cytokine selected from the group consisting of IL-2, IFN-γ, IL-4, IL-10. In some embodiments, the naïve-like CD4+ and/or the naïve-like CD8+ cells are surface positive for a T cell activation marker selected from the group consisting of CD45RA, CD27, CD28, and CCR7; and/or are surface negative for a marker selected from the group consisting of CD45RO, CD56, KLRG1; and/or have low expression of CD95. In some aspects, the naïve-like CD4+ and/or the naïve-like CD8+ cells are surface positive for CD45RA and CCR7. In some embodiments, the naïve-like CD4+ and the naïve-like CD8+ cells are surface positive for CD45RA, CD27 and CCR7 and are surface negative for CD45RO.

In some of any such embodiments, the number, number per volume, number per weight, and/or percentage of naïve-like CD4+ T cells and/or the number, number per volume, number per weight, and/or percentage of naïve-like CD8+ T cells is determined by flow cytometry. In some aspects, the ratio of naïve-like CD4+ T cells to naïve-like CD8+ T cells has been adjusted compared to the ratio of the naïve-like CD4+ T cells to naïve-like CD8+ T cells in a biological sample from the subject.

In some embodiments, the biological sample is or is obtained from a blood, plasma or serum sample. In some aspects, the biological sample is or includes a whole blood sample, a buffy coat sample, a peripheral blood mononuclear cells (PBMC) sample, an unfractionated T cell sample, a lymphocyte sample, a white blood cell sample, an apheresis product, or a leukapheresis product. In some cases, the biological sample is or is obtained from an apheresis or leukapheresis sample. In some embodiments, the subject is a human subject.

In some of any such embodiments, the input composition contains a ratio of naïve-like CD4+ cells to naïve-like CD8+ cells of between or about between 0.8:1 and 2.0:1, 0.8:1 and 1.6:1, 0.8:1 and 1.4:1, 0.8:1 and 1.2:1 or 1.0:1 and 1.2:1, each inclusive. In some embodiments, the input composition includes a ratio of naïve-like CD4+ cells to naïve-like CD8+ cells of or about 1.5:1, 1.4:1, 1.3:1, 1.2:1, 1.1:1, or 1.0:1. In some embodiments, the input composition contains a ratio of naïve-like CD4+ cells to naïve-like CD8+ cells of or about 1.1:1.

In some of any such embodiments, the input composition contains from or from about $1\times10^7$ to $5\times10^9$ total cells or total T cells, from or from about $5\times10^7$ to $1\times10^9$ total cells or total T cells, from or from about $1\times10^8$ to $5\times10^8$ total cells or total T cells, or from or from about $2\times10^8$ to $5\times10^8$ total cells or total T cells, or of viable populations of any of the foregoing. In some cases, the input composition contains at least or at least about $1\times10^8$, $2\times10^8$, $3\times10^8$, $4\times10^8$, or $5\times10^8$ total cells or total T cells or a viable population of any of the foregoing.

In some embodiments, the one or more stimulating agent is capable of activating T cells, CD4+ T cells and/or CD8+ T cells; is capable of inducing a signal through a TCR complex; and/or is capable of inducing proliferation of T cells, CD4+ T cells and/or CD8+ T cells. In some aspects, the one or more stimulating agent contains a primary agent that binds to a member of a TCR complex, optionally that specifically binds to CD3. In some cases, the one or more stimulating agent further contains a secondary agent that specifically binds to a T cell costimulatory molecule. In some examples, the costimulatory molecule is selected from the group consisting of CD28, CD137 (4-1-BB), OX40, or ICOS.

In some embodiments, the primary and secondary agents contain antibodies, optionally wherein the one or more stimulating agent includes incubation with an anti-CD3 antibody and an anti-CD28 antibody. In some embodiments, the one or more stimulating agents are present on the surface of a solid support, optionally a bead. In some embodiments, the one or more stimulating agent are present on the surface of a bead and the bead is a paramagnetic bead. In some aspects, the one or more one stimulating agent is selected from the group consisting of CD3-binding molecules; CD28-binding molecules; recombinant IL-2; recombinant IL-15; and recombinant IL-7, a vaccine containing an antigen specifically recognized by the antigen receptor, and an anti-idiotype antibody that specifically binds the antigen receptor or combinations thereof.

In some of any such embodiments, the incubation is carried out for 2 to 15 days, 2 to 12 days, 2 to 12 days, 2 to 8 days, 2 to 6 days, 2 to 4 days, 4 to 12 days, 4 to 10 days, 4 to 8 days, 4 to 6 days, 6 to 12 days, 6 to 10 days, 6 to 8 days, 8 to 12 days, 8 to 10 days, or 10 to 12 days. In some cases, the incubation is carried out for at least or about at least or 4 days, 6 days, 8 days, 10 days or 12 days.

In some of any such embodiments, the agent containing the nucleic acid molecule is a viral vector or is a transposon. In some cases, the agent containing the nucleic acid molecule is a viral vector and the viral vector is a retroviral vector. In some examples, the viral vector is a lentiviral vector or a gammaretroviral vector.

In some embodiments, the recombinant receptor is capable of binding to a target antigen that is associated with, specific to, and/or expressed on a cell or tissue of a disease, disorder or condition. In some cases, the disease, disorder or condition is an infectious disease or disorder, an autoimmune disease, an inflammatory disease, or a tumor or a cancer. In some instances, the target antigen is a tumor antigen. In some examples, the target antigen is selected from among ROR1, B cell maturation antigen (BCMA), carbonic anhydrase 9 (CAIX), tEGFR, Her2/neu (receptor tyrosine kinase erbB2), CD19, CD20, CD22, mesothelin, CEA, and hepatitis B surface antigen, anti-folate receptor, CD23, CD24, CD30, CD33, CD38, CD44, EGFR, epithelial glycoprotein 2 (EPG-2), epithelial glycoprotein 40 (EPG-40), EPHa2, erb-B2, erb-B3, erb-B4, erbB dimers, EGFR vIII, folate binding protein (FBP), FCRL5, FCRH5, fetal acetylcholine receptor, GD2, GD3, G Protein Coupled Receptor 5D (GPCR5D, HMW-MAA, IL-22R-alpha, kinase insert domain receptor (kdr), kappa light chain, Lewis Y, L1-cell adhesion molecule (L1-CAM), Melanoma-associated antigen (MAGE)-A1, MAGE-A3, MAGE-A6, Preferentially expressed antigen of melanoma (PRAME), survivin, TAG72, B7-H6, IL-13 receptor alpha 2 (IL-13Ra2), CA9, GD3, HMW-MAA, CD171, G250/CAIX, PSCA, folate receptor-a, CD44v6, CD44v7/8, avb6 integrin, 8H9, NCAM, VEGF receptors, 5T4, Foetal AchR, NKG2D ligands, CD44v6, dual antigen, a cancer-testes antigen, mesothelin, murine CMV, mucin 1 (MUC1), MUC16, PSCA, NKG2D, NY-ESO-1, MART-1, gp100, oncofetal antigen, ROR1, TAG72, VEGF-R2, carcinoembryonic antigen (CEA), Her2/neu, estrogen receptor, progesterone receptor, ephrinB2, CD123, c-Met, GD-2, O-acetylated GD2 (OGD2), CE7, Wilms Tumor 1 (WT-1), a cyclin, cyclin A2, CCL-1, CD138, a pathogen-specific antigen and an antigen associated with a universal tag.

In some examples, the target antigen is selected from among Receptor Tyrosine Kinase Like Orphan Receptor 1 (ROR1), B cell maturation antigen (BCMA), carbonic anhydrase 9 (CA9, also known as CAIX or G250), Her2/neu (receptor tyrosine kinase erbB2), CD19, CD20, CD22, mesothelin (MSLN), carcinoembryonic antigen (CEA), and hepatitis B surface antigen, anti-folate receptor, CD23, CD24, CD30, CD33, CD38, CD44, chondroitin sulfate proteoglycan 4 (CSPG4), EGFR, epithelial glycoprotein 2 (EPG-2), epithelial glycoprotein 40 (EPG-40), ephrin receptor A2 (EPHa2), Her3 (erb-B3), Her4 (erb-B4), erbB dimers, type III epidermal growth factor receptor mutation (EGFR vIII), folate binding protein (FBP), Fc receptor like 5 (FCRL5, also known as Fc receptor homolog 5 or FCRH5), fetal acetylcholine receptor (fetal AchR), ganglioside GD2, ganglioside GD3, Human leukocyte antigen A1 (HLA-A1), Human leukocyte antigen A2 (HLA-A2), IL-22 receptor alpha (IL-22Rα), kinase insert domain receptor (kdr), kappa light chain, Leucine Rich Repeat Containing 8 Family Member A (LRRC8A), Lewis Y, L1-cell adhesion molecule (L1-CAM), Melanoma-associated antigen (MAGE)-A1, MAGE-A3, MAGE-A6, MAGE-A10, Preferentially expressed antigen of melanoma (PRAME), survivin, tumor-associated glycoprotein 72 (TAG72), B7-H3, B7-H6, IL-13 receptor alpha 2 (IL-13Rα2), Human high molecular weight-melanoma-associated antigen (HMW-MAA), CD171, folate receptor-alpha, CD44v7/8, αvβ6 integrin (avb6 integrin), 8H9, neural cell adhesion molecule (NCAM), vascular endothelial growth factor receptor (VEGF receptors or VEGFR), Trophoblast glycoprotein (TPBG also known as 5T4), NKG2D ligands, CD44v6, dual antigen, a cancer-testes antigen, murine cytomegalovirus (CMV), mucin 1 (MUC1), MUC16, prostate stem cell antigen (PSCA), prostate specific membrane antigen (PSMA), natural killer group 2 member D (NKG2D) ligands, cancer/testis antigen 1B (CTAG, also known as NY-ESO-1 and LAGE-2), melan A (MART-1), glycoprotein 100 (gp100), glypican-3 (GPC3), G Protein Coupled Receptor 5D (GPRCSD), oncofetal antigen, TAG72, Tyrosinase related protein 1 (TRP1, also known as TYRP1 or gp75), Tyrosinase related protein 2 (TRP2, also known as dopachrome tautomerase, dopachrome delta-isomerase or DCT), vascular endothelial growth factor receptor 2 (VEGF-R2), carcinoembryonic antigen (CEA), estrogen receptor, progesterone receptor, a prostate specific antigen, ephrinB2, CD123, CD133, c-Met, O-acetylated GD2 (OGD2), CE7 epitope of L1-CAM, Wilms Tumor 1 (WT-1), a cyclin, cyclin A2, C—C Motif Chemokine Ligand 1 (CCL-1), CD138, a pathogen-specific antigen or pathogen-expressed antigen, and an antigen associated with a universal tag, and/or biotinylated molecules, and/or molecules expressed by HIV, HCV, HBV or other pathogens.

Antigens targeted by the receptors in some embodiments include antigens associated with a B cell malignancy, such as any of a number of known B cell marker. In some embodiments, the antigen is or includes CD20, CD19, CD22, ROR1, CD45, CD21, CD5, CD33, Igkappa, Iglambda, CD79a, CD79b or CD30.

In some embodiments, the antigen is or includes a pathogen-specific or pathogen-expressed antigen. In some embodiments, the antigen is a viral antigen (such as a viral antigen from HIV, HCV, HBV, etc.), bacterial antigens, and/or parasitic antigens.

In some embodiments, the recombinant receptor is or contains a functional non-TCR antigen receptor or a TCR or antigen-binding fragment thereof. In some embodiments, the recombinant receptor is a chimeric antigen receptor (CAR). In some cases, the chimeric antigen receptor contains an extracellular domain containing an antigen-binding domain. In some instances, the antigen-binding domain is or contains an antibody or an antibody fragment thereof, which optionally is a single chain fragment. In some embodiments, the fragment contains antibody variable regions joined by a flexible linker. In some aspects, the fragment contains an scFv.

In some embodiments, the chimeric antigen receptor further contains a spacer and/or a hinge region. In some embodiments, the chimeric antigen receptor contains an intracellular signaling region. In some cases, the intracellular signaling region contains an intracellular signaling domain. In some embodiments, the intracellular signaling domain is or contains a primary signaling domain, a signaling domain that is capable of inducing a primary activation signal in a T cell, a signaling domain of a T cell receptor (TCR) component, and/or a signaling domain containing an immunoreceptor tyrosine-based activation motif (ITAM). In some embodiments, the intracellular signaling domain is or contains an intracellular signaling domain of a CD3 chain, optionally a CD3-zeta (CD3ζ) chain, or a signaling portion thereof.

In some embodiments, the CAR comprises an scFv specific for the antigen, a transmembrane domain, a cytoplasmic signaling domain derived from a costimulatory molecule, which optionally is or comprises a 4-1BB, and a cytoplasmic signaling domain derived from a primary signaling ITAM-containing molecule, which optionally is or comprises a CD3zeta signaling domain and optionally further comprises a spacer between the transmembrane domain and the scFv; the CAR comprises, in order, an scFv specific for the antigen, a transmembrane domain, a cytoplasmic signaling domain derived from a costimulatory molecule, which optionally is or comprises a 4-1BB signaling domain, and a cytoplasmic signaling domain derived from a primary signaling ITAM-containing molecule, which optionally is a CD3zeta signaling domain; or the CAR comprises, in order, an scFv specific for the antigen, a spacer, a transmembrane domain, a cytoplasmic signaling domain derived from a costimulatory molecule, which optionally is a 4-1BB signaling domain, and a cytoplasmic signaling domain derived from a primary signaling ITAM-containing molecule, which optionally is or comprises a CD3zeta signaling domain.

In some embodiments, the chimeric antigen receptor further contains a transmembrane domain disposed between the extracellular domain and the intracellular signaling region. In some embodiments, the intracellular signaling region further contains a costimulatory signaling region. In some aspects, the costimulatory signaling region contains an intracellular signaling domain of a T cell costimulatory molecule or a signaling portion thereof. In some examples, the costimulatory signaling region contains an intracellular signaling domain of a CD28, a 4-1BB or an ICOS or a signaling portion thereof. In some embodiments, the costimulatory signaling region is between the transmembrane domain and the intracellular signaling region.

In some of any such embodiments, the subject has a disease or condition, optionally wherein the recombinant receptor specifically recognizes or specifically bind to an antigen associated with, or expressed or present on cells of, the disease or condition.

In some embodiments, the method produces an output composition in which the ratio of recombinant receptor-expressing CD4+ T cells to recombinant receptor-expressing CD8+ T cells, optionally the ratio of viable cells thereof, varies by no more than 20% or no more than 10% or no more than 5% from an average of said ratio in a plurality of T cell compositions produced by the method and/or varies from such average by no more than one standard deviation. In some embodiments, the method produces an output composition in which the ratio of recombinant receptor-expressing CD4+ T cells to recombinant receptor-expressing CD8+ T cells, optionally the ratio of viable cells thereof, is between at or about 0.5:1 and 2:1 or 0.8:1 and 1.6:1 or 1:1 and 1.5:1, each inclusive. In some examples, the ratio of recombinant receptor-expressing CD4+ T cells to recombinant receptor-expressing CD8+ T cells, optionally the ratio of viable cells thereof, in the output composition is or is about 1.2:1, 1.1:1, 1:1, 0.9:1, or 0.8:1. In some cases, the ratio of recombinant receptor-expressing CD4+ T cells to recombinant receptor-expressing CD8+ T cells, optionally the ratio of viable cells thereof, in the output composition is or is about 1:1.

In some embodiments, the viable cells contain cells that are apoptotic marker negative (−), optionally wherein the apoptotic marker is Annexin V or active Caspase 3.

In some of any such embodiments, the method is performed in vitro or ex vivo.

Provided herein is an output composition produced by any of the methods described herein. Also provided is a pharmaceutical composition containing the output composition described. In some embodiments, the pharmaceutical composition further contains a pharmaceutical carrier.

Provided herein is a method of treatment including administering to a mammalian subject an output composition produced by any of the described methods or any of the described pharmaceutical compositions. In some embodiments, the cells are derived from the subject to which the cells are administered.

In certain embodiments of the provided methods, the naïve-like CD4+ and/or the naïve-like CD8+ cells are surface positive for CD45RA and CCR7. In some embodiments of the provided methods, the naïve-like CD4+ and/or the naïve-like CD8+ cells are surface positive for CD27 and CCR7. In particular embodiments of the provided methods, the naïve-like CD4+ and the naïve-like CD8+ cells are surface positive for CD45RA, CD27 and CCR7 and are surface negative for CD45RO.

In certain embodiments of the provided methods, the naïve-like CD4+ and/or the naïve-like CD8+ cells are surface positive for CCR7 and surface negative for CD62L. In some embodiments of the provided methods, the input composition comprises a ratio of naïve-like CD4+ cells to naïve-like CD8+ cells that are surface positive for CD45RA and CCR7 of or about 1.1:1. In particular embodiments of the provided methods, the input composition comprises a ratio of naïve-like CD4+ cells to naïve-like CD8+ cells that are surface positive for CD45RA and CD27 of or about 1.69:1. In some embodiments, the input cell composition comprises a ratio of naïve-like CD4+ cells to naïve-like CD8+ cells that are surface positive for CD27 and CCR7 of or about 1.69:1.

In certain embodiments, herein is a method for generating a cell composition, the method comprising: combining a first cell composition comprising CCR7+CD45RA+CD4+ T cells with a second cell composition comprising CCR7+CD45RA+CD8+ T cells to produce an input cell composition in which the ratio of CCR7+CD45RA+CD4+ T cells to CCR7+CD45RA+CD8+ T cells is between or about between 0.8:1 and 2.2:1, inclusive. In some embodiments of the provided methods, the first cell composition is produced by isolating CD4+ T cells from a biological sample obtained from a subject and/or the second cell composition is produced by isolating CD8+ T cells from the biological sample obtained from the subject.

In particular embodiments of the provided methods, prior to the combining, the method comprises determining the number, number per volume, number per weight, and/or percentage of the CCR7+CD45RA+CD4+ T cells in the first cell composition and/or the number, number per volume, number per weight, and/or percentage of the CCR7+CD45RA+CD8+ T cells in the second composition. In certain embodiments of the provided methods, prior to the combining, the method comprises determining the number, number per volume, number per weight, and/or percentage of the CCR7+CD45RA+CD4+ T cells and/or the number, number per volume, number per weight, and/or percentage of CCR7+CD45RA+CD8+ T cells in the biological sample from the subject. In some embodiments of the provided methods, the ratio of the CCR7+CD45RA+CD4+ T cells to CCR7+CD45RA+CD8+ T cells in the input composition is adjusted or altered compared to the ratio of the CCR7+CD45RA+CD4+ T cells to CCR7+CD45RA+CD8+ T cells in the biological sample from the subject.

In particular embodiments, provided herein is a method for generating a cell composition, the method comprising: determining the number, number per volume, number per weight, and/or percentage of CCR7+CD45RA+CD4+ T cells and CCR7+CD45RA+CD8+ T cells in a biological sample obtained from a subject or in one or more samples derived therefrom; and producing an input composition comprising CD4+ T cells and CD8+ T cells in which the ratio of the CCR7+CD45RA+CD4+ T cells to naive-like CD8+ T cells is between or about between 2.2:1 to 0.8:1, inclusive, wherein said ratio in the input composition is adjusted or altered compared to the ratio of the CCR7+CD45RA+CD4+ T cells to naïve-like CD8+ T cells in the biological sample from the subject.

Certain embodiments of the provided methods further comprise contacting the input composition with an agent comprising a nucleic acid molecule encoding a recombinant receptor under conditions to introduce the nucleic acid encoding the recombinant receptor into cells in the input composition.

Provided herein is a method of generating a cell composition, the method comprising: contacting an input composition comprising CCR7+CD45RA+CD4+ T cells and CCR7+CD45RA+CD8+ T cells from a biological sample from a subject with an agent comprising a nucleic acid molecule encoding a recombinant receptor under conditions to introduce the nucleic acid encoding the recombinant receptor into cells in the composition, wherein the ratio of CCR7+CD45RA+CD4+ T cells to CCR7+CD45RA+CD8+ T cells present in the input composition is between or about between 0.8:1 and 2.2:1, inclusive. In some embodiments of the provided methods further comprise stimulating the cells, prior to, during and/or subsequent to said contacting, wherein stimulating comprises incubating the cells in the presence of one or more stimulating agents, wherein stimulating results in activation and/or proliferation of the cells.

In particular embodiments, provided herein is a method of generating a cell composition, the method comprising: combining a first cell composition comprising CCR7+ CD45RA+CD4+ T cells with a second cell composition comprising CCR7+CD45RA+CD8+ T cells to produce an input cell composition in which the ratio of CCR7+ CD45RA+CD4+ T cells to CCR7+CD45RA+CD8+ T cells is between or about between 0.8:1 and 2.2:1, inclusive; contacting the input composition with an agent comprising a nucleic acid molecule encoding a recombinant receptor under conditions to introduce the nucleic acid encoding the recombinant receptor into cells in the composition; and stimulating the cells, prior to, during and/or subsequent to said contacting, wherein stimulating comprises incubating the cells in the presence of one or more stimulating agents, wherein stimulating results in activation and/or proliferation of the cells.

In certain embodiments of the provided methods, the number, number per volume, number per weight, and/or percentage of CCR7+CD45RA+CD4+ T cells and/or the number, number per volume, number per weight, and/or percentage of CCR7+CD45RA+CD8+ T cells is determined by flow cytometry. In some embodiments of the provided methods, the ratio of CCR7+CD45RA+CD4+ T cells to CCR7+CD45RA+CD8+ T cells has been adjusted compared to the ratio of the CCR7+CD45RA+CD4+ T cells to CCR7+ CD45RA+CD8+ T cells in a biological sample from the subject. In particular embodiments of the provided methods, the input composition comprises a ratio of CCR7+ CD45RA+CD4+ cells to CCR7+CD45RA+CD8+ cells of between or about between 0.8:1 and 2.0:1, 0.8:1 and 1.6:1, 0.8:1 and 1.4:1, 0.8:1 and 1.2:1, or 1.0:1 and 1.2:1, each inclusive. In certain embodiments of the provided methods, the input composition comprises a ratio of CCR7+ CD45RA+CD4+ cells to CCR7+CD45RA+CD8+ cells of or about 1.5:1, 1.4:1, 1.3:1, 1.2:1, 1.1:1, or 1.0:1.

In some embodiments of the provided methods, the input composition comprises a ratio of CCR7+CD45RA+CD4+ cells to CCR7+CD45RA+CD8+ cells of or about 1.1:1. In particular embodiments, provided herein is a method for generating a cell composition, the method comprising: combining a first cell composition comprising CD27+CCR7+ CD4+ T cells with a second cell composition comprising CD27+CCR7+CD8+ T cells to produce an input cell composition in which the ratio of CD27+CCR7+CD4+ T cells to CD27+CCR7+CD8+ T cells is between or about between 1.2:1 and 2.4:1, inclusive.

In certain embodiments of the provided methods, the first cell composition is produced by isolating CD4+ T cells from a biological sample obtained from a subject and/or the second cell composition is produced by isolating CD8+ T cells from the biological sample obtained from the subject. In some embodiments of the provided methods, prior to the combining, the method comprises determining the number, number per volume, number per weight, and/or percentage of the CD27+CCR7+CD4+ T cells in the first cell composition and/or the number, number per volume, number per weight, and/or percentage of the CD27+CCR7+CD8+ T cells in the second composition. In particular embodiments of the provided methods, prior to the combining, the method comprises determining the number, number per volume, number per weight, and/or percentage of the CD27+CCR7+ CD4+ T cells and/or the number, number per volume, number per weight, and/or percentage of CD27+CCR7+ CD8+ T cells in the biological sample from the subject.

In certain embodiments of the provided methods, the ratio of the CD27+CCR7+CD4+ T cells to CD27+CCR7+CD8+ T cells in the input composition is adjusted or altered compared to the ratio of the CD27+CCR7+CD4+ T cells to CD27+CCR7+CD8+ T cells in the biological sample from the subject. In certain embodiments provided herein is a method for generating a cell composition, the method comprising: determining the number, number per volume, number per weight, and/or percentage of CD27+CCR7+CD4+ T cells and CD27+CCR7+CD8+ T cells in a biological sample obtained from a subject or in one or more samples derived therefrom; and producing an input composition comprising CD4+ T cells and CD8+ T cells in which the ratio of the CD27+CCR7+CD4+ T cells to naive-like CD8+ T cells is between or about between 2.2:1 to 0.8:1, inclusive, wherein said ratio in the input composition is adjusted or altered compared to the ratio of the CD27+CCR7+CD4+ T cells to naive-like CD8+ T cells in the biological sample from the subject.

Some embodiments of the provided methods further comprise contacting the input composition with an agent comprising a nucleic acid molecule encoding a recombinant receptor under conditions to introduce the nucleic acid encoding the recombinant receptor into cells in the input composition.

In particular embodiments, provided herein is a method of generating a cell composition, the method comprising: contacting an input composition comprising CD27+CCR7+ CD4+ T cells and CD27+CCR7+CD8+ T cells from a biological sample from a subject with an agent comprising a nucleic acid molecule encoding a recombinant receptor under conditions to introduce the nucleic acid encoding the recombinant receptor into cells in the composition, wherein the ratio of CD27+CCR7+CD4+ T cells to CD27+CCR7+ CD8+ T cells present in the input composition is between or about between 0.8:1 and 2.2:1, inclusive. Certain embodiments of the provided methods further comprise stimulating the cells, prior to, during and/or subsequent to said contacting, wherein stimulating comprises incubating the cells in the presence of one or more stimulating agents, wherein stimulating results in activation and/or proliferation of the cells.

In some embodiments, provided herein is a method of generating a cell composition, the method comprising: combining a first cell composition comprising CD27+CCR7+ CD4+ T cells with a second cell composition comprising CD27+CCR7+CD8+ T cells to produce an input cell composition in which the ratio of CD27+CCR7+CD4+ T cells to CD27+CCR7+CD8+ T cells is between or about between 0.8:1 and 2.2:1, inclusive; contacting the input composition with an agent comprising a nucleic acid molecule encoding a recombinant receptor under conditions to introduce the nucleic acid encoding the recombinant receptor into cells in the composition; and stimulating the cells, prior to, during and/or subsequent to said contacting, wherein stimulating comprises incubating the cells in the presence of one or more stimulating agents, wherein stimulating results in activation and/or proliferation of the cells.

In particular embodiments of the provided methods, the number, number per volume, number per weight, and/or percentage of CD27+CCR7+CD4+ T cells and/or the number, number per volume, number per weight, and/or percentage of CD27+CCR7+CD8+ T cells is determined by flow cytometry. In certain embodiments of the provided methods, the ratio of CD27+CCR7+CD4+ T cells to CD27+ CCR7+CD8+ T cells has been adjusted compared to the ratio of the CD27+CCR7+CD4+ T cells to CD27+CCR7+CD8+ T cells in a biological sample from the subject.

In some embodiments of the provided methods, the input composition comprises a ratio of CD27+CCR7+CD4+ cells to CD27+CCR7+CD8+ cells of between or about between 0.8:1 and 2.0:1, 0.8:1 and 1.6:1, 0.8:1 and 1.4:1, 0.8:1 and 1.2:1, or 1.0:1 and 1.2:1, each inclusive. In particular embodiments of the provided methods, the input composition comprises a ratio of CD27+CCR7+CD4+ cells to CD27+CCR7+CD8+ cells of or about 1.5:1, 1.4:1, 1.3:1, 1.2:1, 1.1:1, or 1.0:1. In certain embodiments of the provided methods, the input composition comprises a ratio of CD27+CCR7+CD4+ cells to CD27+CCR7+CD8+ cells of or about 1.1:1. In some embodiments, the input cell composition comprises a ratio of CD27+CCR7+CD4+ cells to CD27+CCR7+CD8+ cells of or about 1.69:1.

In some embodiments, provided herein is a method for generating a cell composition, the method comprising: combining a first cell composition comprising CD62L-CCR7+CD4+ T cells with a second cell composition comprising CD62L-CCR7+CD8+ T cells to produce an input cell composition in which the ratio of CD62L-CCR7+CD4+ T cells to CD62L-CCR7+CD8+ T cells is between or about between 0.5:1 and 2:1, inclusive.

In particular embodiments, provided herein is a method for generating a cell composition, the method comprising: determining the number, number per volume, number per weight, and/or percentage of CD62L-CCR7+CD4+ T cells and CD62L-CCR7+CD8+ T cells in a biological sample obtained from a subject or in one or more samples derived therefrom; and producing an input composition comprising CD4+ T cells and CD8+ T cells in which the ratio of the CD62L-CCR7+CD4+ T cells to naive-like CD8+ cells is between or about between 0.5:1 and 2:1, inclusive, wherein said ratio in the input composition is adjusted or altered compared to the ratio of the CD62L-CCR7+CD4+ T cells to naive-like CD8+ cells in the biological sample from the subject.

Certain embodiments of the provided methods further comprise contacting the input composition with an agent comprising a nucleic acid molecule encoding a recombinant receptor under conditions to introduce the nucleic acid encoding the recombinant receptor into cells in the input composition. In some embodiments, provided herein is a method of generating a cell composition, the method comprising: combining a first cell composition comprising CD62L-CCR7+CD4+ T cells with a second cell composition comprising CD62L-CCR7+CD8+ T cells to produce an input cell composition in which the ratio of CD62L-CCR7+CD4+ T cells to CD62L-CCR7+CD8+ T cells is between or about between 0.5:1 and 2:1, inclusive; contacting the input composition with an agent comprising a nucleic acid molecule encoding a recombinant receptor under conditions to introduce the nucleic acid encoding the recombinant receptor into cells in the composition; and stimulating the cells, prior to, during and/or subsequent to said contacting, wherein stimulating comprises incubating the cells in the presence of one or more stimulating agents, wherein stimulating results in activation and/or proliferation of the cells.

In particular embodiments of the provided methods, the number, number per volume, number per weight, and/or percentage of CD62L-CCR7+CD4+ T cells and/or the number, number per volume, number per weight, and/or percentage of CD62L-CCR7+CD8+ T cells is determined by flow cytometry. In certain embodiments of the provided methods, the ratio of CD62L-CCR7+CD4+ T cells to CD62L-CCR7+CD8+ T cells has been adjusted compared to the ratio of the CD62L-CCR7+CD4+ T cells to CD62L-CCR7+CD8+ T cells in a biological sample from the subject.

In some embodiments of the provided methods, the input composition comprises a ratio of CD62L-CCR7+CD4+ cells to CD62L-CCR7+CD8+ cells of between or about between 0.5:1 and 1.5:1, 1:1 and 2:1, 0.75:1 and 1.5:1, or 0.8:1 and 1.2:1, each inclusive. In particular embodiments of the provided methods, the input composition comprises a ratio of CD62L-CCR7+CD4+ cells to CD62L-CCR7+CD8+ cells of or about 1.2:1, 1.1:1, 1.0:1, 0.9:1, or 0.8:1.

In certain embodiments of the provided methods, the biological sample is or is obtained from a blood, plasma or serum sample. In some embodiments of the provided methods, the biological sample is or comprises a whole blood sample, a buffy coat sample, a peripheral blood mononuclear cells (PBMC) sample, an unfractionated T cell sample, a lymphocyte sample, a white blood cell sample, an apheresis product, or a leukapheresis product. In particular embodiments of the provided methods, the biological sample is or is obtained from an apheresis or leukapheresis sample.

BRIEF DESCRIPTION OF THE DRAWINGS

FIG. 2A shows a plot of bivariate fit analysis of the ratio of CD45RA+/CCR7+/CD4+ to CD45RA+/CCR7+/CD8+ cells in a starting mixture of selected CD4 and CD8 cells compared to the CAR+ CD4+/CD8+ ratio in an engineered CAR+ T cell composition. FIG. 2B shows a plot of bivariate fit analysis of the ratio of the CD62L-/CCR7+/CD4+ T cells to CD62L-/CCR7+/CD8+ T cells in a starting mixture of selected CD4 and CD8 cells compared to the CAR+ CD4+/CD8+ ratio in an engineered CAR+ T cell composition. FIG. 2C shows a plot of bivariate fit analysis of the ratio of the CD27+/CCR7+/CD4+ T cells to CD27+/CCR7+/CD8+ T cells in a starting mixture of selected CD4 and CD8 cells compared to the CAR+ CD4+/CD8+ ratio in an engineered CAR+ T cell composition. The curved lines represent the boundaries of the bivariate normal ellipse at p=0.950. Data points represent the mean ratios of multiple compositions from each subject, including healthy donors (circles) and a patient with multiple myeloma (plus signs).

FIG. 3A shows a plot of bivariate fit analysis of the ratio of CD27+/CCR7+/CD4+ to CD27+/CCR7+/CD8+ cells in a starting mixture of selected CD4 and CD8 cells compared to the CAR+ CD4+/CD8+ ratio in an engineered CAR+ T cell composition.

FIG. 3B shows a plot of bivariate fit analysis of the ratio of the CD27+/CCR7+/CD4+ T cells to CD27+/CCR7+/CD8+ T cells in a starting mixture of selected CD4 and CD8 cells compared to the CAR+ CD4+/CD8+ ratio in an engineered CAR+ T cell composition. FIG. 3C shows a plot of bivariate fit analysis of the ratio of the CD62L−/CCR7+/CD4+ T cells to CD62L−/CCR7+/CD8+ T cells in a starting mixture of selected CD4 and CD8 cells compared to the CAR+ CD4+/CD8+ ratio in an engineered CAR+ T cell composition. The curved lines represent the boundaries of the bivariate normal ellipse at p=0.950.

DETAILED DESCRIPTION

Figure 1A:
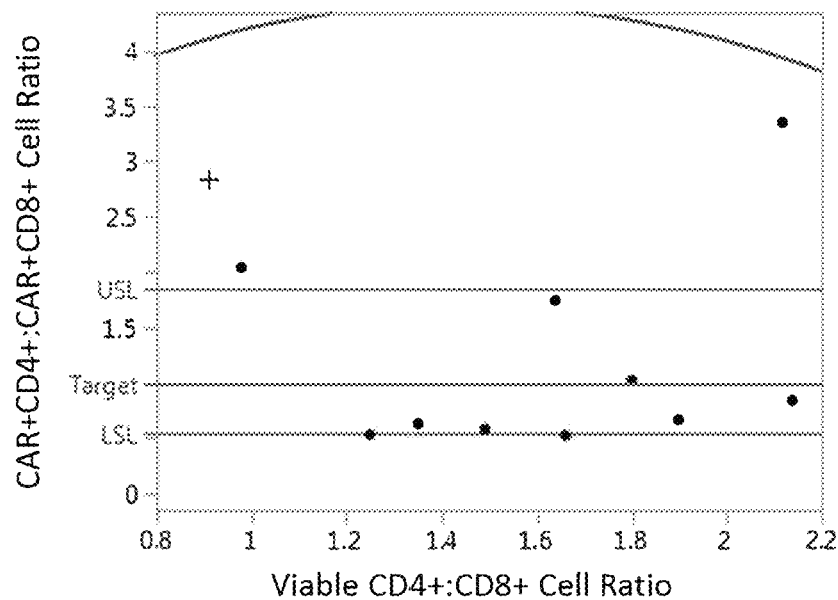
FIG. 1A shows a plot of bivariate fit analysis of the ratio of viable CD4+ cells to viable CD8+ cells (viable CD4+/CD8+ ratio) in an apheresis sample compared to the ratio of CAR+CD4+ T cells to CAR+CD8+ T cells (CAR+CD4+/CD8+ ratio) in a T cell composition after T cell activation, transduction with a chimeric antigen receptor (CAR) construct and expansion. The curved lines represent the boundaries of the bivariate normal ellipse at p=0.990. Data points represent the mean ratios of four samples from each subject, including healthy subjects (circles) and a subject with myeloma (plus sign).

Provided herein are methods for preparing a cell composition, for example an input cell composition, for use in genetically engineering cells to express a recombinant receptor. In some embodiments, the methods include one or more steps for producing an input cell composition containing a defined, controlled, or desired ratio of naïve-like CD4+ T cells to naïve-like CD8+ T cells. In some cases, the provided input composition can be produced by mixing or combining a cell composition containing CD4+ T cells having a known or determined number or percentage of naïve-like CD4+ T cells with a cell composition containing CD8+ T cells having a known or determined number or percentage of naïve-like CD8+ T cells, such as to achieve the chosen or desired ratio. Also provided are methods for stimulating, expanding and/or inducing proliferation of cells in the input composition. The provided methods also can include methods associated with genetic engineering of cells, such as transduction methods, including methods for introducing a recombinant receptor, e.g. chimeric antigen receptor, into such cells for use in connection with adoptive cell therapy.

In one embodiment, processing of the generated input composition includes incubating the cells under stimulating conditions, for example in some aspects, to activate the cells for engineering or transduction or for cell expansion. The methods, in some embodiments, include steps for engineering a plurality of cell types, such as CD4+ cells and CD8+ cells, such as those isolated and present in the input composition. In some aspects, the engineering is carried out to introduce a genetically engineered antigen receptor into the cells, such as a TCR, e.g., a high-affinity TCR, or a functional non-TCR antigen receptor, such as a chimeric antigen receptor (CAR). In some aspects, the methods include further processing, such as further incubation, for example at or about 37° C.±2° C., and/or formulating of cells and compositions containing the same. In some embodiments, the processing produces a resulting output composition containing genetically engineered cells, such as genetically engineered CD4+ cells and CD8+ cells, including cells in which the engineered CD4+ and CD8+ cells are present at a desired ratio. In some embodiments, the resulting processed output composition can be used in methods for administering cells and compositions prepared by the methods to a patient, for example, in connection with adoptive cell therapy.

In some aspects an output composition containing engineered cells, e.g. CAR+ T cells, in which the engineered CD4+ cells and CD8+ cells are present at a desired ratio, or within a certain degree of tolerated error of the desired ratio, is advantageous. For example, engineering cells enriched for a plurality of different cell populations or types of cells, such as isolated CD4+ and CD8+ T cell populations and subpopulations, can improve efficacy of or reduce or avoid unwanted effects. In some cases, such ratios include those deemed optimal for the therapeutic use, e.g., output ratios deemed appropriate or optimal for administration to a patient in connection with adoptive cell therapy. In some embodiments, the desired ratio of CD4+ to CD8+ T cells in an output composition for administration to a subject, such as in connection with adoptive cell therapy, is from or from about 2:1 to 0.5:1, for example at or about 1:1. In some aspects, a composition containing isolated CD8+ and CD4+ T cells, such as containing a certain desired ratio of such cells, increases the ability of cells ultimately administered to a subject to persist, expand, become activated, and/or engraft in vivo or upon administration to a subject. In some aspects, it improves or increases one or more effector function or activation phenotype. For example, such advantages can be achieved in some aspects by administering a CD4+ and a CD8+ population in comparison with a CD8+ population alone.

In some embodiments, the methods provide one or more advantages compared with other preparation, isolation, incubation, and engineering methods, such as cost, time, and/or resource savings. Such advantages can include the ability to isolate, process, e.g., incubate, and/or engineer the plurality of cell populations, present at or near a desired ratio, with increased efficiency and/or reduced complexity, time, cost, and/or use of resources, compared with other methods.

In some embodiments, the provided methods are based on observations that, in certain cell production processes for engineering cells, the input ratio of CD4+ to CD8+ cells, or a ratio of viable cells thereof, may not correlate to the output ratio of the engineered CD4+ to CD8+ cells, or a ratio of viable cells thereof. As shown herein, it is found that the desired ratio of engineered CD4+ to CD8+ T cells (e.g. CAR+ CD4 to CAR+CD8+ T cells or of the ratio of viable cells thereof) in an output composition is correlated or associated with the ratio of the naïve-like CD4+ T cells to naïve-like CD8+ T cells, or a ratio of viable cells thereof, present in an input composition prior to carrying out a production process on the cells to produce the output composition, e.g. involving one or more steps of stimulation, activation, expansion, proliferation and/or transduction of the cells. Exemplary of such naïve-like cells are ratios of CD4+ to CD8+ cells that are CD45RA+ and CCR7+, CD62L−/CCR7+ or CD27+/CCR7+. In some aspects, it is observed that such correlation between the ratio of naïve-like CD4/CD8 cells in an input composition to engineered CD4+ to CD8+ cells (e.g. CAR+ CD4 to CAR+CD8+ T cells or of the ratio of viable cells thereof) in an output composition exists even despite variations in the process used to generate or produce the output compositions. The sources for this variation may include a number of different factors, including particular steps or conditions of the process that might introduce variability from one cell composition to the next, or may come from differences in individuals or samples from which the cells that are engineered are isolated, selected, derived, or obtained.

In certain embodiments, the provided methods are based on observations that the desired ratio of engineered CD4+ to CD8+ T cells (e.g. CAR+ CD4 to CAR+CD8+ T cells or of the ratio of viable cells thereof) in an output composition is correlated or associated with the ratio of the CD45RA+/CCR7+CD4+ T cells to CD45RA+/CCR7+CD8+ T cells, or a ratio of viable cells thereof, present in an input composition prior to carrying out a production process on the cells to produce the output composition, e.g. involving one or more steps of stimulation, activation, expansion, proliferation and/or transduction of the cells. In certain aspects, it is observed that such correlation between the ratio of CD45RA+/CCR7+CD4+ to CD45RA+/CCR7+/CD8+ cells in an input composition to engineered CD4+ to CD8+ cells (e.g. CAR+ CD4 to CAR+CD8+ T cells or of the ratio of viable cells thereof) in an output composition exists even despite variations in the donor and/or process used to generate or produce the output compositions.

In particular embodiments, the provided methods are based on observations that the desired ratio of engineered CD4+ to CD8+ T cells (e.g. CAR+ CD4 to CAR+CD8+ T cells or of the ratio of viable cells thereof) in an output composition is correlated or associated with the ratio of the CD62L−/CCR7+CD4+ T cells to CD62L−/CCR7+CD8+ T cells, or a ratio of viable cells thereof, present in an input composition prior to carrying out a production process on the cells to produce the output composition, e.g. involving one or more steps of stimulation, activation, expansion, proliferation and/or transduction of the cells. In certain aspects, it is observed that such correlation between the ratio of CD62L−/CCR7+CD4+ to CD62L−/CCR7+/CD8+ cells in an input composition to engineered CD4+ to CD8+ cells (e.g. CAR+CD4 to CAR+CD8+ T cells or of the ratio of viable cells thereof) in an output composition exists even despite variations in the donor and/or process used to generate or produce the output compositions.

In some embodiments, the provided methods are based on observations that the desired ratio of engineered CD4+ to CD8+ T cells (e.g. CAR+ CD4 to CAR+CD8+ T cells or of the ratio of viable cells thereof) in an output composition is correlated or associated with the ratio of the CD27+/CCR7+CD4+ T cells to CD27+/CCR7+CD8+ T cells, or a ratio of viable cells thereof, present in an input composition prior to carrying out a production process on the cells to produce the output composition, e.g. involving one or more steps of stimulation, activation, expansion, proliferation and/or transduction of the cells. In certain aspects, it is observed that such correlation between the ratio of CD27+/CCR7+CD4+ to CD27+/CCR7+/CD8+ cells in an input composition to engineered CD4+ to CD8+ cells (e.g. CAR+ CD4 to CAR+CD8+ T cells or of the ratio of viable cells thereof) in an output composition exists even despite variations in the donor and/or process used to generate or produce the output compositions.

In some aspects, the provided methods ensure that an output composition of genetically engineered cells, e.g. CAR+ T cells, generated by a cell production process achieves a relatively consistent and/or controlled desired ratio of the engineered CD4+ to CD8+ T cells, or a ratio of viable cells thereof, that exhibits a variance of such ratio that is low or below an acceptable or threshold variance, among compositions produced by the process, including those derived from samples from a number of different subjects, such as those having different characteristics, such as subjects of different ages, numbers and/or types of prior therapies, and indication and subtype or severity or grade thereof. In some aspects, such processes generate a ratio of such engineered CD4+ to CD8+(e.g. CAR+ CD4 to CAR+CD8+ T cells or of the ratio of viable cells thereof) that varies by no more than 20% or no more than 10% or no more than 5% from an average of said ratio in a plurality of T cell compositions produced by the process and/or varies from such average by no more than one standard deviation or varies by no more than 20% or no more than 10% or no more than 5% among a plurality of T cell compositions produced by the process among such various samples and patients.

In some embodiments, the use of a process that yields greater consistency among the output composition generated among a cell production process, such as with respect to the engineered CD4 to CD8 T cell ratio, can be advantageous to ensure consistency in dosing of a subject, which, in some aspects, can optimize efficacy, potency and/or safety of the administered composition among treated subjects. In some aspects, engineering cells enriched for CD4+ and CD8+ T cell populations at a desired output ratio in the engineered output composition can improve efficacy of or reduce or avoid unwanted effects. In some aspects, the isolation or enrichment increases the ability of cells ultimately administered to a subject to persist, expand, become activated, and/or engraft in vivo or upon administration to a subject. In some aspects, it improves or increases one or more effector function or activation phenotype. Such results can be achieved even where there is donor variability among the starting cell samples for cell engineering.

In some embodiments, the methods provided herein allow for the production of therapeutic cell compositions of engineered cells having a desired output ratio in the output composition without requiring the engineered CD4+ and CD8+ T cells to be processed and/or administered separately. Thus, the provided methods provide for more streamlined and/or controlled methods for preparing a composition having at or near a desired output ratio of engineered CD4+ T cell population and CD8+ T cell population. In particular aspects, after producing an input composition containing the desired ratio of naïve-like CD4 and CD8 cells as described, the provided methods can be used in a cell production process in which the CD4+ and CD8+ T cells are processed, e.g. activated, stimulated, expanded and/or transduced, together in a single stream process. Thus, in some aspects, the methods permit for introduction of a genetically engineered antigen receptor for use in adoptive cell therapy, where the cell populations are isolated, incubated, and/or engineered in combination, and the method is associated with increased efficiency and/or reduced complexity, time, cost, and/or use of resources compared to a method in which the populations are isolated, incubated, and/or engineered separately.

Also provided are cells and compositions prepared by the methods, including pharmaceutical compositions and formulations, and kits, systems, and devices for carrying out the methods. Also provided are methods for use of the cells and compositions prepared by the methods, including therapeutic methods, such as methods for adoptive cell therapy, and pharmaceutical compositions for administration to subjects.

All publications, including patent documents, scientific articles and databases, referred to in this application are incorporated by reference in their entirety for all purposes to the same extent as if each individual publication were individually incorporated by reference. If a definition set forth herein is contrary to or otherwise inconsistent with a definition set forth in the patents, applications, published applications and other publications that are herein incorporated by reference, the definition set forth herein prevails over the definition that is incorporated herein by reference.

The section headings used herein are for organizational purposes only and are not to be construed as limiting the subject matter described.

I. Methods for Generating Engineered Cells with a Controlled Ratio of CD4+ to CD8+ T Cells or Particular Subtypes Thereof Provided herein are methods for generating a cell composition, for example an input cell composition, for use in genetically engineering cells to express a recombinant receptor. In some embodiments, the input cell composition contains CD4+ T cells and CD8+ T cells. In certain embodiments, the input cell composition one or more subtypes or populations of CD4+ and/or CD8+ T cells. In certain embodiments, the one or more subtypes or populations are naïve and/or naïve-like cells. In particular embodiments, the input cell composition contains CD4+ T cells, and at least a portion of the CD4+ T cells are naïve-like CD4 cells. In some embodiments, the input cell composition contains CD8+ T cells, and at least a portion of the CD8+ T cells are naïve cells. In particular embodiments, the input cell composition contains and/or has a fixed, preferred, target, defined, and/or controlled ratio of naïve-like CD4+ T cells to naïve-like CD8+ T cells.

In certain embodiments, the methods include one or more steps of mixing or combining cells or compositions of cells to generate or produce an input cell composition. In certain embodiments, the cells or cell compositions have been selected and/or isolated from a sample. In some embodiments, the cells of the input cell composition have been selected and/or isolated from a sample. In some embodiments, CD4+ T cells and/or a composition of CD4+ T cells are selected or isolated from a sample. In some embodiments, the sample is a biological sample, such as blood sample, apheresis sample, and/or leukapheresis sample. In certain embodiments, the sample is from a subject, e.g. a human subject. In particular embodiments, the composition of CD4+ T cells and the composition of CD8+ T cells are isolated and/or selected from the same sample. In certain embodiments, the composition of CD4+ T cells and the composition of CD8+ T cells are isolated and/or selected from samples taken or obtained from the same subject.

In some embodiments, the generation or production of an input cell composition includes one or more steps of assessing, characterizing, and/or identifying cells. In particular embodiments, the cells are assessed, characterized, and/or identified in a composition of CD4+ T cells. In some embodiments, cells are assessed, characterized, and/or identified in a composition of CD8+ T cells. In some embodiments, the cells are assessed for cells that are positive for a marker that indicates and/or is associated with a naïve-like state in T cells. In certain embodiments, the cells are assessed for cells that are negative for a marker that indicates and/or is associated with a non-naïve-like state in T cells. In particular embodiments, the cells from CD4+ and CD8+ T cell compositions, such as cell compositions isolated from a biological sample from a subject, are assessed, characterized, and/or identified to determine the amount, level, portion, and/or percentage of cells that are positive for one or more markers associated with a naïve-like state and/or are negative for one or more markers associated with a non-naïve-like state. In certain embodiments, the cells from CD4+ and CD8+ T cell compositions, such as cell compositions isolated from a biological sample from a subject, are assessed, characterized, and/or identified to determine the amount, level, portion, and/or percentage of cells that are naïve-like cells.

In some embodiments, the methods include one or more steps of mixing or combining a cell composition containing CD4+ T cells with a cell composition containing CD8+ T cells to generate or produce a cell composition, e.g., an input cell composition, with a defined ratio of naïve-like CD4+ T cells to naïve-like CD8+ T cells. In some embodiments, the generation or production of the input cell composition includes one or more steps of: (i) isolating or selecting a composition of CD4+ T cells and/or a composition of CD8+ T cells from a sample, e.g., a biological sample; (ii) assessing, characterizing, and/or identifying the amount, level, portion, and/or percentage of cells that are positive for one or more markers associated with a naïve-like state and/or are negative for one or more markers associated with a non-naïve-like state in the composition of CD4+ and/or CD8+ T cells; and/or (iii) mixing or combining cells of a composition of CD4+ T cells with cells of a composition of CD8+ T cells at a defined, fixed, and/or preferred ratio of naïve-like CD4+ T cells to naïve-like CD8+ T cells. In particular embodiments, the ratio of the naïve-like CD4+ T cells to naïve-like CD8+ T cells in the input cell composition is different than the ratio that is present in the sample.

In particular embodiments, the content, make-up, and/or constitution of the input cell composition correlates, controls, corresponds, and/or associates with the content, make-up, and/or constitution of the output cell composition. In certain embodiments, the amount, portion, percentage, number, number per volume, number per weight, and/or ratio of naïve and/or naïve-like cells, e.g., naïve-like T cells, in an input cell composition correlates, controls, corresponds, and/or associates with the with the content, make-up, and/or constitution of the output cell composition. In particular embodiments, the amount, portion, number, number per volume, number per weight, and/or ratio of naïve-like CD4+ T cells and/or naïve-like CD8+ T cells in an input cell composition correlates, controls, corresponds, and/or associates with the with the content, make-up, and/or constitution of the output cell composition.

In some embodiments, the methods include one or more steps of genetically engineering the cells of the input composition. In some embodiments, the genetic engineering includes one or more steps of incubating the cells of the input cell composition under conditions that activate and/or simulate the cells, delivering a gene, e.g., a recombinant and/or heterologous gene to the cells, expanding the cells by incubating the cells under activing or stimulating conditions, harvesting the cells, and/or storing the cells by freezing, e.g., cryopreservation. In some embodiments, the one or more steps of genetic engineering produce an output cell composition containing engineered cells. In certain embodiments, engineered cells of the output composition have a fixed, defined, and/or target ratio of CD4+ to CD8+ cells.

In some embodiments, the methods provided herein include one or more steps for generating engineered cells, such as cells expressing a recombinant receptor, that have a defined ratio of CD4+ to CD8+ T cells. In certain embodiments, the methods provided herein include one or more steps for genetically engineering cells from a starting and/or input cell composition to generate a resulting and/or an output cell composition having a defined ratio genetically engineered CD4+ to CD8+ T cells. In particular embodiments, the genetic engineering is or includes transfection or transduction of cells from the input cell composition to introduce an agent containing a nucleic acid into the cells of the input cell composition. In some embodiments, the nucleic acid encodes a recombinant receptor, e.g., a chimeric antigen receptor (CAR). In some embodiments, generating an output cell composition includes one or more steps of activating or stimulating cells of the input cell composition; genetically engineering, transducing or transfecting the cells from the input cell composition; and/or expanding the transfected cells; thereby resulting in output cell composition having a defined ratio genetically engineered CD4+ to CD8+ T cells, such as a 1:1 ratio.

A. Cells and Preparation of Input Cell Compositions

In some embodiments, the methods provided herein include one or more steps for preparing cells for genetic engineering. In certain embodiments, the one or more steps include isolating cells from a biological sample to prepare a composition of cells to be genetically engineered, e.g., an input cell composition. In some embodiments, the preparation of an input cell composition includes one or more steps of isolating two or more cell types and/or compositions of a particular cell type or cell subtype, and mixing or combining the cell types and/or the cell compositions of the particular cell types into a single input cell composition. In particular embodiments, the cell compositions of the particular cell types are assessed to determine the presence, amount, and/or ratios of further subtypes in the compositions. In certain embodiments, the cell compositions of the particular cell types are mixed or combined to achieve input cell compositions of at fixed or determined ratios of cell types or subtypes. In some embodiments, the cell types and/or cell subtypes correlate, control, correspond, and/or associate with the content, make-up, and/or constitution of the output cell composition.

In certain embodiments, the preparation of an input cell composition includes one or more steps of isolating compositions of or including CD4+ T cells, isolating compositions of or including CD8+ T cells, and mixing or combining the CD4+ and CD8+ T cell compositions of the particular cell types into a single input cell composition. In certain embodiments, the preparation of the input cell composition includes one or more steps of assessing, determining, and/or quantifying the portion or amount of a subtype of the CD4+ and/or CD8+ T cells of the cell compositions. In particular embodiments, the subtype of the CD4+ and/or CD8+ T cells are or include naïve and/or naïve-like CD4+ and/or CD8+ T cells. In some embodiments, the portions or amounts of naïve-like cells in the input cell composition correlates, controls, corresponds, and/or associates with the content, make-up, and/or constitution of the output cell composition.

In some embodiments, the cells, e.g., the CD4+ and/or CD8+ T cells, that are isolated from a sample are eukaryotic cells, such as mammalian cells, and in some embodiments are human cells. In some embodiments, the cells are derived from the blood, bone marrow, lymph, or lymphoid organs of a subject, and/or are cells of the immune system, such as cells of the innate or adaptive immunity. In some embodiments, the cells are lymphocytes. In certain embodiments, the lymphocytes are T lymphocytes or T cells. In some embodiments, the cells include CD4+ T cells and CD8+ T cells.

In certain embodiments, compositions of T cells, e.g., CD4+ T cell compositions and/or CD8+ T cell compositions, contain subtypes of cells that are further categorized by function, activation state, maturity, potential for differentiation, expansion, marker or cytokine secretion profile, and/or degree of differentiation. For example, in some embodiments, the cells are or include naïve and/or naïve-like CD4+ and/or CD8+ T cells. With reference to the subject to be treated, the cells may be allogeneic and/or autologous. Among the methods are included off-the-shelf methods. In some embodiments, the methods include isolating cells from the subject, preparing, processing, culturing, and/or engineering the cells, and re-introducing the cells into the same subject, before or after cryopreservation.

In some embodiments, preparation of the engineered cells includes one or more culture and/or preparation steps. The cells for use in an input cell composition, e.g., a composition of cells to be genetically engineered, e.g., to express a recombinant receptor such as the CAR, may contain cells that have been isolated from a sample, such as a biological sample, e.g., one obtained from or derived from a subject. In some embodiments, the subject from which the cell is isolated is one having the disease or condition or in need of a cell therapy or to which cell therapy will be administered. The subject in some embodiments is a human in need of a particular therapeutic intervention, such as the adoptive cell therapy for which cells are being isolated, processed, and/or engineered.

In some aspects, the sample, e.g., a biological sample, from which the cells are derived or isolated is blood or a blood-derived sample, or is derived from an apheresis or leukapheresis product. Exemplary samples include whole blood, peripheral blood mononuclear cells (PBMCs), leukocytes, bone marrow, thymus, and/or cells derived therefrom. In some embodiments, cells are derived, isolated, and/or selected from samples or biological samples that may include a whole blood sample, a buffy coat sample, a peripheral blood mononuclear cells (PBMC) sample, an unfractionated T cell sample, a lymphocyte sample, a white blood cell sample, an apheresis product, or a leukapheresis product. Samples include, in the context of cell therapy, e.g., adoptive cell therapy, samples from autologous and allogeneic sources.

In some embodiments, the cells are derived from cell lines, e.g., T cell lines. The cells in some embodiments are obtained from a xenogeneic source, for example, from mouse, rat, non-human primate, and pig.

In some embodiments, isolation of the cells or the compositions of cells, e.g., T lymphocytes or CD4+ T cell compositions and/or CD8+ T cell compositions, includes one or more preparation and/or non-affinity based cell separation steps. In some examples, cells are washed, centrifuged, and/or incubated in the presence of one or more reagents, for example, to remove unwanted components, enrich for desired components, lyse or remove cells sensitive to particular reagents. In some examples, cells are separated based on one or more property, such as density, adherent properties, size, sensitivity and/or resistance to particular components.

In some examples, cells from the circulating blood of a subject are obtained, e.g., by apheresis or leukapheresis. The samples, in some aspects, contain lymphocytes, including T cells, monocytes, granulocytes, B cells, other nucleated white blood cells, red blood cells, and/or platelets, and in some aspects contains cells other than red blood cells and platelets.

In some embodiments, the blood cells collected from the subject are washed, e.g., to remove the plasma fraction and to place the cells in an appropriate buffer or media for subsequent processing steps. In some embodiments, the cells are washed with phosphate buffered saline (PBS). In some embodiments, the wash solution lacks calcium and/or magnesium and/or many or all divalent cations. In some aspects, a washing step is accomplished a semi-automated "flow-through" centrifuge (for example, the Cobe 2991 cell processor, Baxter) according to the manufacturer's instructions. In some aspects, a washing step is accomplished by tangential flow filtration (TFF) according to the manufacturer's instructions. In some embodiments, the cells are resuspended in a variety of biocompatible buffers after washing, such as, for example, $Ca^{++}/Mg^{++}$ free PBS. In certain embodiments, components of a blood cell sample are removed and the cells directly resuspended in culture media.

In some embodiments, the methods include density-based cell separation methods, such as the preparation of white blood cells from peripheral blood by lysing the red blood cells and centrifugation through a Percoll or Ficoll gradient.

In some embodiments, the isolation methods include the separation of different cell types based on the expression or presence in the cell of one or more specific molecules, such as surface markers, e.g., surface proteins, intracellular markers, or nucleic acid. In some embodiments, any known method for separation based on such markers may be used. In some embodiments, the separation is affinity- or immunoaffinity-based separation. For example, the isolation in some aspects includes separation of cells and cell populations based on the cells' expression or expression level of one or more markers, typically cell surface markers, for example, by incubation with an antibody or binding partner that specifically binds to such markers, followed generally by washing steps and separation of cells having bound the antibody or binding partner, from those cells having not bound to the antibody or binding partner.

Such separation steps can be based on positive selection, in which the cells having bound the reagents are retained for further use, and/or negative selection, in which the cells having not bound to the antibody or binding partner are retained. In some examples, both fractions are retained for further use. In some aspects, negative selection can be particularly useful where no antibody is available that specifically identifies a cell type in a heterogeneous population, such that separation is best carried out based on markers expressed by cells other than the desired population.

The separation need not result in 100% enrichment or removal of a particular cell population or cells expressing a particular marker. For example, positive selection of or enrichment for cells of a particular type, such as those expressing a marker, refers to increasing the number or percentage of such cells, but need not result in a complete absence of cells not expressing the marker. Likewise, negative selection, removal, or depletion of cells of a particular type, such as those expressing a marker, refers to decreasing the number or percentage of such cells, but need not result in a complete removal of all such cells.

In some examples, multiple rounds of separation steps are carried out, where the positively or negatively selected fraction from one step is subjected to another separation step, such as a subsequent positive or negative selection. In some examples, a single separation step can deplete cells expressing multiple markers simultaneously, such as by incubating cells with a plurality of antibodies or binding partners, each specific for a marker targeted for negative selection. Likewise, multiple cell types can simultaneously be positively selected by incubating cells with a plurality of antibodies or binding partners expressed on the various cell types.

For example, in some aspects, specific subpopulations or subtypes of T cells, such as CD4+ T cells and/or CD8+ T cells, are isolated by positive or negative selection techniques. In certain embodiments, CD4+ T cells and/or a cell composition of or including CD4+ T cells are isolated by positive or negative selection techniques. In particular embodiments, CD8+ T cells and/or a cell composition of or including CD8+ T cells are isolated by positive or negative selection techniques. In particular embodiments, a composition of CD4+ T cells and/or a composition of CD8+ T cells are isolated by positive or negative selection techniques.

In some embodiments, isolation is carried out by enrichment for a particular cell population by positive selection, or depletion of a particular cell population, by negative selection. In some embodiments, positive or negative selection is accomplished by incubating cells with one or more antibodies or other binding agent that specifically bind to one or more surface markers expressed (marker$^+$ or marker+) or expressed at a relatively higher level (marker$^{high}$) on the positively or negatively selected cells, respectively.

In some embodiments, T cells are separated from a PBMC sample by negative selection of markers expressed on non-T cells, such as B cells, monocytes, or other white blood cells, such as CD14. In some aspects, a $CD4^+$ or $CD8^+$ selection step is used to separate $CD4^+$ helper and $CD8^+$ cytotoxic T cells. Such $CD4^+$ and $CD8^+$ compositions can contain cells that can be further classified or sorted into sub-populations based on the positive or negative expression of markers and/or the relative level of expression of the markers. Such subtypes may include naïve, naïve-like, and/or non-naïve subtypes or subpopulations.

In certain embodiments, CD4+ T cells, e.g., CD4+ T helper cells, are categorized into naïve and/or naïve-like, and non-naïve and/or non-naïve-like cells by identifying cell populations that have cell surface antigens. In particular embodiments, CD8+ T cells, e.g., CD8+ T helper cells, are categorized into naïve and/or naïve-like, and non-naïve and/or non-naïve-like cells by identifying cell populations that have cell surface antigens.

In certain embodiments, the T lymphocytes are separated or isolated using immunomagnetic (or affinitymagnetic) separation techniques. In particular embodiments, CD4+ T cells and/or compositions of CD4+ T cells are separated or isolated using immunomagnetic separation techniques. In some embodiments, CD8+ T cells and/or compositions of CD8+ T cells are separated or isolated using immunomagnetic separation techniques. Separation and isolation using immunomagnetic (or affinitymagnetic) separation techniques are reviewed in Methods in Molecular Medicine, vol. 58: Metastasis Research Protocols, Vol. 2: Cell Behavior In Vitro and In Vivo, p 17-25 Edited by: S. A. Brooks and U. Schumacher© Humana Press Inc., Totowa, NJ.

In some aspects, the sample or composition of cells to be separated is incubated with small, magnetizable or magnetically responsive material, such as magnetically responsive particles or microparticles, such as paramagnetic beads (e.g., such as Dynalbeads or MACS beads). The magnetically responsive material, e.g., particle, generally is directly or indirectly attached to a binding partner, e.g., an antibody, that specifically binds to a molecule, e.g., surface marker, present on the cell, cells, or population of cells that it is desired to separate, e.g., that it is desired to negatively or positively select.

In some embodiments, the magnetic particle or bead comprises a magnetically responsive material bound to a specific binding member, such as an antibody or other binding partner. There are many well-known magnetically responsive materials used in magnetic separation methods. Suitable magnetic particles include those described in Molday, U.S. Pat. No. 4,452,773, and in European Patent Specification EP 452342 B, which are hereby incorporated by reference. Colloidal sized particles, such as those described in Owen U.S. Pat. No. 4,795,698, and Liberti et al., U.S. Pat. No. 5,200,084 are other examples.

The incubation generally is carried out under conditions whereby the antibodies or binding partners, or molecules, such as secondary antibodies or other reagents, which specifically bind to such antibodies or binding partners, which are attached to the magnetic particle or bead, specifically bind to cell surface molecules if present on cells within the sample.

In some aspects, the sample is placed in a magnetic field, and those cells having magnetically responsive or magnetizable particles attached thereto will be attracted to the magnet and separated from the unlabeled cells. For positive selection, cells that are attracted to the magnet are retained; for negative selection, cells that are not attracted (unlabeled cells) are retained. In some aspects, a combination of positive and negative selection is performed during the same selection step, where the positive and negative fractions are retained and further processed or subject to further separation steps.

In certain embodiments, the magnetically responsive particles are coated in primary antibodies or other binding partners, secondary antibodies, lectins, enzymes, or streptavidin. In certain embodiments, the magnetic particles are attached to cells via a coating of primary antibodies specific for one or more markers. In certain embodiments, the cells, rather than the beads, are labeled with a primary antibody or binding partner, and then cell-type specific secondary antibody- or other binding partner (e.g., streptavidin)-coated magnetic particles, are added. In certain embodiments, streptavidin-coated magnetic particles are used in conjunction with biotinylated primary or secondary antibodies.

In some embodiments, the magnetically responsive particles are left attached to the cells that are to be subsequently incubated, cultured and/or engineered; in some aspects, the particles are left attached to the cells for administration to a patient. In some embodiments, the magnetizable or magnetically responsive particles are removed from the cells. Methods for removing magnetizable particles from cells are known and include, e.g., the use of competing non-labeled antibodies, and magnetizable particles or antibodies conjugated to cleavable linkers. In some embodiments, the magnetizable particles are biodegradable.

In some embodiments, the affinity-based selection is via magnetic-activated cell sorting (MACS) (Miltenyi Biotec, Auburn, CA). Magnetic Activated Cell Sorting (MACS) systems are capable of high-purity selection of cells having magnetized particles attached thereto. In certain embodiments, MACS operates in a mode wherein the non-target and target species are sequentially eluted after the application of the external magnetic field. That is, the cells attached to magnetized particles are held in place while the unattached species are eluted. Then, after this first elution step is completed, the species that were trapped in the magnetic field and were prevented from being eluted are freed in some manner such that they can be eluted and recovered. In certain embodiments, the non-target cells are labelled and depleted from the heterogeneous population of cells.

In certain embodiments, the isolation or separation is carried out using a system, device, or apparatus that carries out one or more of the isolation, cell preparation, separation, processing, incubation, culture, and/or formulation steps of the methods. In some aspects, the system is used to carry out each of these steps in a closed or sterile environment, for example, to minimize error, user handling and/or contamination. In one example, the system is a system as described in International Patent Application, Publication Number WO2009/072003, or US 20110003380 A1.

In some embodiments, the system or apparatus carries out one or more, e.g., all, of the isolation, processing, engineering, and formulation steps in an integrated or self-contained system, and/or in an automated or programmable fashion. In some aspects, the system or apparatus includes a computer and/or computer program in communication with the system or apparatus, which allows a user to program, control, assess the outcome of, and/or adjust various aspects of the processing, isolation, engineering, and formulation steps.

In some aspects, the separation and/or other steps is carried out using CliniMACS system (Miltenyi Biotec), for example, for automated separation of cells on a clinical-scale level in a closed and sterile system. Components can include an integrated microcomputer, magnetic separation unit, peristaltic pump, and various pinch valves. The integrated computer in some aspects controls all components of the instrument and directs the system to perform repeated procedures in a standardized sequence. The magnetic separation unit in some aspects includes a movable permanent magnet and a holder for the selection column. The peristaltic pump controls the flow rate throughout the tubing set and, together with the pinch valves, ensures the controlled flow of buffer through the system and continual suspension of cells.

The CliniMACS system in some aspects uses antibody-coupled magnetizable particles that are supplied in a sterile, non-pyrogenic solution. In some embodiments, after labelling of cells with magnetic particles the cells are washed to remove excess particles. A cell preparation bag is then connected to the tubing set, which in turn is connected to a bag containing buffer and a cell collection bag. The tubing set consists of pre-assembled sterile tubing, including a pre-column and a separation column, and are for single use only. After initiation of the separation program, the system automatically applies the cell sample onto the separation column. Labelled cells are retained within the column, while unlabeled cells are removed by a series of washing steps. In some embodiments, the cell populations for use with the methods described herein are unlabeled and are not retained in the column. In some embodiments, the cell populations for use with the methods described herein are labeled and are retained in the column. In some embodiments, the cell populations for use with the methods described herein are eluted from the column after removal of the magnetic field, and are collected within the cell collection bag.

In certain embodiments, separation and/or other steps are carried out using the CliniMACS Prodigy system (Miltenyi Biotec). The CliniMACS Prodigy system in some aspects is equipped with a cell processing unity that permits automated washing and fractionation of cells by centrifugation. The CliniMACS Prodigy system can also include an onboard camera and image recognition software that determines the optimal cell fractionation endpoint by discerning the macroscopic layers of the source cell product. For example, peripheral blood is automatically separated into erythrocytes, white blood cells and plasma layers. The CliniMACS Prodigy system can also include an integrated cell cultivation chamber which accomplishes cell culture protocols such as, e.g., cell differentiation and expansion, antigen loading, and long-term cell culture. Input ports can allow for the sterile removal and replenishment of media and cells can be monitored using an integrated microscope. See, e.g., Klebanoff et al. (2012) *J Immunother.* 35(9): 651-660, Terakura et al. (2012) Blood. 1:72-82, and Wang et al. (2012) J Immunother. 35(9):689-701.

In some embodiments, a cell population described herein is collected and enriched (or depleted) via flow cytometry, in which cells stained for multiple cell surface markers are carried in a fluidic stream. In some embodiments, a cell population described herein is collected and enriched (or depleted) via preparative scale (FACS)-sorting. In certain embodiments, a cell population described herein is collected and enriched (or depleted) by use of microelectromechanical systems (MEMS) chips in combination with a FACS-based detection system (see, e.g., WO 2010/033140, Cho et al. (2010) *Lab Chip* 10, 1567-1573; and Godin et al. (2008) J Biophoton. 1(5):355-376. In both cases, cells can be labeled with multiple markers, allowing for the isolation of well-defined T cell subsets at high purity.

In some embodiments, the antibodies or binding partners are labeled with one or more detectable marker, to facilitate separation for positive and/or negative selection. For example, separation may be based on binding to fluorescently labeled antibodies. In some examples, separation of cells based on binding of antibodies or other binding partners specific for one or more cell surface markers are carried in a fluidic stream, such as by fluorescence-activated cell sorting (FACS), including preparative scale (FACS) and/or microelectromechanical systems (MEMS) chips, e.g., in combination with a flow-cytometric detection system. Such methods allow for positive and negative selection based on multiple markers simultaneously.

Input Cell Compositions

In certain embodiments, provided herein are methods of producing and/or preparing an input cell composition. In certain embodiments, the input cell composition is a composition of cells for use in genetic engineering, e.g., cells that will be genetically engineered with a nucleic acid encoding a recombinant protein, such as a recombinant receptor, e.g. CAR and/or that will undergo a process to produce genetically engineered cells expressing a recombinant protein, such as a recombinant receptor, e.g. a CAR. In certain embodiments, the cells of the input composition will be treated with, contacted with, and/or incubated with a nucleic acid that encodes a recombinant receptor. In certain embodiments, the input cell composition contains CD4+ T cells and CD8+ T cells. In particular embodiments, the input cell composition contain CD4+ T cells and CD8+ T cells that include a particular desired, fixed and/or controlled ratio of CD4+ to CD8+ T cells that are naïve and/or naïve-like T cells.

In some embodiments, the desired, fixed, and/or controlled ratio of CD4+ to CD8+ T cells that are naïve and/or naïve-like T cells is the ratio or number of cells at which two types of cells or isolated cell populations are included in an input cell composition, designed to result in an output cell composition with a desired, defined, and/or controlled ratio of engineered CD4+ to CD8+ T cells, or within a tolerated error rate or difference thereof, at the completion of the incubation and/or engineering step or other processing steps and/or upon thaw and/or just prior to administration to a subject.

In certain embodiments, the input cell composition contains a ratio, e.g., a defined, controlled, and/or fixed ratio, CD4+ naïve-like T cells to CD8+ naïve-like T cells. In particular embodiments, the ratio of CD4+ naïve-like T cells to CD8+ naïve-like T cells is between 10:1 to 0.05:1, between 8:1 to 0.1:1, between 5:1 to 0.2:1, between 2.5:1 to 0.25:1, between 2.2:1 to 0.8:1, between 2:1 to 0.5:1, or between 1.5:1 to 1:1, inclusive. In particular embodiments, the ratio of CD4+ naïve-like T cells to CD8+ naïve-like T cells is between 2:1 to 0.8:1, between 1.6:1 to 0.8:1, between 1.4:1 to 0.8:1, between 1.2:1 to 0.8:1, or between 1.2:1 to 0.8:1, inclusive. In some embodiments, the ratio is between 2.2:1 to 0.8:1, inclusive. In certain embodiments, the ratio of CD4+ naïve-like T cells to CD8+ naïve-like T cells is or is about 2.2:1, 2.1:1, 2.0:1, 1.9:1, 1.8:1, 1.7:1, 1.6:1, 1.5:1, 1.4:1, 1.3:1, 1.2:1, 1.1:1, 1.0:1, 0.9:1, or 0.8:1. In certain embodiments, the ratio is or is about 1.1:1.

In particular embodiments, the input cell composition has an amount of or about of $1\times10^6$, $5\times10^6$, $1\times10^7$, $5\times10^7$, $1.0\times10^8$, $1.1\times10^8$, $1.2\times10^8$, $1.3\times10^8$, $1.4\times10^8$, $1.5\times10^8$, $1.6\times10^8$, $1.7\times10^8$, $1.8\times10^8$, $1.9\times10^8$, $2.0\times10^8$, $2.1\times10^8$, $2.2\times10^8$, $2.3\times10^8$, $2.4\times10^8$, $2.5\times10^8$, $2.6\times10^8$, $2.7\times10^8$, $2.8\times10^8$, $2.9\times10^8$, $3.0\times10^8$, $3.5\times10^8$, $4.0\times10^8$, $4.5\times10^8$, $5\times10^8$, $5\times10^8$, or $1\times10^9$ total cells or total viable cells. In certain embodiments, the input cell composition has an amount of or about of $1\times10^6$, $5\times10^6$, $1\times10^7$, $5\times10^7$, $1.0\times10^8$, $1.1\times10^8$, $1.2\times10^8$, $1.3\times10^8$, $1.4\times10^8$, $1.5\times10^8$, $1.6\times10^8$, $1.7\times10^8$, $1.8\times10^8$, $1.9\times10^8$, $2.0\times10^8$, $2.1\times10^8$, $2.2\times10^8$, $2.3\times10^8$, $2.4\times10^8$, $2.5\times10^8$, $2.6\times10^8$, $2.7\times10^8$, $2.8\times10^8$, $2.9\times10^8$, $3.0\times10^8$, $3.5\times10^8$, $4.0\times10^8$, $4.5\times10^8$, $5\times10^8$, $5\times10^8$, or $1\times10^9$ cells that express CD4 or CD8. In some embodiments, the input cell composition has an amount of or about of $1\times10^6$, $5\times10^6$, $1\times10^7$, $5\times10^7$, $1.0\times10^8$, $1.1\times10^8$, $1.2\times10^8$, $1.3\times10^8$, $1.4\times10^8$, $1.5\times10^8$, $1.6\times10^8$, $1.7\times10^8$, $1.8\times10^8$, $1.9\times10^8$, $2.0\times10^8$, $2.1\times10^8$, $2.2\times10^8$, $2.3\times10^8$, $2.4\times10^8$, $2.5\times10^8$, $2.6\times10^8$, $2.7\times10^8$, $2.8\times10^8$, $2.9\times10^8$, $3.0\times10^8$, $3.5\times10^8$, $4.0\times10^8$, $4.5\times10^8$, $5\times10^8$, $5\times10^8$, or $1\times10^9$ naïve-like CD4+ and naïve-like CD8+ T cells.

In particular embodiments, the input cell composition has between $1\times10^6$ and $1\times10^{10}$, between $1\times10^7$ and $1\times10^9$, between $5\times10^7$ and $5\times10^8$, or between $1\times10^8$ and $3\times10^8$ total cells or total viable cells. In certain embodiments, the input cell composition has an amount of or about of between $1\times10^6$ and $1\times10^{10}$, between $1\times10^7$ and $1\times10^9$, between $5\times10^7$ and $5\times10^8$, or between $1\times10^8$ and $3\times10^8$ cells that express CD4 or CD8. In some embodiments, the input cell composition has an amount of or about of between $1\times10^6$ and $1\times10^{10}$, between $1\times10^7$ and $1\times10^9$, between $5\times10^7$ and $5\times10^8$, or between $1\times10^8$ and $3\times10^8$ naïve-like CD4+ and naïve-like CD8+ T cells.

In some embodiments, the input cell composition has or contains at least 1%, at least 5%, at least 10%, at least 20%, at least 30%, at least 40%, at least 50%, at least 60%, at least 70%, at least 75%, at least 80%, at least 85%, at least 90%, at least 95%, at least 96%, at least 97%, at least 98%, at least 99%, at least 99.5%, at least 99.9%, or 100% or about 100% naïve-like cells. In particular embodiments, the input cell composition contains or includes no more than 100%, no more than 99%, no more than 98%, no more than 97%, no more than 96%, no more than 95%, no more than 90%, or no more than 85% naïve-like cells.

In particular embodiments, the methods provided herein include one or more steps of producing, generating, and/or making an input cell composition. In certain embodiments, the producing, generating, and/or making an input cell composition includes one or more steps of mixing or combining a cells of a composition of CD4+ T cells with cells of a composition of CD8+ T cells.

In some embodiments, the cells, e.g., the CD4+ T cells CD8+ T cells, of the input composition have been isolated and/or selected from a sample, e.g., a biological sample. In certain embodiments, the source of the cells of the input composition are compositions of cells, e.g., compositions of CD4+ and compositions of CD8+ T cells, that have been isolated and/or selected from the sample, such as separately isolated or selected. In particular embodiments, the composition of CD4+ T cells and the composition of CD8+ T cells are isolated and/or selected, such as separately isolated and/or selected, from a sample, e.g., a biological sample. In certain embodiments, the composition of CD4+ T cells and the composition of CD8+ T cells are isolated and/or selected from the same sample. In certain embodiments, the composition of CD4+ T cells and the composition of CD8+ T cells are isolated and/or selected from samples taken or obtained from the same subject.

In particular embodiments, the composition of CD4+ T cells contains or includes at least 60%, at least 75%, at least 80%, at least 85%, at least 90%, at least 95%, at least 96%, at least 97%, at least 98%, at least 99%, at least 99.5%, at least 99.9%, or 100% or about 100% CD4+ T cells. In some embodiments, the composition of CD4+ T cells contains or includes no more than 100%, no more than 99%, no more than 98%, no more than 97%, no more than 96%, no more than 95%, no more than 90%, or no more than 85% CD4+ T cells.

In certain embodiments, the composition of CD8+ T cells contains or includes at least 60%, at least 75%, at least 80%, at least 85%, at least 90%, at least 95%, at least 96%, at least 97%, at least 98%, at least 99%, at least 99.5%, at least 99.9%, or 100% or about 100% CD8+ T cells. In particular embodiments, the composition of CD8+ T cells contains or includes no more than 100%, no more than 99%, no more than 98%, no more than 97%, no more than 96%, no more than 95%, no more than 90%, or no more than 85% CD8+ T cells.

In certain embodiments, the producing, generating, and/or making an input cell composition includes one or more steps of measuring, determining, and/or quantifying the amount, portion, number, number per volume, number per weight, and/or percentage of viable CD4+ T cells and/or viable CD8+ T cells that are present in the composition of CD4+ T cells and/or the composition of CD8+ T cells, e.g., prior to combining or mixing the cells of the cell compositions. In particular embodiments, the producing, generating, and/or making an input cell composition includes one or more steps of measuring, determining, and/or quantifying the amount, portion, number, number per volume, number per weight, and/or percentage of naïve-like CD4+ T cells and/or naïve-like CD8+ T cells that are present in the composition of CD4+ T cells and/or the composition of CD8+ T cells. In some embodiments, the naïve-like CD4+ and/or naïve-like CD8+ T cells are viable naïve-like cells.

In certain embodiments, the producing, generating, and/or making an input cell composition includes one or more steps of measuring, determining, and/or quantifying the amount, portion, number, number per volume, number per weight, and/or percentage of viable CD4+ T cells and/or viable CD8+ T cells that are present in the sample, e.g., the biological sample. In particular embodiments, the producing, generating, and/or making an input cell composition includes one or more steps of measuring, determining, and/or quantifying the amount, portion, number, number per volume, number per weight, and/or percentage of naïve-like CD4+ T cells and/or naïve-like CD8+ T cells that are present in the sample. In some embodiments, the naïve-like CD4+ and/or naïve-like CD8+ T cells are viable naïve-like cells.

In some embodiments, the cells of the input composition are isolated and/or selected from a sample, e.g., a biological sample. In particular embodiments, the portions of naïve-like cells in the sample, e.g., portion of naïve-like CD4+ and CD8+ T cells are known or have been determined, measured, or assessed. In some embodiments, cells from the sample are isolated and/or selected to directly produce a cell composition, e.g., an input cell composition, with a defined, fixed, or controlled ratio of naïve-like CD4+ T cells to naïve-like CD8+ T cells. In certain embodiments, the cells are isolated and/or selected with immunoaffinity bead selection. In some embodiments, the cells are isolated and/or selected with affinity columns. In particular embodiments, the cells from the sample are isolated or selected according to any of the methods described in WO 2015/164675 to produce a cell composition with a defined, controlled, and/or fixed ratio of naïve-like CD4+ cells to naïve-like CD8+ cells.

In certain embodiments, the input cell composition contains cells that were directly isolated and/or selected from a sample by a first and second isolation or selection. In certain embodiments, the input composition is produced by performing a first and second selection to isolate an amount, number, or concentration of CD4+ T cells and CD8+ T cells sufficient to produce the defined, fixed, and/or controlled ratio of naïve-like CD4+ to naïve-like CD8+ T cells.

In some embodiments, the cells from the sample are directly isolated, selected, and/or enriched to produce an input cell composition enriched for CD4+ cells and CD8+ cells. In some embodiments, the amount, number, percentage, number per volume, and/or number per weight of naïve-like CD4+ and naïve-like CD8+ cells have been measured, assessed, and/or determined in the sample, and the CD4+ and CD8+ cells are isolated, selected, and/or enriched in sufficient amounts to achieve an input cell composition with the defined, fixed, or controlled ratio of naïve-like CD4+ to naïve-like CD8+ T cells. In some embodiments, the cells that are directly isolated, selected, and/or enriched from the sample are the input cell composition and are used in subsequent processing steps, such as subsequent processing steps involving incubation, stimulation, activation, engineering and/or formulation of the enriched cells.

In some embodiments, the isolated, selected, and/or enriched cells from the sample, such as an input cell composition, contain a ratio of CD4+ cells to CD8+ cells at a defined, fixed, or controlled ratio of naïve-like CD4+ cells to naïve-like CD8+ cells. In embodiments of the methods provided herein, the first and/or second selections, or selections for sub-populations thereof, of the sample can be performed in a manner to result in an input cell composition with a desired ratio of naïve-like CD4+ T cells to naïve-like CD8+ cells.

In some embodiments, prior to performing the first and/or second selection from the sample, the ratio of CD4+ to CD8+ T cells in the sample, e.g., the biological sample, is determined. In certain embodiments, prior to performing the first and/or second selection, the ratio of naïve-like CD4+ to naïve-like CD8+ T cells in the sample is determined. Based on the particular ratio of the CD4+ to CD8+ T cells and/or naïve-like CD4+ to CD8+ T cells in the sample, which can vary among samples, the particular mode of selection can be individualized to the sample, for example by sizing of chromatography columns or selection of amount or concentration of immunoaffinity reagents, to achieve the desired, fixed, or controlled ratio. The relative level or frequency of various cell populations in a subject can be determined based on assessing surface expression of a marker or markers present on such populations or sub-populations. A number of well-known methods for assessing expression level of surface markers or proteins may be used, such as detection by affinity-based methods, e.g., immunoaffinity-based methods, e.g., in the context of cell surface proteins, such as by flow cytometry.

In some contexts, the appropriate ratio for naïve-like CD4+ and CD8+ T cells can vary depending on context, e.g., for example, for a particular disease, condition, or prior treatment of a subject from which cells are derived, and/or a particular antigen-specificity of the cells, relative representation among cells of a particular type (e.g., CD4+ cells) of various subpopulations, e.g., effector versus memory versus naïve cells, and/or one or more conditions under which cells will be incubated, such as medium, stimulating agents, time of culture, buffers, oxygen content carbon dioxide content, antigen, cytokine, antibodies, and other components. Thus, it may be that a cell type which typically or in general is known to proliferate or expand more rapidly than another will not always have such a property in every context. Thus, in some aspects, the ratio of naïve-like CD4+ T cells and naïve-like CD8+ T cells is determined based on known capacities of cell types in a normal or typical context, coupled with assessment of phenotypes or states of the cells or subject from which the cells are derived, and/or empirical evidence.

In some embodiments, the separation and/or steps is carried out using immunomagnetic beads. In some embodiments, a cell sample containing CD4+ and CD8+ cells is contacted with magnetic beads containing a first immunoaffinity reagent that binds to CD4 or CD8 and magnetic beads containing a second immunoaffinity reagent that binds to the other of the CD4 or CD8. The separation and/or steps can occur simultaneously and/or sequentially.

In some embodiments, the first and/or second immunoaffinity reagent are present in the incubation composition at a sub-optimal yield concentration, whereby the enriched composition contains less than all, e.g., 70%, of the total CD4+ cells in the incubation composition and/or less than all, e.g., 70%, of the CD8+ cells in the incubation composition, thereby producing a composition enriched for CD4+ and CD8+ T cells.

In some embodiments, the suboptimal yield concentration of the affinity reagent is a concentration below a concentration used or required to achieve an optimal or maximal yield of bound cells in a given selection or enrichment involving incubating cells with the reagent and recovering or separating cells having bound to the reagent ("yield," for example, being the number of the cells so-recovered or selected compared to the total number of cells in the incubation that are targeted by the reagent or to which the reagent is specific or that have a marker for which the reagent is specific and capable of binding). The suboptimal yield concentration generally is a concentration or amount of the reagent that in such process or step achieves less than all, e.g., no more than 70% yield of bound cells, e.g., CD4+ and/or CD8+ T cells, upon recovery of the cells having bound to the reagent. In some embodiments, no more than at or about 50%, 45%, 40%, 30%, or 25% yield is achieved by the suboptimal concentration of the affinity reagent. The concentration may be expressed in terms of number or mass of particles or surfaces per cell and/or number of mass or molecules of agent (e.g., antibody, such as antibody fragment) per cell. In particular embodiments, the suboptimal yield concentrations are sufficient to derive or achieve the fixed, controlled, and/or defined ratio of naïve-like CD4+ T cells to naïve-like CD8+ T cells.

In some embodiments, e.g., when operating in a suboptimal yield concentration for each or one or more of two or more selection reagents with affinity to CD4+ and/or CD8+ T cells, one or more of such reagents is used at a concentration that is higher than one or more of the other such reagent(s), in order to bias the ratio of the cell type recognized by that reagent as compared to the cell type(s) recognized by the other(s). For example, the reagent specifically binding to the marker for which it is desired to bias the ratio may be included at a concentration (e.g., agent or mass per cells) that is increased by half, 1-fold, 2-fold, 3-fold, 4-fold, 5-fold, 10-fold, or more, compared to other(s), depending on how much it is desired to increase the ratio.

In some embodiments, when operating in the suboptimal range and/or with enough cells to achieve saturation of reagents, the amount of immunoaffinity reagent is proportional to the approximate yield of enriched cells. In certain embodiments, an appropriate amount or concentration of immunoaffinity reagents that depend on the desired ratio of the generated composition containing the enriched or selected CD4+ and CD8+ T cells can be determined as a matter of routine.

In some embodiments, the separation and/or isolation steps are carried out using magnetic beads in which immunoaffinity reagents are reversibly bound, such as via a peptide ligand interaction with a streptavidin mutein as described in WO 2015/164675. Exemplary of such magnetic beads are Streptamers®. In some embodiments, the separation and/or steps is carried out using magnetic beads, such as those commercially available from Miltenyi Biotec.

In some embodiments, the first selection or enrichment of CD4+ and CD8+ cells from a sample are performed using immunoaffinity-based reagents that include at least a first and second affinity chromatography matrix, respectively, having immobilized thereon an antibody. In some embodiments, one or both of the first and/or second selection can employ a plurality of affinity chromatography matrices and/or antibodies, whereby the plurality of matrices and/or antibodies employed for the same selection, i.e. the first selection or the second selection, are serially connected. In some embodiments, the affinity chromatography matrix or matrices employed in a first and/or second selection adsorbs or is capable of selecting or enriching at least about $50 \times 10^6$ cells/mL, $100 \times 10^6$ cells/mL, $200 \times 10^6$ cells/mL or $400 \times 10^6$ cells/mL. In some embodiments, the adsorption capacity can be modulated based on the diameter and/or length of the column. In some embodiments, the culture-initiating ratio of the selected or enriched composition is achieved by choosing a sufficient amount of matrix and/or at a sufficient relative amount to achieve the culture-initiating ratio assuming based on, for example, the adsorption capacity of the column or columns for selecting cells.

In one exemplary embodiment, the CD4+ T cells and CD8+ T cells have an equal or similar portion of naïve-like cells, and the adsorption capacity of the matrix or matrices is the same between the first and second selection, e.g. is or is about $1 \times 10^8$ cells/mL for both, whereby enrichment or selection of cells in the first selection and second selection results in a composition containing a CD4+ cells to CD8+ cells with a naïve-like CD4+ to CD8+ T cell ratio of or of about 1:1. In particular embodiments, an appropriate volume, diameter or number of affinity matrix chromatography columns for the first and/or second selection depending on portions of naïve-like cells and on the desired ratio of the generated input cell composition can be chosen or determined as a matter of routine.

In some embodiments, the adsorption capacity of a column matrix or matrices is adjusted to account for differences in the frequency of a naïve-like cells, e.g., naïve like CD4+ or CD8+ cells, compared to the frequency of cells of the respective CD4+ or CD8+ parent population in the starting sample from the subject. The relative level or frequency of various cell populations in a subject can be determined based on assessing surface expression of a marker or markers present on such populations or sub-populations. A number of well-known methods for assessing expression level of surface markers or proteins may be used, such as detection by affinity-based methods, e.g., immunoaffinity-based methods, e.g., in the context of cell surface proteins, such as by flow cytometry.

In some embodiments, naïve-like cells, e.g., naïve-like CD4+ and/or CD8+ T cells, are assessed, measured, and/or detected in cell compositions, e.g., CD4+ and/or CD8+ T cell compositions, or in a sample, e.g., a biological sample. In some embodiments, a naïve-like T cell is a T cell that is positive for the expression of one or more markers that indicate that the cell is naïve and/or is a naïve-like cell. In certain embodiments, a naïve-like T cell is a cell that is positive for the expression of a marker that is associated with a naïve or naïve-like state in T cells. In particular embodiments, a naïve-like T cell is a T cell that is negative for the expression of one or more markers that indicates that the cell is not naïve and/or is a not a naïve-like cell. In certain embodiments, a naïve-like T cell is a cell that is negative for the expression of a marker that is associated with a non-naïve or non-naïve-like state in T cells. In certain embodiments, a non-naïve or non-naïve-like state in a T cells includes, for example but not limited to, effector T (TEFF) cells, memory T cells, central memory T cells (TCM), effector memory T (TEM) cells, and combinations thereof.

In some embodiments, a naïve-like T cell is positive for the expression of at least one, two, three, four, five, six, seven, eight, nine, ten, or more than ten markers that indicate that the cell is naïve and/or is a naïve-like cell, and/or is associated with a naïve or naïve-like state in T cells. In some embodiments, the markers are expressed on the cell surface. In certain embodiments, the naïve-like T cell is negative for the expression of at least one, two, three, four, five, six, seven, eight, nine, ten, or more than ten markers that indicate that the cell is non-naïve and/or is a non-naïve-like cell, and/or is associated with a non-naïve or non-naïve-like state in T cells.

Markers that indicate that the T cell is naïve and/or is a naïve-like T cell, and/or are associated with a naïve or naïve-like state in T cells include, but are not limited to, CD27, CD28, CD45RA, CD62L, and/or CCR7. In some embodiments, the naïve-like T cell, e.g., the naïve-like CD4+ and/or CD8+ T cell, is positive for expression of CD27, CD28, CD45RA, and/or CCR7. In certain embodiments, the naïve-like T cell is positive for the surface expression of one or more of CD27, CD28, CD45RA, and/or CCR7. In some embodiments, the naïve-like T cell, e.g., the naïve-like CD4+ and/or CD8+ T cell, is negative for expression of CD62L. Markers that indicate that the cell is a non-naïve and/or is a non-naïve-like T cell, and/or are associated with a non-naïve or non-naïve-like state in T cells include, but are not limited to, CD25, CD45RO, CD56, KLRG1, and/or CD95. In some embodiments, the naïve-like T cell, e.g., a naïve-like CD4+ and/or CD8+ T cell, is negative for expression of CD25, CD45RO, CD56, and/or KLRG1. In particular embodiments, the naïve-like T cell, e.g., a naïve-like CD4+ and/or CD8+ T cell, has low expression of a marker associated with non-naïve or non-naïve-like cells. In particular embodiments, the naïve-like T cell has low expression of CD95. In certain embodiments, the naïve-like T cell is negative for the surface expression of one or more of CD25, CD45RO, CD56, and/or KLRG1.

In some embodiments, low expression of a marker associated with non-naïve or non-naïve-like cells is or includes at least 10%, at least 20%, at least 30%, at least 40%, at least 50%, at least 60%, at least 70%, at least 80%, at least 90%, at least 95%, or at least 99% less expression than the expression of the marker in a cell that is a non-naïve-like cells, and/or a cell that is positive for one or more markers that indicate that the cell is a non-naïve and/or is a non-naïve-like T cell, and/or are associated with a non-naïve or non-naïve-like state in T cells. In certain embodiments, low expression of a marker associated with non-naïve or non-naïve-like cells is or includes at least 10%, at least 20%, at least 30%, at least 40%, at least 50%, at least 60%, at least 70%, at least 80%, at least 90%, at least 95%, or at least 99% less expression than the expression of the marker in an effector T ($T_{EFF}$) cell, a memory T cell, a central memory T cell ($T_{CM}$), and/or an effector memory T ($T_{EM}$) cell.

In some embodiments, markers that indicate that the cell is a non-naïve and/or is a non-naïve-like T cell, and/or are associated with a non-naïve or non-naïve-like state in T cells include, one or more cytokines. For example, in certain embodiments, a non-naïve or non-naïve-like T cells is negative for the expression and/or the production of one or more of IL-2, IFN-γ, IL-4, and IL-10. In some embodiments, the one or more cytokines are secreted. In particular embodiments, the one or more cytokines are expressed internally by the non-naïve-like T cells, for example, during or after treatment with an agent that prevents, inhibits, or reduces secretion.

In certain embodiments, a naïve-like T cell is positive for the expression, e.g., surface expression, of CD45RA and CCR7. In particular embodiments, a naïve-like CD4+ T cell is positive for the expression, e.g., surface expression, of CD45RA and CCR7. In some embodiments, a naïve-like CD8+ T cell is positive for the expression, e.g., surface expression, of CD45RA and CCR7. In particular embodiments, a naïve-like T cell is positive for the expression, e.g., surface expression, of CD45RA, CD27, and CCR7 and is negative for the expression, e.g., surface expression of CD45RO. In particular embodiments, a naïve-like CD4+ T cell is positive for the expression, e.g., surface expression, of CD45RA, CD27, and CCR7 and is negative for the expression, e.g., surface expression of CD45RO. In some embodiments, a naïve-like CD8+ T cell is positive for the expression, e.g., surface expression, of CD45RA, CD27, and CCR7 and is negative for the expression, e.g., surface expression of CD45RO.

In certain embodiments, the CD4+ and/or CD8+ T cells are viable cells. In certain embodiments, the CD4+ and/or CD8+ T cells are viable naïve-like cells. The viable cell is positive for the expression of a marker that indicates that the cell undergoes normal functional cellular processes and/or has not undergone or is not under the process of undergoing necrosis or programmed cell death. In some embodiments, viability can be assessed by the redox potential of the cell, the integrity of the cell membrane, or the activity or function of mitochondria. In some embodiments, viability is the absence of a specific molecule associated with cell death, or the absence of the indication of cell death in an assay.

In certain embodiments, cell viability is assessed with an assay that may include, but is not limited to, dye uptake assays (e.g., calcein AM assays), XTT cell viability assays, and dye exclusion assays (e.g., trypan blue, Eosin, or propidium dye exclusion assays). In particular embodiments, a viable cell has negative expression of one or more apoptotic markers, e.g., annexin V or active Caspase 3. In some embodiments, the viable cell is negative for the expression or activation of one or more apoptosis marker that may include, but are not limited to, a caspase, e.g., caspase 2, caspase 3, caspase 6, caspase 7, caspase 8, caspase 9, and caspase 10, Bcl-2 family members, e.g., Bax, Bad, and Bid, Annexin V, and/or TUNEL staining.

In some embodiments, expression is or includes an amount, level, concentration, and/or presence of the marker. In particular embodiments, the marker is polypeptide. In some embodiments, the marker is an mRNA. In some embodiments, the expression is or includes an amount, level, concentration, and/or presence of a polypeptide, e.g., the marker polypeptide. In certain embodiments, an amount, level, concentration, and/or presence of a polynucleotide, e.g., an mRNA or a cDNA derived from the mRNA, that encodes the marker. In certain embodiments, expression is or includes an amount, level, concentration, and/or presence of the marker on or exposed on the cell surface or within the cell membrane. In certain embodiments, expression is or includes an amount, level, concentration, and/or presence of the marker on or exposed on the cell surface or within the cell membrane. In particular embodiments, the expression is or includes internal expression, e.g., an amount, level, concentration, and/or presence of the marker within the cell internally, such as within the cytosol, nucleus, endoplasmic reticulum, and/or the Golgi apparatus.

In some embodiments, the markers are measured, assessed, and/or quantified by performing an in vitro assay. In some examples, the in vitro assay is an immunoassay, an aptamer-based assay, a histological or cytological assay, or an mRNA expression level assay. In some cases, the in vitro assay used can be an enzyme-linked immunosorbent assay (ELISA), immunoblotting, immunoprecipitation, radioimmunoassay (RIA), immunostaining, flow cytometry assay, surface plasmon resonance (SPR), chemiluminescence assay, lateral flow immunoassay, inhibition assay or avidity assay. In some embodiments, the expression of the markers is measured, assessed, and/or quantified by RNA-seq. In particular embodiments, the expression of the markers is measured, assessed, and/or quantified by immunostaining techniques. In particular embodiments, the expression of the markers is measured, assessed, and/or quantified by flow cytometry analysis. In some embodiments, the expression of the markers is measured, assessed, and/or quantified by internal cytokine staining.

In some embodiments, the markers are measured, assessed, and/or quantified in cells of the CD4+ T cell composition. In particular embodiments, at least 1%, at least 5%, at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, at least 95%, at least 97%, or at least 99% of the CD4+ T cells are naïve-like CD4+ T cells. In certain embodiments, between 10% and 50%, between 20% and 60%, between 25% and 75%, between 30% and 80%, between 40% and 90%, between 50% and 100%, between 30% and 50%, between 40% and 60%, between 50% and 70%, between 60% and 80%, between 70% and 90%, between 80% and 100%, between 5% and 25%, between 25% and 50%, between 50% and 75%, or between 75% and 99% of the CD4+ T cells are naïve-like CD4+ T cells. In certain embodiments, the naïve-like CD4+ T cells are viable naïve-like CD4+ T cells.

In certain embodiments, the markers are measured, assessed, and/or quantified in cells of the CD8+ T cell composition. In particular embodiments, at least 1%, at least 5%, at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, at least 95%, at least 97%, or at least 99% of the CD8+ T cells are naïve-like CD8+ T cells. In certain embodiments, between 10% and 50%, between 20% and 60%, between 25% and 75%, between 30% and 80%, between 40% and 90%, between 50% and 100%, between 30% and 50%, between 40% and 60%, between 50% and 70%, between 60% and 80%, between 70% and 90%, between 80% and 100%, between 5% and 25%, between 25% and 50%, between 50% and 75%, or between 75% and 99% of the CD8+ T cells are naïve-like CD4+ T cells. In certain embodiments, the naïve-like CD8+ T cells are viable naïve-like CD8+ T cells.

In some embodiments, cells from a composition of CD4+ T cells are mixed or combined with cells from a composition of CD8+ T cells in amounts and/or proportions sufficient to produce an input cell composition with a ratio of CD4+ naïve-like T cells to CD8+ naïve-like T cells between 10:1 and 0.05:1, between 8:1 and 0.1:1, between 5:1 and 0.2:1, between 2.5:1 and 0.25:1, between 2.2:1 and 0.8:1, between 2:1 and 0.5:1, or between 1.5:1 and 1:1, inclusive. In some embodiments, the cells are mixed in amounts and/or proportions sufficient to a ratio of CD4+ naïve-like T cells to CD8+ naïve-like T cells of between 2.2:1 and 0.8:1, inclusive. In certain embodiments, the cells are mixed or combined to a ratio of CD4+ naïve-like T cells to CD8+ naïve-like T cells of or of about 2.2:1, 2.1:1, 2.0:1, 1.9:1, 1.8:1, 1.7:1, 1.6:1, 1.5:1, 1.4:1, 1.3:1, 1.2:1, 1.1:1, 1.0:1, 0.9:1, or 0.8:1. In certain embodiments, the cells are mixed or combined to a ratio of or of about 1.1:1.

In some embodiments, an amount of or about of $5 \times 10^5$, $1 \times 10^6$, $5 \times 10^6$, $1 \times 10^7$, $5 \times 10^7$, $1.0 \times 10^8$, $1.1 \times 10^8$, $1.2 \times 10^8$, $1.3 \times 10^8$, $1.4 \times 10^8$, $1.5 \times 10^8$, $1.6 \times 10^8$, $1.7 \times 10^8$, $1.8 \times 10^8$, $1.9 \times 10^8$, $2.0 \times 10^8$, $2.1 \times 10^8$, $2.2 \times 10^8$, $2.3 \times 10^8$, $2.4 \times 10^8$, $2.5 \times 10^8$, $2.6 \times 10^8$, $2.7 \times 10^8$, $2.8 \times 10^8$, $2.9 \times 10^8$, $3.0 \times 10^8$, $3.5 \times 10^8$, $4.0 \times 10^8$, $4.5 \times 10^8$, $5 \times 10^8$, $5 \times 10^8$, or $1 \times 10^9$, total or total viable CD4+ T cells are mixed or combined with an amount of or about of $5 \times 10^5$, $1 \times 10^6$, $5 \times 10^6$, $1 \times 10^7$, $5 \times 10^7$, $1.0 \times 10^8$, $1.1 \times 10^8$, $1.2 \times 10^8$, $1.3 \times 10^8$, $1.4 \times 10^8$, $1.5 \times 10^8$, $1.6 \times 10^8$, $1.7 \times 10^8$, $1.8 \times 10^8$, $1.9 \times 10^8$, $2.0 \times 10^8$, $2.1 \times 10^8$, $2.2 \times 10^8$, $2.3 \times 10^8$, $2.4 \times 10^8$, $2.5 \times 10^8$, $2.6 \times 10^8$, $2.7 \times 10^8$, $2.8 \times 10^8$, $2.9 \times 10^8$, $3.0 \times 10^8$, $3.5 \times 10^8$, $4.0 \times 10^8$, $4.5 \times 10^8$, $5 \times 10^8$, $5.5 \times 10^8$, or $1 \times 10^9$ total or total viable CD8+ T cells to produce an input cell composition with a defined ratio of CD4+ naïve-like T cells to CD8+ naïve-like T cells. In certain embodiments, between $1 \times 10^6$ and $1 \times 10^{10}$, between $1 \times 10^7$ and $1 \times 10^9$, between $5 \times 10^7$ and $5 \times 10^8$, or between $1 \times 10^8$ and $3 \times 10^8$ total or total viable CD4+ T cells are mixed or combined with an amount of or about of between $1 \times 10^6$ and $1 \times 10^{10}$, between $1 \times 10^7$ and $1 \times 10^9$, between $5 \times 10^7$ and $5 \times 10^8$, or between $1 \times 10^8$ and $3 \times 10^8$ total or total viable CD8+ T cells to produce an input cell composition with a defined ratio of CD4+ naïve-like T cells to CD8+ naïve-like T cells.

In some embodiments, an amount of or about of $5 \times 10^5$, $1 \times 10^6$, $5 \times 10^6$, $1 \times 10^7$, $5 \times 10^7$, $1.0 \times 10^8$, $1.1 \times 10^8$, $1.2 \times 10^8$, $1.3 \times 10^8$, $1.4 \times 10^8$, $1.5 \times 10^8$, $1.6 \times 10^8$, $1.7 \times 10^8$, $1.8 \times 10^8$, $1.9 \times 10^8$, $2.0 \times 10^8$, $2.1 \times 10^8$, $2.2 \times 10^8$, $2.3 \times 10^8$, $2.4 \times 10^8$, $2.5 \times 10^8$, $2.6 \times 10^8$, $2.7 \times 10^8$, $2.8 \times 10^8$, $2.9 \times 10^8$, $3.0 \times 10^8$, $3.5 \times 10^8$, $4.0 \times 10^8$, $4.5 \times 10^8$, $5 \times 10^8$, $5 \times 10^8$, or $1 \times 10^9$ naïve-like CD4+ T cells are mixed or combined with an amount of or about of $5 \times 10^5$, $1 \times 10^6$, $5 \times 10^6$, $1 \times 10^7$, $5 \times 10^7$, $1.0 \times 10^8$, $1.1 \times 10^8$, $1.2 \times 10^8$, $1.3 \times 10^8$, $1.4 \times 10^8$, $1.5 \times 10^8$, $1.6 \times 10^8$, $1.7 \times 10^8$, $1.8 \times 10^8$, $1.9 \times 10^8$, $2.0 \times 10^8$, $2.1 \times 10^8$, $2.2 \times 10^8$, $2.3 \times 10^8$, $2.4 \times 10^8$, $2.5 \times 10^8$, $2.6 \times 10^8$, $2.7 \times 10^8$, $2.8 \times 10^8$, $2.9 \times 10^8$, $3.0 \times 10^8$, $3.5 \times 10^8$, $4.0 \times 10^8$, $4.5 \times 10^8$, $5 \times 10^8$, $5.5 \times 10^8$, or $1 \times 10^9$ naïve-like CD8+ T cells to produce an input cell composition with a defined ratio of CD4+ naïve-like T cells to CD8+ naïve-like T cells. In certain embodiments, between $5 \times 10^5$ and $1 \times 10^{10}$, $1 \times 10^6$ and $1 \times 10^{10}$, between $1 \times 10^7$ and $1 \times 10^9$, between $5 \times 10^7$ and $5 \times 10^8$, or between $1 \times 10^8$ and $3 \times 10^8$ naïve-like CD4+ T cells are mixed or combined with an amount of or about of between $5\times10^5$ and $1\times10^{10}$, $1\times10^6$ and $1\times10^{10}$, between $1\times10^7$ and $1\times10^9$, between $5\times10^7$ and $5\times10^8$, or between $1\times10^8$ and $3\times10^8$ naïve-like CD8+ T cells to produce an input cell composition with a defined ratio of CD4+ naïve-like T cells to CD8+ naïve-like T cells.

In particular embodiments, the ratio of naïve-like CD4+ T cells to naïve-like CD8+ T cells of the input cell composition has been adjusted, changed, and/or altered compared to the ratio of the naïve-like CD4+ T cells to naïve-like CD8+ T cells of a sample, e.g., a biological sample. In particular embodiments, the ratio of naïve-like CD4+ T cells to naïve-like CD8+ T cells is or is about or is at least 5%, 10%, 20%, 30%, 40%, 50%, 60%, 70%, 80%, 90%, 95%, 100%, 1-fold, 1.5-fold, 2-fold, 2.5-fold, 3-fold, 4-fold, 5-fold, 10-fold, 20-fold, 50-fold, 100-fold adjusted, changed, or altered from the biological sample. In certain embodiments, the sample is the sample from where cells of the input cell composition were derived, isolated, selected, and/or obtained.

In certain embodiments, the input cell composition contains a ratio, e.g., a defined, controlled, and/or fixed ratio, of CD45RA+/CCR7+/CD4+ T cells to CD45RA+/CCR7+/CD8+ T cells. In particular embodiments, the ratio of CD45RA+/CCR7+/CD4+ T cells to CD45RA+/CCR7+/CD8+ T cells is between 10:1 to 0.05:1, between 8:1 and 0.1:1, between 5:1 and 0.2:1, between 2.5:1 and 0.25:1, between 2.2:1 and 0.8:1, between 2:1 and 0.5:1, or between 1.5:1 and 1:1, inclusive. In particular embodiments, the ratio of CD45RA+/CCR7+/CD4+ T cells to CD45RA+/CCR7+/CD8+ T cells is between 2:1 and 0.8:1, between 1.6:1 and 0.8:1, between 1.4:1 and 0.8:1, between 1.2:1 and 0.8:1, or between 1.2:1 and 0.8:1, inclusive. In some embodiments, the ratio is between 2.2:1 and 0.8:1, inclusive. In certain embodiments, the ratio of CD45RA+/CCR7+/CD4+ T cells to CD45RA+/CCR7+/CD8+ T cells is or is about 2.2:1, 2.1:1, 2.0:1, 1.9:1, 1.8:1, 1.7:1, 1.6:1, 1.5:1, 1.4:1, 1.3:1, 1.2:1, 1.1:1, 1.0:1, 0.9:1, or 0.8:1. In certain embodiments, the ratio is or is about 1.1:1.

In particular embodiments, the input cell composition has an amount of or about of $1\times10^6$, $5\times10^6$, $1\times10^7$, $5\times10^7$, $1.0\times10^8$, $1.1\times10^8$, $1.2\times10^8$, $1.3\times10^8$, $1.4\times10^8$, $1.5\times10^8$, $1.6\times10^8$, $1.7\times10^8$, $1.8\times10^8$, $1.9\times10^8$, $2.0\times10^8$, $2.1\times10^8$, $2.2\times10^8$, $2.3\times10^8$, $2.4\times10^8$, $2.5\times10^8$, $2.6\times10^8$, $2.7\times10^8$, $2.8\times10^8$, $2.9\times10^8$, $3.0\times10^8$, $3.5\times10^8$, $4.0\times10^8$, $4.5\times10^8$, $5\times10^8$, $5\times10^8$, or $1\times10^9$ total cells or total viable cells. In certain embodiments, the input cell composition has an amount of or about of $5\times10^5$, $1\times10^6$, $5\times10^6$, $1\times10^7$, $5\times10^7$, $1.0\times10^8$, $1.1\times10^8$, $1.2\times10^8$, $1.3\times10^8$, $1.4\times10^8$, $1.5\times10^8$, $1.6\times10^8$, $1.7\times10^8$, $1.8\times10^8$, $1.9\times10^8$, $2.0\times10^8$, $2.1\times10^8$, $2.2\times10^8$, $2.3\times10^8$, $2.4\times10^8$, $2.5\times10^8$, $2.6\times10^8$, $2.7\times10^8$, $2.8\times10^8$, $2.9\times10^8$, $3.0\times10^8$, $3.5\times10^8$, $4.0\times10^8$, $4.5\times10^8$, $5\times10^8$, $5\times10^8$, or $1\times10^9$ cells that express CD4 or CD8. In some embodiments, the input cell composition has an amount of or about of $5\times10^5$, $1\times10^6$, $5\times10^6$, $1\times10^7$, $5\times10^7$, $1.0\times10^8$, $1.1\times10^8$, $1.2\times10^8$, $1.3\times10^8$, $1.4\times10^8$, $1.5\times10^8$, $1.6\times10^8$, $1.7\times10^8$, $1.8\times10^8$, $1.9\times10^8$, $2.0\times10^8$, $2.1\times10^8$, $2.2\times10^8$, $2.3\times10^8$, $2.4\times10^8$, $2.5\times10^8$, $2.6\times10^8$, $2.7\times10^8$, $2.8\times10^8$, $2.9\times10^8$, $3.0\times10^8$, $3.5\times10^8$, $4.0\times10^8$, $4.5\times10^8$, $5\times10^8$, $5\times10^8$, or $1\times10^9$ CD45RA+/CCR7+/CD4+ and CD45RA+/CCR7+/CD8+ T cells.

In particular embodiments, the input cell composition has between $1\times10^6$ and $1\times10^{10}$, between $1\times10^7$ and $1\times10^9$, between $5\times10^7$ and $5\times10^8$, or between $1\times10^8$ and $3\times10^8$ total cells or total viable cells. In certain embodiments, the input cell composition has an amount of or about of between $5\times10^5$ and $1\times10^{10}$, $1\times10^6$ and $1\times10^{10}$, between $1\times10^7$ and $1\times10^9$, between $5\times10^7$ and $5\times10^8$, or between $1\times10^8$ and $3\times10^8$ cells that express CD4 or CD8. In some embodiments, the input cell composition has an amount of or about of between $5\times10^5$ and $1\times10^{10}$, $1\times10^6$ and $1\times10^{10}$, between $1\times10^7$ and $1\times10^9$, between $5\times10^7$ and $5\times10^8$, or between $1\times10^8$ and $3\times10^8$ CD45RA+/CCR7+/CD4+ and CD45RA+/CCR7+/CD8+ T cells.

In some embodiments, the input cell composition has or contains at least 1%, at least 5%, at least 10%, at least 20%, at least 30%, at least 40%, at least 50%, at least 60%, at least 70%, at least 75%, at least 80%, at least 85%, at least 90%, at least 95%, at least 96%, at least 97%, at least 98%, at least 99%, at least 99.5%, at least 99.9%, or 100% or about 100% CD45RA+/CCR7+ cells. In particular embodiments, the input cell composition contains or includes no more than 100%, no more than 99%, no more than 98%, no more than 97%, no more than 96%, no more than 95%, no more than 90%, or no more than 85% CD45RA+/CCR7+ cells.

In some embodiments, an amount of or about of $5\times10^5$, $1\times10^6$, $5\times10^6$, $1\times10^7$, $5\times10^7$, $1.0\times10^8$, $1.1\times10^8$, $1.2\times10^8$, $1.3\times10^8$, $1.4\times10^8$, $1.5\times10^8$, $1.6\times10^8$, $1.7\times10^8$, $1.8\times10^8$, $1.9\times10^8$, $2.0\times10^8$, $2.1\times10^8$, $2.2\times10^8$, $2.3\times10^8$, $2.4\times10^8$, $2.5\times10^8$, $2.6\times10^8$, $2.7\times10^8$, $2.8\times10^8$, $2.9\times10^8$, $3.0\times10^8$, $3.5\times10^8$, $4.0\times10^8$, $4.5\times10^8$, $5\times10^8$, $5\times10^8$, or $1\times10^9$, total or total viable CD4+ T cells are mixed or combined with an amount of or about of $5\times10^5$, $1\times10^6$, $5\times10^6$, $1\times10^7$, $5\times10^7$, $1.0\times10^8$, $1.1\times10^8$, $1.2\times10^8$, $1.3\times10^8$, $1.4\times10^8$, $1.5\times10^8$, $1.6\times10^8$, $1.7\times10^8$, $1.8\times10^8$, $1.9\times10^8$, $2.0\times10^8$, $2.1\times10^8$, $2.2\times10^8$, $2.3\times10^8$, $2.4\times10^8$, $2.5\times10^8$, $2.6\times10^8$, $2.7\times10^8$, $2.8\times10^8$, $2.9\times10^8$, $3.0\times10^8$, $3.5\times10^8$, $4.0\times10^8$, $4.5\times10^8$, $5\times10^8$, $5.5\times10^8$, or $1\times10^9$ total or total viable CD8+ T cells to produce an input cell composition with a defined ratio of CD45RA+/CCR7+/CD4+ T cells to CD45RA+/CCR7+/CD8+ T cells. In certain embodiments, between $5\times10^5$ and $1\times10^{10}$, $1\times10^6$ and $1\times10^{10}$, between $1\times10^7$ and $1\times10^9$, between $5\times10^7$ and $5\times10^8$, or between $1\times10^8$ and $3\times10^8$ total or total viable CD4+ T cells are mixed or combined with an amount of or about of between $5\times10^5$ and $1\times10^{10}$, $1\times10^6$ and $1\times10^{10}$, between $1\times10^7$ and $1\times10^9$, between $5\times10^7$ and $5\times10^8$, or between $1\times10^8$ and $3\times10^8$ total or total viable CD8+ T cells to produce an input cell composition with a defined ratio of CD45RA+/CCR7+/CD4+ T cells to CD45RA+/CCR7+/CD8+ T cells.

In particular embodiments, the ratio of CD45RA+/CCR7+/CD4+ T cells to CD45RA+/CCR7+/CD8+ T cells of the input cell composition has been adjusted, changed, and/or altered compared to the ratio of the CD45RA+/CCR7+/CD4+ T cells to CD45RA+/CCR7+/CD8+ T cells of a sample, e.g., a biological sample. In particular embodiments, the ratio of CD45RA+/CCR7+/CD4+ T cells to CD45RA+/CCR7+/CD8+ T cells is or is about or is at least 5%, 10%, 20%, 30%, 40%, 50%, 60%, 70%, 80%, 90%, 95%, 100%, 1-fold, 1.5-fold, 2-fold, 2.5-fold, 3-fold, 4-fold, 5-fold, 10-fold, 20-fold, 50-fold, 100-fold adjusted, changed, or altered from the biological sample. In certain embodiments, the sample is the sample from where cells of the input cell composition were derived, isolated, selected, and/or obtained.

In certain embodiments, the input cell composition contains a ratio, e.g., a defined, controlled, and/or fixed ratio, of CD27+/CCR7+/CD4+ T cells to CD27+/CCR7+/CD8+ T cells. In particular embodiments, the ratio of CD27+/CCR7+/CD4+ T cells to CD27+/CCR7+/CD8+ T cells is between 10:1 and 0.05:1, between 8:1 and 0.1:1, between 5:1 and 0.2:1, between 2.5:1 and 0.25:1, between 2.2:1 and 0.8:1, between 2:1 and 0.5:1, or between 2:1 and 1:1, inclusive. In particular embodiments, the ratio of CD27+/CCR7+/CD4+ T cells to CD27+/CCR7+/CD8+ T cells is between 2:1 and 0.8:1, between 1.8:1 and 1:1, between 1.8:1 and 1.2:1, between 1.2:1 and 1.4:1, or between 1.8:1 and 1.6:1, inclusive. In some embodiments, the ratio is between 1.8:1 and 1.6:1, inclusive. In certain embodiments, the ratio of CD27+/CCR7+/CD4+ T cells to CD27+/CCR7+/CD8+ T cells is or is about 2.2:1, 2.1:1, 2.0:1, 1.9:1, 1.8:1, 1.7:1, 1.69:1, 1.6:1, 1.5:1, 1.4:1, or 1.3:1. In certain embodiments, the ratio is or is about 1.69:1.

In particular embodiments, the input cell composition has an amount of or about of $1 \times 10^6$, $5 \times 10^6$, $1 \times 10^7$, $5 \times 10^7$, $1.0 \times 10^8$, $1.1 \times 10^8$, $1.2 \times 10^8$, $1.3 \times 10^8$, $1.4 \times 10^8$, $1.5 \times 10^8$, $1.6 \times 10^8$, $1.7 \times 10^8$, $1.8 \times 10^8$, $1.9 \times 10^8$, $2.0 \times 10^8$, $2.1 \times 10^8$, $2.2 \times 10^8$, $2.3 \times 10^8$, $2.4 \times 10^8$, $2.5 \times 10^8$, $2.6 \times 10^8$, $2.7 \times 10^8$, $2.8 \times 10^8$, $2.9 \times 10^8$, $3.0 \times 10^8$, $3.5 \times 10^8$, $4.0 \times 10^8$, $4.5 \times 10^8$, $5 \times 10^8$, $5 \times 10^8$, or $1 \times 10^9$ total cells or total viable cells. In certain embodiments, the input cell composition has an amount of or about of $5 \times 10^5$, $1 \times 10^6$, $5 \times 10^6$, $1 \times 10^7$, $5 \times 10^7$, $1.0 \times 10^8$, $1.1 \times 10^8$, $1.2 \times 10^8$, $1.3 \times 10^8$, $1.4 \times 10^8$, $1.5 \times 10^8$, $1.6 \times 10^8$, $1.7 \times 10^8$, $1.8 \times 10^8$, $1.9 \times 10^8$, $2.0 \times 10^8$, $2.1 \times 10^8$, $2.2 \times 10^8$, $2.3 \times 10^8$, $2.4 \times 10^8$, $2.5 \times 10^8$, $2.6 \times 10^8$, $2.7 \times 10^8$, $2.8 \times 10^8$, $2.9 \times 10^8$, $3.0 \times 10^8$, $3.5 \times 10^8$, $4.0 \times 10^8$, $4.5 \times 10^8$, $5 \times 10^8$, $5 \times 10^8$, or $1 \times 10^9$ cells that express CD4 or CD8. In some embodiments, the input cell composition has an amount of or about of $5 \times 10^5$, $1 \times 10^6$, $5 \times 10^6$, $1 \times 10^7$, $5 \times 10^7$, $1.0 \times 10^8$, $1.1 \times 10^8$, $1.2 \times 10^8$, $1.3 \times 10^8$, $1.4 \times 10^8$, $1.5 \times 10^8$, $1.6 \times 10^8$, $1.7 \times 10^8$, $1.8 \times 10^8$, $1.9 \times 10^8$, $2.0 \times 10^8$, $2.1 \times 10^8$, $2.2 \times 10^8$, $2.3 \times 10^8$, $2.4 \times 10^8$, $2.5 \times 10^8$, $2.6 \times 10^8$, $2.7 \times 10^8$, $2.8 \times 10^8$, $2.9 \times 10^8$, $3.0 \times 10^8$, $3.5 \times 10^8$, $4.0 \times 10^8$, $4.5 \times 10^8$, $5 \times 10^8$, $5 \times 10^8$, or $1 \times 10^9$ CD27+/CCR7+/CD4+ and CD27+/CCR7+/CD8+ T cells.

In particular embodiments, the input cell composition has between $1 \times 10^6$ and $1 \times 10^{10}$, between $1 \times 10^7$ and $1 \times 10^9$, between $5 \times 10^7$ and $5 \times 10^8$, or between $1 \times 10^8$ and $3 \times 10^8$ total cells or total viable cells. In certain embodiments, the input cell composition has an amount of or about of between $5 \times 10^5$ and $1 \times 10^{10}$, $1 \times 10^6$ and $1 \times 10^{10}$, between $1 \times 10^7$ and $1 \times 10^9$, between $5 \times 10^7$ and $5 \times 10^8$, or between $1 \times 10^8$ and $3 \times 10^8$ cells that express CD4 or CD8. In some embodiments, the input cell composition has an amount of or about of between $5 \times 10^5$ and $1 \times 10^{10}$, $1 \times 10^6$ and $1 \times 10^{10}$, between $1 \times 10^7$ and $1 \times 10^9$, between $5 \times 10^7$ and $5 \times 10^8$, or between $1 \times 10^8$ and $3 \times 10^8$ CD27+/CCR7+/CD4+ and CD27+/CCR7+/CD8+ T cells.

In some embodiments, the input cell composition has or contains at least 1%, at least 5%, at least 10%, at least 20%, at least 30%, at least 40%, at least 50%, at least 60%, at least 70%, at least 75%, at least 80%, at least 85%, at least 90%, at least 95%, at least 96%, at least 97%, at least 98%, at least 99%, at least 99.5%, at least 99.9%, or 100% or about 100% CD27+/CCR7+ cells. In particular embodiments, the input cell composition contains or includes no more than 100%, no more than 99%, no more than 98%, no more than 97%, no more than 96%, no more than 95%, no more than 90%, or no more than 85% CD27+/CCR7+ cells.

In some embodiments, an amount of or about of $5 \times 10^5$, $1 \times 10^6$, $5 \times 10^6$, $1 \times 10^7$, $5 \times 10^7$, $1.0 \times 10^8$, $1.1 \times 10^8$, $1.2 \times 10^8$, $1.3 \times 10^8$, $1.4 \times 10^8$, $1.5 \times 10^8$, $1.6 \times 10^8$, $1.7 \times 10^8$, $1.8 \times 10^8$, $1.9 \times 10^8$, $2.0 \times 10^8$, $2.1 \times 10^8$, $2.2 \times 10^8$, $2.3 \times 10^8$, $2.4 \times 10^8$, $2.5 \times 10^8$, $2.6 \times 10^8$, $2.7 \times 10^8$, $2.8 \times 10^8$, $2.9 \times 10^8$, $3.0 \times 10^8$, $3.5 \times 10^8$, $4.0 \times 10^8$, $4.5 \times 10^8$, $5 \times 10^8$, $5 \times 10^8$, or $1 \times 10^9$, total or total viable CD4+ T cells are mixed or combined with an amount of or about of $5 \times 10^5$, $1 \times 10^6$, $5 \times 10^6$, $1 \times 10^7$, $5 \times 10^7$, $1.0 \times 10^8$, $1.1 \times 10^8$, $1.2 \times 10^8$, $1.3 \times 10^8$, $1.4 \times 10^8$, $1.5 \times 10^8$, $1.6 \times 10^8$, $1.7 \times 10^8$, $1.8 \times 10^8$, $1.9 \times 10^8$, $2.0 \times 10^8$, $2.1 \times 10^8$, $2.2 \times 10^8$, $2.3 \times 10^8$, $2.4 \times 10^8$, $2.5 \times 10^8$, $2.6 \times 10^8$, $2.7 \times 10^8$, $2.8 \times 10^8$, $2.9 \times 10^8$, $3.0 \times 10^8$, $3.5 \times 10^8$, $4.0 \times 10^8$, $4.5 \times 10^8$, $5 \times 10^8$, $5.5 \times 10^8$, or $1 \times 10^9$ total or total viable CD8+ T cells to produce an input cell composition with a defined ratio of CD27+/CCR7+/CD4+ T cells to CD27+/CCR7+/CD8+ T cells. In certain embodiments, between $5 \times 10^5$ and $1 \times 10^{10}$, $1 \times 10^6$ and $1 \times 10^{10}$, between $1 \times 10^7$ and $1 \times 10^9$, between $5 \times 10^7$ and $5 \times 10^8$, or between $1 \times 10^8$ and $3 \times 10^8$ total or total viable CD4+ T cells are mixed or combined with an amount of or about of between $5 \times 10^5$ and $1 \times 10^{10}$, $1 \times 10^6$ and $1 \times 10^{10}$, between $1 \times 10^7$ and $1 \times 10^9$, between $5 \times 10^7$ and $5 \times 10^8$, or between $1 \times 10^8$ and $3 \times 10^8$ total or total viable CD8+ T cells to produce an input cell composition with a defined ratio of CD27+/CCR7+/CD4+ T cells to CD27+/CCR7+/CD8+ T cells.

In particular embodiments, the ratio of CD27+/CCR7+/CD4+ T cells to CD27+/CCR7+/CD8+ T cells of the input cell composition has been adjusted, changed, and/or altered compared to the ratio of the CD27+/CCR7+/CD4+ T cells to CD27+/CCR7+/CD8+ T cells of a sample, e.g., a biological sample. In particular embodiments, the ratio of CD27+/CCR7+/CD4+ T cells to CD27+/CCR7+/CD8+ T cells is or is about or is at least 5%, 10%, 20%, 30%, 40%, 50%, 60%, 70%, 80%, 90%, 95%, 100%, 1-fold, 1.5-fold, 2-fold, 2.5-fold, 3-fold, 4-fold, 5-fold, 10-fold, 20-fold, 50-fold, 100-fold adjusted, changed, or altered from the biological sample. In certain embodiments, the sample is the sample from where cells of the input cell composition were derived, isolated, selected, and/or obtained.

In certain embodiments, the input cell composition contains a ratio, e.g., a defined, controlled, and/or fixed ratio, of CD62L−/CCR7+/CD4+ T cells to CD62L−/CCR7+/CD8+ T cells. In particular embodiments, the ratio of CD62L−/CCR7+/CD4+ T cells to CD62L−/CCR7+/CD8+ T cells is between 10:1 and 0.05:1, between 8:1 and 0.1:1, between 5:1 and 0.2:1, between 2.5:1 and 0.25:1, between 2.2:1 and 0.8:1, between 2:1 and 0.5:1, or between 1.5:1 and 1:1, inclusive. In particular embodiments, the ratio of CD62L−/CCR7+/CD4+ T cells to CD62L−/CCR7+/CD8+ T cells is between 2:1 and 0.8:1, between 1.6:1 and 0.8:1, between 1.4:1 and 0.8:1, between 1.2:1 and 0.8:1, or between 1.2:1 and 0.8:1, inclusive. In some embodiments, the ratio is between 2.2:1 and 0.8:1, inclusive. In certain embodiments, the ratio of CD62L−/CCR7+/CD4+ T cells to CD62L−/CCR7+/CD8+ T cells is or is about 2.2:1, 2.1:1, 2.0:1, 1.9:1, 1.8:1, 1.7:1, 1.6:1, 1.5:1, 1.4:1, 1.3:1, 1.2:1, 1.1:1, 1.0:1, 0.9:1, or 0.8:1. In certain embodiments, the ratio is or is about 1.1:1.

In particular embodiments, the input cell composition has between $1 \times 10^6$ and $1 \times 10^{10}$, between $1 \times 10^7$ and $1 \times 10^9$, between $5 \times 10^7$ and $5 \times 10^8$, or between $1 \times 10^8$ and $3 \times 10^8$ total cells or total viable cells. In certain embodiments, the input cell composition has an amount of or about of between $1 \times 10^6$ and $1 \times 10^{10}$, between $1 \times 10^7$ and $1 \times 10^9$, between $5 \times 10^7$ and $5 \times 10^8$, or between $1 \times 10^8$ and $3 \times 10^8$ cells that express CD4 or CD8. In some embodiments, the input cell composition has an amount of or about of between $1 \times 10^6$ and $1 \times 10^{10}$, between $1 \times 10^7$ and $1 \times 10^9$, between $5 \times 10^7$ and $5 \times 10^8$, or between $1 \times 10^8$ and $3 \times 10^8$ CD62L−/CCR7+/CD4+ and CD62L−/CCR7+/CD8+ T cells.

In some embodiments, the input cell composition has or contains at least 1%, at least 5%, at least 10%, at least 20%, at least 30%, at least 40%, at least 50%, at least 60%, at least 70%, at least 75%, at least 80%, at least 85%, at least 90%, at least 95%, at least 96%, at least 97%, at least 98%, at least 99%, at least 99.5%, at least 99.9%, or 100% or about 100% CD62L−/CCR7+ cells. In particular embodiments, the input cell composition contains or includes no more than 100%, no more than 99%, no more than 98%, no more than 97%, no more than 96%, no more than 95%, no more than 90%, or no more than 85% CD62L−/CCR7+ cells.

In some embodiments, an amount of or about of $1\times10^6$, $5\times10^6$, $1\times10^7$, $5\times10^7$, $1.0\times10^8$, $1.1\times10^8$, $1.2\times10^8$, $1.3\times10^8$, $1.4\times10^8$, $1.5\times10^8$, $1.6\times10^8$, $1.7\times10^8$, $1.8\times10^8$, $1.9\times10^8$, $2.0\times10^8$, $2.1\times10^8$, $2.2\times10^8$, $2.3\times10^8$, $2.4\times10^8$, $2.5\times10^8$, $2.6\times10^8$, $2.7\times10^8$, $2.8\times10^8$, $2.9\times10^8$, $3.0\times10^8$, $3.5\times10^8$, $4.0\times10^8$, $4.5\times10^8$, $5\times10^8$, $5\times10^8$, or $1\times10^9$, total or total viable CD4+ T cells are mixed or combined with an amount of or about of $1\times10^6$, $5\times10^6$, $1\times10^7$, $5\times10^7$, $1.0\times10^8$, $1.1\times10^8$, $1.2\times10^8$, $1.3\times10^8$, $1.4\times10^8$, $1.5\times10^8$, $1.6\times10^8$, $1.7\times10^8$, $1.8\times10^8$, $1.9\times10^8$, $2.0\times10^8$, $2.1\times10^8$, $2.2\times10^8$, $2.3\times10^8$, $2.4\times10^8$, $2.5\times10^8$, $2.6\times10^8$, $2.7\times10^8$, $2.8\times10^8$, $2.9\times10^8$, $3.0\times10^8$, $3.5\times10^8$, $4.0\times10^8$, $4.5\times10^8$, $5\times10^8$, $5.5\times10^8$, or $1\times10^9$ total or total viable CD8+ T cells to produce an input cell composition with a defined ratio of CD62L−/CCR7+/CD4+ T cells to CD62L−/CCR7+/CD8+ T cells. In certain embodiments, between $1\times10^6$ and $1\times10^{10}$, between $1\times10^7$ and $1\times10^9$, between $5\times10^7$ and $5\times10^8$, or between $1\times10^8$ and $3\times10^8$ total or total viable CD4+ T cells are mixed or combined with an amount of or about of between $1\times10^6$ and $1\times10^{10}$, between $1\times10^7$ and $1\times10^9$, between $5\times10^7$ and $5\times10^8$, or between $1\times10^8$ and $3\times10^8$ total or total viable CD8+ T cells to produce an input cell composition with a defined ratio of CD62L−/CCR7+/CD4+ T cells to CD62L−/CCR7+/CD8+ T cells.

In particular embodiments, the ratio of CD62L−/CCR7+/CD4+ T cells to CD62L−/CCR7+/CD8+ T cells of the input cell composition has been adjusted, changed, and/or altered compared to the ratio of the CD62L−/CCR7+/CD4+ T cells to CD62L−/CCR7+/CD8+ T cells of a sample, e.g., a biological sample. In particular embodiments, the ratio of CD62L−/CCR7+/CD4+ T cells to CD62L−/CCR7+/CD8+ T cells is or is about or is at least 5%, 10%, 20%, 30%, 40%, 50%, 60%, 70%, 80%, 90%, 95%, 100%, 1-fold, 1.5-fold, 2-fold, 2.5-fold, 3-fold, 4-fold, 5-fold, 10-fold, 20-fold, 50-fold, 100-fold adjusted, changed, or altered from the biological sample. In certain embodiments, the sample is the sample from where cells of the input cell composition were derived, isolated, selected, and/or obtained.

In some embodiments, producing, generating, and/or making an input cell composition includes one or more steps of mixing or combining cells of a CD4+ T cell composition with cells of a CD8+ T cell compositions to produce an input cell composition with a ratio of between 2.2:1 to 0.8:1 CD45RA+/CCR7+/CD4+ T cells to CD45RA+/CCR7+/CD8+ T cells. In particular embodiments, number, number per volume, number per weight, and/or the amount, level, or percentage of CD45RA+/CCR7+ cells are measured, assessed, and/or quantified in the CD4+ T cell composition and the CD8+ T cell composition prior to the mixing or combining. In some embodiments, the amount, level, number, number per volume, number per weight, and/or percentage of CD45RA+/CCR7+ cells are measured, assessed, and/or quantified by detecting CD45RA+; CCR7+ T cells. In particular embodiments, the input cell composition has a ratio of between 2.2:1 to 0.8:1 CD45RA+/CCR7+/CD4+ T cells to CD45RA+/CCR7+/CD8+ T cells. In some embodiments, the input cell composition has a ratio of or of about 1.1:1 CD45RA+/CCR7+/CD4+ T cells to CD45RA+/CCR7+/CD8+ T cells.

In some embodiments, producing, generating, and/or making an input cell composition includes one or more steps of mixing or combining cells of a CD4+ T cell composition with cells of a CD8+ T cell compositions to produce an input cell composition with a ratio of between 2.4:1 to 1:1 CD27+/CCR7+/CD4+ T cells to CD27+/CCR7+/CD8+ T cells. In particular embodiments, number, number per volume, number per weight, and/or the amount, level, or percentage of CD27+/CCR7+ cells are measured, assessed, and/or quantified in the CD4+ T cell composition and the CD8+ T cell composition prior to the mixing or combining. In some embodiments, the amount, level, number, number per volume, number per weight, and/or percentage of CD27+/CCR7+ cells are measured, assessed, and/or quantified by detecting CD45RA+; CCR7+ T cells. In particular embodiments, the input cell composition has a ratio of between 2.4:1 to 1:1 CD27+/CCR7+/CD4+ T cells to CD27+/CCR7+/CD8+ T cells. In some embodiments, the input cell composition has a ratio of or of about 1.69:1 CD27+/CCR7+/CD4+ T cells to CD27+/CCR7+/CD8+ T cells.

In some embodiments, producing, generating, and/or making an input cell composition includes one or more steps of mixing or combining cells of a CD4+ T cell composition with cells of a CD8+ T cell compositions to produce an input cell composition with a ratio of between 2.2:1 to 0.8:1 CD62L−/CCR7+/CD4+ T cells to CD62L−/CCR7+/CD8+ T cells. In particular embodiments, number, number per volume, number per weight, and/or the amount, level, or percentage of CD62L−/CCR7+ cells are measured, assessed, and/or quantified in the CD4+ T cell composition and the CD8+ T cell composition prior to the mixing or combining. In some embodiments, the amount, level, number, number per volume, number per weight, and/or percentage of CD62L−/CCR7+ cells are measured, assessed, and/or quantified by detecting CD62L−/CCR7+ T cells. In particular embodiments, the input cell composition has a ratio of between 2.2:1 to 0.8:1 CD62L−/CCR7+/CD4+ T cells to CD62L−/CCR7+/CD8+ T cells. In some embodiments, the input cell composition has a ratio of or of about 1.1:1 CD62L−/CCR7/CD4+ T cells to CD62L−/CCR7/CD8+ T cells.

In some embodiments, producing, generating, and/or making an input cell composition includes one or more steps of mixing or combining cells of a CD4+ T cell composition with cells of a CD8+ T cell compositions to produce an input cell composition with a ratio of between 2.2:1 to 0.8:1 naïve-like CD4+ T cells to naïve-like CD8+ T cells. In particular embodiments, number, number per volume, number per weight, and/or the amount, level, or percentage of naïve-like cells are measured, assessed, and/or quantified in the CD4+ T cell composition and the CD8+ T cell composition prior to the mixing or combining. In some embodiments, the amount, level, number, number per volume, number per weight, and/or percentage of naïve-like cells are measured, assessed, and/or quantified by detecting CD45RA+; CCR7+ T cells. In particular embodiments, the input cell composition has a ratio of between 2.2:1 to 0.8:1 CD45RA+/CCR7+/CD4+ T cells to CD45RA+/CCR7+/CD8+ T cells. In some embodiments, the input cell composition has a ratio of or of about 1.1:1 CD45RA+/CCR7+/CD4+ T cells to CD45RA+/CCR7+/CD8+ T cells.

B. Activation or Stimulation of Cells

In some embodiments, the cells are incubated and/or cultured prior to, in connection with, and/or subsequent to a process for genetic engineering. In certain embodiments, the cells are incubated and/or cultured prior to, during, or immediately after one or more steps associated with the genetic engineering protocol or process. The incubation steps can include culture, cultivation, stimulation, activation, and/or propagation. The incubation and/or engineering may be carried out in a culture vessel, such as a unit, chamber, well, column, tube, tubing set, valve, vial, culture dish, bag, or other container for culture or cultivating cells. In some embodiments, the compositions or cells are incubated in the presence of stimulating conditions or a stimulatory agent. Such conditions include those designed to induce proliferation, expansion, activation, and/or survival of cells in the population, to mimic antigen exposure, and/or to prime the cells for genetic engineering, such as for the introduction of a recombinant antigen receptor.

In some embodiments, methods provided herein include on or more steps of incubating cells under stimulating or activating conditions. In some embodiments, the cells are incubated for or for about 15 minutes, 30 minutes, 45 minutes, 60 minutes, 90 minutes, 120 minutes, 2 hours, 3 hours, 4 hours, 6 hours, 8 hours, 12 hours, 16 hours, 18 hours, 24 hours, 36 hours, 1 day, 2 days, 3 days, 4 days, 5 days, 6 days, 7 days, or more than 7 days. In some embodiments, the cells are incubated for between 5 minutes and 90 minutes, between 1 hour and 4 hours, between 2 hours and 8 hours, between 6 hours and 24 hours, between 12 hours and 48 hours, between 16 hours and 32 hours, between 18 hours and 30 hours, between 1 day and 4 days, or between 2 days and 7 days. In some embodiments, the cells are incubated for between 2 and 15 days, between 2 and 12 days, between 2 and 10 days, between 2 and 8 days, between 2 and 6 days, between 2 and 4 days, between 4 and 12 days, between 4 and 10 days, between 4 and 8 days, between 4 and 6 days, between 6 and 12 days, between 6 and 10 days, between 6 and 8 days, between 8 and 12 days, between 8 and 10 days, or between 10 and 12 days. In some embodiments, the cells are incubated for at least 2 days, 3 days, 4 days, 5 days, 6 days, 7 days, 8 days, 9 days, 10 days, 11 days, 12 days, 13 days, 14 days, or more than 14 days.

In some embodiments, the cells are genetically engineered by a method or process that includes one or more steps for gene transfer. In some embodiments, the gene transfer is accomplished by first stimulating the cells, such as by incubating the cells under stimulating conditions, e.g., incubating the cells with a stimulus that induces a response such as proliferation, survival, and/or activation, followed by the gene transfer. In some embodiments, the cells are incubated under stimulating conditions for the purposes of activating the cells prior to the gene transfer. In some embodiments, the gene transfer is or includes transduction of the activated cells. In particular embodiments, the stimulating agents or conditions induce and/or are capable of inducing primary signal, signaling, stimulation, activation and/or expansion of the cells.

In some embodiments, the cells, e.g., the cells of the input cell composition are incubated under stimulating or activating conditions prior to gene transfer. In some embodiments, the cells are incubated under stimulating or activating conditions for or for about 15 minutes, 30 minutes, 45 minutes, 60 minutes, 90 minutes, 120 minutes, 2 hours, 3 hours, 4 hours, 6 hours, 8 hours, 12 hours, 16 hours, 18 hours, 24 hours, 36 hours, 1 day, 2 days, 3 days, 4 days, 5 days, 6 days, 7 days, or more than 7 days. In some embodiments, the cells of the input cell composition are incubated under stimulating or activating conditions for between 5 minutes and 90 minutes, between 1 hour and 4 hours, between 2 hours and 8 hours, between 6 hours and 24 hours, between 12 hours and 48 hours, between 16 hours and 32 hours, between 18 hours and 30 hours, between 1 day and 4 days, or between 2 days and 7 days prior to gene transfer. In particular embodiments, the cells of the input cell composition are incubated under stimulating or activating conditions for between 2 and 15 days, between 2 and 12 days, between 2 and 12 days, between 2 and 8 days, between 2 and 6 days, between 2 and 4 days, between 4 and 12 days, between 4 and 10 days, between 4 and 8 days, between 4 and 6 days, between 6 and 12 days, between 6 and 10 days, between 6 and 8 days, between 8 and 12 days, between 8 and 10 days, or between 10 and 12 days. In some embodiments, the cells are incubated for at least 2 days, 3 days, 4 days, 5 days, 6 days, 7 days, 8 days, 9 days, 10 days, 11 days, 12 days, 13 days, 14 days, or more than 14 days.

In some embodiments, the cells are incubated under stimulating or activating conditions during some or all of a gene transfer. For example, in certain embodiments, the cells are incubated under stimulating conditions during all or a portion of transducing or transfecting the cells to introduce a heterologous nucleic acid. In certain embodiments, the cells are incubated under stimulating or activating conditions in the presence of a viral vector, e.g., a retroviral vector such a gammaretroviral vector or a lentiviral vector.

In particular embodiments, the cells are incubated under stimulating or activating conditions after, e.g., immediately after the gene transfer. In some embodiments, the cells are incubated under stimulating or activating conditions after the gene transfer to expand the cells e.g., to expand the cells into numbers that are sufficient for clinical applications. In some embodiments, the cells are incubated after the gene transfer under stimulating or activating conditions for or for about 15 minutes, 30 minutes, 45 minutes, 60 minutes, 90 minutes, 120 minutes, 2 hours, 3 hours, 4 hours, 6 hours, 8 hours, 12 hours, 16 hours, 18 hours, 24 hours, 36 hours, 1 day, 2 days, 3 days, 4 days, 5 days, 6 days, 7 days, or more than 7 days. In some embodiments, the cells composition are incubated after the gene transfer under stimulating or activating conditions for between 5 minutes and 90 minutes, between 1 hour and 4 hours, between 2 hours and 8 hours, between 6 hours and 24 hours, between 12 hours and 48 hours, between 16 hours and 32 hours, between 18 hours and 30 hours, between 1 day and 4 days, or between 2 days and 7 days prior to gene transfer. In some embodiments, the cells of the composition are incubated after the gene transfer under stimulating or activating conditions for between 2 and 15 days, between 2 and 12 days, between 2 and 12 days, between 2 and 8 days, between 2 and 6 days, between 2 and 4 days, between 4 and 12 days, between 4 and 10 days, between 4 and 8 days, between 4 and 6 days, between 6 and 12 days, between 6 and 10 days, between 6 and 8 days, between 8 and 12 days, between 8 and 10 days, or between 10 and 12 days. In some embodiments, the cells are incubated for at least 2 days, 3 days, 4 days, 5 days, 6 days, 7 days, 8 days, 9 days, 10 days, 11 days, 12 days, 13 days, 14 days, or more than 14 days. In some embodiments, the cells are expanded for an amount of time sufficient to generate a suitable number of cells for a clinical application.

The conditions can include one or more of particular media, temperature, oxygen content, carbon dioxide content, time, agents, e.g., nutrients, amino acids, antibiotics, ions, and/or stimulatory factors, such as cytokines, chemokines, antigens, binding partners, fusion proteins, recombinant soluble receptors, and any other agents designed to activate the cells.

In some embodiments, stimulatory conditions or agents induce and/or are capable of inducing primary signal, signaling, stimulation, activation and/or expansion of the cells.

In some embodiments, the stimulating conditions or agents include one or more agent, e.g., ligand, which is capable of activating an intracellular signaling domain of a TCR complex. In some aspects, the agent turns on or initiates TCR/CD3 intracellular signaling cascade in a T cell. Such agents can include antibodies, such as those specific for a TCR, e.g. anti-CD3. In some embodiments, the stimulating conditions include one or more agent, e.g. ligand, which is capable of stimulating a costimulatory receptor, e.g., anti-CD28. In some embodiments, such agents and/or ligands may be, bound to solid support such as a bead, and/or one or more cytokines. Optionally, the expansion method may further comprise the step of adding anti-CD3 and/or anti-CD28 antibody to the culture medium (e.g., at a concentration of at least about 0.5 ng/ml). In some embodiments, the stimulating agents include IL-2, IL-15 and/or IL-7. In particular embodiments, the agent is an antibody that specifically binds to the recombinant receptor. In particular embodiments, the recombinant receptor is an antigen binding receptor, e.g., a CAR, and the agent is an anti-idiotype antibody that specifically binds to the antigen binding receptor.

In some embodiments, the agents and/or ligands are attached to magnetic beads, such as paramagnetic beads (e.g., such as Dynalbeads or MACS beads). In certain embodiments, the beads may be removed from the cells by placing the cells in a magnetic field, thus removing and/or separating the beads from the cells, e.g., debeading the cells. In certain embodiments, the beads are removed immediately after an incubation to activate the cells. In some embodiments, the beads are removed prior to gene delivery, for example by transduction or transfection. In certain embodiments, the beads are removed during or immediately after the gene delivery. In particular embodiments, the beads are removed prior to or during an incubation to expanding the cells. In some embodiments, the beads are removed prior to harvesting and/or cryoprotecting the cells.

In some aspects, incubation is carried out in accordance with techniques such as those described in U.S. Pat. No. 6,040,177 to Riddell et al., Klebanoff et al. (2012) J Immunother. 35(9): 651-660, Terakura et al. (2012) Blood. 1:72-82, and/or Wang et al. (2012) J Immunother. 35(9):689-701.

In some embodiments, the T cells are expanded by adding to a culture-initiating composition feeder cells, such as non-dividing peripheral blood mononuclear cells (PBMC), (e.g., such that the resulting population of cells contains at least about 5, 10, 20, or 40 or more PBMC feeder cells for each T lymphocyte in the initial population to be expanded); and incubating the culture (e.g. for a time sufficient to expand the numbers of T cells). In some aspects, the non-dividing feeder cells can comprise gamma-irradiated PBMC feeder cells. In some embodiments, the PBMC are irradiated with gamma rays in the range of about 3000 to 3600 rads to prevent cell division. In some aspects, the feeder cells are added to culture medium prior to the addition of the populations of T cells.

In some embodiments, the stimulating conditions include temperature suitable for the growth of human T lymphocytes, for example, at least about 25 degrees Celsius, generally at least about 30 degrees, and generally at or about 37 degrees Celsius. Optionally, the incubation may further comprise adding non-dividing EBV-transformed lymphoblastoid cells (LCL) as feeder cells. LCL can be irradiated with gamma rays in the range of about 6000 to 10,000 rads. The LCL feeder cells in some aspects is provided in any suitable amount, such as a ratio of LCL feeder cells to initial T lymphocytes of at least about 10:1.

In embodiments, antigen-specific T cells, such as antigen-specific CD4+ and/or CD8+ T cells, are obtained by stimulating naïve or antigen specific T lymphocytes with antigen. For example, antigen-specific T cell lines or clones can be generated to cytomegalovirus antigens by isolating T cells from infected subjects and stimulating the cells in vitro with the same antigen.

C. Genetic Engineering

In some embodiments, the provided methods involve generating or producing a composition of engineered cells, e.g., a cell composition containing cells that express a recombinant antigen receptor. Various methods for the introduction of genetically engineered components, e.g., recombinant receptors, e.g., CARs or TCRs, are well known and may be used with the provided methods and compositions. Exemplary methods include those for transfer of nucleic acids encoding the receptors, including via viral, e.g., retroviral or lentiviral, transduction, transposons, and electroporation.

In certain embodiments, cells of the input cell composition are contacted with and/or introduced with one or more agents containing a nucleic acid, for example that encode a recombinant receptor such as a CAR. In some embodiments, the agent is a vector, e.g., a viral vector, a plasmid, or a transposon. In some embodiments, the cells are CD4+ T cells. In certain embodiments, the cells are CD8+ T cells. In particular embodiments, the introducing and/or contacting the cells with the nucleic acid results in engineered cells with a defined, desired, or fixed ratio of engineered CD4+ T cells to engineered CD8+ T cells. In some embodiments, the nucleic acids are heterologous, i.e., normally not present in a cell or sample obtained from the cell, such as one obtained from another organism or cell, which for example, is not ordinarily found in the cell being engineered and/or an organism from which such cell is derived. In some embodiments, the nucleic acids are not naturally occurring, such as a nucleic acid not found in nature, including one comprising chimeric combinations of nucleic acids encoding various domains from multiple different cell types.

In some embodiments, the preparation methods include steps for freezing, e.g., cryopreserving, the cells, either before, such as immediately before, during, or after, such as immediately after, any of the steps or stages for genetic engineering and/or producing an output cell composition that contains genetically engineered cells. In certain embodiments, the cells are cryofrozen before, during, or after the steps of isolating or selecting the cells, mixing or combining cells into an input cell composition, incubation, activation, gene transfer, transduction, transfection, expansion, and/or harvesting. In some embodiments, all or a portion of the cells are collected for freezing. In some embodiments, a portion of the cells are collecting before, during, or after a stage or step in the process of genetically engineering the cells for later or subsequent analysis, e.g., such as an analysis after a composition of the engineered cells has been administered to a subject.

In some embodiments, the freeze and subsequent thaw step removes granulocytes and, to some extent, monocytes in the cell population. In some embodiments, the cells are suspended in a freezing solution, e.g., following a washing step to remove plasma and platelets. Any of a variety of known freezing solutions and parameters in some aspects may be used. One example involves using PBS containing 20% DMSO and 8% human serum albumin (HSA), or other suitable cell freezing media. This is then diluted 1:1 with media so that the final concentration of DMSO and HSA are 10% and 4%, respectively. The cells are generally then frozen to $-80°$ C. at a rate of 1° per minute and stored in the vapor phase of a liquid nitrogen storage tank.

1. Vectors and Methods for Genetic Engineering

In some embodiments, recombinant nucleic acids are transferred into cells using recombinant infectious virus particles, such as, e.g., vectors derived from simian virus 40 (SV40), adenoviruses, adeno-associated virus (AAV). In some embodiments, recombinant nucleic acids are transferred into T cells using recombinant lentiviral vectors or retroviral vectors, such as gamma-retroviral vectors (see, e.g., Koste et al. (2014) Gene Therapy 2014 Apr. 3. doi: 10.1038/gt.2014.25; Carlens et al. (2000) Exp Hematol 28(10): 1137-46; Alonso-Camino et al. (2013) Mol Ther Nucl Acids 2, e93; Park et al., Trends Biotechnol. 2011 Nov. 29(11): 550-557. In some embodiments, the virus is adeno-associated virus (AAV).

In some embodiments, the retroviral vector has a long terminal repeat sequence (LTR), e.g., a retroviral vector derived from the Moloney murine leukemia virus (MoMLV), myeloproliferative sarcoma virus (MPSV), murine embryonic stem cell virus (MESV), murine stem cell virus (MSCV), spleen focus forming virus (SFFV). Most retroviral vectors are derived from murine retroviruses. In some embodiments, the retroviruses include those derived from any avian or mammalian cell source. The retroviruses typically are amphotropic, meaning that they are capable of infecting host cells of several species, including humans. In one embodiment, the gene to be expressed replaces the retroviral gag, pol and/or env sequences. A number of illustrative retroviral systems have been described (e.g., U.S. Pat. Nos. 5,219,740; 6,207,453; 5,219,740; Miller and Rosman (1989) BioTechniques 7:980-990; Miller, A. D. (1990) Human Gene Therapy 1:5-14; Scarpa et al. (1991) Virology 180:849-852; Burns et al. (1993) Proc. Natl. Acad. Sci. USA 90:8033-8037; and Boris-Lawrie and Temin (1993) Cur. Opin. Genet. Develop. 3:102-109.

Methods of lentiviral transduction are known. Exemplary methods are described in, e.g., Wang et al. (2012) J. Immunother. 35(9): 689-701; Cooper et al. (2003) Blood. 101: 1637-1644; Verhoeyen et al. (2009) Methods Mol Biol. 506: 97-114; and Cavalieri et al. (2003) Blood. 102(2): 497-505.

In some embodiments, the viral vector particles contain a genome derived from a retroviral genome based vector, such as derived from a lentiviral genome or a gammaretroviral based vector. In some aspects of the provided viral vectors, the heterologous nucleic acid encoding a recombinant receptor, such as an antigen receptor, such as a CAR, is contained and/or located between the 5' LTR and 3' LTR sequences of the vector genome.

In some embodiments, the viral vector genome is a lentivirus genome, such as an HIV-1 genome or an SIV genome. For example, lentiviral vectors have been generated by multiply attenuating virulence genes, for example, the genes env, vif; vpu and nef can be deleted, making the vector safer for therapeutic purposes. Lentiviral vectors are known. See Naldini et al., (1996 and 1998); Zufferey et al., (1997); Dull et al., 1998, U.S. Pat. Nos. 6,013,516; and 5,994,136). In some embodiments, these viral vectors are plasmid-based or virus-based, and are configured to carry the essential sequences for incorporating foreign nucleic acid, for selection, and for transfer of the nucleic acid into a host cell. Known lentiviruses can be readily obtained from depositories or collections such as the American Type Culture Collection ("ATCC"; 10801 University Blvd., Manassas, Va. 20110-2209), or isolated from known sources using commonly available techniques.

Non-limiting examples of lentiviral vectors include those derived from a lentivirus, such as Human Immunodeficiency Virus 1 (HIV-1), HIV-2, an Simian Immunodeficiency Virus (SIV), Human T-lymphotropic virus 1 (HTLV-1), HTLV-2 or equine infection anemia virus (E1AV). For example, lentiviral vectors have been generated by multiply attenuating the HIV virulence genes, for example, the genes env, vif; vpr, vpu and nef are deleted, making the vector safer for therapeutic purposes. Lentiviral vectors are known in the art, see Naldini et al., (1996 and 1998); Zufferey et al., (1997); Dull et al., 1998, U.S. Pat. Nos. 6,013,516; and 5,994,136). In some embodiments, these viral vectors are plasmid-based or virus-based, and are configured to carry the essential sequences for incorporating foreign nucleic acid, for selection, and for transfer of the nucleic acid into a host cell. Known lentiviruses can be readily obtained from depositories or collections such as the American Type Culture Collection ("ATCC"; 10801 University Blvd., Manassas, Va. 20110-2209), or isolated from known sources using commonly available techniques.

In some embodiments, the viral genome vector can contain sequences of the 5' and 3' LTRs of a retrovirus, such as a lentivirus. In some aspects, the viral genome construct may contain sequences from the 5' and 3' LTRs of a lentivirus, and in particular can contain the R and U5 sequences from the 5' LTR of a lentivirus and an inactivated or self-inactivating 3' LTR from a lentivirus. The LTR sequences can be LTR sequences from any lentivirus from any species. For example, they may be LTR sequences from HIV, SIV, FIV or BIV. Typically, the LTR sequences are HIV LTR sequences.

In some embodiments, the nucleic acid of a viral vector, such as an HIV viral vector, lacks additional transcriptional units. The vector genome can contain an inactivated or self-inactivating 3' LTR (Zufferey et al. J Virol 72: 9873, 1998; Miyoshi et al., J Virol 72:8150, 1998). For example, deletion in the U3 region of the 3' LTR of the nucleic acid used to produce the viral vector RNA can be used to generate self-inactivating (SIN) vectors. This deletion can then be transferred to the 5' LTR of the proviral DNA during reverse transcription. A self-inactivating vector generally has a deletion of the enhancer and promoter sequences from the 3' long terminal repeat (LTR), which is copied over into the 5' LTR during vector integration. In some embodiments enough sequence can be eliminated, including the removal of a TATA box, to abolish the transcriptional activity of the LTR. This can prevent production of full-length vector RNA in transduced cells. In some aspects, the U3 element of the 3' LTR contains a deletion of its enhancer sequence, the TATA box, Sp1, and NF-kappa B sites. As a result of the self-inactivating 3' LTR, the provirus that is generated following entry and reverse transcription contains an inactivated 5' LTR. This can improve safety by reducing the risk of mobilization of the vector genome and the influence of the LTR on nearby cellular promoters. The self-inactivating 3' LTR can be constructed by any method known in the art. In some embodiments, this does not affect vector titers or the in vitro or in vivo properties of the vector.

Optionally, the U3 sequence from the lentiviral 5' LTR can be replaced with a promoter sequence in the viral construct, such as a heterologous promoter sequence. This can increase the titer of virus recovered from the packaging cell line. An enhancer sequence can also be included. Any enhancer/promoter combination that increases expression of the viral RNA genome in the packaging cell line may be used. In one example, the CMV enhancer/promoter sequence is used (U.S. Pat. Nos. 5,385,839 and 5,168,062).

In certain embodiments, the risk of insertional mutagenesis can be minimized by constructing the retroviral vector genome, such as lentiviral vector genome, to be integration defective. A variety of approaches can be pursued to produce a non-integrating vector genome. In some embodiments, a mutation(s) can be engineered into the integrase enzyme component of the pol gene, such that it encodes a protein with an inactive integrase. In some embodiments, the vector genome itself can be modified to prevent integration by, for example, mutating or deleting one or both attachment sites, or making the 3' LTR-proximal polypurine tract (PPT) non-functional through deletion or modification. In some embodiments, non-genetic approaches are available; these include pharmacological agents that inhibit one or more functions of integrase. The approaches are not mutually exclusive; that is, more than one of them can be used at a time. For example, both the integrase and attachment sites can be non-functional, or the integrase and PPT site can be non-functional, or the attachment sites and PPT site can be non-functional, or all of them can be non-functional. Such methods and viral vector genomes are known and available (see Philpott and Thrasher, *Human Gene Therapy* 18:483, 2007; Engelman et al. J Virol 69:2729, 1995; Brown et al *J Virol* 73:9011 (1999); WO 2009/076524; McWilliams et al., *J Virol* 77:11150, 2003; Powell and Levin *J Virol* 70:5288, 1996).

In some embodiments, the provided methods involve methods of transducing cells by contacting, e.g., incubating, a cell composition comprising a plurality of cells with a viral particle. In some embodiments, the cells to be transfected or transduced are or comprise primary cells obtained from a subject, such as cells enriched and/or selected from a subject.

In some embodiments, the concentration of cells to be transduced of the composition is from or from about $1.0 \times 10^5$ cells/mL to $1.0 \times 10^8$ cells/mL, such as at least or about at least or about $1.0 \times 10^5$ cells/mL, $5 \times 10^5$ cells/mL, $1 \times 10^6$ cells/mL, $5 \times 10^6$ cells/mL, $1 \times 10^7$ cells/mL, $5 \times 10^7$ cells/mL or $1 \times 10^8$ cells/mL.

In some embodiments, the viral particles are provided at a certain ratio of copies of the viral vector particles or infectious units (IU) thereof, per total number of cells to be transduced (IU/cell). For example, in some embodiments, the viral particles are present during the contacting at or about or at least at or about 0.5, 1, 2, 3, 4, 5, 10, 15, 20, 30, 40, 50, or 60 IU of the viral vector particles per one of the cells.

In some embodiments, the titer of viral vector particles is between or between about $1 \times 10^6$ IU/mL and $1 \times 10^8$ IU/mL, such as between or between about $5 \times 10^6$ IU/mL and $5 \times 10^7$ IU/mL, such as at least $6 \times 10^6$ IU/mL, $7 \times 10^6$ IU/mL, $8 \times 10^6$ IU/mL, $9 \times 10^6$ IU/mL, $1 \times 10^7$ IU/mL, $2 \times 10^7$ IU/mL, $3 \times 10^7$ IU/mL, $4 \times 10^7$ IU/mL, or $5 \times 10^7$ IU/mL.

In some embodiments, transduction can be achieved at a multiplicity of infection (MOI) of less than 100, such as generally less than 60, 50, 40, 30, 20, 10, 5 or less.

In some embodiments, the method involves contacting or incubating, the cells with the viral particles. In some embodiments, the contacting is for 30 minutes to 72 hours, such as 30 minute to 48 hours, 30 minutes to 24 hours or 1 hour to 24 hours, such as at least or about at least 30 minutes, 1 hour, 2 hours, 6 hours, 12 hours, 24 hours, 36 hours or more.

In some embodiments, when the contacting can be effected with centrifugation, such as spinoculation (e.g., centrifugal inoculation). In some embodiments, the composition containing cells, viral particles and reagent can be rotated, generally at relatively low force or speed, such as speed lower than that used to pellet the cells, such as from or from about 600 rpm to 1700 rpm (e.g., at or about or at least 600 rpm, 1000 rpm, or 1500 rpm or 1700 rpm). In some embodiments, the rotation is carried at a force, e.g., a relative centrifugal force, of from or from about 100 g to 3200 g (e.g., at or about or at least at or about 100 g, 200 g, 300 g, 400 g, 500 g, 1000 g, 1500 g, 2000 g, 2500 g, 3000 g or 3200 g), as measured for example at an internal or external wall of the chamber or cavity. The term "relative centrifugal force" or RCF is generally understood to be the effective force imparted on an object or substance (such as a cell, sample, or pellet and/or a point in the chamber or other container being rotated), relative to the earth's gravitational force, at a particular point in space as compared to the axis of rotation. The value may be determined using well-known formulas, taking into account the gravitational force, rotation speed and the radius of rotation (distance from the axis of rotation and the object, substance, or particle at which RCF is being measured).

In certain embodiments, the input cells are treated, incubated, or contacted with particles that comprise binding molecules that bind to or recognize the recombinant receptor that is encoded by the viral DNA.

In some embodiments, recombinant nucleic acids are transferred into T cells via electroporation (see, e.g., Chicaybam et al, (2013) PLoS ONE 8(3): e60298 and Van Tedeloo et al. (2000) Gene Therapy 7(16): 1431-1437). In some embodiments, recombinant nucleic acids are transferred into T cells via transposition (see, e.g., Manuri et al. (2010) Hum Gene Ther 21(4): 427-437; Sharma et al. (2013) Molec Ther Nucl Acids 2, e74; and Huang et al. (2009) Methods Mol Biol 506: 115-126). Other methods of introducing and expressing genetic material in immune cells include calcium phosphate transfection (e.g., as described in Current Protocols in Molecular Biology, John Wiley & Sons, New York. N.Y.), protoplast fusion, cationic liposome-mediated transfection; tungsten particle-facilitated microparticle bombardment (Johnston, Nature, 346: 776-777 (1990)); and strontium phosphate DNA co-precipitation (Brash et al., Mol. Cell Biol., 7: 2031-2034 (1987)).

Other approaches and vectors for transfer of the nucleic acids encoding the recombinant products are those described, e.g., in international patent application, Publication No.: WO2014055668, and U.S. Pat. No. 7,446,190.

In some embodiments, recombinant nucleic acids are transferred into T cells via transposons. Examples of transposons suitable for use with mammalian cells, e.g., human primary leukocytes, include but are not limited to Sleeping Beauty and Piggybac. Transposon-based transfection is a two-component system consisting of a transposase and a transposon. In some embodiments, the system comprises a transposon is engineered to comprise a foreign DNA (also referred herein as cargo DNA), e.g., a gene encoding a recombinant receptor, that is flanked by inverted repeat/direct repeat (IR/DR) sequences that are recognized by an accompanying tranposase. In some embodiments, a non-viral plasmid encodes a transposase under the control of a promoter. In some embodiments, transfection of the plasmid into a host cell results in a transitory expression of the transposase at sufficiently levels to integrate the transposon into the genomic DNA.

Sleeping Beauty (SB) is a synthetic member of the Tc/1-mariner superfamily of transposons, reconstructed from dormant elements harbored in the salmonid fish genome. SB transposon-based transfection is a two-component system consisting of a transposase and a transposon containing inverted repeat/direct repeat (IR/DR) sequences that result in precise integration into a TA dinucleotide. The transposon is designed with an expression cassette of interest flanked by IR/DRs. The SB transposase binds specific binding sites that are located on the IR of the Sleeping beauty transposon. The SB transposase mediates integration of the transposon, a mobile element encoding a cargo sequence flanked on both sides by inverted terminal repeats that harbor binding sites for the catalytic enzyme (SB). Stable expression results when SB inserts gene sequences into vertebrate chromosomes at a TA target dinucleotide through a cut-and-paste mechanism. This system has been used to engineer a variety of vertebrate cell types, including primary human peripheral blood leukocytes. In some embodiments, the cells are contacted, incubated, and/or treated with an SB transposon comprising a cargo gene, e.g., a gene encoding a recombinant receptor or a CAR, flanked by SB IR sequences. In particular embodiments, the cells to be transfected are contacted, incubated, and/or treated with a plasmid comprising an SB transposon comprising a cargo gene, e.g., a gene encoding a CAR, flanked by SB IR sequences. In certain embodiments, the plasmid further comprises a gene encoding an SB transposase that is not flanked by SB IR sequences.

PiggyBac (PB) is another transposon system that can be used to integrate cargo DNA into a host's, e.g., a human's, genomic DNA. The PB transposase recognizes PB transposon-specific inverted terminal repeat sequences (LTRs) located on both ends of the transposon and efficiently moves the contents from the original sites and efficiently integrates them into TTAA chromosomal sites. The PB transposon system enables genes of interest between the two LTRs in the PB vector to be mobilized into target genomes. The PB system has been used to engineer a variety of vertebrate cell types, including primary human cells. In some embodiments, the cells to be transfected are contacted, incubated, and/or treated with an PB transposon comprising a cargo gene, e.g., a gene encoding a CAR, flanked by PB IR sequences. In particular embodiments, the cells to be transfected are contacted, incubated, and/or treated with a plasmid comprising a PB transposon comprising a cargo gene, e.g., a gene encoding a CAR, flanked by PB IR sequences. In certain embodiments, the plasmid further comprises a gene encoding an SB transposase that is not flanked by PB IR sequences.

In some embodiments, transduction with transposons is performed with a plasmid that comprises a transposase gene and a plasmid that comprises a transposon that contains a cargo DNA sequence that is flanked by inverted repeat/direct repeat (IR/DR) sequences that are recognized by the transposase. In certain embodiments, the cargo DNA sequence encodes a heterologous protein, e.g., a recombinant T cell receptor or a CAR. In some embodiments, the plasmid comprises transposase and the transposon. In some embodiments, the transposase is under control of a ubiquitous promoter, or any promoter suitable to drive expression of the transposase in the target cell. Ubiquitous promoters include, but are not limited to, EF1a, CMB, SV40, PGK1, Ubc, human β-actin, CAG, TRE, UAS, Ac5, CaMKIIa, and U6. In some embodiments, the cargo DNA comprises a selection cassette allowing for the selection of cells with stable integration of the cargo DNA into the genomic DNA. Suitable selection cassettes include, but are not limited to, selection cassettes encoding a kanamycin resistance gene, spectinomycin resistance gene, streptomycin resistance gene, ampicillin resistance gene, carbenicillin resistance gene, hygromycin resistance gene, bleomycin resistance gene, erythromycin resistance gene, and polymyxin B resistance gene.

In some embodiments, the components for transduction with a transposon, e.g., plasmids comprising an SB transposase and SB transposon, are introduced into the target cell. Any convenient protocol may be employed, where the protocol may provide for in vitro or in vivo introduction of the system components into the target cell, depending on the location of the target cell. For example, where the target cell is an isolated cell, the system may be introduced directly into the cell under cell culture conditions permissive of viability of the target cell, e.g., by using standard transformation techniques. Such techniques include, but are not necessarily limited to: viral infection, transformation, conjugation, protoplast fusion, electroporation, particle gun technology, calcium phosphate precipitation, direct microinjection, viral vector delivery, and the like. The choice of method is generally dependent on the type of cell being transformed and the circumstances under which the transformation is taking place (i.e. in vitro, ex vivo, or in vivo). A general discussion of these methods can be found in Ausubel, et al, Short Protocols in Molecular Biology, 3rd ed., Wiley & Sons, 1995.

In some embodiments, the SB transposon and the SB transposase source are introduced into a target cell of a multicellular organism, e.g., a mammal or a human, under conditions sufficient for excision of the inverted repeat flanked nucleic acid from the vector carrying the transposon and subsequent integration of the excised nucleic acid into the genome of the target cell. Some embodiments further comprise a step of ensuring that the requisite transposase activity is present in the target cell along with the introduced transposon. Depending on the structure of the transposon vector itself, i.e. whether or not the vector includes a region encoding a product having transposase activity, the method may further include introducing a second vector into the target cell which encodes the requisite transposase activity.

In some embodiments, the amount of vector nucleic acid comprising the transposon and the amount of vector nucleic acid encoding the transposase that is introduced into the cell is sufficient to provide for the desired excision and insertion of the transposon nucleic acid into the target cell genome. As such, the amount of vector nucleic acid introduced should provide for a sufficient amount of transposase activity and a sufficient copy number of the nucleic acid that is desired to be inserted into the target cell. The amount of vector nucleic acid that is introduced into the target cell varies depending on the efficiency of the particular introduction protocol that is employed, e.g., the particular ex vivo administration protocol that is employed.

Once the vector DNA has entered the target cell in combination with the requisite transposase, the nucleic acid region of the vector that is flanked by inverted repeats, i.e. the vector nucleic acid positioned between the Sleeping Beauty transposase recognized inverted repeats, is excised from the vector via the provided transposase and inserted into the genome of the targeted cell. As such, introduction of the vector DNA into the target cell is followed by subsequent transposase mediated excision and insertion of the exogenous nucleic acid carried by the vector into the genome of the targeted cell. In particular embodiments, the vector is integrated into the genomes of at least 1%, at least 2%, at least 3%, at least 4%, at least 5%, at least 6% at least 7% at least 8%, at least 9%, at least 10%, at least 15%, or at least 20% of the cells that are transfected with the SB transposon and/or SB transposase. In some embodiments, integration of the nucleic acid into the target cell genome is stable, i.e., the vector nucleic acid remains present in the target cell genome for more than a transient period of time and is passed on a part of the chromosomal genetic material to the progeny of the target cell.

In certain embodiments, the transposons are used to integrate nucleic acids, i.e. polynucleotides, of various sizes into the target cell genome. In some embodiments, the size of DNA that is inserted into a target cell genome using the subject methods ranges from about 0.1 kb to 200 kb, from about 0.5 kb to 100 kb, from about 1.0 kb to about 8.0 kb, from about 1.0 to about 200 kb, from about 1.0 to about 10 kb, from about 10 kb to about 50 kb, from about 50 kb to about 100 kb, or from about 100 kb to about 200 kb. In some embodiments, the size of DNA that is inserted into a target cell genome using the subject methods ranges from about 1.0 kb to about 8.0 kb. In some embodiments, the size of DNA that is inserted into a target cell genome using the subject methods ranges from about 1.0 to about 200 kb. In particular embodiments, the size of DNA that is inserted into a target cell genome using the subject methods ranges from about 1.0 kb to about 8.0 kb.

In some embodiments, the cells, e.g., T cells, may be transfected either during or after expansion e.g. with a T cell receptor (TCR) or a chimeric antigen receptor (CAR). This transfection for the introduction of the gene of the desired receptor can be carried out with any suitable retroviral vector, for example. The genetically modified cell population can then be liberated from the initial stimulus (the anti-CD3/anti-CD28 stimulus, for example) and subsequently be stimulated with a second type of stimulus e.g. via a de novo introduced receptor). This second type of stimulus may include an antigenic stimulus in form of a peptide/MHC molecule, the cognate (cross-linking) ligand of the genetically introduced receptor (e.g. natural ligand of a CAR) or any ligand (such as an antibody) that directly binds within the framework of the new receptor (e.g. by recognizing constant regions within the receptor). See, for example, Cheadle et al, "Chimeric antigen receptors for T-cell based therapy" Methods Mol Biol. 2012; 907:645-66 or Barrett et al., Chimeric Antigen Receptor Therapy for Cancer Annual Review of Medicine Vol. 65: 333-347 (2014).

In some cases, a vector may be used that does not require that the cells, e.g., T cells, are activated. In some such instances, the cells may be selected and/or transduced prior to activation. Thus, the cells may be engineered prior to, or subsequent to culturing of the cells, and in some cases at the same time as or during at least a portion of the culturing.

Among additional nucleic acids, e.g., genes for introduction are those to improve the efficacy of therapy, such as by promoting viability and/or function of transferred cells; genes to provide a genetic marker for selection and/or evaluation of the cells, such as to assess in vivo survival or localization; genes to improve safety, for example, by making the cell susceptible to negative selection in vivo as described by Lupton S. D. et al., *Mol. and Cell Biol.,* 11:6 (1991); and Riddell et al., *Human Gene Therapy* 3:319-338 (1992); see also the publications of PCT/US91/08442 and PCT/US94/05601 by Lupton et al. describing the use of bifunctional selectable fusion genes derived from fusing a dominant positive selectable marker with a negative selectable marker. See, e.g., Riddell et al., U.S. Pat. No. 6,040,177, at columns 14-17.

2. Recombinant Receptors

In some embodiments, the cells for use in or administered in connection with the provided methods contain or are engineered to contain an engineered receptor, e.g., an engineered antigen receptor, such as a chimeric antigen receptor (CAR), or a T cell receptor (TCR). Also provided are populations of such cells, compositions containing such cells and/or enriched for such cells, such as in which cells of a certain type such as T cells or CD8+ or CD4+ T cells are enriched or selected. Among the compositions are pharmaceutical compositions and formulations for administration, such as for adoptive cell therapy. Also provided are methods for administering the cells and compositions to subjects, e.g., patients, in accord with the provided methods, and/or with the provided articles of manufacture or compositions.

In some embodiments, the cells include one or more nucleic acids introduced via genetic engineering, and thereby express recombinant or genetically engineered products of such nucleic acids. In some embodiments, gene transfer is accomplished by first stimulating the cells, such as by combining it with a stimulus that induces a response such as proliferation, survival, and/or activation, e.g., as measured by expression of a cytokine or activation marker, followed by transduction of the activated cells, and expansion in culture to numbers sufficient for clinical applications.

The cells generally express recombinant receptors, such as antigen receptors including functional non-TCR antigen receptors, e.g., chimeric antigen receptors (CARs), and other antigen-binding receptors such as transgenic T cell receptors (TCRs). Also among the receptors are other chimeric receptors.

a. Chimeric Antigen Receptors (CARs)

In some embodiments of the provided methods and uses, chimeric receptors, such as a chimeric antigen receptors, contain one or more domains that combine a ligand-binding domain (e.g. antibody or antibody fragment) that provides specificity for a desired antigen (e.g., tumor antigen) with intracellular signaling domains. In some embodiments, the intracellular signaling domain is an activating intracellular domain portion, such as a T cell activating domain, providing a primary activation signal. In some embodiments, the intracellular signaling domain contains or additionally contains a costimulatory signaling domain to facilitate effector functions. In some embodiments, chimeric receptors when genetically engineered into immune cells can modulate T cell activity, and, in some cases, can modulate T cell differentiation or homeostasis, thereby resulting in genetically engineered cells with improved longevity, survival and/or persistence in vivo, such as for use in adoptive cell therapy methods.

In some embodiments, engineered cells, such as T cells, are provided that express a CAR with specificity for a particular antigen (or marker or ligand), such as an antigen expressed on the surface of a particular cell type. In some embodiments, the antigen is a polypeptide. In some embodiments, it is a carbohydrate or other molecule. In some embodiments, the antigen is selectively expressed or over-expressed on cells of the disease or condition, e.g., the tumor or pathogenic cells, as compared to normal or non-targeted cells or tissues. In other embodiments, the antigen is expressed on normal cells and/or is expressed on the engineered cells.

In particular embodiments, the recombinant receptor, such as chimeric receptor, contains an intracellular signaling region, which includes a cytoplasmic signaling domain (also interchangeably called an intracellular signaling domain), such as a cytoplasmic (intracellular) region capable of inducing a primary activation signal in a T cell, for example, a cytoplasmic signaling domain of a T cell receptor (TCR) component (e.g. a cytoplasmic signaling domain of a zeta chain of a CD3-zeta (CD3ζ) chain or a functional variant or signaling portion thereof) and/or that comprises an immunoreceptor tyrosine-based activation motif (ITAM).

In some embodiments, the chimeric receptor further contains an extracellular ligand-binding domain that specifically binds to a ligand (e.g. antigen) antigen. In some embodiments, the chimeric receptor is a CAR that contains an extracellular antigen-recognition domain that specifically binds to an antigen. In some embodiments, the ligand, such as an antigen, is a protein expressed on the surface of cells.

In some embodiments, the CAR is a TCR-like CAR and the antigen is a processed peptide antigen, such as a peptide antigen of an intracellular protein, which, like a TCR, is recognized on the cell surface in the context of a major histocompatibility complex (MHC) molecule.

Exemplary antigen receptors, including CARs, and methods for engineering and introducing such receptors into cells, include those described, for example, in international patent application publication numbers WO200014257, WO2013126726, WO2012/129514, WO2014031687, WO2013/166321, WO2013/071154, WO2013/123061 U.S. patent application publication numbers US2002131960, US2013287748, US20130149337, U.S. Pat. Nos. 6,451,995, 7,446,190, 8,252,592, 8,339,645, 8,398,282, 7,446,179, 6,410,319, 7,070,995, 7,265,209, 7,354,762, 7,446,191, 8,324,353, and 8,479,118, and European patent application number EP2537416, and/or those described by Sadelain et al., Cancer Discov. 2013 April; 3(4): 388-398; Davila et al. (2013) PLoS ONE 8(4): e61338; Turtle et al., Curr Opin. Immunol., 2012 October; 24(5): 633-39; Wu et al., Cancer, 2012 Mar. 18(2): 160-75. In some aspects, the antigen receptors include a CAR as described in U.S. Pat. No. 7,446,190, and those described in International Patent Application Publication No.: WO/2014055668 A1. Examples of the CARs include CARs as disclosed in any of the aforementioned publications, such as WO2014031687, U.S. Pat. Nos. 8,339,645, 7,446,179, US 2013/0149337, U.S. Pat. Nos. 7,446,190, 8,389,282, Kochenderfer et al., 2013, Nature Reviews Clinical Oncology, 10, 267-276 (2013); Wang et al. (2012) J. Immunother. 35(9): 689-701; and Brentjens et al., Sci Transl Med. 2013 5(177). See also WO2014031687, U.S. Pat. Nos. 8,339,645, 7,446,179, US 2013/0149337, U.S. Pat. Nos. 7,446,190, and 8,389,282.

In some embodiments, the CAR is constructed with a specificity for a particular antigen (or marker or ligand), such as an antigen expressed in a particular cell type to be targeted by adoptive therapy, e.g., a cancer marker, and/or an antigen intended to induce a dampening response, such as an antigen expressed on a normal or non-diseased cell type. Thus, the CAR typically includes in its extracellular portion one or more antigen binding molecules, such as one or more antigen-binding fragment, domain, or portion, or one or more antibody variable domains, and/or antibody molecules. In some embodiments, the CAR includes an antigen-binding portion or portions of an antibody molecule, such as a single-chain antibody fragment (scFv) derived from the variable heavy (VH) and variable light (VL) chains of a monoclonal antibody (mAb).

In some embodiments, the antibody or antigen-binding portion thereof is expressed on cells as part of a recombinant receptor, such as an antigen receptor. Among the antigen receptors are functional non-TCR antigen receptors, such as chimeric antigen receptors (CARs). Generally, a CAR containing an antibody or antigen-binding fragment that exhibits TCR-like specificity directed against peptide-MHC complexes also may be referred to as a TCR-like CAR. In some embodiments, the extracellular antigen binding domain specific for an MHC-peptide complex of a TCR-like CAR is linked to one or more intracellular signaling components, in some aspects via linkers and/or transmembrane domain(s). In some embodiments, such molecules can typically mimic or approximate a signal through a natural antigen receptor, such as a TCR, and, optionally, a signal through such a receptor in combination with a costimulatory receptor.

In some embodiments, the recombinant receptor, such as a chimeric receptor (e.g. CAR), includes a ligand-binding domain that binds, such as specifically binds, to an antigen (or a ligand). Among the antigens targeted by the chimeric receptors are those expressed in the context of a disease, condition, or cell type to be targeted via the adoptive cell therapy. Among the diseases and conditions are proliferative, neoplastic, and malignant diseases and disorders, including cancers and tumors, including hematologic cancers, cancers of the immune system, such as lymphomas, leukemias, and/or myelomas, such as B, T, and myeloid leukemias, lymphomas, and multiple myelomas.

In some embodiments, the antigen (or a ligand) is a polypeptide. In some embodiments, it is a carbohydrate or other molecule. In some embodiments, the antigen (or a ligand) is selectively expressed or overexpressed on cells of the disease or condition, e.g., the tumor or pathogenic cells, as compared to normal or non-targeted cells or tissues. In other embodiments, the antigen is expressed on normal cells and/or is expressed on the engineered cells.

In some embodiments, the CAR contains an antibody or an antigen-binding fragment (e.g. scFv) that specifically recognizes an antigen, such as an intact antigen, expressed on the surface of a cell.

In some embodiments, the antigen (or a ligand) is a tumor antigen or cancer marker. In some embodiments, the antigen (or a ligand) is or includes orphan tyrosine kinase receptor (ROR1), B cell maturation antigen (BCMA), carbonic anhydrase 9 (CA9, also known as CAIX or G250), Her2/neu (receptor tyrosine kinase erbB2), CD19, CD20, CD22, mesothelin (MSLN), carcinoembryonic antigen (CEA), and hepatitis B surface antigen, anti-folate receptor, CD23, CD24, CD30, CD33, CD38, CD44, chondroitin sulfate proteoglycan 4 (CSPG4), EGFR, epithelial glycoprotein 2 (EPG-2), epithelial glycoprotein 40 (EPG-40), ephrin receptor A2 (EPHa2), Her3 (erb-B3), Her4 (erb-B4), erbB dimers, type III epidermal growth factor receptor mutation (EGFR vIII), folate binding protein (FBP), Fc receptor like 5 (FCRL5, also known as Fc receptor homolog 5 or FCRH5), fetal acetylcholine receptor (fetal AchR), ganglioside GD2, ganglioside GD3, Human leukocyte antigen A1 (HLA-A1), Human leukocyte antigen A2 (HLA-A2), IL-22 receptor alpha (IL-22Rα), kinase insert domain receptor (kdr), kappa light chain, Leucine Rich Repeat Containing 8 Family Member A (LRRC8A), Lewis Y, L1-cell adhesion molecule (L1-CAM), Melanoma-associated antigen (MAGE)-A1, MAGE-A3, MAGE-A6, MAGE-A10, Preferentially expressed antigen of melanoma (PRAME), survivin, tumor-associated glycoprotein 72 (TAG72), B7-H3, B7-H6, IL-13 receptor alpha 2 (IL-13Rα2), Human high molecular weight-melanoma-associated antigen (HMW-MAA), CD171, folate receptor-alpha, CD44v7/8, avf3.6 integrin (avb6 integrin), 8H9, neural cell adhesion molecule (NCAM), vascular endothelial growth factor receptor (VEGF receptors or VEGFR), Trophoblast glycoprotein (TPBG also known as 5T4), NKG2D ligands, CD44v6, dual antigen, a cancer-testes antigen, murine cytomegalovirus (CMV), mucin 1 (MUC1), MUC16, prostate stem cell antigen (PSCA), prostate specific membrane antigen (PSMA), natural killer group 2 member D (NKG2D) ligands, cancer/testis antigen 1B (CTAG, also known as NY-ESO-1 and LAGE-2), melan A (MART-1), glycoprotein 100 (gp100), glypican-3 (GPC3), G Protein Coupled Receptor 5D (GPRCSD), oncofetal antigen, TAG72, Tyrosinase related protein 1 (TRP1, also known as TYRP1 or gp75), Tyrosinase related protein 2 (TRP2, also known as dopachrome tautomerase, dopachrome delta-isomerase or DCT), vascular endothelial growth factor receptor 2 (VEGF-R2), carcinoembryonic antigen (CEA), estrogen receptor, progesterone receptor, a prostate specific antigen, ephrinB2, CD123, CD133, c-Met, O-acetylated GD2 (OGD2), CE7 epitope of L1-CAM, Wilms Tumor 1 (WT-1), a cyclin, cyclin A2, C—C Motif Chemokine Ligand 1 (CCL-1), CD138, a pathogen-specific antigen or pathogen-expressed antigen, and an antigen associated with a universal tag, and/or biotinylated molecules, and/or molecules expressed by HIV, HCV, HBV or other pathogens. Antigens targeted by the receptors in some embodiments include antigens associated with a B cell malignancy, such as any of a number of known B cell marker. In some embodiments, the antigen targeted by the receptor is CD20, CD19, CD22, ROR1, CD45, CD21, CD5, CD33, Igkappa, Iglambda, CD79a, CD79b or CD30.

In some embodiments, the antigen is a pathogen-specific antigen. In some embodiments, the antigen is a viral antigen (such as a viral antigen from HIV, HCV, HBV, etc.), bacterial antigens, and/or parasitic antigens.

In some embodiments, the antigen or antigen binding domain is CD19. In some embodiments, the scFv contains a VH and a VL derived from an antibody or an antibody fragment specific to CD19. In some embodiments, the antibody or antibody fragment that binds CD19 is a mouse derived antibody such as FMC63 and SJ25C1. In some embodiments, the antibody or antibody fragment is a human antibody, e.g., as described in U.S. Patent Publication No. US 2016/0152723.

In some embodiments, the scFv is derived from FMC63. FMC63 generally refers to a mouse monoclonal IgG1 antibody raised against Nalm-1 and -16 cells expressing CD19 of human origin (Ling, N. R., et al. (1987). *Leucocyte typing III*. 302). The FMC63 antibody comprises CDRH1 and H2 set forth in SEQ ID NOS: 38, 39 respectively, and CDRH3 set forth in SEQ ID NOS: 40 or 54 and CDRL1 set forth in SEQ ID NOS: 35 and CDR L2 36 or 55 and CDR L3 sequences 37 or 34. The FMC63 antibody comprises the heavy chain variable region ($V_H$) comprising the amino acid sequence of SEQ ID NO: 41 and the light chain variable region ($V_L$) comprising the amino acid sequence of SEQ ID NO: 42. In some embodiments, the svFv comprises a variable light chain containing the CDRL1 sequence of SEQ ID NO:35, a CDRL2 sequence of SEQ ID NO:36, and a CDRL3 sequence of SEQ ID NO:37 and/or a variable heavy chain containing a CDRH1 sequence of SEQ ID NO:38, a CDRH2 sequence of SEQ ID NO:39, and a CDRH3 sequence of SEQ ID NO:40. In some embodiments, the scFv comprises a variable heavy chain region of FMC63 set forth in SEQ ID NO:41 and a variable light chain region of FMC63 set forth in SEQ ID NO:42. In some embodiments, the variable heavy and variable light chain are connected by a linker. In some embodiments, the linker is set forth in SEQ ID NO:56. In some embodiments, the scFv comprises, in order, a $V_H$, a linker, and a $V_L$. In some embodiments, the scFv comprises, in order, a $V_L$, a linker, and a $V_H$. In some embodiments, the svFc is encoded by a sequence of nucleotides set forth in SEQ ID NO:57 or a sequence that exhibits at least 85%, 86%, 87%, 88%, 89%, 90%, 91%, 92%, 93%, 94%, 95%, 96%, 97%, 98%, or 99% sequence identity to SEQ ID NO:57. In some embodiments, the scFv comprises the sequence of amino acids set forth in SEQ ID NO:43 or a sequence that exhibits at least 85%, 86%, 87%, 88%, 89%, 90%, 91%, 92%, 93%, 94%, 95%, 96%, 97%, 98%, or 99% sequence identity to SEQ ID NO:43.

In some embodiments the scFv is derived from SJ25C1. SJ25C1 is a mouse monoclonal IgG1 antibody raised against Nalm-1 and -16 cells expressing CD19 of human origin (Ling, N. R., et al. (1987). *Leucocyte typing III*. 302). The SJ25C1 antibody comprises CDRH1, H2 and H3 set forth in SEQ ID NOS: 47-49, respectively, and CDRL1, L2 and L3 sequences set forth in SEQ ID NOS: 44-46, respectively. The SJ25C1 antibody comprises the heavy chain variable region ($V_H$) comprising the amino acid sequence of SEQ ID NO: 50 and the light chain variable region ($V_L$) comprising the amino acid sequence of SEQ ID NO: 51. In some embodiments, the svFv comprises a variable light chain containing the CDRL1 sequence of SEQ ID NO:44, a CDRL2 sequence of SEQ ID NO: 45, and a CDRL3 sequence of SEQ ID NO:46 and/or a variable heavy chain containing a CDRH1 sequence of SEQ ID NO:47, a CDRH2 sequence of SEQ ID NO:48, and a CDRH3 sequence of SEQ ID NO:49. In some embodiments, the scFv comprises a variable heavy chain region of SJ25C1 set forth in SEQ ID NO:50 and a variable light chain region of SJ25C1 set forth in SEQ ID NO:51. In some embodiments, the variable heavy and variable light chain are connected by a linker. In some embodiments, the linker is set forth in SEQ ID NO:52. In some embodiments, the scFv comprises, in order, a $V_H$, a linker, and a $V_L$. In some embodiments, the scFv comprises, in order, a $V_L$, a linker, and a $V_H$. In some embodiments, the scFv comprises the sequence of amino acids set forth in SEQ ID NO:53 or a sequence that exhibits at least 85%, 86%, 87%, 88%, 89%, 90%, 91%, 92%, 93%, 94%, 95%, 96%, 97%, 98%, or 99% sequence identity to SEQ ID NO:53.

In some embodiments, the antigen or antigen binding domain is BCMA. In some embodiments, the scFv contains a VH and a VL derived from an antibody or an antibody fragment specific for BCMA. In some embodiments, the antibody or antibody fragment that binds BCMA is or contains a VH and a VL from an antibody or antibody fragment set forth in International Patent Applications, Publication Number WO 2016/090327 and WO 2016/090320.

In some embodiments, the antigen or antigen binding domain is GPRCSD. In some embodiments, the scFv contains a VH and a VL derived from an antibody or an antibody fragment specific for GPRCSD. In some embodiments, the antibody or antibody fragment that binds GPRCSD is or contains a VH and a VL from an antibody or antibody fragment set forth in International Patent Applications, Publication Number WO 2016/090329 and WO 2016/090312.

In some embodiments, the CAR contains a TCR-like antibody, such as an antibody or an antigen-binding fragment (e.g. scFv) that specifically recognizes an intracellular antigen, such as a tumor-associated antigen, presented on the cell surface as a MHC-peptide complex. In some embodiments, an antibody or antigen-binding portion thereof that recognizes an MHC-peptide complex can be expressed on cells as part of a recombinant receptor, such as an antigen receptor. Among the antigen receptors are functional non-TCR antigen receptors, such as chimeric antigen receptors (CARs). Generally, a CAR containing an antibody or antigen-binding fragment that exhibits TCR-like specificity directed against peptide-MHC complexes also may be referred to as a TCR-like CAR.

Reference to "Major histocompatibility complex" (MHC) refers to a protein, generally a glycoprotein, that contains a polymorphic peptide binding site or binding groove that can, in some cases, complex with peptide antigens of polypeptides, including peptide antigens processed by the cell machinery. In some cases, MHC molecules can be displayed or expressed on the cell surface, including as a complex with peptide, i.e. MHC-peptide complex, for presentation of an antigen in a conformation recognizable by an antigen receptor on T cells, such as a TCRs or TCR-like antibody. Generally, MHC class I molecules are heterodimers having a membrane spanning α chain, in some cases with three a domains, and a non-covalently associated (β2 microglobulin. Generally, WIC class II molecules are composed of two transmembrane glycoproteins, α and β, both of which typically span the membrane. An WIC molecule can include an effective portion of an MHC that contains an antigen binding site or sites for binding a peptide and the sequences necessary for recognition by the appropriate antigen receptor. In some embodiments, MHC class I molecules deliver peptides originating in the cytosol to the cell surface, where a MHC-peptide complex is recognized by T cells, such as generally CD8+ T cells, but in some cases CD4+ T cells. In some embodiments, MHC class II molecules deliver peptides originating in the vesicular system to the cell surface, where they are typically recognized by CD4+ T cells. Generally, MHC molecules are encoded by a group of linked loci, which are collectively termed H-2 in the mouse and human leukocyte antigen (HLA) in humans. Hence, typically human MHC can also be referred to as human leukocyte antigen (HLA).

The term "MHC-peptide complex" or "peptide-WIC complex" or variations thereof, refers to a complex or association of a peptide antigen and an MHC molecule, such as, generally, by non-covalent interactions of the peptide in the binding groove or cleft of the MHC molecule. In some embodiments, the MHC-peptide complex is present or displayed on the surface of cells. In some embodiments, the MHC-peptide complex can be specifically recognized by an antigen receptor, such as a TCR, TCR-like CAR or antigen-binding portions thereof.

In some embodiments, a peptide, such as a peptide antigen or epitope, of a polypeptide can associate with an MHC molecule, such as for recognition by an antigen receptor. Generally, the peptide is derived from or based on a fragment of a longer biological molecule, such as a polypeptide or protein. In some embodiments, the peptide typically is about 8 to about 24 amino acids in length. In some embodiments, a peptide has a length of from or from about 9 to 22 amino acids for recognition in the MHC Class II complex. In some embodiments, a peptide has a length of from or from about 8 to 13 amino acids for recognition in the MHC Class I complex. In some embodiments, upon recognition of the peptide in the context of an MHC molecule, such as MHC-peptide complex, the antigen receptor, such as TCR or TCR-like CAR, produces or triggers an activation signal to the T cell that induces a T cell response, such as T cell proliferation, cytokine production, a cytotoxic T cell response or other response.

In some embodiments, a TCR-like antibody or antigen-binding portion, are known or can be produced by methods that are known (see e.g. US Published Application Nos. US 2002/0150914; US 2003/0223994; US 2004/0191260; US 2006/0034850; US 2007/00992530; US20090226474; US20090304679; and International PCT Publication No. WO 03/068201).

In some embodiments, an antibody or antigen-binding portion thereof that specifically binds to a MHC-peptide complex, can be produced by immunizing a host with an effective amount of an immunogen containing a specific MHC-peptide complex. In some cases, the peptide of the MHC-peptide complex is an epitope of antigen capable of binding to the MHC, such as a tumor antigen, for example a universal tumor antigen, myeloma antigen or other antigen as described below. In some embodiments, an effective amount of the immunogen is then administered to a host for eliciting an immune response, wherein the immunogen retains a three-dimensional form thereof for a period of time sufficient to elicit an immune response against the three-dimensional presentation of the peptide in the binding groove of the MHC molecule. Serum collected from the host is then assayed to determine if desired antibodies that recognize a three-dimensional presentation of the peptide in the binding groove of the MHC molecule is being produced. In some embodiments, the produced antibodies can be assessed to confirm that the antibody can differentiate the MHC-peptide complex from the MHC molecule alone, the peptide of interest alone, and a complex of MHC and irrelevant peptide. The desired antibodies can then be isolated.

In some embodiments, an antibody or antigen-binding portion thereof that specifically binds to an MHC-peptide complex can be produced by employing antibody library display methods, such as phage antibody libraries. In some embodiments, phage display libraries of mutant Fab, scFv or other antibody forms can be generated, for example, in which members of the library are mutated at one or more residues of a CDR or CDRs. See e.g. US published application No. US20020150914, US2014/0294841; and Cohen CJ. et al. (2003) *J Mol. Recogn.* 16:324-332.

The term "antibody" herein is used in the broadest sense and includes polyclonal and monoclonal antibodies, including intact antibodies and functional (antigen-binding) antibody fragments, including fragment antigen binding (Fab) fragments, F(ab')2 fragments, Fab' fragments, Fv fragments, recombinant IgG (rIgG) fragments, variable heavy chain ($V_H$) regions capable of specifically binding the antigen, single chain antibody fragments, including single chain variable fragments (scFv), and single domain antibodies (e.g., sdAb, sdFv, nanobody) fragments. The term encompasses genetically engineered and/or otherwise modified forms of immunoglobulins, such as intrabodies, peptibodies, chimeric antibodies, fully human antibodies, humanized antibodies, and heteroconjugate antibodies, multispecific, e.g., bispecific, antibodies, diabodies, triabodies, and tetrabodies, tandem di-scFv, tandem tri-scFv. Unless otherwise stated, the term "antibody" should be understood to encompass functional antibody fragments thereof. The term also encompasses intact or full-length antibodies, including antibodies of any class or sub-class, including IgG and subclasses thereof, IgM, IgE, IgA, and IgD.

In some embodiments, the antigen-binding proteins, antibodies and antigen binding fragments thereof specifically recognize an antigen of a full-length antibody. In some embodiments, the heavy and light chains of an antibody can be full-length or can be an antigen-binding portion (a Fab, F(ab')2, Fv or a single chain Fv fragment (scFv)). In other embodiments, the antibody heavy chain constant region is chosen from, e.g., IgG1, IgG2, IgG3, IgG4, IgM, IgA1, IgA2, IgD, and IgE, particularly chosen from, e.g., IgG1, IgG2, IgG3, and IgG4, more particularly, IgG1 (e.g., human IgG1). In another embodiment, the antibody light chain constant region is chosen from, e.g., kappa or lambda, particularly kappa.

Among the provided antibodies are antibody fragments. An "antibody fragment" refers to a molecule other than an intact antibody that comprises a portion of an intact antibody that binds the antigen to which the intact antibody binds. Examples of antibody fragments include but are not limited to Fv, Fab, Fab', Fab'-SH, F(ab')$_2$; diabodies; linear antibodies; variable heavy chain ($V_H$) regions, single-chain antibody molecules such as scFvs and single-domain $V_H$ single antibodies; and multispecific antibodies formed from antibody fragments. In particular embodiments, the antibodies are single-chain antibody fragments comprising a variable heavy chain region and/or a variable light chain region, such as scFvs.

The term "variable region" or "variable domain" refers to the domain of an antibody heavy or light chain that is involved in binding the antibody to antigen. The variable domains of the heavy chain and light chain ($V_H$ and $V_L$, respectively) of a native antibody generally have similar structures, with each domain comprising four conserved framework regions (FRs) and three CDRs. (See, e.g., Kindt et al. Kuby Immunology, 6th ed., W.H. Freeman and Co., page 91 (2007). A single $V_H$ or $V_L$ domain may be sufficient to confer antigen-binding specificity. Furthermore, antibodies that bind a particular antigen may be isolated using a $V_H$ or $V_L$ domain from an antibody that binds the antigen to screen a library of complementary $V_L$ or $V_H$ domains, respectively. See, e.g., Portolano et al., J. Immunol. 150: 880-887 (1993); Clarkson et al., Nature 352:624-628 (1991).

Single-domain antibodies are antibody fragments comprising all or a portion of the heavy chain variable domain or all or a portion of the light chain variable domain of an antibody. In certain embodiments, a single-domain antibody is a human single-domain antibody. In some embodiments, the CAR comprises an antibody heavy chain domain that specifically binds the antigen, such as a cancer marker or cell surface antigen of a cell or disease to be targeted, such as a tumor cell or a cancer cell, such as any of the target antigens described herein or known in the art.

Antibody fragments can be made by various techniques, including but not limited to proteolytic digestion of an intact antibody as well as production by recombinant host cells. In some embodiments, the antibodies are recombinantly-produced fragments, such as fragments comprising arrangements that do not occur naturally, such as those with two or more antibody regions or chains joined by synthetic linkers, e.g., peptide linkers, and/or that are may not be produced by enzyme digestion of a naturally-occurring intact antibody. In some embodiments, the antibody fragments are scFvs.

A "humanized" antibody is an antibody in which all or substantially all CDR amino acid residues are derived from non-human CDRs and all or substantially all FR amino acid residues are derived from human FRs. A humanized antibody optionally may include at least a portion of an antibody constant region derived from a human antibody. A "humanized form" of a non-human antibody, refers to a variant of the non-human antibody that has undergone humanization, typically to reduce immunogenicity to humans, while retaining the specificity and affinity of the parental non-human antibody. In some embodiments, some FR residues in a humanized antibody are substituted with corresponding residues from a non-human antibody (e.g., the antibody from which the CDR residues are derived), e.g., to restore or improve antibody specificity or affinity.

Thus, in some embodiments, the chimeric antigen receptor, including TCR-like CARs, includes an extracellular portion containing an antibody or antibody fragment. In some embodiments, the antibody or fragment includes an scFv. In some aspects, the chimeric antigen receptor includes an extracellular portion containing the antibody or fragment and an intracellular signaling region. In some embodiments, the intracellular signaling region comprises an intracellular signaling domain. In some embodiments, the intracellular signaling domain is or comprises a primary signaling domain, a signaling domain that is capable of inducing a primary activation signal in a T cell, a signaling domain of a T cell receptor (TCR) component, and/or a signaling domain comprising an immunoreceptor tyrosine-based activation motif (ITAM).

In some embodiments, the recombinant receptor such as the CAR, such as the antibody portion thereof, further includes a spacer, which may be or include at least a portion of an immunoglobulin constant region or variant or modified version thereof, such as a hinge region, e.g., an IgG4 hinge region, and/or a $C_H1/C_L$ and/or Fc region. In some embodiments, the recombinant receptor further comprises a spacer and/or a hinge region. In some embodiments, the constant region or portion is of a human IgG, such as IgG4 or IgG1. In some aspects, the portion of the constant region serves as a spacer region between the antigen-recognition component, e.g., scFv, and transmembrane domain. The spacer can be of a length that provides for increased responsiveness of the cell following antigen binding, as compared to in the absence of the spacer. In some examples, the spacer is at or about 12 amino acids in length or is no more than 12 amino acids in length. Exemplary spacers include those having at least about 10 to 229 amino acids, about 10 to 200 amino acids, about 10 to 175 amino acids, about 10 to 150 amino acids, about 10 to 125 amino acids, about 10 to 100 amino acids, about 10 to 75 amino acids, about 10 to 50 amino acids, about 10 to 40 amino acids, about 10 to 30 amino acids, about 10 to 20 amino acids, or about 10 to 15 amino acids, and including any integer between the endpoints of any of the listed ranges. In some embodiments, a spacer region has about 12 amino acids or less, about 119 amino acids or less, or about 229 amino acids or less. Exemplary spacers include IgG4 hinge alone, IgG4 hinge linked to CH2 and CH3 domains, or IgG4 hinge linked to the CH3 domain. Exemplary spacers include, but are not limited to, those described in Hudecek et al. (2013) *Clin. Cancer Res.,* 19:3153 or international patent application publication number WO2014031687. In some embodiments, the spacer has the sequence set forth in SEQ ID NO: 1, and is encoded by the sequence set forth in SEQ ID NO: 2. In some embodiments, the spacer has the sequence set forth in SEQ ID NO: 3. In some embodiments, the spacer has the sequence set forth in SEQ ID NO: 4.

In some embodiments, the constant region or portion is of IgD. In some embodiments, the spacer has the sequence set forth in SEQ ID NO: 5. In some embodiments, the spacer has a sequence of amino acids that exhibits at least 85%, 86%, 87%, 88%, 89%, 90%, 91%, 92%, 93%, 94%, 95%, 96%, 97%, 98%, 99% or more sequence identity to any of SEQ ID NOS: 1, 3, 4 and 5. In some embodiments, the spacer has the sequence set forth in SEQ ID NOS: 23-31. In some embodiments, the spacer has a sequence of amino acids that exhibits at least 85%, 86%, 87%, 88%, 89%, 90%, 91%, 92%, 93%, 94%, 95%, 96%, 97%, 98%, 99% or more sequence identity to any of SEQ ID NOS: 23-31.

In some embodiments, the antigen receptor comprises an intracellular domain linked directly or indirectly to the extracellular domain. In some embodiments, the chimeric antigen receptor includes a transmembrane domain linking the extracellular domain and the intracellular signaling domain. In some embodiments, the intracellular signaling domain comprises an ITAM. For example, in some aspects, the antigen recognition domain (e.g. extracellular domain) is linked to one or more intracellular signaling components, such as signaling components that mimic activation through an antigen receptor complex, such as a TCR complex, in the case of a CAR, and/or signal via another cell surface receptor domains. In some embodiments, the chimeric receptor comprises a transmembrane domain linked or fused between the extracellular domain (e.g. scFv) and intracellular signaling domain. Thus, in some embodiments, the antigen binding component (e.g., antibody) is linked to one or more transmembrane and intracellular signaling regions. In some embodiments, the transmembrane domain is fused to the extracellular domain. In one embodiment, a transmembrane domain that naturally is associated with one of the domains in the receptor, e.g., CAR, is used. In some instances, the transmembrane domain is selected or modified by amino acid substitution to avoid binding of such domains to the transmembrane domains of the same or different surface membrane proteins to minimize interactions with other members of the receptor complex.

The transmembrane domain in some embodiments is derived either from a natural or from a synthetic source. Where the source is natural, the domain in some aspects is derived from any membrane-bound or transmembrane protein. Transmembrane regions include those derived from (i.e. comprise at least the transmembrane region(s) of) the alpha, beta or zeta chain of the T-cell receptor, CD28, CD3 epsilon, CD45, CD4, CD5, CD8, CD9, CD 16, CD22, CD33, CD37, CD64, CD80, CD86, CD 134, CD137, CD154. Alternatively the transmembrane domain in some embodiments is synthetic. In some aspects, the synthetic transmembrane domain comprises predominantly hydrophobic residues such as leucine and valine. In some aspects, a triplet of phenylalanine, tryptophan and valine will be found at each end of a synthetic transmembrane domain. In some embodiments, the linkage is by linkers, spacers, and/or transmembrane domain(s). In some aspects, the transmembrane domain contains a transmembrane portion of CD28.

In some embodiments, the extracellular domain and transmembrane domain can be linked directly or indirectly. In some embodiments, the extracellular domain and transmembrane are linked by a spacer, such as any described herein. In some embodiments, the receptor contains extracellular portion of the molecule from which the transmembrane domain is derived, such as a CD28 extracellular portion Among the intracellular signaling domains are those that mimic or approximate a signal through a natural antigen receptor, a signal through such a receptor in combination with a costimulatory receptor, and/or a signal through a costimulatory receptor alone. In some embodiments, a short oligo- or polypeptide linker, for example, a linker of between 2 and 10 amino acids in length, such as one containing glycines and serines, e.g., glycine-serine doublet, is present and forms a linkage between the transmembrane domain and the cytoplasmic signaling domain of the CAR.

The receptor, e.g., the CAR, generally includes at least one intracellular signaling component or components. In some embodiments, the receptor includes an intracellular component of a TCR complex, such as a TCR CD3 chain that mediates T-cell activation and cytotoxicity, e.g., CD3 zeta chain. Thus, in some aspects, the ROR1-binding antibody is linked to one or more cell signaling modules. In some embodiments, cell signaling modules include CD3 transmembrane domain, CD3 intracellular signaling domains, and/or other CD transmembrane domains. In some embodiments, the receptor, e.g., CAR, further includes a portion of one or more additional molecules such as Fc receptor γ, CD8, CD4, CD25, or CD16. For example, in some aspects, the CAR includes a chimeric molecule between CD3-zeta (CD3ζ) or Fc receptor γ and CD8, CD4, CD25 or CD16.

In some embodiments, upon ligation of the CAR, the cytoplasmic domain or intracellular signaling domain of the receptor activates at least one of the normal effector functions or responses of the immune cell, e.g., T cell engineered to express the CAR. For example, in some contexts, the CAR induces a function of a T cell such as cytolytic activity or T-helper activity, such as secretion of cytokines or other factors. In some embodiments, a truncated portion of an intracellular signaling region of an antigen receptor component or costimulatory molecule is used in place of an intact immunostimulatory chain, for example, if it transduces the effector function signal. In some embodiments, the intracellular signaling domain or domains, include the cytoplasmic sequences of the T cell receptor (TCR), and in some aspects also those of co-receptors that in the natural context act in concert with such receptor to initiate signal transduction following antigen receptor engagement, and/or any derivative or variant of such molecules, and/or any synthetic sequence that has the same functional capability.

In the context of a natural TCR, full activation generally requires not only signaling through the TCR, but also a costimulatory signal. Thus, in some embodiments, to promote full activation, a component for generating secondary or co-stimulatory signal is also included in the CAR. In other embodiments, the CAR does not include a component for generating a costimulatory signal. In some aspects, an additional CAR is expressed in the same cell and provides the component for generating the secondary or costimulatory signal.

T cell activation is in some aspects described as being mediated by two classes of cytoplasmic signaling sequences: those that initiate antigen-dependent primary activation through the TCR (primary cytoplasmic signaling sequences), and those that act in an antigen-independent manner to provide a secondary or co-stimulatory signal (secondary cytoplasmic signaling sequences). In some aspects, the CAR includes one or both of such signaling components.

In some aspects, the CAR includes a primary cytoplasmic signaling sequence that regulates primary activation of the TCR complex. Primary cytoplasmic signaling sequences that act in a stimulatory manner may contain signaling motifs which are known as immunoreceptor tyrosine-based activation motifs or ITAMs. Examples of ITAM containing primary cytoplasmic signaling sequences include those derived from TCR or CD3 zeta, FcR gamma or FcR beta. In some embodiments, cytoplasmic signaling molecule(s) in the CAR contain(s) a cytoplasmic signaling domain, portion thereof, or sequence derived from CD3 zeta.

In some embodiments, the CAR includes a signaling region and/or transmembrane portion of a costimulatory receptor, such as CD28, 4-1BB, OX40, DAP10, and ICOS. In some aspects, the same CAR includes both the signaling region and costimulatory components. In some embodiments, the chimeric antigen receptor contains an intracellular domain derived from a T cell costimulatory molecule or a functional variant thereof, such as between the transmembrane domain and intracellular signaling domain. In some aspects, the T cell costimulatory molecule is CD28 or 41BB.

In some embodiments, the signaling region and/or activating domain is included within one CAR, whereas the costimulatory component is provided by another CAR recognizing another antigen. In some embodiments, the CARs include activating or stimulatory CARs, and costimulatory CARs, both expressed on the same cell (see WO2014/055668). In some aspects, the cells include one or more stimulatory or activating CAR and/or a costimulatory CAR. In some embodiments, the cells further include inhibitory CARs (iCARs, see Fedorov et al., Sci. Transl. Medicine, 5(215) (December, 2013), such as a CAR recognizing an antigen other than the one associated with and/or specific for the disease or condition whereby an activating signal delivered through the disease-targeting CAR is diminished or inhibited by binding of the inhibitory CAR to its ligand, e.g., to reduce off-target effects.

In certain embodiments, the intracellular signaling domain comprises a CD28 transmembrane and signaling domain linked to a CD3 (e.g., CD3-zeta) intracellular domain. In some embodiments, the intracellular signaling domain comprises a chimeric CD28 and CD137 (4-1BB, TNFRSF9) co-stimulatory domains, linked to a CD3 zeta intracellular domain.

In some embodiments, the CAR encompasses one or more, e.g., two or more, costimulatory domains and an activation domain, e.g., primary activation domain, in the cytoplasmic portion. Exemplary CARs include intracellular components of CD3-zeta, CD28, and 4-1BB.

In some embodiments, the antigen receptor further includes a marker and/or cells expressing the CAR or other antigen receptor further includes a surrogate marker, such as a cell surface marker, which may be used to confirm transduction or engineering of the cell to express the receptor. In some aspects, the marker includes all or part (e.g., truncated form) of CD34, a NGFR, or epidermal growth factor receptor, such as truncated version of such a cell surface receptor (e.g., tEGFR). Exemplary surrogate markers can include truncated forms of cell surface polypeptides, such as truncated forms that are non-functional and to not transduce or are not capable of transducing a signal or a signal ordinarily transduced by the full-length form of the cell surface polypeptide, and/or do not or are not capable of internalizing. Exemplary truncated cell surface polypeptides including truncated forms of growth factors or other receptors such as a truncated human epidermal growth factor receptor 2 (tHER2), a truncated epidermal growth factor receptor (tEGFR, exemplary tEGFR sequence set forth in SEQ ID NO: 7 or 16) or a prostate-specific membrane antigen (PSMA) or modified form thereof. tEGFR may contain an epitope recognized by the antibody cetuximab (Erbitux®) or other therapeutic anti-EGFR antibody or binding molecule, which can be used to identify or select cells that have been engineered with the tEGFR construct and an encoded exogenous protein, and/or to eliminate or separate cells expressing the encoded exogenous protein. See U.S. Pat. No. 8,802,374 and Liu et al., Nature Biotech. 2016 April; 34(4): 430-434). In some aspects, the marker, e.g. surrogate marker, includes all or part (e.g., truncated form) of CD34, a NGFR, a CD19 or a truncated CD19, e.g., a truncated non-human CD19, or epidermal growth factor receptor (e.g., tEGFR). In some embodiments, the marker is or comprises a fluorescent protein, such as green fluorescent protein (GFP), enhanced green fluorescent protein (EGFP), such as super-fold GFP (sfGFP), red fluorescent protein (RFP), such as tdTomato, mCherry, mStrawberry, AsRed2, DsRed or DsRed2, cyan fluorescent protein (CFP), blue green fluorescent protein (BFP), enhanced blue fluorescent protein (EBFP), and yellow fluorescent protein (YFP), and variants thereof, including species variants, monomeric variants, and codon-optimized and/or enhanced variants of the fluorescent proteins. In some embodiments, the marker is or comprises an enzyme, such as a luciferase, the lacZ gene from E. coli, alkaline phosphatase, secreted embryonic alkaline phosphatase (SEAP), chloramphenicol acetyl transferase (CAT). Exemplary light-emitting reporter genes include luciferase (luc), β-galactosidase, chloramphenicol acetyl-transferase (CAT), β-glucuronidase (GUS) or variants thereof.

In some embodiments, the marker is a selection marker. In some embodiments, the selection marker is or comprises a polypeptide that confers resistance to exogenous agents or drugs. In some embodiments, the selection marker is an antibiotic resistance gene. In some embodiments, the selection marker is an antibiotic resistance gene confers antibiotic resistance to a mammalian cell. In some embodiments, the selection marker is or comprises a Puromycin resistance gene, a Hygromycin resistance gene, a Blasticidin resistance gene, a Neomycin resistance gene, a Geneticin resistance gene or a Zeocin resistance gene or a modified form thereof.

In some embodiments, the nucleic acid encoding the marker is operably linked to a polynucleotide encoding for a linker sequence, such as a cleavable linker sequence, e.g., a T2A. For example, a marker, and optionally a linker sequence, can be any as disclosed in PCT Pub. No. WO2014031687. For example, the marker can be a truncated EGFR (tEGFR) that is, optionally, linked to a linker sequence, such as a T2A cleavable linker sequence. An exemplary polypeptide for a truncated EGFR (e.g. tEGFR) comprises the sequence of amino acids set forth in SEQ ID NO: 7 or 16 or a sequence of amino acids that exhibits at least 85%, 86%, 87%, 88%, 89%, 90%, 91%, 92%, 93%, 94%, 95%, 96%, 97%, 98%, 99% or more sequence identity to SEQ ID NO: 7 or 16.

In some embodiments, the nucleic acid encoding the marker is operably linked to a polynucleotide encoding for a linker sequence, such as a cleavable linker sequence, e.g., MMP cleavable linker sequence. For example, a marker, and optionally a linker sequence, can be any as disclosed in published patent application No. WO2014031687. For example, the marker can be a truncated EGFR (tEGFR) that is, optionally, linked to a linker sequence, such as a T2A cleavable linker sequence.

In some embodiments, the marker is a molecule, e.g., cell surface protein, not naturally found on T cells or not naturally found on the surface of T cells, or a portion thereof. In some embodiments, the molecule is a non-self molecule, e.g., non-self protein, i.e., one that is not recognized as "self" by the immune system of the host into which the cells will be adoptively transferred.

In some embodiments, the marker serves no therapeutic function and/or produces no effect other than to be used as a marker for genetic engineering, e.g., for selecting cells successfully engineered. In other embodiments, the marker may be a therapeutic molecule or molecule otherwise exerting some desired effect, such as a ligand for a cell to be encountered in vivo, such as a costimulatory or immune checkpoint molecule to enhance and/or dampen responses of the cells upon adoptive transfer and encounter with ligand.

In some cases, CARs are referred to as first, second, and/or third generation CARs. In some aspects, a first generation CAR is one that solely provides a CD3-chain induced signal upon antigen binding; in some aspects, a second-generation CARs is one that provides such a signal and costimulatory signal, such as one including an intracellular signaling domain from a costimulatory receptor such as CD28 or CD137; in some aspects, a third generation CAR in some aspects is one that includes multiple costimulatory domains of different costimulatory receptors.

In some embodiments, the chimeric antigen receptor includes an extracellular portion containing the antibody or fragment described herein. In some aspects, the chimeric antigen receptor includes an extracellular portion containing the antibody or fragment described herein and an intracellular signaling domain. In some embodiments, the antibody or fragment includes an scFv or a single-domain $V_H$ antibody and the intracellular domain contains an ITAM. In some aspects, the intracellular signaling domain includes a signaling domain of a zeta chain of a CD3-zeta (CD3ζ) chain. In some embodiments, the chimeric antigen receptor includes a transmembrane domain disposed between the extracellular domain and the intracellular signaling region.

In some aspects, the transmembrane domain contains a transmembrane portion of CD28. The extracellular domain and transmembrane can be linked directly or indirectly. In some embodiments, the extracellular domain and transmembrane are linked by a spacer, such as any described herein. In some embodiments, the chimeric antigen receptor contains an intracellular domain of a T cell costimulatory molecule, such as between the transmembrane domain and intracellular signaling domain. In some aspects, the T cell costimulatory molecule is CD28 or 4-1BB.

In some embodiments, the CAR contains an antibody, e.g., an antibody fragment, a transmembrane domain that is or contains a transmembrane portion of CD28 or a functional variant thereof, and an intracellular signaling domain containing a signaling portion of CD28 or functional variant thereof and a signaling portion of CD3 zeta or functional variant thereof. In some embodiments, the CAR contains an antibody, e.g., antibody fragment, a transmembrane domain that is or contains a transmembrane portion of CD28 or a functional variant thereof, and an intracellular signaling domain containing a signaling portion of a 4-1BB or functional variant thereof and a signaling portion of CD3 zeta or functional variant thereof. In some such embodiments, the receptor further includes a spacer containing a portion of an Ig molecule, such as a human Ig molecule, such as an Ig hinge, e.g. an IgG4 hinge, such as a hinge-only spacer.

In some embodiments, the transmembrane domain of the receptor, e.g., the CAR is a transmembrane domain of human CD28 or variant thereof, e.g., a 27-amino acid transmembrane domain of a human CD28 (Accession No.: P10747.1), or is a transmembrane domain that comprises the sequence of amino acids set forth in SEQ ID NO: 8 or a sequence of amino acids that exhibits at least 85%, 86%, 87%, 88%, 89%, 90%, 91%, 92%, 93%, 94%, 95%, 96%, 97%, 98%, 99% or more sequence identity to SEQ ID NO:8; in some embodiments, the transmembrane-domain containing portion of the recombinant receptor comprises the sequence of amino acids set forth in SEQ ID NO: 9 or a sequence of amino acids having at least at or about 85%, 86%, 87%, 88%, 89%, 90%, 91%, 92%, 93%, 94%, 95%, 96%, 97%, 98%, 99% or more sequence identity thereto.

In some embodiments, the chimeric antigen receptor contains an intracellular domain of a T cell costimulatory molecule. In some aspects, the T cell costimulatory molecule is CD28 or 4-1BB.

In some embodiments, the intracellular signaling region comprises an intracellular costimulatory signaling domain of human CD28 or functional variant or portion thereof, such as a 41 amino acid domain thereof and/or such a domain with an LL to GG substitution at positions 186-187 of a native CD28 protein. In some embodiments, the intracellular signaling domain can comprise the sequence of amino acids set forth in SEQ ID NO: 10 or 11 or a sequence of amino acids that exhibits at least 85%, 86%, 87%, 88%, 89%, 90%, 91%, 92%, 93%, 94%, 95%, 96%, 97%, 98%, 99% or more sequence identity to SEQ ID NO: 10 or 11. In some embodiments, the intracellular region comprises an intracellular costimulatory signaling domain of 4-1BB or functional variant or portion thereof, such as a 42-amino acid cytoplasmic domain of a human 4-1BB (Accession No. Q07011.1) or functional variant or portion thereof, such as the sequence of amino acids set forth in SEQ ID NO: 12 or a sequence of amino acids that exhibits at least 85%, 86%, 87%, 88%, 89%, 90%, 91%, 92%, 93%, 94%, 95%, 96%, 97%, 98%, 99% or more sequence identity to SEQ ID NO: 12.

In some embodiments, the intracellular signaling region comprises a human CD3 chain, optionally a CD3 zeta stimulatory signaling domain or functional variant thereof, such as an 112 AA cytoplasmic domain of isoform 3 of human CD3 (Accession No.: P20963.2) or a CD3 zeta signaling domain as described in U.S. Pat. No. 7,446,190 or U.S. Pat. No. 8,911,993. In some embodiments, the intracellular signaling region comprises the sequence of amino acids set forth in SEQ ID NO: 13, 14 or 15 or a sequence of amino acids that exhibits at least 85%, 86%, 87%, 88%, 89%, 90%, 91%, 92%, 93%, 94%, 95%, 96%, 97%, 98%, 99% or more sequence identity to SEQ ID NO: 13, 14 or 15.

In some aspects, the spacer contains only a hinge region of an IgG, such as only a hinge of IgG4 or IgG1, such as the hinge only spacer set forth in SEQ ID NO:1. In other embodiments, the spacer is an Ig hinge, e.g., and IgG4 hinge, linked to a $C_H2$ and/or $C_H3$ domains. In some embodiments, the spacer is an Ig hinge, e.g., an IgG4 hinge, linked to $C_H2$ and $C_H3$ domains, such as set forth in SEQ ID NO:3. In some embodiments, the spacer is an Ig hinge, e.g., an IgG4 hinge, linked to a $C_H3$ domain only, such as set forth in SEQ ID NO:4. In some embodiments, the spacer is or comprises a glycine-serine rich sequence or other flexible linker such as known flexible linkers.

For example, in some embodiments, the CAR includes an antibody such as an antibody fragment, including scFvs, a spacer, such as a spacer containing a portion of an immunoglobulin molecule, such as a hinge region and/or one or more constant regions of a heavy chain molecule, such as an Ig-hinge containing spacer, a transmembrane domain containing all or a portion of a CD28-derived transmembrane domain, a CD28-derived intracellular signaling domain, and a CD3 zeta signaling domain. In some embodiments, the CAR includes an antibody or fragment, such as scFv, a spacer such as any of the Ig-hinge containing spacers, a CD28-derived transmembrane domain, a 4-1BB-derived intracellular signaling domain, and a CD3 zeta-derived signaling domain.

In some embodiments, nucleic acid molecules encoding such CAR constructs further includes a sequence encoding a T2A ribosomal skip element and/or a tEGFR sequence, e.g., downstream of the sequence encoding the CAR. In some embodiments, the sequence encodes a T2A ribosomal skip element set forth in SEQ ID NO: 6 or 17, or a sequence of amino acids that exhibits at least 85%, 86%, 87%, 88%, 89%, 90%, 91%, 92%, 93%, 94%, 95%, 96%, 97%, 98%, 99% or more sequence identity to SEQ ID NO: 6 or 17. In some embodiments, T cells expressing an antigen receptor (e.g. CAR) can also be generated to express a truncated EGFR (EGFRt) as a non-immunogenic selection epitope (e.g. by introduction of a construct encoding the CAR and EGFRt separated by a T2A ribosome switch to express two proteins from the same construct), which then can be used as a marker to detect such cells (see e.g. U.S. Pat. No. 8,802,374). In some embodiments, the sequence encodes an tEGFR sequence set forth in SEQ ID NO: 7 or 16, or a sequence of amino acids that exhibits at least 85%, 86%, 87%, 88%, 89%, 90%, 91%, 92%, 93%, 94%, 95%, 96%, 97%, 98%, 99% or more sequence identity to SEQ ID NO: 7 or 16. In some cases, the peptide, such as T2A, can cause the ribosome to skip (ribosome skipping) synthesis of a peptide bond at the C-terminus of a 2A element, leading to separation between the end of the 2A sequence and the next peptide downstream (see, for example, de Felipe. *Genetic Vaccines and Ther.* 2:13 (2004) and de Felipe et al. *Traffic* 5:616-626 (2004)). Many 2A elements are known. Examples of 2A sequences that can be used in the methods and nucleic acids disclosed herein, without limitation, 2A sequences from the foot-and-mouth disease virus (F2A, e.g., SEQ ID NO: 22), equine rhinitis A virus (E2A, e.g., SEQ ID NO: 21), Thosea asigna virus (T2A, e.g., SEQ ID NO: 6 or 17), and porcine teschovirus-1 (P2A, e.g., SEQ ID NO: 19 or 20) as described in U.S. Patent Publication No. 20070116690.

The recombinant receptors, such as CARs, expressed by the cells administered to the subject generally recognize or specifically bind to a molecule that is expressed in, associated with, and/or specific for the disease or condition or cells thereof being treated. Upon specific binding to the molecule, e.g., antigen, the receptor generally delivers an immunostimulatory signal, such as an ITAM-transduced signal, into the cell, thereby promoting an immune response targeted to the disease or condition. For example, in some embodiments, the cells express a CAR that specifically binds to an antigen expressed by a cell or tissue of the disease or condition or associated with the disease or condition.

b. Chimeric Auto-Antibody Receptors (CAARs)

In some embodiments, among the recombinant receptor expressed by the engineered cells used in connection with the provided methods, uses, articles of manufacture and compositions is a chimeric autoantibody receptor (CAAR). In some embodiments, the CAAR is specific for an autoantibody. In some embodiments, a cell expressing the CAAR, such as a T cell engineered to express a CAAR, can be used to specifically bind to and kill autoantibody-expressing cells, but not normal antibody expressing cells. In some embodiments, CAAR-expressing cells can be used to treat an autoimmune disease associated with expression of self-antigens, such as autoimmune diseases. In some embodiments, CAAR-expressing cells can target B cells that ultimately produce the autoantibodies and display the autoantibodies on their cell surfaces, mark these B cells as disease-specific targets for therapeutic intervention. In some embodiments, CAAR-expressing cells can be used to efficiently targeting and killing the pathogenic B cells in autoimmune diseases by targeting the disease-causing B cells using an antigen-specific chimeric autoantibody receptor. In some embodiments, the recombinant receptor is a CAAR, such as any described in U.S. Patent Application Pub. No. US 2017/0051035.

In some embodiments, the CAAR comprises an autoantibody binding domain, a transmembrane domain, and an intracellular signaling region. In some embodiments, the intracellular signaling region comprises an intracellular signaling domain. In some embodiments, the intracellular signaling domain is or comprises a primary signaling domain, a signaling domain that is capable of inducing a primary activation signal in a T cell, a signaling domain of a T cell receptor (TCR) component, and/or a signaling domain comprising an immunoreceptor tyrosine-based activation motif (ITAM). In some embodiments, the intracellular signaling region comprises a secondary or costimulatory signaling region (secondary intracellular signaling regions).

In some embodiments, the autoantibody binding domain comprises an autoantigen or a fragment thereof. The choice of autoantigen can depend upon the type of autoantibody being targeted. For example, the autoantigen may be chosen because it recognizes an autoantibody on a target cell, such as a B cell, associated with a particular disease state, e.g. an autoimmune disease, such as an autoantibody-mediated autoimmune disease. In some embodiments, the autoimmune disease includes pemphigus vulgaris (PV). Exemplary autoantigens include desmoglein 1 (Dsg1) and Dsg3.

c. Multi-Targeting

In some embodiments, the cells used in connection with the provided methods, uses, articles of manufacture and compositions include cells employing multi-targeting strategies. In some embodiments, the cells express multi-chain chimeric antigen receptors (CAR) or express two or more genetically engineered receptors on the cell, each recognizing the same of a different antigen and typically each including a different intracellular signaling component. Such multi-targeting strategies are described, for example, in International Patent Application, Publication No.: WO 2014055668 A1 (describing combinations of activating and costimulatory CARs, e.g., targeting two different antigens present individually on off-target, e.g., normal cells, but present together only on cells of the disease or condition to be treated) and Fedorov et al., *Sci. Transl. Medicine,* 5(215) (2013) (describing cells expressing an activating and an inhibitory CAR, such as those in which the activating CAR binds to one antigen expressed on both normal or non-diseased cells and cells of the disease or condition to be treated, and the inhibitory CAR binds to another antigen expressed only on the normal cells or cells which it is not desired to treat).

For example, in some embodiments, the cells include a receptor expressing a first genetically engineered antigen receptor (e.g., CAR or TCR) which is capable of inducing an activating or stimulatory signal to the cell, generally upon specific binding to the antigen recognized by the first receptor, e.g., the first antigen. In some embodiments, the cell further includes a second genetically engineered antigen receptor (e.g., CAR or TCR), e.g., a chimeric costimulatory receptor, which is capable of inducing a costimulatory signal to the immune cell, generally upon specific binding to a second antigen recognized by the second receptor. In some embodiments, the first antigen and second antigen are the same. In some embodiments, the first antigen and second antigen are different.

In some embodiments, the first and/or second genetically engineered antigen receptor (e.g. CAR or TCR) is capable of inducing an activating signal to the cell. In some embodiments, the receptor includes an intracellular signaling component containing ITAM or ITAM-like motifs. In some embodiments, the activation induced by the first receptor involves a signal transduction or change in protein expression in the cell resulting in initiation of an immune response, such as ITAM phosphorylation and/or initiation of ITAM-mediated signal transduction cascade, formation of an immunological synapse and/or clustering of molecules near the bound receptor (e.g. CD4 or CD8, etc.), activation of one or more transcription factors, such as NF-κB and/or AP-1, and/or induction of gene expression of factors such as cytokines, proliferation, and/or survival.

In some embodiments, the first and/or second receptor includes intracellular signaling domains or regions of costimulatory receptors such as CD28, CD137 (4-1BB), OX40, and/or ICOS. In some embodiments, the first and second receptor include an intracellular signaling domain of a costimulatory receptor that are different. In one embodiment, the first receptor contains a CD28 costimulatory signaling region and the second receptor contain a 4-1BB co-stimulatory signaling region or vice versa.

In some embodiments, the first and/or second receptor includes both an intracellular signaling domain containing ITAM or ITAM-like motifs and an intracellular signaling domain of a costimulatory receptor.

In some embodiments, the first receptor contains an intracellular signaling domain containing ITAM or ITAM-like motifs and the second receptor contains an intracellular signaling domain of a costimulatory receptor. The costimulatory signal in combination with the activating signal induced in the same cell is one that results in an immune response, such as a robust and sustained immune response, such as increased gene expression, secretion of cytokines and other factors, and T cell mediated effector functions such as cell killing.

In some embodiments, neither ligation of the first receptor alone nor ligation of the second receptor alone induces a robust immune response. In some aspects, if only one receptor is ligated, the cell becomes tolerized or unresponsive to antigen, or inhibited, and/or is not induced to proliferate or secrete factors or carry out effector functions. In some such embodiments, however, when the plurality of receptors are ligated, such as upon encounter of a cell expressing the first and second antigens, a desired response is achieved, such as full immune activation or stimulation, e.g., as indicated by secretion of one or more cytokine, proliferation, persistence, and/or carrying out an immune effector function such as cytotoxic killing of a target cell.

In some embodiments, the two receptors induce, respectively, an activating and an inhibitory signal to the cell, such that binding by one of the receptor to its antigen activates the cell or induces a response, but binding by the second inhibitory receptor to its antigen induces a signal that suppresses or dampens that response. Examples are combinations of activating CARs and inhibitory CARs or iCARs. Such a strategy may be used, for example, in which the activating CAR binds an antigen expressed in a disease or condition but which is also expressed on normal cells, and the inhibitory receptor binds to a separate antigen which is expressed on the normal cells but not cells of the disease or condition.

In some embodiments, the multi-targeting strategy is employed in a case where an antigen associated with a particular disease or condition is expressed on a non-diseased cell and/or is expressed on the engineered cell itself, either transiently (e.g., upon stimulation in association with genetic engineering) or permanently. In such cases, by requiring ligation of two separate and individually specific antigen receptors, specificity, selectivity, and/or efficacy may be improved.

In some embodiments, the plurality of antigens, e.g., the first and second antigens, are expressed on the cell, tissue, or disease or condition being targeted, such as on the cancer cell. In some aspects, the cell, tissue, disease or condition is multiple myeloma or a multiple myeloma cell. In some embodiments, one or more of the plurality of antigens generally also is expressed on a cell which it is not desired to target with the cell therapy, such as a normal or non-diseased cell or tissue, and/or the engineered cells themselves. In such embodiments, by requiring ligation of multiple receptors to achieve a response of the cell, specificity and/or efficacy is achieved.

d. T Cell Receptors (TCRs)

In some embodiments, engineered cells, such as T cells, are provided that express a T cell receptor (TCR) or antigen-binding portion thereof that recognizes an peptide epitope or T cell epitope of a target polypeptide, such as an antigen of a tumor, viral or autoimmune protein.

In some embodiments, a "T cell receptor" or "TCR" is a molecule that contains a variable α and β chains (also known as TCRα and TCRβ, respectively) or a variable γ and δ chains (also known as TCRα and TCRβ, respectively), or antigen-binding portions thereof, and which is capable of specifically binding to a peptide bound to an MHC molecule. In some embodiments, the TCR is in the αβ form. Typically, TCRs that exist in αβ and γδ forms are generally structurally similar, but T cells expressing them may have distinct anatomical locations or functions. A TCR can be found on the surface of a cell or in soluble form. Generally, a TCR is found on the surface of T cells (or T lymphocytes) where it is generally responsible for recognizing antigens bound to major histocompatibility complex (MHC) molecules.

Unless otherwise stated, the term "TCR" should be understood to encompass full TCRs as well as antigen-binding portions or antigen-binding fragments thereof. In some embodiments, the TCR is an intact or full-length TCR, including TCRs in the αβ form or γδ form. In some embodiments, the TCR is an antigen-binding portion that is less than a full-length TCR but that binds to a specific peptide bound in an MHC molecule, such as binds to an MHC-peptide complex. In some cases, an antigen-binding portion or fragment of a TCR can contain only a portion of the structural domains of a full-length or intact TCR, but yet is able to bind the peptide epitope, such as MHC-peptide complex, to which the full TCR binds. In some cases, an antigen-binding portion contains the variable domains of a TCR, such as variable α chain and variable β chain of a TCR, sufficient to form a binding site for binding to a specific MHC-peptide complex. Generally, the variable chains of a TCR contain complementarity determining regions involved in recognition of the peptide, MHC and/or MHC-peptide complex.

In some embodiments, the variable domains of the TCR contain hypervariable loops, or complementarity determining regions (CDRs), which generally are the primary contributors to antigen recognition and binding capabilities and specificity. In some embodiments, a CDR of a TCR or combination thereof forms all or substantially all of the antigen-binding site of a given TCR molecule. The various CDRs within a variable region of a TCR chain generally are separated by framework regions (FRs), which generally display less variability among TCR molecules as compared to the CDRs (see, e.g., Jores et al., Proc. Nat'l Acad. Sci. U.S.A. 87:9138, 1990; Chothia et al., EMBO J. 7:3745, 1988; see also Lefranc et al., Dev. Comp. Immunol. 27:55, 2003). In some embodiments, CDR3 is the main CDR responsible for antigen binding or specificity, or is the most important among the three CDRs on a given TCR variable region for antigen recognition, and/or for interaction with the processed peptide portion of the peptide-MHC complex. In some contexts, the CDR1 of the alpha chain can interact with the N-terminal part of certain antigenic peptides. In some contexts, CDR1 of the beta chain can interact with the C-terminal part of the peptide. In some contexts, CDR2 contributes most strongly to or is the primary CDR responsible for the interaction with or recognition of the MHC portion of the MHC-peptide complex. In some embodiments, the variable region of the β-chain can contain a further hypervariable region (CDR4 or HVR4), which generally is involved in superantigen binding and not antigen recognition (Kotb (1995) Clinical Microbiology Reviews, 8:411-426).

In some embodiments, a TCR also can contain a constant domain, a transmembrane domain and/or a short cytoplasmic tail (see, e.g., Janeway et al., Immunobiology: The Immune System in Health and Disease, 3rd Ed., Current Biology Publications, p. 4:33, 1997). In some aspects, each chain of the TCR can possess one N-terminal immunoglobulin variable domain, one immunoglobulin constant domain, a transmembrane region, and a short cytoplasmic tail at the C-terminal end. In some embodiments, a TCR is associated with invariant proteins of the CD3 complex involved in mediating signal transduction.

In some embodiments, a TCR chain contains one or more constant domain. For example, the extracellular portion of a given TCR chain (e.g., α-chain or β-chain) can contain two immunoglobulin-like domains, such as a variable domain (e.g., Vα or Vβ; typically amino acids 1 to 116 based on Kabat numbering Kabat et al., "Sequences of Proteins of Immunological Interest, US Dept. Health and Human Services, Public Health Service National Institutes of Health, 1991, 5th ed.) and a constant domain (e.g., α-chain constant domain or Cα, typically positions 117 to 259 of the chain based on Kabat numbering or β chain constant domain or $C_β$, typically positions 117 to 295 of the chain based on Kabat) adjacent to the cell membrane. For example, in some cases, the extracellular portion of the TCR formed by the two chains contains two membrane-proximal constant domains, and two membrane-distal variable domains, which variable domains each contain CDRs. The constant domain of the TCR may contain short connecting sequences in which a cysteine residue forms a disulfide bond, thereby linking the two chains of the TCR. In some embodiments, a TCR may have an additional cysteine residue in each of the α and β chains, such that the TCR contains two disulfide bonds in the constant domains.

In some embodiments, the TCR chains contain a transmembrane domain. In some embodiments, the transmembrane domain is positively charged. In some cases, the TCR chain contains a cytoplasmic tail. In some cases, the structure allows the TCR to associate with other molecules like CD3 and subunits thereof. For example, a TCR containing constant domains with a transmembrane region may anchor the protein in the cell membrane and associate with invariant subunits of the CD3 signaling apparatus or complex. The intracellular tails of CD3 signaling subunits (e.g. CD3γ, CD3δ, CD3ε and CD3ζ chains) contain one or more immunoreceptor tyrosine-based activation motif or ITAM that are involved in the signaling capacity of the TCR complex.

In some embodiments, the TCR may be a heterodimer of two chains α and β (or optionally γ and δ) or it may be a single chain TCR construct. In some embodiments, the TCR is a heterodimer containing two separate chains (α and β chains or γ and δ chains) that are linked, such as by a disulfide bond or disulfide bonds.

In some embodiments, the TCR can be generated from a known TCR sequence(s), such as sequences of Vα,β chains, for which a substantially full-length coding sequence is readily available. Methods for obtaining full-length TCR sequences, including V chain sequences, from cell sources are well known. In some embodiments, nucleic acids encoding the TCR can be obtained from a variety of sources, such as by polymerase chain reaction (PCR) amplification of TCR-encoding nucleic acids within or isolated from a given cell or cells, or synthesis of publicly available TCR DNA sequences.

In some embodiments, the TCR is obtained from a biological source, such as from cells such as from a T cell (e.g. cytotoxic T cell), T-cell hybridomas or other publicly available source. In some embodiments, the T-cells can be obtained from in vivo isolated cells. In some embodiments, the TCR is a thymically selected TCR. In some embodiments, the TCR is a neoepitope-restricted TCR. In some embodiments, the T-cells can be a cultured T-cell hybridoma or clone. In some embodiments, the TCR or antigen-binding portion thereof or antigen-binding fragment thereof can be synthetically generated from knowledge of the sequence of the TCR.

In some embodiments, the TCR is generated from a TCR identified or selected from screening a library of candidate TCRs against a target polypeptide antigen, or target T cell epitope thereof. TCR libraries can be generated by amplification of the repertoire of Vα and Vβ from T cells isolated from a subject, including cells present in PBMCs, spleen or other lymphoid organ. In some cases, T cells can be amplified from tumor-infiltrating lymphocytes (TILs). In some embodiments, TCR libraries can be generated from CD4+ or CD8+ T cells. In some embodiments, the TCRs can be amplified from a T cell source of a normal of healthy subject, i.e. normal TCR libraries. In some embodiments, the TCRs can be amplified from a T cell source of a diseased subject, i.e. diseased TCR libraries. In some embodiments, degenerate primers are used to amplify the gene repertoire of Vα and Vβ, such as by RT-PCR in samples, such as T cells, obtained from humans. In some embodiments, scTv libraries can be assembled from naïve Vα and Vβ libraries in which the amplified products are cloned or assembled to be separated by a linker. Depending on the source of the subject and cells, the libraries can be HLA allele-specific. Alternatively, in some embodiments, TCR libraries can be generated by mutagenesis or diversification of a parent or scaffold TCR molecule. In some aspects, the TCRs are subjected to directed evolution, such as by mutagenesis, e.g., of the α or β chain. In some aspects, particular residues within CDRs of the TCR are altered. In some embodiments, selected TCRs can be modified by affinity maturation. In some embodiments, antigen-specific T cells may be selected, such as by screening to assess CTL activity against the peptide. In some aspects, TCRs, e.g. present on the antigen-specific T cells, may be selected, such as by binding activity, e.g., particular affinity or avidity for the antigen.

In some embodiments, the TCR or antigen-binding portion thereof is one that has been modified or engineered. In some embodiments, directed evolution methods are used to generate TCRs with altered properties, such as with higher affinity for a specific MHC-peptide complex. In some embodiments, directed evolution is achieved by display methods including, but not limited to, yeast display (Holler et al. (2003) Nat Immunol, 4, 55-62; Holler et al. (2000) Proc Natl Acad Sci USA, 97, 5387-92), phage display (Li et al. (2005) Nat Biotechnol, 23, 349-54), or T cell display (Chervin et al. (2008) J Immunol Methods, 339, 175-84). In some embodiments, display approaches involve engineering, or modifying, a known, parent or reference TCR. For example, in some cases, a wild-type TCR can be used as a template for producing mutagenized TCRs in which in one or more residues of the CDRs are mutated, and mutants with an desired altered property, such as higher affinity for a desired target antigen, are selected.

In some embodiments, peptides of a target polypeptide for use in producing or generating a TCR of interest are known or can be readily identified. In some embodiments, peptides suitable for use in generating TCRs or antigen-binding portions can be determined based on the presence of an HLA-restricted motif in a target polypeptide of interest, such as a target polypeptide described below. In some embodiments, peptides are identified using available computer prediction models. In some embodiments, for predicting MHC class I binding sites, such models include, but are not limited to, ProPred1 (Singh and Raghava (2001) Bioinformatics 17(12):1236-1237, and SYFPEITHI (see Schuler et al. (2007) Immunoinformatics Methods in Molecular Biology, 409(1): 75-93 2007). In some embodiments, the MHC-restricted epitope is HLA-A0201, which is expressed in approximately 39-46% of all Caucasians and therefore, represents a suitable choice of MHC antigen for use preparing a TCR or other MHC-peptide binding molecule.

HLA-A0201-binding motifs and the cleavage sites for proteasomes and immune-proteasomes using computer prediction models are known. For predicting MHC class I binding sites, such models include, but are not limited to, ProPred1 (described in more detail in Singh and Raghava, ProPred: prediction of HLA-DR binding sites. BIOINFORMATICS 17(12):1236-1237 2001), and SYFPEITHI (see Schuler et al. SYFPEITHI, Database for Searching and T-Cell Epitope Prediction. in Immunoinformatics Methods in Molecular Biology, vol 409(1): 75-93 2007)

In some embodiments, the TCR or antigen binding portion thereof may be a recombinantly produced natural protein or mutated form thereof in which one or more property, such as binding characteristic, has been altered. In some embodiments, a TCR may be derived from one of various animal species, such as human, mouse, rat, or other mammal. A TCR may be cell-bound or in soluble form. In some embodiments, for purposes of the provided methods, the TCR is in cell-bound form expressed on the surface of a cell.

In some embodiments, the TCR is a full-length TCR. In some embodiments, the TCR is an antigen-binding portion. In some embodiments, the TCR is a dimeric TCR (dTCR). In some embodiments, the TCR is a single-chain TCR (sc-TCR). In some embodiments, a dTCR or scTCR have the structures as described in WO 03/020763, WO 04/033685, WO 2011/044186.

In some embodiments, the TCR contains a sequence corresponding to the transmembrane sequence. In some embodiments, the TCR does contain a sequence corresponding to cytoplasmic sequences. In some embodiments, the TCR is capable of forming a TCR complex with CD3. In some embodiments, any of the TCRs, including a dTCR or scTCR, can be linked to signaling domains that yield an active TCR on the surface of a T cell. In some embodiments, the TCR is expressed on the surface of cells.

In some embodiments a dTCR contains a first polypeptide wherein a sequence corresponding to a TCR α chain variable region sequence is fused to the N terminus of a sequence corresponding to a TCR α chain constant region extracellular sequence, and a second polypeptide wherein a sequence corresponding to a TCR β chain variable region sequence is fused to the N terminus a sequence corresponding to a TCR β chain constant region extracellular sequence, the first and second polypeptides being linked by a disulfide bond. In some embodiments, the bond can correspond to the native inter-chain disulfide bond present in native dimeric αβ TCRs. In some embodiments, the interchain disulfide bonds are not present in a native TCR. For example, in some embodiments, one or more cysteines can be incorporated into the constant region extracellular sequences of dTCR polypeptide pair. In some cases, both a native and a non-native disulfide bond may be desirable. In some embodiments, the TCR contains a transmembrane sequence to anchor to the membrane.

In some embodiments, a dTCR contains a TCR α chain containing a variable α domain, a constant α domain and a first dimerization motif attached to the C-terminus of the constant α domain, and a TCR β chain comprising a variable β domain, a constant β domain and a first dimerization motif attached to the C-terminus of the constant β domain, wherein the first and second dimerization motifs easily interact to form a covalent bond between an amino acid in the first dimerization motif and an amino acid in the second dimerization motif linking the TCR α chain and TCR β chain together.

In some embodiments, the TCR is a scTCR. Typically, a scTCR can be generated using methods known, See e.g., Soo Hoo, W. F. et al. PNAS (USA) 89, 4759 (1992); Wiilfing, C. and Plückthun, A., J. Mol. Biol. 242, 655 (1994); Kurucz, I. et al. PNAS (USA) 90 3830 (1993); International published PCT Nos. WO 96/13593, WO 96/18105, WO99/60120, WO99/18129, WO 03/020763, WO2011/044186; and Schlueter, C. J. et al. J. Mol. Biol. 256, 859 (1996). In some embodiments, a scTCR contains an introduced non-native disulfide interchain bond to facilitate the association of the TCR chains (see e.g. International published PCT No. WO 03/020763). In some embodiments, a scTCR is a non-disulfide linked truncated TCR in which heterologous leucine zippers fused to the C-termini thereof facilitate chain association (see e.g. International published PCT No. WO99/60120). In some embodiments, a scTCR contain a TCRα variable domain covalently linked to a TCRβ variable domain via a peptide linker (see e.g., International published PCT No. WO99/18129).

In some embodiments, a scTCR contains a first segment constituted by an amino acid sequence corresponding to a TCR α chain variable region, a second segment constituted by an amino acid sequence corresponding to a TCR β chain variable region sequence fused to the N terminus of an amino acid sequence corresponding to a TCR β chain constant domain extracellular sequence, and a linker sequence linking the C terminus of the first segment to the N terminus of the second segment.

In some embodiments, a scTCR contains a first segment constituted by an α chain variable region sequence fused to the N terminus of an α chain extracellular constant domain sequence, and a second segment constituted by a β chain variable region sequence fused to the N terminus of a sequence β chain extracellular constant and transmembrane sequence, and, optionally, a linker sequence linking the C terminus of the first segment to the N terminus of the second segment.

In some embodiments, a scTCR contains a first segment constituted by a TCR β chain variable region sequence fused to the N terminus of a β chain extracellular constant domain sequence, and a second segment constituted by an α chain variable region sequence fused to the N terminus of a sequence α chain extracellular constant and transmembrane sequence, and, optionally, a linker sequence linking the C terminus of the first segment to the N terminus of the second segment.

In some embodiments, the linker of a scTCRs that links the first and second TCR segments can be any linker capable of forming a single polypeptide strand, while retaining TCR binding specificity. In some embodiments, the linker sequence may, for example, have the formula —P-AA-P— wherein P is proline and AA represents an amino acid sequence wherein the amino acids are glycine and serine. In some embodiments, the first and second segments are paired so that the variable region sequences thereof are orientated for such binding. Hence, in some cases, the linker has a sufficient length to span the distance between the C terminus of the first segment and the N terminus of the second segment, or vice versa, but is not too long to block or reduces bonding of the scTCR to the target ligand. In some embodiments, the linker can contain from or from about 10 to 45 amino acids, such as 10 to 30 amino acids or 26 to 41 amino acids residues, for example 29, 30, 31 or 32 amino acids. In some embodiments, the linker has the formula —PGGG-(SGGGG)5—P— wherein P is proline, G is glycine and S is serine (SEQ ID NO:32). In some embodiments, the linker has the sequence GSADDAKKDAAKKDGKS (SEQ ID NO:33).

In some embodiments, the scTCR contains a covalent disulfide bond linking a residue of the immunoglobulin region of the constant domain of the α chain to a residue of the immunoglobulin region of the constant domain of the β chain. In some embodiments, the interchain disulfide bond in a native TCR is not present. For example, in some embodiments, one or more cysteines can be incorporated into the constant region extracellular sequences of the first and second segments of the scTCR polypeptide. In some cases, both a native and a non-native disulfide bond may be desirable.

In some embodiments of a dTCR or scTCR containing introduced interchain disulfide bonds, the native disulfide bonds are not present. In some embodiments, the one or more of the native cysteines forming a native interchain disulfide bonds are substituted to another residue, such as to a serine or alanine. In some embodiments, an introduced disulfide bond can be formed by mutating non-cysteine residues on the first and second segments to cysteine. Exemplary non-native disulfide bonds of a TCR are described in published International PCT No. WO2006/000830.

In some embodiments, the TCR or antigen-binding fragment thereof exhibits an affinity with an equilibrium binding constant for a target antigen of between or between about 10-5 and 10-12 M and all individual values and ranges therein. In some embodiments, the target antigen is an MHC-peptide complex or ligand.

In some embodiments, nucleic acid or nucleic acids encoding a TCR, such as α and β chains, can be amplified by PCR, cloning or other suitable means and cloned into a suitable expression vector or vectors. The expression vector can be any suitable recombinant expression vector, and can be used to transform or transfect any suitable host. Suitable vectors include those designed for propagation and expansion or for expression or both, such as plasmids and viruses.

In some embodiments, the vector can a vector of the pUC series (Fermentas Life Sciences), the pBluescript series (Stratagene, LaJolla, Calif.), the pET series (Novagen, Madison, Wis.), the pGEX series (Pharmacia Biotech, Uppsala, Sweden), or the pEX series (Clontech, Palo Alto, Calif). In some cases, bacteriophage vectors, such as XG10, XGT11, λZapII (Stratagene), XEMBL4, and λNM1149, also can be used. In some embodiments, plant expression vectors can be used and include pBI01, pBI101.2, pBI101.3, pBI121 and pBIN19 (Clontech). In some embodiments, animal expression vectors include pEUK-Cl, pMAM and pMAMneo (Clontech). In some embodiments, a viral vector is used, such as a retroviral vector.

In some embodiments, the recombinant expression vectors can be prepared using standard recombinant DNA techniques. In some embodiments, vectors can contain regulatory sequences, such as transcription and translation initiation and termination codons, which are specific to the type of host (e.g., bacterium, fungus, plant, or animal) into which the vector is to be introduced, as appropriate and taking into consideration whether the vector is DNA- or RNA-based. In some embodiments, the vector can contain a nonnative promoter operably linked to the nucleotide sequence encoding the TCR or antigen-binding portion (or other MHC-peptide binding molecule). In some embodiments, the promoter can be a non-viral promoter or a viral promoter, such as a cytomegalovirus (CMV) promoter, an SV40 promoter, an RSV promoter, and a promoter found in the long-terminal repeat of the murine stem cell virus. Other known promoters also are contemplated.

In some embodiments, to generate a vector encoding a TCR, the α and β chains are PCR amplified from total cDNA isolated from a T cell clone expressing the TCR of interest and cloned into an expression vector. In some embodiments, the α and β chains are cloned into the same vector. In some embodiments, the α and β chains are cloned into different vectors. In some embodiments, the generated α and β chains are incorporated into a retroviral, e.g. lentiviral, vector.

D. Features of the Output Cell Composition

In particular embodiments, the methods provided herein produce or generate a composition of cells that contain genetically engineered cells, e.g., an output cell composition. In certain embodiments, an output cell composition is a cell composition that results from some or all of the steps for genetically engineering cells. In certain embodiments, the output cell composition results from a process of genetically engineering cells of an input cell composition. In certain embodiments, process contains one or more steps for activating, transducing or transfecting, expanding, and/or harvesting cells, such as cells that were obtained from an input cell composition. In certain embodiments, the output cell composition contains cells that have been genetically engineered. In particular embodiments, the cells of the output cell composition have undergone all of the steps for a process of genetic engineering.

In some embodiments, the output cell composition contains cells that include one or more nucleic acids introduced via genetic engineering, and thereby express recombinant or genetically engineered products of such nucleic acids. In some embodiments, the nucleic acids are heterologous, i.e., normally not present in a cell or sample obtained from the cell, such as one obtained from another organism or cell, which for example, is not ordinarily found in the cell being engineered and/or an organism from which such cell is derived. In some embodiments, the nucleic acids are not naturally occurring, such as a nucleic acid not found in nature, including one comprising chimeric combinations of nucleic acids encoding various domains from multiple different cell types.

In some embodiments, the output cell composition contains cells that have been genetically engineered. In particular embodiments, the output cell composition contains engineered T cells. In some embodiments, the engineered T cells include engineered CD4+ T cells and engineered CD8+ T cells. In particular embodiments, the output cell composition contains or includes at least 25%, at least 30%, at least 40%, at least 50%, at least 60%, at least 70%, at least 75%, at least 80%, at least 85%, at least 90%, at least 95%, at least 96%, at least 97%, at least 98%, at least 99%, at least 99.5%, at least 99.9%, or 100% or about 100% engineered T cells. In certain embodiments, the engineered cells express a recombinant receptor. In particular embodiments, the output cell composition contains or includes at least 25%, at least 30%, at least 40%, at least 50%, at least 60%, at least 70%, at least 75%, at least 80%, at least 85%, at least 90%, at least 95%, at least 96%, at least 97%, at least 98%, at least 99%, at least 99.5%, at least 99.9%, or 100% or about 100% T cells that express a recombinant receptor. In some embodiments, the recombinant receptor is a TCR or a CAR. In particular embodiments, the recombinant receptor is a CAR.

In certain embodiments, the output cell composition has a ratio of engineered CD4+ T cells to CD8+ T cells of between 5:1 to 0.2:1, between 4:1 to 0.25:1, between 3:1 to 0.33:1, between 2:1 to 0.5:1, between 1.5:1 to 0.66:1, or between 1.25:1 to 0.8:1. In particular embodiments, the output cell composition has a ratio of engineered CD4+ T cells to CD8+ T cells of between 2:1 to 0.5:1. In some embodiments, the output cell composition has a ratio of engineered CD4+ T cells to CD8+ T cells of or of about 2.0:1, 1.9:1, 1.8:1, 1.7:1, 1.6:1, 1.5:1, 1.4:1, 1.3:1, 1.2:1, 1.1:1, 1.0:1, 0.9:1, 0.8:1, 0.7:1, 0.6:1, or 0.5:1. In particular embodiments, the output cell composition has a ratio of engineered CD4+ T cells to CD8+ T cells of or of about 1:1. In particular embodiments, the engineered T cells express a recombinant receptor. In particular embodiments, the output cell composition has a ratio of recombinant receptor expressing CD4+ T cells to recombinant receptor expressing CD8+ T cells of or of about 2.0:1, 1.9:1, 1.8:1, 1.7:1, 1.6:1, 1.5:1, 1.4:1, 1.3:1, 1.2:1, 1.1:1, 1.0:1, 0.9:1, 0.8:1, 0.7:1, 0.6:1, or 0.5:1. In particular embodiments, the output cell composition has a ratio of recombinant receptor expressing CD4+ T cells to recombinant receptor expressing CD8+ T cells of or of about 1:1. In some embodiments, the recombinant receptor is a TCR or a CAR. In particular embodiments, the recombinant receptor is a CAR.

In some embodiments, the methods result in an output cell composition having a ratio of engineered CD4+ T cells to engineered CD8+ T cells, a ratio of CD4+ T cells expressing a recombinant receptor to CD8+ T cells expressing a recombinant receptor, and/or a ratio of a ratio of CD4+ T cells expressing a CAR to CD8+ T cells expressing a CAR that is within a certain tolerated difference or range of error of such a defined, desired, or fixed ratio, and/or results in such a ratio a certain percentage of the time that the method is performed, such as at least at or about 50%, 55%, 60%, 65%, 70%, 75%, 80%, 85%, 90%, 95%, or more than 95% of the time. In some embodiments, the tolerated difference is within about 1%, about 2%, about 3%, about 4% about 5%, about 10%, about 15%, about 20%, about 25%, about 30%, about 35%, about 40%, about 45%, about 50%, about 60%, about 70%, or about 75% of the ratio. In some aspects, the ratio is within 10%, 20%, or 30%, of the desired ratio and/or is within that ratio at least 70%, 80%, or 90% of the time the methods are performed. In certain embodiments, the ratio is within 50% of a 1:1 ratio at least 90% of the time the methods are performed.

In some embodiments, the tolerated difference and/or the defined ratio of engineered, recombinant receptor expressing, and/or CAR expressing CD4+ to CD8+ T cells is or has been determined by administering different cell types, such as administering CD4+ and CD8+ T cells, to one or more subjects at a plurality of test ratios or numbers, and assessing one or more parameters. In some aspects, the determination of the defined or fixed ratio or tolerated difference includes assessing one or more outcomes following administration to the subject. In some aspects, the outcomes include those selected from among amelioration of a disease symptom and outcomes indicating safety and/or low or absence of toxicity.

In certain embodiments, an output cell composition produced by the methods provided herein has a ratio of engineered CD4+ T cells to engineered CD8+ T cells of between 2:1 and 0.5:1. In certain embodiments, the output composition contains a ratio of engineered CD4+ T cells to engineered CD8+ T cells of or of about 1:1. In some embodiments, the output cell composition was produced from an input cell composition described herein, e.g., an input cell composition described in Section I-A, and has a ratio of engineered CD4+ T cells to engineered CD8+ T cells of between 2:1 and 0.5:1. In particular embodiments, the output cell composition produced from an input cell composition has a ratio of engineered CD4+ T cells to engineered CD8+ T cells of 1:1 with a tolerated different of 50%, 25%, 10%, or less. In certain embodiments, the engineered T cells express a recombinant receptor. In certain embodiments, the engineered T cells express a CAR.

II. Compositions and Formulations

Provided herein are compositions or formulations containing cells prepared according to the methods of incubating (e.g., stimulating) described herein. In some embodiments, the compositions and methods described herein can be used to obtain an output cell composition of cells with a defined ratio of recombinant receptor expressing CD4+ to CD8+ T cells, such as for use as a therapeutic cell composition. Also provided herein is an output cell composition produced by any of the methods described herein.

In some embodiments, the cells produced using any of the methods described herein, e.g., cells of the output cell composition, are provided as compositions, including pharmaceutical compositions and formulations, such as unit dose form compositions including the number of cells for administration in a given dose or fraction thereof. In particular embodiments, the cells of the output cell composition are genetically engineered with a recombinant receptor (e.g., CAR-T cells). In certain embodiments, the pharmaceutical compositions and formulations generally include one or more optional pharmaceutically acceptable carrier or excipient. In some embodiments, the composition includes at least one additional therapeutic agent.

In some embodiments, a composition of cells, e.g., an output cell composition, is generated or manufactured for the purposes of a cell therapy. In some embodiments, the cell composition is a pharmaceutical composition or formulation. Such compositions can be used in accord with the provided methods, for example, to assess their release for use in the prevention or treatment of diseases, conditions, and disorders, or in detection, diagnostic, and prognostic methods.

The term "pharmaceutical formulation" refers to a preparation which is in such form as to permit the biological activity of an active ingredient contained therein to be effective, and which contains no additional components which are unacceptably toxic to a subject to which the formulation would be administered. In some embodiments, methods provided herein may be used to compare surface glycan expression of cell compositions composed of the same engineered cells, but with different pharmaceutical formulations.

A "pharmaceutically acceptable carrier" refers to an ingredient in a pharmaceutical formulation, other than an active ingredient, which is nontoxic to a subject. A pharmaceutically acceptable carrier includes, but is not limited to, a buffer, excipient, stabilizer, or preservative. In particular embodiments, methods provided herein may be used to compare surface glycan expression of cell compositions composed of the same engineered cells, but with different pharmaceutically acceptable carriers.

In some embodiments, the T cell therapy, such as engineered T cells (e.g., CAR T cells), are formulated with a pharmaceutically acceptable carrier. In some aspects, the choice of carrier is determined in part by the particular cell and/or by the method of administration. Accordingly, there are a variety of suitable formulations. For example, the pharmaceutical composition can contain preservatives. Suitable preservatives may include, for example, methylparaben, propylparaben, sodium benzoate, and benzalkonium chloride. In some aspects, a mixture of two or more preservatives is used. The preservative or mixtures thereof are typically present in an amount of about 0.0001% to about 2% by weight of the total composition. Carriers are described, e.g., by Remington's Pharmaceutical Sciences 16th edition, Osol, A. Ed. (1980). Pharmaceutically acceptable carriers are generally nontoxic to recipients at the dosages and concentrations employed, and include, but are not limited to: buffers such as phosphate, citrate, and other organic acids; antioxidants including ascorbic acid and methionine; preservatives (such as octadecyldimethylbenzyl ammonium chloride; hexamethonium chloride; benzalkonium chloride; benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g., Zn-protein complexes); and/or non-ionic surfactants such as polyethylene glycol (PEG).

Buffering agents in some aspects are included in the compositions. Suitable buffering agents include, for example, citric acid, sodium citrate, phosphoric acid, potassium phosphate, and various other acids and salts. In some aspects, a mixture of two or more buffering agents is used. The buffering agent or mixtures thereof are typically present in an amount of about 0.001% to about 4% by weight of the total composition. Methods for preparing administrable pharmaceutical compositions are known. Exemplary methods are described in more detail in, for example, Remington: The Science and Practice of Pharmacy, Lippincott Williams & Wilkins; 21st ed. (May 1, 2005).

The formulations can include aqueous solutions. The formulation or composition may also contain more than one active ingredient useful for the particular indication, disease, or condition being prevented or treated with the cells, including one or more active ingredients where the activities are complementary to the cells and/or the respective activities do not adversely affect one another. Such active ingredients are suitably present in combination in amounts that are effective for the purpose intended. Thus, in some embodiments, the pharmaceutical composition further includes other pharmaceutically active agents or drugs, such as chemotherapeutic agents, e.g., asparaginase, busulfan, carboplatin, cisplatin, daunorubicin, doxorubicin, fluorouracil, gemcitabine, hydroxyurea, methotrexate, paclitaxel, rituximab, vinblastine, vincristine, etc.

The pharmaceutical composition, in some embodiments, contain cells, e.g., cells of the output cell composition, in amounts effective to treat or prevent the disease or condition, such as a therapeutically effective or prophylactically effective amount. Therapeutic or prophylactic efficacy in some embodiments is monitored by periodic assessment of treated subjects. For repeated administrations over several days or longer, depending on the condition, the treatment is repeated until a desired suppression of disease symptoms occurs. However, other dosage regimens may be useful and can be determined. The desired dosage can be delivered by a single bolus administration of the composition, by multiple bolus administrations of the composition, or by continuous infusion administration of the composition.

The cells, e.g., cells of the output cell composition, may be formulated for administration using standard administration techniques, formulations, and/or devices. Provided are formulations and devices, such as syringes and vials, for storage and administration of the compositions. With respect to cells, administration can be autologous or heterologous. For example, immunoresponsive cells or progenitors can be obtained from one subject, and administered to the same subject or a different, compatible subject. Peripheral blood derived immunoresponsive cells or their progeny (e.g., in vivo, ex vivo or in vitro derived) can be administered via localized injection, including catheter administration, systemic injection, localized injection, intravenous injection, or parenteral administration. When administering a therapeutic composition (e.g., a pharmaceutical composition containing a genetically modified immunoresponsive cell), it will generally be formulated in a unit dosage injectable form (solution, suspension, emulsion).

Formulations include those for oral, intravenous, intraperitoneal, subcutaneous, pulmonary, transdermal, intramuscular, intranasal, buccal, sublingual, or suppository administration. In some embodiments, the agent or cell populations are administered parenterally. The term "parenteral," as used herein, includes intravenous, intramuscular, subcutaneous, rectal, vaginal, and intraperitoneal administration. In some embodiments, the agent or cell populations are administered to a subject using peripheral systemic delivery by intravenous, intraperitoneal, or subcutaneous injection.

Compositions in some embodiments are provided as sterile liquid preparations, e.g., isotonic aqueous solutions, suspensions, emulsions, dispersions, or viscous compositions, which may in some aspects be buffered to a selected pH. Liquid preparations are normally easier to prepare than gels, other viscous compositions, and solid compositions. Additionally, liquid compositions are somewhat more convenient to administer, especially by injection. Viscous compositions, on the other hand, can be formulated within the appropriate viscosity range to provide longer contact periods with specific tissues. Liquid or viscous compositions can comprise carriers, which can be a solvent or dispersing medium containing, for example, water, saline, phosphate buffered saline, polyol (for example, glycerol, propylene glycol, liquid polyethylene glycol) and suitable mixtures thereof.

Sterile injectable solutions can be prepared by incorporating the cells in a solvent, such as in admixture with a suitable carrier, diluent, or excipient such as sterile water, physiological saline, glucose, dextrose, or the like. The compositions can also be lyophilized. The compositions can contain auxiliary substances such as wetting, dispersing, or emulsifying agents (e.g., methylcellulose), pH buffering agents, gelling or viscosity enhancing additives, preservatives, flavoring agents, colors, and the like, depending upon the route of administration and the preparation desired. Standard texts may in some aspects be consulted to prepare suitable preparations.

Various additives which enhance the stability and sterility of the compositions, including antimicrobial preservatives, antioxidants, chelating agents, and buffers, can be added. Prevention of the action of microorganisms can be ensured by various antibacterial and antifungal agents, for example, parabens, chlorobutanol, phenol, sorbic acid, and the like. Prolonged absorption of the injectable pharmaceutical form can be brought about by the use of agents delaying absorption, for example, aluminum monostearate and gelatin.

The formulations to be used for in vivo administration are generally sterile. Sterility may be readily accomplished, e.g., by filtration through sterile filtration membranes.

For the prevention or treatment of disease, the appropriate dosage may depend on the type of disease to be treated, the type of agent or agents, the type of cells or recombinant receptors, the severity and course of the disease, whether the agent or cells are administered for preventive or therapeutic purposes, previous therapy, the subject's clinical history and response to the agent or the cells, and the discretion of the attending physician. The compositions are in some embodiments suitably administered to the subject at one time or over a series of treatments.

III. Methods of Administration

Also provided are methods of using and uses of the cells and compositions, such as those present in an output composition described herein, in the treatment of diseases, conditions, and disorders in which the antigen recognized by the recombinant receptor (e.g. CAR) is expressed. Also provided herein are methods of treatment including administering to a subject an output cell composition produced by any of the methods of engineering described. In some embodiments, the method includes generating genetically engineered T cells, such as genetically engineered T cells of the output cell composition, using any of the methods described herein and administering the genetically engineered T cells from produced by the methods described herein.

Provided are methods of administering the engineered cells and compositions, and uses of such engineered cells and compositions to treat or prevent diseases, conditions, and disorders, including cancers. The provided methods and uses include methods and uses for adoptive cell therapy. In some embodiments, the methods include administration of the engineered cells or a composition containing the cells, such as cells from an output composition as described, to a subject, tissue, or cell, such as one having, at risk for, or suspected of having the disease, condition or disorder. In some embodiments, the cells, populations, and compositions are administered to a subject having the particular disease or condition to be treated, e.g., via adoptive cell therapy, such as adoptive T cell therapy. In some embodiments, the cells or compositions are administered to the subject, such as a subject having or at risk for the disease or condition, ameliorate one or more symptom of the disease or condition, such as by lessening tumor burden in a cancer expressing an antigen recognized by an engineered T cell.

The disease or condition that is treated in some aspects can be any in which expression of an antigen is associated with, specific to, and/or expressed on a cell or tissue of a disease, disorder or condition and/or involved in the etiology of a disease, condition or disorder, e.g. causes, exacerbates or otherwise is involved in such disease, condition, or disorder. Exemplary diseases and conditions can include diseases or conditions associated with malignancy or transformation of cells (e.g. cancer), autoimmune or inflammatory disease, or an infectious disease, e.g. caused by a bacterial, viral or other pathogen. Exemplary antigens, which include antigens associated with various diseases and conditions that can be treated, are described above. In particular embodiments, the immunomodulatory polypeptide and/or recombinant receptor, e.g., the chimeric antigen receptor or TCR, specifically binds to an antigen associated with the disease or condition. In some embodiments, the subject has a disease, disorder or condition, optionally a cancer, a tumor, an autoimmune disease, disorder or condition, or an infectious disease.

In some embodiments, the disease, disorder or condition includes tumors associated with various cancers. The cancer can in some embodiments be any cancer located in the body of a subject, such as, but not limited to, cancers located at the head and neck, breast, liver, colon, ovary, prostate, pancreas, brain, cervix, bone, skin, eye, bladder, stomach, esophagus, peritoneum, or lung. For example, the anti-cancer agent can be used for the treatment of colon cancer, cervical cancer, cancer of the central nervous system, breast cancer, bladder cancer, anal carcinoma, head and neck cancer, ovarian cancer, endometrial cancer, small cell lung cancer, non-small cell lung carcinoma, neuroendocrine cancer, soft tissue carcinoma, penile cancer, prostate cancer, pancreatic cancer, gastric cancer, gall bladder cancer or espohageal cancer. In some cases, the cancer can be a cancer of the blood. In some embodiments, the disease, disorder or condition is a tumor, such as a solid tumor, lymphoma, leukemia, blood tumor, metastatic tumor, or other cancer or tumor type. In some embodiments, the disease, disorder or condition is selected from among cancers of the colon, lung, liver, breast, prostate, ovarian, skin, melanoma, bone, brain cancer, ovarian cancer, epithelial cancers, renal cell carcinoma, pancreatic adenocarcinoma, cervical carcinoma, colorectal cancer, glioblastoma, neuroblastoma, Ewing sarcoma, medulloblastoma, osteosarcoma, synovial sarcoma, and/or mesothelioma.

Among the diseases, conditions, and disorders are tumors, including solid tumors, hematologic malignancies, and melanomas, and including localized and metastatic tumors, infectious diseases, such as infection with a virus or other pathogen, e.g., HIV, HCV, HBV, CMV, HPV, and parasitic disease, and autoimmune and inflammatory diseases. In some embodiments, the disease, disorder or condition is a tumor, cancer, malignancy, neoplasm, or other proliferative disease or disorder. Such diseases include but are not limited to leukemia, lymphoma, e.g., acute myeloid (or myelogenous) leukemia (AML), chronic myeloid (or myelogenous) leukemia (CML), acute lymphocytic (or lymphoblastic) leukemia (ALL), chronic lymphocytic leukemia (CLL), hairy cell leukemia (HCL), small lymphocytic lymphoma (SLL), Mantle cell lymphoma (MCL), Marginal zone lymphoma, Burkitt lymphoma, Hodgkin lymphoma (HL), non-Hodgkin lymphoma (NHL), Anaplastic large cell lymphoma (ALCL), follicular lymphoma, refractory follicular lymphoma, diffuse large B-cell lymphoma (DLBCL) and multiple myeloma (MM), a B cell malignancy is selected from among acute lymphoblastic leukemia (ALL), adult ALL, chronic lymphoblastic leukemia (CLL), non-Hodgkin lymphoma (NHL), and Diffuse Large B-Cell Lymphoma (DLBCL).

In some embodiments, the disease or condition is an infectious disease or condition, such as, but not limited to, viral, retroviral, bacterial, and protozoal infections, immunodeficiency, Cytomegalovirus (CMV), Epstein-Barr virus (EBV), adenovirus, BK polyomavirus. In some embodiments, the disease or condition is an autoimmune or inflammatory disease or condition, such as arthritis, e.g., rheumatoid arthritis (RA), Type I diabetes, systemic lupus erythematosus (SLE), inflammatory bowel disease, psoriasis, scleroderma, autoimmune thyroid disease, Grave's disease, Crohn's disease, multiple sclerosis, asthma, and/or a disease or condition associated with transplant.

In some embodiments, the antigen associated with the disease or disorder is selected from the group consisting of orphan tyrosine kinase receptor ROR1, B cell maturation antigen (BCMA), carbonic anhydrase 9 (CAIX), tEGFR, Her2/neu (receptor tyrosine kinase erbB2), L1-CAM, CD19, CD20, CD22, mesothelin, CEA, hepatitis B surface antigen, anti-folate receptor, CD23, CD24, CD30, CD33, CD38, CD44, EGFR, epithelial glycoprotein 2 (EPG-2), epithelial glycoprotein 40 (EPG-40), ephrine receptor A2 (EPHa2), Her2/neu (receptor tyrosine kinase erb-B2), Her3 (erb-B3), Her4 (erb-B4), erbB dimers, type III epidermal growth factor receptor mutation (EGFR vIII), folate binding protein (FBP), FCRL5, Fc receptor like 5 (FCRL5; also known as Fc receptor homolog 5 or FCRH5), fetal acetylcholine receptor, ganglioside GD2, ganglioside GD3, G Protein Coupled Receptor 5D (GPCR5D), HMW-MAA, IL-22R-alpha, IL-13R-alpha2, kinase insert domain receptor (kdr), kappa light chain, Leucine Rich Repeat Containing 8 Family Member A (LRRC8A), Lewis Y, L1-cell adhesion molecule, (L1-CAM), Melanoma-associated antigen (MAGE)-A1, MAGE-A3, MAGE-A6, Preferentially expressed antigen of melanoma (PRAME), survivin, TAG72, B7-H6, IL-13 receptor alpha 2 (IL-13Rα2), CA9, GD3, HMW-MAA, CD171, G250/CAIX, Human leukocyte antigen A1 (HLA-A1), MAGE A1, HLA-A2, NY-ESO-1, PSCA, folate receptor-a, CD44v6, CD44v7/8, avf3.6 integrin (avb6 integrin), 8H9, NCAM, VEGF receptors, 5T4, Foetal AchR, natural killer group 2 member D (NKG2D) ligands, CD44v6, dual antigen, a cancer-testes antigen, mesothelin, murine CMV, mucin 1 (MUC1), MUC16, prostate stem cell antigen (PSCA), NKG2D, a cancer-testis antigen cancer/testis antigen 1B (CTAG, also known as NY-ESO-1 and LAGE-2), MART-1, glycoprotein 100 (gp100), oncofetal antigen, ROR1, Trophoblast glycoprotein (TPBG also known as 5T4), TAG72, VEGF-R2, carcinoembryonic antigen (CEA), Her2/neu, estrogen receptor, progesterone receptor, ephrinB2, CD123, c-Met, GD-2, O-acetylated GD2 (OGD2), CE7, Wilms Tumor 1 (WT-1), a cyclin, cyclin A2, C—C Motif Chemokine Ligand 1 (CCL-1), CD138, a pathogen-specific antigen and an antigen associated with a universal tag, and/or biotinylated molecules, and/or molecules expressed by HIV, HCV, HBV or other pathogens.

In some embodiments, the antigen or ligand is a tumor antigen or cancer marker. In some embodiments, the antigen or ligand the antigen is or includes orphan tyrosine kinase receptor (ROR1), B cell maturation antigen (BCMA), carbonic anhydrase 9 (CA9, also known as CAIX or G250), Her2/neu (receptor tyrosine kinase erbB2), CD19, CD20, CD22, mesothelin (MSLN), carcinoembryonic antigen (CEA), and hepatitis B surface antigen, anti-folate receptor, CD23, CD24, CD30, CD33, CD38, CD44, chondroitin sulfate proteoglycan 4 (CSPG4), EGFR, epithelial glycoprotein 2 (EPG-2), epithelial glycoprotein 40 (EPG-40), ephrin receptor A2 (EPHa2), Her3 (erb-B3), Her4 (erb-B4), erbB dimers, type III epidermal growth factor receptor mutation (EGFR vIII), folate binding protein (FBP), Fc receptor like 5 (FCRL5, also known as Fc receptor homolog 5 or FCRH5), fetal acetylcholine receptor (fetal AchR), ganglioside GD2, ganglioside GD3, Human leukocyte antigen A1 (HLA-A1), Human leukocyte antigen A2 (HLA-A2), IL-22 receptor alpha (IL-22Rα), kinase insert domain receptor (kdr), kappa light chain, Leucine Rich Repeat Containing 8 Family Member A (LRRC8A), Lewis Y, L1-cell adhesion molecule (L1-CAM), Melanoma-associated antigen (MAGE)-A1, MAGE-A3, MAGE-A6, MAGE-A10, Preferentially expressed antigen of melanoma (PRAME), survivin, tumor-associated glycoprotein 72 (TAG72), B7-H3, B7-H6, IL-13 receptor alpha 2 (IL-13Rα2), Human high molecular weight-melanoma-associated antigen (HMW-MAA), CD171, folate receptor-alpha, CD44v7/8, avf3.6 integrin (avb6 integrin), 8H9, neural cell adhesion molecule (NCAM), vascular endothelial growth factor receptor (VEGF receptors or VEGFR), Trophoblast glycoprotein (TPBG also known as 5T4), NKG2D ligands, CD44v6, dual antigen, a cancer-testes antigen, murine cytomegalovirus (CMV), mucin 1 (MUC1), MUC16, prostate stem cell antigen (PSCA), prostate specific membrane antigen (PSMA), natural killer group 2 member D (NKG2D) ligands, cancer/testis antigen 1B (CTAG, also known as NY-ESO-1 and LAGE-2), melan A (MART-1), glycoprotein 100 (gp100), glypican-3 (GPC3), G Protein Coupled Receptor 5D (GPRCSD), oncofetal antigen, TAG72, Tyrosinase related protein 1 (TRP1, also known as TYRP1 or gp75), Tyrosinase related protein 2 (TRP2, also known as dopachrome tautomerase, dopachrome delta-isomerase or DCT), vascular endothelial growth factor receptor 2 (VEGF-R2), carcinoembryonic antigen (CEA), estrogen receptor, progesterone receptor, a prostate specific antigen, ephrinB2, CD123, CD133, c-Met, O-acetylated GD2 (OGD2), CE7 epitope of L1-CAM, Wilms Tumor 1 (WT-1), a cyclin, cyclin A2, C—C Motif Chemokine Ligand 1 (CCL-1), CD138, a pathogen-specific antigen or pathogen-expressed antigen, and an antigen associated with a universal tag, and/or biotinylated molecules, and/or molecules expressed by HIV, HCV, HBV or other pathogens.

In some embodiments, the disease or condition is a B cell malignancy. In some embodiments, the B cell malignancy is a leukemia or a lymphoma. In some aspects, the disease or condition is acute lymphoblastic leukemia (ALL), adult ALL, chronic lymphoblastic leukemia (CLL), non-Hodgkin lymphoma (NHL), or Diffuse Large B-Cell Lymphoma (DLBCL). In some cases, the disease or condition is an NHL, such as or including an NHL that is an aggressive NHL, diffuse large B cell lymphoma (DLBCL), NOS (de novo and transformed from indolent), primary mediastinal large B cell lymphoma (PMBCL), T cell/histocyte-rich large B cell lymphoma (TCHRBCL), Burkitt's lymphoma, mantle cell lymphoma (MCL), and/or follicular lymphoma (FL), optionally, follicular lymphoma Grade 3B (FL3B). In some aspects, the recombinant receptor, such as a CAR, specifically binds to an antigen associated with the disease or condition or expressed in cells of the environment of a lesion associated with the B cell malignancy. Antigens targeted by the receptors in some embodiments include antigens associated with a B cell malignancy, such as any of a number of known B cell marker. In some embodiments, the antigen targeted by the receptor is CD20, CD19, CD22, ROR1, CD45, CD21, CD5, CD33, Igkappa, Iglambda, CD79a, CD79b or CD30.

In some embodiments, the disease or condition is a myeloma, such as a multiple myeloma. In some aspects, the recombinant receptor, such as a CAR, specifically binds to an antigen associated with the disease or condition or expressed in cells of the environment of a lesion associated with the multiple myeloma. Antigens targeted by the receptors in some embodiments include antigens associated with multiple myeloma, such as GPRCSD or BCMA.

In some embodiments, the antigen is a pathogen-specific or pathogen-expressed antigen. In some embodiments, the antigen is a viral antigen (such as a viral antigen from HIV, HCV, HBV, etc.), bacterial antigens, and/or parasitic antigens.

In some embodiments, the cell-based therapy is or comprises administration of cells, such as T cells, that target a molecule expressed on the surface of a lesion, such as a tumor or a cancer. In some embodiments, the immune cells express a T cell receptor (TCR) or other antigen-binding receptor. In some embodiments, the immune cells express a recombinant receptor, such as a transgenic TCR or a chimeric antigen receptor (CAR). In some embodiments, the cells are autologous to the subject. In some embodiments, the cells are allogeneic to the subject.

Methods for administration of engineered cells for adoptive cell therapy are known and may be used in connection with the provided methods and compositions. For example, adoptive T cell therapy methods are described, e.g., in US Patent Application Publication No. 2003/0170238 to Gruenberg et al; U.S. Pat. No. 4,690,915 to Rosenberg; Rosenberg (2011) *Nat Rev Clin Oncol.* 8(10):577-85). See, e.g., Themeli et al., (2013) *Nat Biotechnol.* 31(10): 928-933; Tsukahara et al., (2013) *Biochem Biophys Res Commun* 438(1): 84-9; Davila et al., (2013) *PLoS ONE* 8(4): e61338.

In some embodiments, the cell therapy, e.g., adoptive T cell therapy, is carried out by autologous transfer, in which the cells are isolated and/or otherwise prepared from the subject who is to receive the cell therapy, or from a sample derived from such a subject. Thus, in some aspects, the cells are derived from a subject, e.g., patient, in need of a treatment and the cells, following isolation and processing are administered to the same subject.

In some embodiments, the cell therapy, e.g., adoptive T cell therapy, is carried out by allogeneic transfer, in which the cells are isolated and/or otherwise prepared from a subject other than a subject who is to receive or who ultimately receives the cell therapy, e.g., a first subject. In such embodiments, the cells then are administered to a different subject, e.g., a second subject, of the same species. In some embodiments, the first and second subjects are genetically identical. In some embodiments, the first and second subjects are genetically similar. In some embodiments, the second subject expresses the same HLA class or supertype as the first subject. The cells can be administered by any suitable means. Dosing and administration may depend in part on whether the administration is brief or chronic. Various dosing schedules include but are not limited to single or multiple administrations over various timepoints, bolus administration, and pulse infusion.

In some embodiments, the provided methods include one or more steps administering to a subject cells of the output cell composition, such as a composition of cells described in Section I. In certain embodiments, the cells of the output cell composition include engineered CD4+ T cells and engineered CD8+ T cells. In some embodiments, the engineered CD4+ and CD8+ T cells express a T cell receptor (TCR) or other antigen-binding receptor. In some embodiments, the immune cells express a recombinant receptor, such as a transgenic TCR or a chimeric antigen receptor (CAR). In some embodiments, the cells of the output cell composition are autologous to the subject. In some embodiments, the cells are allogeneic to the subject.

In certain embodiments, the CD4+ T cells and CD8+ T cells of the output cell composition are administered to the subject in the same composition, dose, or mixture. Thus, in some embodiments, the recombinant receptor expressing CD4+ T cells and recombinant receptor expressing CD8+ T cells, e.g., CAR+ CD4+ and CAR+CD8+ are administered to the subject in the same composition, dose, or mixture.

In certain embodiments, the cells, e.g., the cells of the output cell composition or individual populations of subtypes of cells, are administered to the subject at a range of about one million to about 100 billion cells and/or that amount of cells per kilogram of body weight, such as, e.g., 1 million to about 50 billion cells (e.g., about 5 million cells, about 25 million cells, about 500 million cells, about 1 billion cells, about 5 billion cells, about 20 billion cells, about 30 billion cells, about 40 billion cells, or a range defined by any two of the foregoing values), such as about 10 million to about 100 billion cells (e.g., about 20 million cells, about 30 million cells, about 40 million cells, about 60 million cells, about 70 million cells, about 80 million cells, about 90 million cells, about 10 billion cells, about 25 billion cells, about 50 billion cells, about 75 billion cells, about 90 billion cells, or a range defined by any two of the foregoing values), and in some cases about 100 million cells to about 50 billion cells (e.g., about 120 million cells, about 250 million cells, about 350 million cells, about 450 million cells, about 650 million cells, about 800 million cells, about 900 million cells, about 3 billion cells, about 30 billion cells, about 45 billion cells) or any value in between these ranges and/or per kilogram of body weight. Dosages may vary depending on attributes particular to the disease or disorder and/or patient and/or other treatments.

In some embodiments, for example, where the subject is a human, the dose includes fewer than about $1 \times 10^8$ total recombinant receptor (e.g., CAR)-expressing cells, T cells, or peripheral blood mononuclear cells (PBMCs), e.g., in the range of about $1 \times 10^6$ to $1 \times 10^8$ such cells, such as $2 \times 10^6$, $5 \times 10^6$, $1 \times 10^7$, $5 \times 10^7$, or $1 \times 10^8$ or total such cells, or the range between any two of the foregoing values.

In some embodiments, the dose of genetically engineered cells comprises from or from about $1 \times 10^5$ to $5 \times 10^8$ total CAR-expressing T cells, $1 \times 10^5$ to $2.5 \times 10^8$ total CAR-expressing T cells, $1 \times 10^5$ to $1 \times 10^8$ total CAR-expressing T cells, $1 \times 10^5$ to $5 \times 10^7$ total CAR-expressing T cells, $1 \times 10^5$ to $2.5 \times 10^7$ total CAR-expressing T cells, $1 \times 10^5$ to $1 \times 10^7$ total CAR-expressing T cells, $1 \times 10^5$ to $5 \times 10^6$ total CAR-expressing T cells, $1 \times 10^5$ to $2.5 \times 10^6$ total CAR-expressing T cells, $1 \times 10^5$ to $1 \times 10^6$ total CAR-expressing T cells, $1 \times 10^6$ to $5 \times 10^8$ total CAR-expressing T cells, $1 \times 10^6$ to $2.5 \times 10^8$ total CAR-expressing T cells, $1 \times 10^6$ to $1 \times 10^8$ total CAR-expressing T cells, $1 \times 10^6$ to $5 \times 10^7$ total CAR-expressing T cells, $1 \times 10^6$ to $2.5 \times 10^7$ total CAR-expressing T cells, $1 \times 10^6$ to $1 \times 10^7$ total CAR-expressing T cells, $1 \times 10^6$ to $5 \times 10^6$ total CAR-expressing T cells, $1 \times 10^6$ to $2.5 \times 10^6$ total CAR-expressing T cells, $2.5 \times 10^6$ to $5 \times 10^8$ total CAR-expressing T cells, $2.5 \times 10^6$ to $2.5 \times 10^8$ total CAR-expressing T cells, $2.5 \times 10^6$ to $1 \times 10^8$ total CAR-expressing T cells, $2.5 \times 10^6$ to $5 \times 10^7$ total CAR-expressing T cells, $2.5 \times 10^6$ to $2.5 \times 10^7$ total CAR-expressing T cells, $2.5 \times 10^6$ to $1 \times 10^7$ total CAR-expressing T cells, $2.5 \times 10^6$ to $5 \times 10^6$ total CAR-expressing T cells, $5 \times 10^6$ to $5 \times 10^8$ total CAR-expressing T cells, $5 \times 10^6$ to $2.5 \times 10^8$ total CAR-expressing T cells, $5 \times 10^6$ to $1 \times 10^8$ total CAR-expressing T cells, $5 \times 10^6$ to $5 \times 10^7$ total CAR-expressing T cells, $5 \times 10^6$ to $2.5 \times 10^7$ total CAR-expressing T cells, $5 \times 10^6$ to $1 \times 10^7$ total CAR-expressing T cells, $1 \times 10^7$ to $5 \times 10^8$ total CAR-expressing T cells, $1 \times 10^7$ to $2.5 \times 10^8$ total CAR-expressing T cells, $1 \times 10^7$ to $1 \times 10^8$ total CAR-expressing T cells, $1 \times 10^7$ to $5 \times 10^7$ total CAR-expressing T cells, $1 \times 10^7$ to $2.5 \times 10^7$ total CAR-expressing T cells, $2.5 \times 10^7$ to $5 \times 10^8$ total CAR-expressing T cells, $2.5 \times 10^7$ to $2.5 \times 10^8$ total CAR-expressing T cells, $2.5 \times 10^7$ to $1 \times 10^8$ total CAR-expressing T cells, $2.5 \times 10^7$ to $5 \times 10^7$ total CAR-expressing T cells, $5 \times 10^7$ to $5 \times 10^8$ total CAR-expressing T cells, $5 \times 10^7$ to $2.5 \times 10^8$ total CAR-expressing T cells, $5 \times 10^7$ to $1 \times 10^8$ total CAR-expressing T cells, $1 \times 10^8$ to $5 \times 10^8$ total CAR-expressing T cells, $1 \times 10^8$ to $2.5 \times 10^8$ total CAR-expressing T cells, or $2.5 \times 10^8$ to $5 \times 10^8$ total CAR-expressing T cells.

In some embodiments, the dose of genetically engineered cells comprises at least or at least about $1\times10^5$ CAR-expressing cells, at least or at least about $2.5\times10^5$ CAR-expressing cells, at least or at least about $5\times10^5$ CAR-expressing cells, at least or at least about $1\times10^6$ CAR-expressing cells, at least or at least about $2.5\times10^6$ CAR-expressing cells, at least or at least about $5\times10^6$ CAR-expressing cells, at least or at least about $1\times10^7$ CAR-expressing cells, at least or at least about $2.5\times10^7$ CAR-expressing cells, at least or at least about $5\times10^7$ CAR-expressing cells, at least or at least about $1\times10^8$ CAR-expressing cells, at least or at least about $2.5\times10^8$ CAR-expressing cells, or at least or at least about $5\times10^8$ CAR-expressing cells.

In some embodiments, the cell therapy comprises administration of a dose comprising a number of cell from or from about $1\times10^5$ to $5\times10^8$ total recombinant receptor-expressing cells, total T cells, or total peripheral blood mononuclear cells (PBMCs), from or from about $5\times10^5$ to $1\times10^7$ total recombinant receptor-expressing cells, total T cells, or total peripheral blood mononuclear cells (PBMCs) or from or from about $1\times10^6$ to $1\times10^7$ total recombinant receptor-expressing cells, total T cells, or total peripheral blood mononuclear cells (PBMCs), each inclusive. In some embodiments, the cell therapy comprises administration of a dose of cells comprising a number of cells at least or at least about $1\times10^5$ total recombinant receptor-expressing cells, total T cells, or total peripheral blood mononuclear cells (PBMCs), such at least or at least $1\times10^6$, at least or at least about $1\times10^7$, at least or at least about $1\times10^8$ of such cells. In some embodiments, the number is with reference to the total number of CD3+ or CD8+, in some cases also recombinant receptor-expressing (e.g. CAR+) cells. In some embodiments, the cell therapy comprises administration of a dose comprising a number of cell from or from about $1\times10^5$ to $5\times10^8$ CD3+ or CD8+ total T cells or CD3+ or CD8+ recombinant receptor-expressing cells, from or from about $5\times10^5$ to $1\times10^7$ CD3+ or CD8+ total T cells or CD3+ or CD8+ recombinant receptor-expressing cells, or from or from about $1\times10^6$ to $1\times10^7$ CD3+ or CD8+ total T cells or CD3+ or CD8+ recombinant receptor-expressing cells, each inclusive. In some embodiments, the cell therapy comprises administration of a dose comprising a number of cell from or from about $1\times10^5$ to $5\times10^8$ total CD3+/CAR+ or CD8+/CAR+ cells, from or from about $5\times10^5$ to $1\times10^7$ total CD3+/CAR+ or CD8+/CAR+ cells, or from or from about $1\times10^6$ to $1\times10^7$ total CD3+/CAR+ or CD8+/CAR+ cells, each inclusive.

In some embodiments, for example, where the subject is human, the CD8+ T cells of the dose, including in a dose including CD4+ and CD8+ T cells, includes between about $1\times10^6$ and $5\times10^8$ total recombinant receptor (e.g., CAR)-expressing CD8+ cells, e.g., in the range of about $5\times10^6$ to $1\times10^8$ such cells, such cells $1\times10^7$, $2.5\times10^7$, $5\times10^7$, $7.5\times10^7$, $1\times10^8$, or $5\times10^8$ total such cells, or the range between any two of the foregoing values. In some embodiments, the patient is administered multiple doses, and each of the doses or the total dose can be within any of the foregoing values. In some embodiments, the dose of cells comprises the administration of from or from about $1\times10^7$ to $0.75\times10^8$ total recombinant receptor-expressing CD8+ T cells, $1\times10^7$ to $2.5\times10^7$ total recombinant receptor-expressing CD8+ T cells, from or from about $1\times10^7$ to $0.75\times10^8$ total recombinant receptor-expressing CD8+ T cells, each inclusive. In some embodiments, the dose of cells comprises the administration of or about $1\times10^7$, $2.5\times10^7$, $5\times10^7$, $7.5\times10^7$, $1\times10^8$, or $5\times10^8$ total recombinant receptor-expressing CD8+ T cells.

In some embodiments, the dose of cells, e.g., recombinant receptor-expressing T cells, is administered to the subject as a single dose or is administered only one time within a period of two weeks, one month, three months, six months, 1 year or more.

In some aspects, the pharmaceutical compositions and formulations are provided as unit dose form compositions including the number of cells for administration in a given dose or fraction thereof. In some embodiments, the provided methods produce cells in a predictable timeline to dosing as compared to other methods of incubating (e.g., stimulating) cells. In some cases, the dose of cells for administration is determined based on the number of naïve-like cells in the input cell composition.

In some aspects, the size of the dose is determined by the burden of the disease or condition in the subject. For example, in some aspects, the number of cells administered in the dose is determined based on the tumor burden that is present in the subject immediately prior to administration of the initiation of the dose of cells. In some embodiments, the size of the first and/or subsequent dose is inversely correlated with disease burden. In some aspects, as in the context of a large disease burden, the subject is administered a low number of cells. In other embodiments, as in the context of a lower disease burden, the subject is administered a larger number of cells.

Following administration of the cells, the biological activity of the engineered cell populations in some embodiments is measured, e.g., by any of a number of known methods. Parameters to assess include specific binding of an engineered or natural T cell or other immune cell to antigen, in vivo, e.g., by imaging, or ex vivo, e.g., by ELISA or flow cytometry. In certain embodiments, the ability of the engineered cells to destroy target cells can be measured using any suitable method, such as cytotoxicity assays described in, for example, Kochenderfer et al., J. Immunotherapy, 32(7): 689-702 (2009), and Herman et al. J. Immunological Methods, 285(1): 25-40 (2004). In certain embodiments, the biological activity of the cells is measured by assaying expression and/or secretion of one or more cytokines, such as CD 107a, IFNγ, IL-2, and TNF. In some aspects the biological activity is measured by assessing clinical outcome, such as reduction in tumor burden or load.

The cells can be administered by any suitable means. The cells are administered in a dosing regimen to achieve a therapeutic effect, such as a reduction in tumor burden. Dosing and administration may depend in part on the schedule of administration of the immunomodulatory compound, which can be administered prior to, subsequent to and/or simultaneously with initiation of administration of the T cell therapy. Various dosing schedules of the T cell therapy include but are not limited to single or multiple administrations over various time-points, bolus administration, and pulse infusion. In certain embodiments, the engineered T cells express a recombinant receptor. In certain embodiments, the engineered T cells express a CAR.

In particular embodiments, the ratio of the CD4+ T cells to CD8+ T cells that are administered to the subject in the same composition, dose, or mixture is between 5:1 to 0.2:1, between 4:1 to 0.25:1, between 3:1 to 0.33:1, between 2:1 to 0.5:1, between 1.5:1 to 0.66:1, or between 1.25:1 to 0.8:1. In some embodiments, the ratio of CD4+ T cells to CD8+ T cells administered to the subject in the same composition, dose, or mixture is or is about 2.0:1, 1.9:1, 1.8:1, 1.7:1, 1.6:1, 1.5:1, 1.4:1, 1.3:1, 1.2:1, 1.1:1, 1.0:1, 0.9:1, 0.8:1, 0.7:1, 0.6:1, or 0.5:1.

In particular embodiments, the ratio of recombinant receptor expressing CD4+ T cells to recombinant receptor expressing CD8+ T cells that are administered to the subject in the same composition, dose, or mixture is between 5:1 and 0.2:1, between 4:1 and 0.25:1, between 3:1 and 0.33:1, between 2:1 and 0.5:1, between 1.5:1 and 0.66:1, or between 1.25:1 and 0.8:1. In certain embodiments, the ratio of recombinant receptor expressing CD4+ T cells to recombinant receptor expressing CD8+ T cells that are administered to the subject in the same composition, dose, or mixture is or is about 2.0:1, 1.9:1, 1.8:1, 1.7:1, 1.6:1, 1.5:1, 1.4:1, 1.3:1, 1.2:1, 1.1:1, 1.0:1, 0.9:1, 0.8:1, 0.7:1, 0.6:1, or 0.5:1. In particular embodiments, ratio of the administered recombinant receptor expressing CD4+ T cells to recombinant receptor expressing CD8+ T cells is or is about 1:1. In some embodiments, the recombinant receptor is a TCR or a CAR. In particular embodiments, the recombinant receptor is a CAR.

In some embodiments, the ratio of engineered CD4+ T cells to engineered CD8+ T cells of the dose, composition, or mixture that is administered to the subject is within a certain tolerated difference or range of error of such a defined, desired, or fixed ratio. In some embodiments, the tolerated difference is within of or of about 1%, 2%, 3%, 4%, 5%, 10%, 15%, 20%, 25%, 30%, 35%, 40%, 45%, or 50%, of the target, defined, preferred, and/or fixed ratio.

In some embodiments, a composition of cells produced by the methods provided herein, e.g., an output composition, having a ratio of engineered CD4+ T cells to engineered CD8+ T cells of between 2:1 and 0.5:1 is administered to a subject in a single composition, dose, or mixture. In certain embodiments, the composition contains a ratio of engineered CD4+ T cells to engineered CD8+ T cells of or of about 1:1. In some embodiments, a cell composition produced from an input cell composition, e.g., an input cell composition described in Section I-A1, has a ratio of engineered CD4+ T cells to engineered CD8+ T cells of between 2:1 and 0.5:1 and is administered to a subject in a single composition, dose, or mixture. In particular embodiments, the cell composition produced from an input cell composition has a ratio of engineered CD4+ T cells to engineered CD8+ T cells of 1:1 with a tolerated difference of 50%, 25%, 10%, or less.

In some embodiments, the cells are administered as part of a further combination treatment, such as simultaneously with or sequentially with, in any order, another therapeutic intervention, such as an antibody or engineered cell or receptor or agent, such as a cytotoxic or therapeutic agent. For example, in some embodiments, an anti-cancer agent or immunomodulatory agent can be used in combination therapy with adoptive cell therapy with engineered cell expressing a recombinant receptor, e.g. a CAR. In some contexts, the cells are co-administered with another therapy sufficiently close in time such that the cell populations enhance the effect of the P one or more additional therapeutic agents, or vice versa. In some embodiments, the cells are administered prior to the one or more additional therapeutic agents. In some embodiments, the cells are administered after the one or more additional therapeutic agents.

In some embodiments, the one or more additional therapeutic agents include a cytokine, such as IL-2, for example, to enhance persistence. In some embodiments, the methods comprise administration of a chemotherapeutic agent. In some embodiments, the one or more additional therapeutic agents include one or more lymphodepleting therapies, such as prior to or simultaneous with initiation of administration of the engineered cells. In some embodiments, the lymphodepleting therapy comprises administration of a phosphamide, such as cyclophosphamide. In some embodiments, the lymphodepleting therapy can include administration of fludarabine. In some embodiments, fludarabine is excluded in the lymphodepleting therapy. In some embodiments, a lymphodepleting therapy is not administered.

In some embodiments, the methods include administering a preconditioning agent, such as a lymphodepleting or chemotherapeutic agent, such as cyclophosphamide, fludarabine, or combinations thereof, to a subject prior to the initiation of the cell therapy. For example, the subject may be administered a preconditioning agent at least 2 days prior, such as at least 3, 4, 5, 6, or 7 days prior, to the initiation of the cell therapy. In some embodiments, the subject is administered a preconditioning agent no more than 7 days prior, such as no more than 6, 5, 4, 3, or 2 days prior, to the initiation of the cell therapy.

In some embodiments, the subject is preconditioned with cyclophosphamide at a dose between or between about 20 mg/kg and 100 mg/kg, such as between or between about 40 mg/kg and 80 mg/kg. In some aspects, the subject is preconditioned with or with about 60 mg/kg of cyclophosphamide. In some embodiments, the cyclophosphamide can be administered in a single dose or can be administered in a plurality of doses, such as given daily, every other day or every three days. In some embodiments, the cyclophosphamide is administered once daily for one or two days. In some embodiments, where the lymphodepleting agent comprises cyclophosphamide, the subject is administered cyclophosphamide at a dose between or between about 100 $mg/m^2$ and 500 $mg/m^2$, such as between or between about 200 $mg/m^2$ and 400 $mg/m^2$, or 250 $mg/m^2$ and 350 $mg/m^2$, inclusive. In some instances, the subject is administered about 300 $mg/m^2$ of cyclophosphamide. In some embodiments, the cyclophosphamide can be administered in a single dose or can be administered in a plurality of doses, such as given daily, every other day or every three days. In some embodiments, cyclophosphamide is administered daily, such as for 1-5 days, for example, for 3 to 5 days. In some instances, the subject is administered about 300 $mg/m^2$ of cyclophosphamide, daily for 3 days, prior to initiation of the cell therapy.

In some embodiments, where the lymphodepleting agent comprises fludarabine, the subject is administered fludarabine at a dose between or between about 1 $mg/m^2$ and 100 $mg/m^2$, such as between or between about 10 $mg/m^2$ and 75 $mg/m^2$, 15 $mg/m^2$ and 50 $mg/m^2$, 20 $mg/m^2$ and 40 $mg/m^2$, or 24 $mg/m^2$ and 35 $mg/m^2$, inclusive. In some instances, the subject is administered about 30 $mg/m^2$ of fludarabine. In some embodiments, the fludarabine can be administered in a single dose or can be administered in a plurality of doses, such as given daily, every other day or every three days. In some embodiments, fludarabine is administered daily, such as for 1-5 days, for example, for 3 to 5 days. In some instances, the subject is administered about 30 $mg/m^2$ of fludarabine, daily for 3 days, prior to initiation of the cell therapy.

In some embodiments, the lymphodepleting agent comprises a combination of agents, such as a combination of cyclophosphamide and fludarabine. Thus, the combination of agents may include cyclophosphamide at any dose or administration schedule, such as those described above, and fludarabine at any dose or administration schedule, such as those described above. For example, in some aspects, the subject is administered 60 mg/kg (~2 g/m$^2$) of cyclophosphamide and 3 to 5 doses of 25 mg/m$^2$ fludarabine prior to the first or subsequent dose.

IV. Articles of Manufacture and Kits

Also provided are articles of manufacture, such as kits and devices, for the administration of the cells to subjects in according to the provided methods for adoptive cell therapy, and for storage and administration of the cells and compositions, such as the input compositions or output compositions as described.

The articles of manufacture include one or more containers, typically a plurality of containers, packaging material, and a label or package insert on or associated with the container or containers and/or packaging, generally including instructions for administration of the cells to a subject.

In some embodiments, the containers contain the cells to be administered, e.g., one or more unit doses thereof. The article of manufacture typically includes a plurality of containers, each containing a single unit dose of the cells. The unit dose may be an amount or number of the cells to be administered to the subject in the first dose or twice the number (or more) the cells to be administered in the first or any one or more consecutive dose(s). It may be the lowest dose or lowest possible dose of the cells that would be administered to the subject in connection with the administration method. In some embodiments, the unit dose is the minimum number of cells or number of cells or the minimum number of reference units or the target reference units or reference units within a target range that would be administered in a single dose to any subject having a particular disease or condition or any subject, according to the methods herein.

Suitable containers include, for example, bottles, vials, syringes, and flexible bags, such as infusion bags. In particular embodiments, the containers are bags, e.g., flexible bags, such as those suitable for infusion of cells to subjects, e.g., flexible plastic or PVC bags, and/or IV solution bags. The bags in some embodiments are sealable and/or able to be sterilized, so as to provide sterile solution and delivery of the cells and compositions. In some embodiments, the containers, e.g., bags, have a capacity of at or about or at least at or about 10, 20, 30, 40, 50, 60, 70, 80, 90, 100, 200, 300, 400, 500, or 1000 mL capacity, such as between at or about 10 and at or about 100 or between at or about 10 and at or about 500 mL capacity, each inclusive. In some embodiments, the containers, e.g., bags, are and/or are made from material which is stable and/or provide stable storage and/or maintenance of cells at one or more of various temperatures, such as in cold temperatures, e.g. below at or about or at or about −20° C., −80° C., −120° C., 135° C. and/or temperatures suitable for cryopreservation, and/or other temperatures, such as temperatures suitable for thawing the cells and body temperature such as at or about 37° C., for example, to permit thawing, e.g., at the subject's location or location of treatment, e.g., at bedside, immediately prior to treatment.

The containers may be formed from a variety of materials such as glass or plastic. In some embodiments, the container has one or more port, e.g., sterile access ports, for example, for connection of tubing or cannulation to one or more tubes, e.g., for intravenous or other infusion and/or for connection for purposes of transfer to and from other containers, such as cell culture and/or storage bags or other containers. Exemplary containers include infusion bags, intravenous solution bags, vials, including those with stoppers pierceable by a needle for injection.

The article of manufacture may further include a package insert or label with one or more pieces of identifying information and/or instructions for use. In some embodiments, the information or instructions indicates that the contents can or should be used to treat a particular condition or disease, and/or providing instructions therefor. The label or package insert may indicate that the contents of the article of manufacture are to be used for treating the disease or condition. In some embodiments, the label or package insert provides instructions to treat a subject, e.g., the subject from which the cells have been derived, via a method involving the administration of a first and one or more consecutive doses of the cells, e.g., according to any of the embodiments of the provided methods. In some embodiments, the instructions specify administration, in a first dose, of one unit dose, e.g., the contents of a single individual container in the article of manufacture, followed by one or more consecutive doses at a specified time point or within a specified time window and/or after the detection of the presence or absence or amount or degree of one or more factors or outcomes in the subject.

In some embodiments, the instructions specify administering one or more of the unit doses to the subject.

In some embodiments, the label or package insert or packaging comprises an identifier to indicate the specific identity of the subject from which the cells are derived and/or are to be administered. In the case of autologous transfer, the identity of the subject from which the cells are derived is the same as the identity of the subject to which the cells are to be administered. Thus, the identifying information may specify that the cells are to be administered to a particular patient, such as the one from which the cells were originally derived. Such information may be present in the packaging material and/or label in the form of a bar code or other coded identifier, or may indication the name and/or other identifying characteristics of the subject.

The article of manufacture in some embodiments includes one or more, typically a plurality, of containers containing compositions comprising the cells, e.g., individual unit dose forms thereof, and further include one or more additional containers with a composition contained therein which includes a further agent, such as a cytotoxic or otherwise therapeutic agent, for example, which is to be administered in combination, e.g., simultaneously or sequentially in any order, with the cells. Alternatively, or additionally, the article of manufacture may further include another or the same container comprising a pharmaceutically-acceptable buffer. It may further include other materials such as other buffers, diluents, filters, tubing, needles, and/or syringes.

The term "package insert" is used to refer to instructions customarily included in commercial packages of therapeutic products, that contain information about the indications, usage, dosage, administration, combination therapy, contraindications and/or warnings concerning the use of such therapeutic products.

V. Definitions

Unless defined otherwise, all terms of art, notations and other technical and scientific terms or terminology used herein are intended to have the same meaning as is commonly understood by one of ordinary skill in the art to which the claimed subject matter pertains. In some cases, terms with commonly understood meanings are defined herein for clarity and/or for ready reference, and the inclusion of such definitions herein should not necessarily be construed to represent a substantial difference over what is generally understood in the art.

As used herein, a "subject" is a mammal, such as a human or other animal, and typically is human. In some embodiments, the subject, e.g., patient, to whom the immunomodulatory polypeptides, engineered cells, or compositions are administered, is a mammal, typically a primate, such as a human. In some embodiments, the primate is a monkey or an ape. The subject can be male or female and can be any suitable age, including infant, juvenile, adolescent, adult, and geriatric subjects. In some embodiments, the subject is a non-primate mammal, such as a rodent.

As used herein, "treatment" (and grammatical variations thereof such as "treat" or "treating") refers to complete or partial amelioration or reduction of a disease or condition or disorder, or a symptom, adverse effect or outcome, or phenotype associated therewith. Desirable effects of treatment include, but are not limited to, preventing occurrence or recurrence of disease, alleviation of symptoms, diminishment of any direct or indirect pathological consequences of the disease, preventing metastasis, decreasing the rate of disease progression, amelioration or palliation of the disease state, and remission or improved prognosis. The terms do not imply complete curing of a disease or complete elimination of any symptom or effect(s) on all symptoms or outcomes.

As used herein, "delaying development of a disease" means to defer, hinder, slow, retard, stabilize, suppress and/or postpone development of the disease (such as cancer). This delay can be of varying lengths of time, depending on the history of the disease and/or individual being treated. As is evident, a sufficient or significant delay can, in effect, encompass prevention, in that the individual does not develop the disease. For example, a late stage cancer, such as development of metastasis, may be delayed.

"Preventing," as used herein, includes providing prophylaxis with respect to the occurrence or recurrence of a disease in a subject that may be predisposed to the disease but has not yet been diagnosed with the disease. In some embodiments, the provided cells and compositions are used to delay development of a disease or to slow the progression of a disease.

As used herein, to "suppress" a function or activity is to reduce the function or activity when compared to otherwise same conditions except for a condition or parameter of interest, or alternatively, as compared to another condition. For example, cells that suppress tumor growth reduce the rate of growth of the tumor compared to the rate of growth of the tumor in the absence of the cells.

An "effective amount" of an agent, e.g., a pharmaceutical formulation, cells, or composition, in the context of administration, refers to an amount effective, at dosages/amounts and for periods of time necessary, to achieve a desired result, such as a therapeutic or prophylactic result.

A "therapeutically effective amount" of an agent, e.g., a pharmaceutical formulation or engineered cells, refers to an amount effective, at dosages and for periods of time necessary, to achieve a desired therapeutic result, such as for treatment of a disease, condition, or disorder, and/or pharmacokinetic or pharmacodynamic effect of the treatment. The therapeutically effective amount may vary according to factors such as the disease state, age, sex, and weight of the subject, and the immunomodulatory polypeptides or engineered cells administered. In some embodiments, the provided methods involve administering the immunomodulatory polypeptides, engineered cells, or compositions at effective amounts, e.g., therapeutically effective amounts.

A "prophylactically effective amount" refers to an amount effective, at dosages and for periods of time necessary, to achieve the desired prophylactic result. Typically but not necessarily, since a prophylactic dose is used in subjects prior to or at an earlier stage of disease, the prophylactically effective amount will be less than the therapeutically effective amount.

The term "pharmaceutical formulation" refers to a preparation which is in such form as to permit the biological activity of an active ingredient contained therein to be effective, and which contains no additional components which are unacceptably toxic to a subject to which the formulation would be administered.

A "pharmaceutically acceptable carrier" refers to an ingredient in a pharmaceutical formulation, other than an active ingredient, which is nontoxic to a subject. A pharmaceutically acceptable carrier includes, but is not limited to, a buffer, excipient, stabilizer, or preservative.

As used herein, recitation that nucleotides or amino acid positions "correspond to" nucleotides or amino acid positions in a disclosed sequence, such as set forth in the Sequence listing, refers to nucleotides or amino acid positions identified upon alignment with the disclosed sequence to maximize identity using a standard alignment algorithm, such as the GAP algorithm. By aligning the sequences, one can identify corresponding residues, for example, using conserved and identical amino acid residues as guides. In general, to identify corresponding positions, the sequences of amino acids are aligned so that the highest order match is obtained (see, e.g.: Computational Molecular Biology, Lesk, A. M., ed., Oxford University Press, New York, 1988; Biocomputing: Informatics and Genome Projects, Smith, D. W., ed., Academic Press, New York, 1993; Computer Analysis of Sequence Data, Part I, Griffin, A. M., and Griffin, H. G., eds., Humana Press, New Jersey, 1994; Sequence Analysis in Molecular Biology, von Heinje, G., Academic Press, 1987; and Sequence Analysis Primer, Gribskov, M. and Devereux, J., eds., M Stockton Press, New York, 1991; Carrillo et al. (1988) SIAM J Applied Math 48: 1073).

An amino acid substitution may include replacement of one amino acid in a polypeptide with another amino acid. The substitution may be a conservative amino acid substitution or a non-conservative amino acid substitution. Amino acid substitutions may be introduced into a binding molecule, e.g., antibody, of interest and the products screened for a desired activity, e.g., retained/improved antigen binding, decreased immunogenicity, or improved ADCC or CDC.

Amino acids generally can be grouped according to the following common side-chain properties:

(1) hydrophobic: Norleucine, Met, Ala, Val, Leu, Ile;
(2) neutral hydrophilic: Cys, Ser, Thr, Asn, Gln;
(3) acidic: Asp, Glu;
(4) basic: His, Lys, Arg;
(5) residues that influence chain orientation: Gly, Pro;
(6) aromatic: Trp, Tyr, Phe.

In some embodiments, conservative substitutions can involve the exchange of a member of one of these classes for another member of the same class. In some embodiments, non-conservative amino acid substitutions can involve exchanging a member of one of these classes for another class.

As used herein, the singular forms "a," "an," and "the" include plural referents unless the context clearly dictates otherwise. For example, "a" or "an" means "at least one" or "one or more." It is understood that aspects and variations described herein include "consisting" and/or "consisting essentially of" aspects and variations.

Throughout this disclosure, various aspects of the claimed subject matter are presented in a range format. It should be understood that the description in range format is merely for convenience and brevity and should not be construed as an inflexible limitation on the scope of the claimed subject matter. Accordingly, the description of a range should be considered to have specifically disclosed all the possible sub-ranges as well as individual numerical values within that range. For example, where a range of values is provided, it is understood that each intervening value, between the upper and lower limit of that range and any other stated or intervening value in that stated range is encompassed within the claimed subject matter. The upper and lower limits of these smaller ranges may independently be included in the smaller ranges, and are also encompassed within the claimed subject matter, subject to any specifically excluded limit in the stated range. Where the stated range includes one or both of the limits, ranges excluding either or both of those included limits are also included in the claimed subject matter. This applies regardless of the breadth of the range.

The term "about" as used herein refers to the usual error range for the respective value readily known to the skilled person in this technical field. Reference to "about" a value or parameter herein includes (and describes) embodiments that are directed to that value or parameter per se. For example, description referring to "about X" includes description of "X". In certain embodiments, "about" a stated value refers to a value within ±25%, ±20%, ±10%, ±5%, ±1%, ±0.1%, or ±0.01% of the stated value.

As used herein, a composition refers to any mixture of two or more products, substances, or compounds, including cells. It may be a solution, a suspension, liquid, powder, a paste, aqueous, non-aqueous or any combination thereof.

As used herein, a statement that a cell or population of cells is "positive" for a particular marker refers to the detectable presence on or in the cell of a particular marker, typically a surface marker. When referring to a surface marker, the term refers to the presence of surface expression as detected by flow cytometry, for example, by staining with an antibody that specifically binds to the marker and detecting said antibody, wherein the staining is detectable by flow cytometry at a level substantially above the staining detected carrying out the same procedure with an isotype-matched control under otherwise identical conditions and/or at a level substantially similar to that for cell known to be positive for the marker, and/or at a level substantially higher than that for a cell known to be negative for the marker.

As used herein, a statement that a cell or population of cells is "negative" for a particular marker refers to the absence of substantial detectable presence on or in the cell of a particular marker, typically a surface marker. When referring to a surface marker, the term refers to the absence of surface expression as detected by flow cytometry, for example, by staining with an antibody that specifically binds to the marker and detecting said antibody, wherein the staining is not detected by flow cytometry at a level substantially above the staining detected carrying out the same procedure with an isotype-matched control under otherwise identical conditions, and/or at a level substantially lower than that for cell known to be positive for the marker, and/or at a level substantially similar as compared to that for a cell known to be negative for the marker.

The term "vector," as used herein, refers to a nucleic acid molecule capable of propagating another nucleic acid to which it is linked. The term includes the vector as a self-replicating nucleic acid structure as well as the vector incorporated into the genome of a host cell into which it has been introduced. Certain vectors are capable of directing the expression of nucleic acids to which they are operatively linked. Such vectors are referred to herein as "expression vectors."

The terms "host cell," "host cell line," and "host cell culture" are used interchangeably and refer to cells into which exogenous nucleic acid has been introduced, including the progeny of such cells. Host cells include "transformants" and "transformed cells," which include the primary transformed cell and progeny derived therefrom without regard to the number of passages. Progeny may not be completely identical in nucleic acid content to a parent cell, but may contain mutations. Mutant progeny that have the same function or biological activity as screened or selected for in the originally transformed cell are included herein.

VI. Exemplary Embodiments

Among the provided embodiments are:

1. A method for generating a cell composition, the method comprising:
  combining a first cell composition comprising naïve-like CD4+ T cells with a second cell composition comprising naïve-like CD8+ T cells to produce an input cell composition in which the ratio of naïve-like CD4+ T cells to naïve-like CD8+ T cells is between or about between 0.8:1 and 2.2:1, inclusive.

2. The method of embodiment 1, wherein the first cell composition is produced by isolating CD4+ T cells from a biological sample obtained from a subject and/or the second cell composition is produced by isolating CD8+ T cells from the biological sample obtained from the subject.

3. The method of embodiment 1 or embodiment 2, wherein, prior to the combining, the method comprises determining the number, number per volume, number per weight, and/or percentage of the naïve-like CD4+ T cells in the first composition and/or the number, number per volume, number per weight, and/or percentage of the naïve-like CD8+ T cells in the second composition.

4. The method of embodiment 2, wherein, prior to the combining, the method comprises determining the number, number per volume, number per weight, and/or percentage of the naïve-like CD4+ T cells and/or the number, number per volume, number per weight, and/or percentage of naïve-like CD8+ T cells in the biological sample from the subject.

5. The method of any of embodiments 1-4, wherein the ratio of the naïve-like CD4+ T cells to naïve-like CD8+ T cells in the input composition is adjusted or altered compared to the ratio of the naïve-like CD4+ T cells to naïve-like CD8+ T cells in the biological sample from the subject.

6. A method for generating a cell composition, the method comprising:
  determining the number, number per volume, number per weight, and/or percentage of naïve-like CD4+ T cells and naïve-like CD8+ T cells in a biological sample obtained from a subject or in one or more samples derived therefrom; and
  producing an input composition comprising CD4+ T cells and CD8+ T cells in which the ratio of the naïve-like CD4+ T cells to naive-like CD8+ T cells is between or about between 2.2:1 to 0.8:1, inclusive, wherein said ratio in the input composition is adjusted or altered compared to the ratio of the naïve-like CD4+ T cells to naive-like CD8+ T cells in the biological sample from the subject.

7. The method of any of embodiments 1-6, further comprising contacting the input composition with an agent comprising a nucleic acid molecule encoding a recombinant receptor under conditions to introduce the nucleic acid encoding the recombinant receptor into cells in the input composition.

8. A method of generating a cell composition, the method comprising:
   contacting an input composition comprising naïve-like CD4+ T cells and naïve-like CD8+ T cells from a biological sample from a subject with an agent comprising a nucleic acid molecule encoding a recombinant receptor under conditions to introduce the nucleic acid encoding the recombinant receptor into cells in the composition,
   wherein the ratio of naïve-like CD4+ T cells to naïve-like CD8+ T cells present in the input composition is between or about between 0.8:1 and 2.2:1, inclusive.

9. The method of embodiment 7 or embodiment 8, further comprising stimulating the cells, prior to, during and/or subsequent to said contacting, wherein stimulating comprises incubating the cells in the presence of one or more stimulating agents, wherein stimulating results in activation and/or proliferation of the cells.

10. A method of generating a cell composition, the method comprising:
    combining a first cell composition comprising naïve-like CD4+ T cells with a second cell composition comprising naïve-like CD8+ T cells to produce an input cell composition in which the ratio of naïve-like CD4+ T cells to naïve-like CD8+ T cells is between or about between 0.8:1 and 2.2:1, inclusive;
    contacting the input composition with an agent comprising a nucleic acid molecule encoding a recombinant receptor under conditions to introduce the nucleic acid encoding the recombinant receptor into cells in the composition; and
    stimulating the cells, prior to, during and/or subsequent to said contacting, wherein stimulating comprises incubating the cells in the presence of one or more stimulating agents, wherein stimulating results in activation and/or proliferation of the cells.

11. The method of any of embodiments 1-10, wherein the naïve-like CD4+ and/or the naïve-like CD8+ cells:
    are surface positive for a marker selected from the group consisting of CD45RA, CD27, CD28, and CCR7; and/or
    are surface negative for a marker selected from the group consisting of CD25, CD45RO, CD56, CD62L, and KLRG1; and/or
    have low expression of CD95; and/or
    are negative for intracellular expression of a cytokine selected from the group consisting of IL-2, IFN-γ, IL-4, IL-10.

12. The method of any of embodiments 1-11, wherein the naïve-like CD4+ and/or the naïve-like CD8+ cells:
    are surface positive for a T cell activation marker selected from the group consisting of CD45RA, CD27, CD28, and CCR7; and/or
    are surface negative for a marker selected from the group consisting of CD45RO, CD56, CD62L, and KLRG1; and/or
    have low expression of CD95.

13. The method of any of embodiments 1-12, wherein the naïve-like CD4+ and/or the naïve-like CD8+ cells are surface positive for CD45RA and CCR7.

14. The method of any of embodiments 1-12, wherein the naïve-like CD4+ and/or the naïve-like CD8+ cells are surface positive for CD27 and CCR7.

15. The method of any of embodiments 1-14, wherein the naïve-like CD4+ and the naïve-like CD8+ cells are surface positive for CD45RA, CD27 and CCR7 and are surface negative for CD45RO.

16. The method of any of embodiments 1-12, wherein the naïve-like CD4+ and/or the naïve-like CD8+ cells are surface positive for CCR7 and surface negative for CD62L.

17. The method of any of embodiments 3-16, wherein the number, number per volume, number per weight, and/or percentage of naïve-like CD4+ T cells and/or the number, number per volume, number per weight, and/or percentage of naïve-like CD8+ T cells is determined by flow cytometry.

18. The method of any of embodiments 8-17, wherein the ratio of naïve-like CD4+ T cells to naïve-like CD8+ T cells has been adjusted compared to the ratio of the naïve-like CD4+ T cells to naïve-like CD8+ T cells in a biological sample from the subject.

19. The method of any of embodiments 1-18, wherein the input composition comprises a ratio of naïve-like CD4+ cells to naïve-like CD8+ cells of between or about between 0.8:1 and 2.0:1, 0.8:1 and 1.6:1, 0.8:1 and 1.4:1, 0.8:1 and 1.2:1, 1.5:1 and 2:1, 1.6:1 and 1.8:1, or 1.0:1 and 1.2:1, each inclusive.

20. The method of any of embodiments 1-19, wherein the input composition comprises a ratio of naïve-like CD4+ cells to naïve-like CD8+ cells of or about 2:1, 1.9:1, 1.8:1, 1.7:1, 1.69:1, 1.6:1, 1.5:1, 1.4:1, 1.3:1, 1.2:1, 1.1:1, or 1.0:1.

21. The method of any of embodiments 1-20, wherein the input composition comprises a ratio of naïve-like CD4+ cells to naïve-like CD8+ cells of or about 1.1:1.

22. The method of any of embodiments 1-20, wherein the input composition comprises a ratio of naïve-like CD4+ cells to naïve-like CD8+ cells that are surface positive for CD45RA and CCR7 of or about 1.1:1.

23. The method of any of embodiments 1-20, wherein the input composition comprises a ratio of naïve-like CD4+ cells to naïve-like CD8+ cells that are surface positive for CD45RA and CD27 of or about 1.69:1.

24. A method for generating a cell composition, the method comprising:
    combining a first cell composition comprising CCR7+CD45RA+CD4+ T cells with a second cell composition comprising CCR7+CD45RA+CD8+ T cells to produce an input cell composition in which the ratio of CCR7+CD45RA+CD4+ T cells to CCR7+CD45RA+CD8+ T cells is between or about between 0.8:1 and 2.2:1, inclusive.

25. The method of embodiment 24, wherein the first cell composition is produced by isolating CD4+ T cells from a biological sample obtained from a subject and/or the second cell composition is produced by isolating CD8+ T cells from the biological sample obtained from the subject.

26. The method of embodiment 24 or embodiment 25, wherein, prior to the combining, the method comprises determining the number, number per volume, number per weight, and/or percentage of the CCR7+CD45RA+CD4+ T cells in the first composition and/or the number, number per volume, number per weight, and/or percentage of the CCR7+CD45RA+CD8+ T cells in the second composition.

27. The method of any of embodiments 24-26, wherein, prior to the combining, the method comprises determining the number, number per volume, number per weight, and/or percentage of the CCR7+CD45RA+CD4+ T cells and/or the number, number per volume, number per weight, and/or percentage of CCR7+CD45RA+CD8+ T cells in the biological sample from the subject.

28. The method of any of embodiments 24-27 wherein the ratio of the CCR7+CD45RA+CD4+ T cells to CCR7+CD45RA+CD8+ T cells in the input composition is adjusted or altered compared to the ratio of the CCR7+CD45RA+CD4+ T cells to CCR7+CD45RA+CD8+ T cells in the biological sample from the subject.

29. A method for generating a cell composition, the method comprising:
  determining the number, number per volume, number per weight, and/or percentage of CCR7+CD45RA+CD4+ T cells and CCR7+CD45RA+CD8+ T cells in a biological sample obtained from a subject or in one or more samples derived therefrom; and
  producing an input composition comprising CD4+ T cells and CD8+ T cells in which the ratio of the CCR7+CD45RA+CD4+ T cells to naive-like CD8+ T cells is between or about between 2.2:1 to 0.8:1, inclusive, wherein said ratio in the input composition is adjusted or altered compared to the ratio of the CCR7+CD45RA+CD4+ T cells to naive-like CD8+ T cells in the biological sample from the subject.

30. The method of any of embodiments 29, further comprising contacting the input composition with an agent comprising a nucleic acid molecule encoding a recombinant receptor under conditions to introduce the nucleic acid encoding the recombinant receptor into cells in the input composition.

31. A method of generating a cell composition, the method comprising:
  contacting an input composition comprising CCR7+CD45RA+CD4+ T cells and CCR7+CD45RA+CD8+ T cells from a biological sample from a subject with an agent comprising a nucleic acid molecule encoding a recombinant receptor under conditions to introduce the nucleic acid encoding the recombinant receptor into cells in the composition,
  wherein the ratio of CCR7+CD45RA+CD4+ T cells to CCR7+CD45RA+CD8+ T cells present in the input composition is between or about between 0.8:1 and 2.2:1, inclusive.

32. The method of embodiment 31, further comprising stimulating the cells, prior to, during and/or subsequent to said contacting, wherein stimulating comprises incubating the cells in the presence of one or more stimulating agents, wherein stimulating results in activation and/or proliferation of the cells.

33. A method of generating a cell composition, the method comprising:
  combining a first cell composition comprising CCR7+CD45RA+CD4+ T cells with a second cell composition comprising CCR7+CD45RA+CD8+ T cells to produce an input cell composition in which the ratio of CCR7+CD45RA+CD4+ T cells to CCR7+CD45RA+CD8+ T cells is between or about between 0.8:1 and 2.2:1, inclusive;
  contacting the input composition with an agent comprising a nucleic acid molecule encoding a recombinant receptor under conditions to introduce the nucleic acid encoding the recombinant receptor into cells in the composition; and
  stimulating the cells, prior to, during and/or subsequent to said contacting, wherein stimulating comprises incubating the cells in the presence of one or more stimulating agents, wherein stimulating results in activation and/or proliferation of the cells.

34. The method of any of embodiments 24-33, wherein the number, number per volume, number per weight, and/or percentage of CCR7+CD45RA+CD4+ T cells and/or the number, number per volume, number per weight, and/or percentage of CCR7+CD45RA+CD8+ T cells is determined by flow cytometry.

35. The method of any of embodiments 31-34, wherein the ratio of CCR7+CD45RA+CD4+ T cells to CCR7+CD45RA+CD8+ T cells has been adjusted compared to the ratio of the CCR7+CD45RA+CD4+ T cells to CCR7+CD45RA+CD8+ T cells in a biological sample from the subject.

36. The method of any of embodiments 24-35, wherein the input composition comprises a ratio of CCR7+CD45RA+CD4+ cells to CCR7+CD45RA+CD8+ cells of between or about between 0.8:1 and 2.0:1, 0.8:1 and 1.6:1, 0.8:1 and 1.4:1, 0.8:1 and 1.2:1, or 1.0:1 and 1.2:1, each inclusive.

37. The method of any of embodiments 24-36, wherein the input composition comprises a ratio of CCR7+CD45RA+CD4+ cells to CCR7+CD45RA+CD8+ cells of or about 1.5:1, 1.4:1, 1.3:1, 1.2:1, 1.1:1, or 1.0:1.

38. The method of any of embodiments 24-37, wherein the input composition comprises a ratio of CCR7+CD45RA+CD4+ cells to CCR7+CD45RA+CD8+ cells of or about 1.1:1.

39. A method for generating a cell composition, the method comprising:
  combining a first cell composition comprising CD27+CCR7+CD4+ T cells with a second cell composition comprising CD27+CCR7+CD8+ T cells to produce an input cell composition in which the ratio of CD27+CCR7+CD4+ T cells to CD27+CCR7+CD8+ T cells is between or about between 1.2:1 and 2.4:1, inclusive.

40. The method of embodiment 39, wherein the first cell composition is produced by isolating CD4+ T cells from a biological sample obtained from a subject and/or the second cell composition is produced by isolating CD8+ T cells from the biological sample obtained from the subject.

41. The method of embodiment 39 or embodiment 40, wherein, prior to the combining, the method comprises determining the number, number per volume, number per weight, and/or percentage of the CD27+CCR7+CD4+ T cells in the first composition and/or the number, number per volume, number per weight, and/or percentage of the CD27+CCR7+CD8+ T cells in the second composition.

42. The method of any of embodiments 39-41, wherein, prior to the combining, the method comprises determining the number, number per volume, number per weight, and/or percentage of the CD27+CCR7+CD4+ T cells and/or the number, number per volume, number per weight, and/or percentage of CD27+CCR7+CD8+ T cells in the biological sample from the subject.

43. The method of any of embodiments 39-42, wherein the ratio of the CD27+CCR7+CD4+ T cells to CD27+CCR7+CD8+ T cells in the input composition is adjusted or altered compared to the ratio of the CD27+CCR7+CD4+ T cells to CD27+CCR7+CD8+ T cells in the biological sample from the subject.

44. A method for generating a cell composition, the method comprising:
  determining the number, number per volume, number per weight, and/or percentage of CD27+CCR7+CD4+ T cells and CD27+CCR7+CD8+ T cells in a biological sample obtained from a subject or in one or more samples derived therefrom; and producing an input composition comprising CD4+ T cells and CD8+ T cells in which the ratio of the CD27+CCR7+CD4+ T cells to naive-like CD8+ T cells is between or about between 2.2:1 to 0.8:1, inclusive, wherein said ratio in the input composition is adjusted or altered compared to the ratio of the CD27+CCR7+CD4+ T cells to naive-like CD8+ T cells in the biological sample from the subject.

45. The method of any of embodiments 39-44, further comprising contacting the input composition with an agent comprising a nucleic acid molecule encoding a recombinant receptor under conditions to introduce the nucleic acid encoding the recombinant receptor into cells in the input composition.

46. A method of generating a cell composition, the method comprising:
contacting an input composition comprising CD27+CCR7+CD4+ T cells and CD27+CCR7+CD8+ T cells from a biological sample from a subject with an agent comprising a nucleic acid molecule encoding a recombinant receptor under conditions to introduce the nucleic acid encoding the recombinant receptor into cells in the composition,
wherein the ratio of CD27+CCR7+CD4+ T cells to CD27+CCR7+CD8+ T cells present in the input composition is between or about between 0.8:1 and 2.2:1, inclusive.

47. The method of embodiment 46 or embodiment 47, further comprising stimulating the cells, prior to, during and/or subsequent to said contacting, wherein stimulating comprises incubating the cells in the presence of one or more stimulating agents, wherein stimulating results in activation and/or proliferation of the cells.

48. A method of generating a cell composition, the method comprising:
combining a first cell composition comprising CD27+CCR7+CD4+ T cells with a second cell composition comprising CD27+CCR7+CD8+ T cells to produce an input cell composition in which the ratio of CD27+CCR7+CD4+ T cells to CD27+CCR7+CD8+ T cells is between or about between 0.8:1 and 2.2:1, inclusive;
contacting the input composition with an agent comprising a nucleic acid molecule encoding a recombinant receptor under conditions to introduce the nucleic acid encoding the recombinant receptor into cells in the composition; and
stimulating the cells, prior to, during and/or subsequent to said contacting, wherein stimulating comprises incubating the cells in the presence of one or more stimulating agents, wherein stimulating results in activation and/or proliferation of the cells.

49. The method of any of embodiments 39-48, wherein the number, number per volume, number per weight, and/or percentage of CD27+CCR7+CD4+ T cells and/or the number, number per volume, number per weight, and/or percentage of CD27+CCR7+CD8+ T cells is determined by flow cytometry.

50. The method of any of embodiments 39-49, wherein the ratio of CD27+CCR7+CD4+ T cells to CD27+CCR7+CD8+ T cells has been adjusted compared to the ratio of the CD27+CCR7+CD4+ T cells to CD27+CCR7+CD8+ T cells in a biological sample from the subject.

51. The method of any of embodiments 39-50, wherein the input composition comprises a ratio of CD27+CCR7+CD4+ cells to CD27+CCR7+CD8+ cells of between or about between 0.8:1 and 2.0:1, 0.8:1 and 1.6:1, 0.8:1 and 1.4:1, 0.8:1 and 1.2:1, or 1.0:1 and 1.2:1, each inclusive.

52. The method of any of embodiments 39-51, wherein the input composition comprises a ratio of CD27+CCR7+CD4+ cells to CD27+CCR7+CD8+ cells of or about 1.5:1, 1.4:1, 1.3:1, 1.2:1, 1.1:1, or 1.0:1.

53. The method of any of embodiments 39-52, wherein the input composition comprises a ratio of CD27+CCR7+CD4+ cells to CD27+CCR7+CD8+ cells of or about 1.1:1.

54. A method for generating a cell composition, the method comprising:
combining a first cell composition comprising CD62L-CCR7+CD4+ T cells with a second cell composition comprising CD62L-CCR7+CD8+ T cells to produce an input cell composition in which the ratio of CD62L-CCR7+CD4+ T cells to CD62L-CCR7+CD8+ T cells is between or about between 0.5:1 and 2:1, inclusive.

55. A method for generating a cell composition, the method comprising:
determining the number, number per volume, number per weight, and/or percentage of CD62L-CCR7+CD4+ T cells and CD62L-CCR7+CD8+ T cells in a biological sample obtained from a subject or in one or more samples derived therefrom; and
producing an input composition comprising CD4+ T cells and CD8+ T cells in which the ratio of the CD62L-CCR7+CD4+ T cells to naive-like CD8+ T cells is between or about between 0.5:1 and 2:1, inclusive, wherein said ratio in the input composition is adjusted or altered compared to the ratio of the CD62L-CCR7+CD4+ T cells to naive-like CD8+ T cells in the biological sample from the subject.

56. The method of embodiments 54 or 55, further comprising contacting the input composition with an agent comprising a nucleic acid molecule encoding a recombinant receptor under conditions to introduce the nucleic acid encoding the recombinant receptor into cells in the input composition.

57. A method of generating a cell composition, the method comprising:
combining a first cell composition comprising CD62L-CCR7+CD4+ T cells with a second cell composition comprising CD62L-CCR7+CD8+ T cells to produce an input cell composition in which the ratio of CD62L-CCR7+CD4+ T cells to CD62L-CCR7+CD8+ T cells is between or about between 0.5:1 and 2:1, inclusive;
contacting the input composition with an agent comprising a nucleic acid molecule encoding a recombinant receptor under conditions to introduce the nucleic acid encoding the recombinant receptor into cells in the composition; and
stimulating the cells, prior to, during and/or subsequent to said contacting, wherein stimulating comprises incubating the cells in the presence of one or more stimulating agents, wherein stimulating results in activation and/or proliferation of the cells.

58. The method of embodiment 56 or 57, wherein the number, number per volume, number per weight, and/or percentage of CD62L-CCR7+CD4+ T cells and/or the number, number per volume, number per weight, and/or percentage of CD62L-CCR7+CD8+ T cells is determined by flow cytometry.

59. The method of any of embodiments 55-58, wherein the ratio of CD62L-CCR7+CD4+ T cells to CD62L-CCR7+CD8+ T cells has been adjusted compared to the ratio of the CD62L-CCR7+CD4+ T cells to CD62L-CCR7+CD8+ T cells in a biological sample from the subject.

60. The method of any of embodiments 55-59, wherein the input composition comprises a ratio of CD62L-CCR7+CD4+ cells to CD62L-CCR7+CD8+ cells of between or about between 0.5:1 and 1.5:1, 1:1 and 2:1, 0.75:1 and 1.5:1, or 0.8:1 and 1.2:1, each inclusive.

61. The method of 55-60, wherein the input composition comprises a ratio of CD62L-CCR7+CD4+ cells to CD62L-CCR7+CD8+ cells of or about 1.2:1, 1.1:1, 1.0:1, 0.9:1, or 0.8:1.

62. The method of any of embodiments 2-9, 18-23, 25-32, 34-38, 40-47, 50-53, 55-56, or 59-61, wherein the biological sample is or is obtained from a blood, plasma or serum sample.

63. The method of any of embodiments 2-9, 18-23, 25-32, 34-38, 40-47, 50-53, 55-56, or 59-62, wherein the biological sample is or comprises a whole blood sample, a buffy coat sample, a peripheral blood mononuclear cells (PBMC) sample, an unfractionated T cell sample, a lymphocyte sample, a white blood cell sample, an apheresis product, or a leukapheresis product.

64. The method of any of embodiments 2-9, 18-23, 25-32, 34-38, 40-47, 50-53, 55-56, or 59-63, wherein the biological sample is or is obtained from an apheresis or leukapheresis sample.

65. The method of any of embodiments 2-9, 18-23, 25-32, 34-38, 40-47, 50-53, 55-56, or 59-64, wherein the subject is a human subject.

66. The method of any of embodiments 1-65, wherein the input composition comprises from or from about $1 \times 10^7$ to $5 \times 10^9$ total cells or total T cells, from or from about $5 \times 10^7$ to $1 \times 10^9$ total cells or total T cells, from or from about $1 \times 10^8$ to $5 \times 10^8$ total cells or total T cells, or from or from about $2 \times 10^8$ to $5 \times 10^8$ total cells or total T cells, or of viable populations of any of the foregoing.

67. The method of any of embodiments 1-66, wherein the input composition comprises at least or at least about $1 \times 10^8$, $2 \times 10^8$, $3 \times 10^8$, $4 \times 10^8$, or $5 \times 10^8$ total cells or total T cells or a viable population of any of the foregoing.

68. The method of any of embodiments 9-23, 32-38, 47-53, 57-67, wherein the one or more stimulating agent is capable of activating T cells, CD4+ T cells and/or CD8+ T cells; is capable of inducing a signal through a TCR complex; and/or is capable of inducing proliferation of T cells, CD4+ T cells and/or CD8+ T cells.

69. The method of any of embodiments 9-23, 32-38, 47-53, 57-68, wherein the one or more stimulating agent comprises a primary agent that binds to a member of a TCR complex, optionally that specifically binds to CD3.

70. The method of embodiment 69, wherein the one or more stimulating agent further comprises a secondary agent that specifically binds to a T cell costimulatory molecule.

71. The method of embodiment 70, wherein the costimulatory molecule is selected from the group consisting of CD28, CD137 (4-1-BB), OX40, or ICOS.

72. The method of embodiment 70 or embodiment 71, wherein the primary and secondary agents comprise antibodies, optionally wherein the one or more stimulating agent comprises incubation with an anti-CD3 antibody and an anti-CD28 antibody.

73. The method of any of embodiments 9-23, 32-38, 47-53, 57-72, wherein the one or more stimulating agents are present on the surface of a solid support, optionally a bead.

74. The method of any of embodiments 9-23, 32-38, 47-53, 57-73, wherein the one or more one stimulating agent is selected from the group consisting of CD3-binding molecules; CD28-binding molecules; recombinant IL-2; recombinant IL-15; and recombinant IL-7, a vaccine comprising an antigen specifically recognized by the antigen receptor, and an anti-idiotype antibody that specifically binds the antigen receptor or combinations thereof.

75. The method of any of embodiments 9-23, 32-38, 47-53, 57-74, wherein the incubation is carried out for 2 to 15 days, 2 to 12 days, 2 to 12 days, 2 to 8 days, 2 to 6 days, 2 to 4 days, 4 to 12 days, 4 to 10 days, 4 to 8 days, 4 to 6 days, 6 to 12 days, 6 to 10 days, 6 to 8 days, 8 to 12 days, 8 to 10 days, or 10 to 12 days.

76. The method of any of embodiments 9-23, 32-38, 47-53, 57-75, wherein the incubation is carried out for at least or about at least or 4 days, 6 days, 8 days, 10 days or 12 days.

77. The method of any of embodiments 7-23, 30-39, 45-53, or 57-76, wherein the agent comprising the nucleic acid molecule is a viral vector or is a transposon.

78. The method of embodiment 77, wherein the agent comprising the nucleic acid molecule is a viral vector and the viral vector is a retroviral vector.

79. The method of embodiment 78, wherein the viral vector is a lentiviral vector or a gammaretroviral vector.

80. The method of any of embodiments 7-23, 30-38, 45-53, or 56-79, wherein the recombinant receptor is capable of binding to a target antigen that is associated with, specific to, and/or expressed on a cell or tissue of a disease, disorder or condition.

81. The method of embodiment 80, wherein the disease, disorder or condition is an infectious disease or disorder, an autoimmune disease, an inflammatory disease, or a tumor or a cancer.

82. The method of embodiment 80 or embodiment 81, wherein the target antigen is a tumor antigen.

83. The method of any of embodiments 80-82, wherein the target antigen is selected from among Receptor Tyrosine Kinase Like Orphan Receptor 1 (ROR1), B cell maturation antigen (BCMA), carbonic anhydrase 9 (CA9, also known as CAIX or G250), Her2/neu (receptor tyrosine kinase erbB2), CD19, CD20, CD22, mesothelin (MSLN), carcinoembryonic antigen (CEA), and hepatitis B surface antigen, anti-folate receptor, CD23, CD24, CD30, CD33, CD38, CD44, chondroitin sulfate proteoglycan 4 (CSPG4), EGFR, epithelial glycoprotein 2 (EPG-2), epithelial glycoprotein 40 (EPG-40), ephrin receptor A2 (EPHa2), Her3 (erb-B3), Her4 (erb-B4), erbB dimers, type III epidermal growth factor receptor mutation (EGFR vIII), folate binding protein (FBP), Fc receptor like 5 (FCRL5, also known as Fc receptor homolog 5 or FCRH5), fetal acetylcholine receptor (fetal AchR), ganglioside GD2, ganglioside GD3, Human leukocyte antigen A1 (HLA-A1), Human leukocyte antigen A2 (HLA-A2), IL-22 receptor alpha(IL-22Rα), kinase insert domain receptor (kdr), kappa light chain, Leucine Rich Repeat Containing 8 Family Member A (LRRC8A), Lewis Y, L1-cell adhesion molecule (L1-CAM), Melanoma-associated antigen (MAGE)-A1, MAGE-A3, MAGE-A6, MAGE-A10, Preferentially expressed antigen of melanoma (PRAME), survivin, tumor-associated glycoprotein 72 (TAG72), B7-H3, B7-H6, IL-13 receptor alpha 2 (IL-13Rα2), Human high molecular weight-melanoma-associated antigen (HMW-MAA), CD171, folate receptor-alpha, CD44v7/8, avf3.6 integrin (avb6 integrin), 8H9, neural cell adhesion molecule (NCAM), vascular endothelial growth factor receptor (VEGF receptors or VEGFR), Trophoblast glycoprotein (TPBG also known as 5T4), NKG2D ligands, CD44v6, dual antigen, a cancer-testes antigen, murine cytomegalovirus (CMV), mucin 1 (MUC1), MUC16, prostate stem cell antigen (PSCA), prostate specific membrane antigen (PSMA), natural killer group 2 member D (NKG2D) ligands, cancer/testis antigen 1B (CTAG, also known as NY-ESO-1 and LAGE-2), melan A (MART-1), glycoprotein 100 (gp100), glypican-3 (GPC3), G Protein Coupled Receptor 5D (GPRCSD), oncofetal antigen, TAG72, Tyrosinase related protein 1 (TRP1, also known as TYRP1 or gp75), Tyrosinase related protein 2 (TRP2, also known as dopachrome tautomerase, dopachrome delta-isomerase or DCT), vascular endothelial growth factor receptor 2 (VEGF-R2), carcinoembryonic antigen (CEA), estrogen receptor, progesterone receptor, a prostate specific antigen, ephrinB2, CD123, CD133, c-Met, O-acetylated GD2 (OGD2), CE7 epitope of L1-CAM, Wilms Tumor 1 (WT-1), a cyclin, cyclin A2, C—C Motif Chemokine Ligand 1 (CCL-1), CD138, a pathogen-specific antigen or pathogen-expressed antigen, and an antigen associated with a universal tag.

84. The method of any of embodiments 7-23, 30-38, 45-53, or 56-83, wherein the recombinant receptor is or comprises a functional non-TCR α ntigen receptor or a TCR or antigen-binding fragment thereof.

85. The method of any of embodiments 7-23, 30-38, 45-53, or 56-83, wherein the recombinant receptor is a chimeric antigen receptor (CAR).

86. The method of embodiment 85, wherein the chimeric antigen receptor comprises an extracellular domain comprising an antigen-binding domain.

87. The method of embodiment 86, wherein the antigen-binding domain is or comprises an antibody or an antibody fragment thereof, which optionally is a single chain fragment.

88. The method of embodiment 87, wherein the fragment comprises antibody variable regions joined by a flexible linker.

89. The method of embodiment 87 or embodiment 88, wherein the fragment comprises an scFv.

90. The method of any of embodiments 86-89, wherein the chimeric antigen receptor further comprises a spacer and/or a hinge region.

91. The method of any of embodiments 86-90, wherein the chimeric antigen receptor comprises an intracellular signaling region.

92. The method of embodiment 91, wherein the intracellular signaling region comprises an intracellular signaling domain.

93. The method of embodiment 92, wherein the intracellular signaling domain is or comprises a primary signaling domain, a signaling domain that is capable of inducing a primary activation signal in a T cell, a signaling domain of a T cell receptor (TCR) component, and/or a signaling domain comprising an immunoreceptor tyrosine-based activation motif (ITAM).

94. The method of embodiment 93, wherein the intracellular signaling domain is or comprises an intracellular signaling domain of a CD3 chain, optionally a CD3-zeta (CD3ζ) chain, or a signaling portion thereof.

95. The method of any of embodiments 91-94, wherein the chimeric antigen receptor further comprises a transmembrane domain disposed between the extracellular domain and the intracellular signaling region.

96. The method of any of embodiments 91-95, wherein the intracellular signaling region further comprises a costimulatory signaling region.

97. The method of embodiment 96, wherein the costimulatory signaling region comprises an intracellular signaling domain of a T cell costimulatory molecule or a signaling portion thereof.

98. The method of embodiment 96 or embodiment 97, wherein the costimulatory signaling region comprises an intracellular signaling domain of a CD28, a 4-1BB or an ICOS or a signaling portion thereof.

99. The method of any of embodiments 96-98, wherein the costimulatory signaling region is between the transmembrane domain and the intracellular signaling region.

100. The method of any of embodiments 2-9, 11-23, 25-32, 34-38, 40-47, 50-53, 55-56, or 59-99, wherein the subject has a disease or condition, optionally wherein the recombinant receptor specifically recognizes or specifically bind to an antigen associated with, or expressed or present on cells of, the disease or condition.

101. The method of any of embodiments 1-100, wherein the method produces an output composition in which the ratio of recombinant receptor-expressing CD4+ T cells to recombinant receptor-expressing CD8+ T cells, optionally the ratio of viable cells thereof, varies by no more than 20% or no more than 10% or no more than 5% from an average of said ratio in a plurality of T cell compositions produced by the method and/or varies from such average by no more than one standard deviation.

102. The method of any of embodiments 1-101, wherein the method produces an output composition in which the ratio of recombinant receptor-expressing CD4+ T cells to recombinant receptor-expressing CD8+ T cells, optionally the ratio of viable cells thereof, is between at or about 0.5:1 and 2:1 or 0.8:1 and 1.6:1 or 1:1 and 1.5:1, each inclusive.

103. The method of any of embodiment 101 or embodiment 102, wherein the ratio of recombinant receptor-expressing CD4+ T cells to recombinant receptor-expressing CD8+ T cells, optionally the ratio of viable cells thereof, in the output composition is or is about 1.2:1, 1.1:1, 1:1, 0.9:1, or 0.8:1.

104. The method of any of embodiments 101-103, wherein the ratio of recombinant receptor-expressing CD4+ T cells to recombinant receptor-expressing CD8+ T cells, optionally the ratio of viable cells thereof, in the output composition is or is about 1:1.

105. The method of any of embodiments 66-104, wherein the viable cells comprise cells that are apoptotic marker negative (−), optionally wherein the apoptotic marker is Annexin V or active Caspase 3.

106. The method of any of embodiments 1-105 that is performed in vitro or ex vivo.

107. An output composition produced by the method of any of embodiments 104.

108. A pharmaceutical composition comprising the output composition of embodiment 107.

109. The pharmaceutical composition of embodiment 108, further comprising a pharmaceutical carrier.

110. A method of treatment, comprising administering to a mammalian subject an output composition produced by the method of any of embodiments 105 or a pharmaceutical composition of embodiment 108 or embodiment 109.

111. The method of embodiment 110, wherein the cells are derived from the subject to which the cells are administered.

VII. EXAMPLES

The following examples are included for illustrative purposes only and are not intended to limit the scope of the invention.

Example 1: Correlation Between Phenotype of Starting Composition and the Ratio of CD4+ to CD8+ CAR Expressing Cells in a CAR+ T Cell Composition CAR+ T cell compositions containing autologous T cells expressing a chimeric antigen receptor (CAR) were generated from apheresis collected from 11 separate donors with four test samples separately processed from each donor sample. One donor was a patient with myeloma and the remaining donors were healthy subjects. After washing each apheresis sample, each sample was assessed by flow cytometry for cell viability using an apoptotic marker and for surface expression of CD4 and CD8 to determine the ratio of viable CD4+ to CD8+ T cells (CD4/CD8 ratio) in each apheresis sample run.

CD4+ and CD8+ T cells were selected from apheresis samples by immuno-affinity-based selection. CD4+ T cells and CD8+ T cells were combined at a 1:1 ratio of viable CD4+ to CD8+ cells. A sample of the combined cells was assessed by flow cytometry for cell viability using an apoptotic specific marker and for surface expression of markers that included CD4, CD8, CD45RA and CCR7. The ratio of viable CD45RA+/CCR7+CD4+ to viable CD45RA+/CCR7+CD8+(CD45RA+/CCR7+CD4/CD8 ratio) in the mixture of selected CD4 and CD8 cells was determined.

To generate a CAR+ T cell composition, the combined CD4+ and CD8+ T cells were activated by incubation with anti-CD3 and anti-CD28 antibody-coated beads in the presence of cytokines, and then were transduced with a lentiviral vector encoding an anti-BCMA CAR. The CAR contained an scFv antigen-binding domain specific for BCMA, a spacer, a CD28 transmembrane region, a 4-1BB costimulatory signaling region, and a CD3-zeta derived intracellular signaling domain. After transduction, cells were expanded and then frozen by cryopreservation. The cells in the frozen composition were thawed and assessed by flow cytometry for viability, surface expression of CD4 and CD8, and CAR expression using a BCMA-Fc reagent. The ratio of viable CAR+ cells that were CD4+ to viable CAR+ cells that were CD8+ was determined (CAR+ CD4/CD8 ratio).

The CD4/CD8 ratio in the apheresis samples, or the CD45RA+/CCR7+CD4/CD8 ratio in the mixture of selected CD4 and CD8 cells, was compared, post facto, to the CAR+CD4/CD8 ratio in the engineered CAR-T cell composition. The degree of correlation of the mean ratios from each subject was assessed by bivariate analysis and the bivariate normal ellipse representing the 0.990 probability region for the plotted data are shown in in FIGS. 1A and 1B, respectively. Table 1A and Table 1B display the results of a Pearson correlation analysis carried out with respect to the data plotted in FIG. 1A and FIG. 1B, respectively.

TABLE 1A

Bivariate Normal Ellipse P = 0.990;
CD4/CD8 ratio in apheresis sample

| Variable | Mean | Std. Dev. | Correlation | Signif. Prob. |
|---|---|---|---|---|
| Starting CD4/CD8 Ratio | 1.57 | 0.42 | −0.11 | 0.75 |
| Final CAR+ CD4/CD8 ratio | 1.35 | 1.00 | | |

TABLE 1B

Bivariate Normal Ellipse P = 0.990; CD45RA+/CCR7+
CD4/CD8 ratio in mixture of selected CD4 and CD8 cells

| Variable | Mean | Std. Dev. | Correlation | Signif. Prob. |
|---|---|---|---|---|
| Starting CD45RA+/CCR7+ CD4/CD8 Ratio | 1.52 | 1.09 | 0.99 | <0.0001 |
| Final CAR+ CD4/CD8 ratio | 1.35 | 1.00 | | |

As shown in FIG. 1A and Table 1A, in this experiment the viable CD4/CD8 ratio of CD4+ and CD8+ T cells from the apheresis sample did not correlate with the CAR+ CD4/CD8 ratio in the final composition. This result is consistent with observations that mixing of purified CD4 and CD8 T cells at a 1:1 ratio prior to activation based on total viable cells does not necessarily correlate with a 1:1 ratio of CD4+ and CD8+ T cells in an output T cell composition.

Figure 1B:
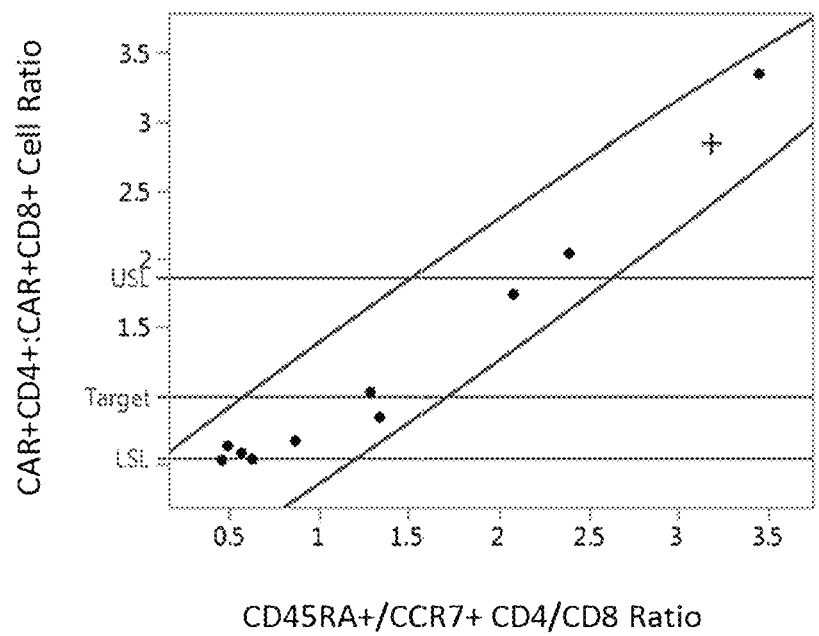
FIG. 1B shows a plot of bivariate fit analysis of the CD45RA+/CCR7+CD4/CD8 ratio in a starting mixture of selected CD4 and CD8 cells compared to the CAR+ CD4+/CD8+ ratio in a T cell composition after T cell activation, transduction with a chimeric antigen receptor (CAR) construct and expansion. The curved lines represent the boundaries of the bivariate normal ellipse at p=0.990. Data points represent the mean ratios of four samples from each subject, including healthy subjects (circles) and a subject with myeloma (plus sign).

As shown in FIG. 1B and Table 1B, in this experiment, the CAR+ CD4/CD8 ratio in the final T cell composition positively correlated with the starting naïve-like cell CD4/CD8 T cell ratio, as determined by the ratio of CD45RA+/CCR7+CD4/CD8 ratio in the mixture of CD4 and CD8 cells. In particular, the results in FIG. 1B show that the correlation between the ratio of CD45RA+/CCR7+/CD4+ cells to CD45RA+/CCR7+/CD8+ cells in the starting sample to the CAR+ CD4/CD8 ratio in the T cell composition is high based on Pearson correlation coefficient and p value <0.0001. This correlation held despite variations in input composition and between process runs. Based on this model fit from this exemplary sample set, a CD45RA+/CCR7+/CD4+ to CD45RA+/CCR7+/CD8+ ratio of about 1.1:1 was determined to result in a CAR+ CD4/CD8 ratio of about 1:1 in the output T cell composition.

These data support the hypothesis that it is possible to control and/or adjust the ratio and/or composition of CD4+ cells and CD8+ cells in an output T cell composition by controlling the ratio of a naïve-like CD4+ subset to a naïve-like CD8+ T cell subject, such as determined by CD45RA+ and CCR7+ surface expression.

Example 2: Correlation Between Phenotypes of the Starting T Cell Population and the Ratio of CAR+ CD4+ to CAR+CD8+ T Cells in Engineered CAR+ T Cell Compositions A total of 50 engineered CAR+ T cell compositions were generated from apheresis samples collected from 15 healthy donors and one multiple myeloma patient. To generate the CAR-T compositions, viable selected CD4+ and CD8+ T cells were combined into a starting cell composition at a 1:1 ratio and then activated, transduced, and expanded as described in Example 1. Samples from the starting compositions of combined viable CD4+ and CD8+ T cells were assessed by flow cytometry for viability and for surface expression of markers that included CD4, CD8, CD27, CD45RA, CCR7, and CD62L.

Samples from the engineered CAR+ T cell compositions were assessed for CAR expression and for surface expression of markers that included CD4 and CD8. Averages were calculated for ratios of CD4+CAR+ T cells to CD8+CAR+ T cells (CAR+ CD4/CD8 ratio) of individual CAR+ T cell compositions of the same donor that were generated using the same exemplary process as described in Example 1, except that certain process parameters were varied. The average CAR+ CD4/CD8 ratios were analyzed for correlations with various phenotypes of the starting compositions of combined viable CD4+ to CD8+ cells. Combining the selected CD4+ and CD8+ T-cells at 1:1 ratio prior to the activation did not necessarily correlate with a 1:1 CAR+ CD4/CD8 ratio in the generated output cell compositions.

Figure 2A:
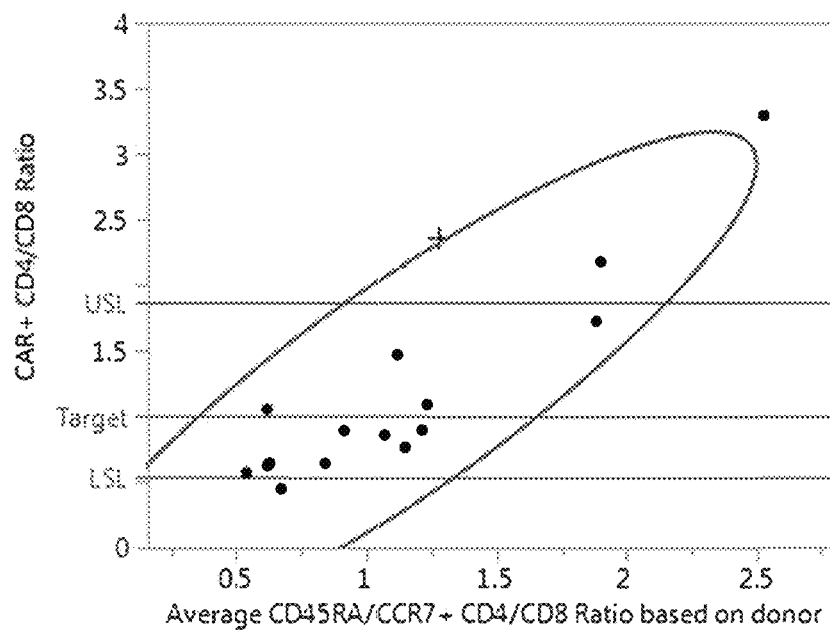
FIGS. 2A-2C show plots of bivariate fit analysis of the ratio of the different phenotypes cells of in a starting mixture of selected CD4 and CD8 cells compared to the CAR+ CD4+/CD8+ ratio in an engineered CAR+ T cell composition.
Figure 2B:
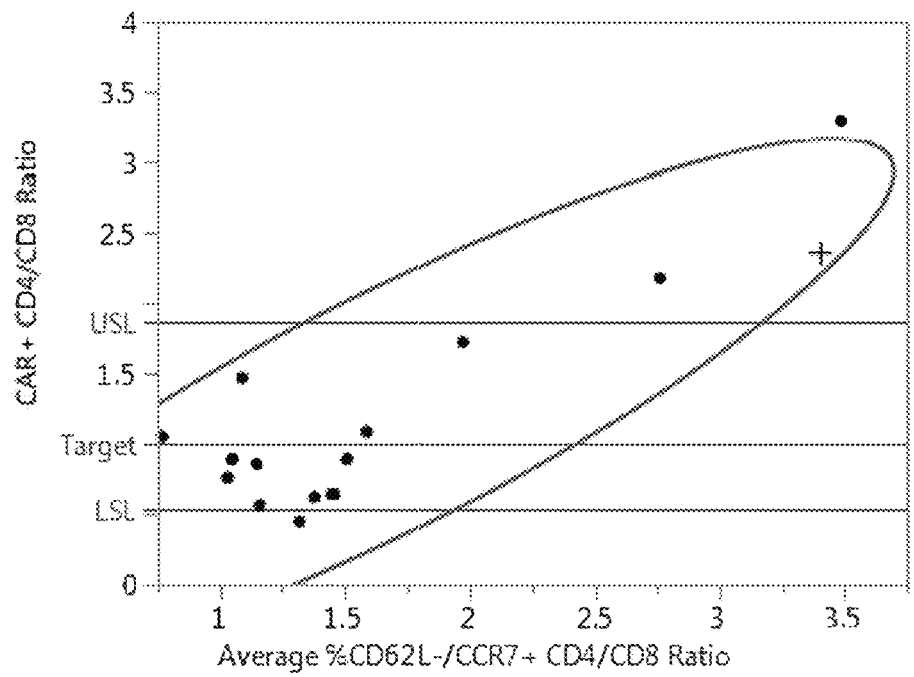
Figure 2C:
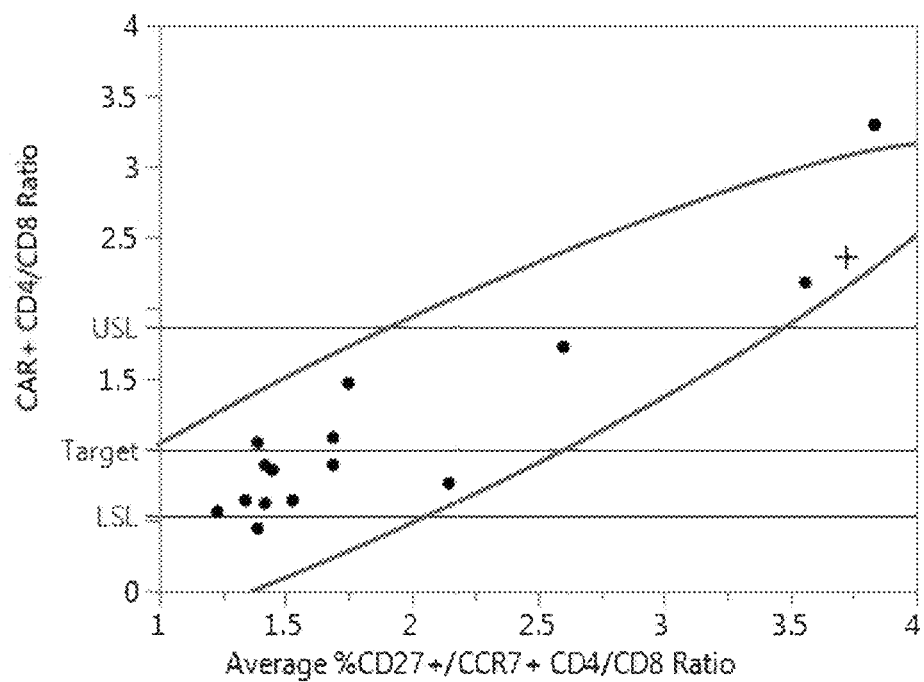

The degree of the correlations between the average CAR+ CD4/CD8 ratios and the phenotypes from each donor were assessed by bivariate analysis. The bivariate normal ellipses representing the 0.950 probability are shown for ratios for CD45RA+/CCR7+/CD4+ T cell to CD45RA+/CCR7+/CD8+(CD45RA+/CCR7+CD4/CD8 ratio; FIG. 2A); CD62L−/CCR7+/CD4+ to CD62L−/CCR7+/CD8+ (CD62L−/CCR7+CD4/CD8 ratio; FIG. 2B); and CD27+/CCR7+/CD4+ to CD27+/CCR7+/CD8+ ratio (CD27+/CCR7+CD4/CD8 ratio; FIG. 2C) Table 2 displays the results of Pearson correlation analysis carried out with respect to the data plotted in FIGS. 2A-2C.

TABLE 2

| Bivariate Normal Ellipse P = 0.950 for Exemplary Phenotypes | | | | |
|---|---|---|---|---|
| Phenotype | Mean | Std. Dev. | Correlation | Signif. Prob. | Number |
| CD45RA+/CCR7+ CD4/CD8 Ratio | 1.14 | 0.56 | 0.88 | <0.0001 | 16 |
| % CD62L−/CCR7+ CD4/CD8 Ratio) | 1.66 | 0.83 | 0.88 | <0.0001 | 16 |
| % CD27+/CCR7+ CD4/CD8 Ratio | 2.01 | 0.91 | 0.93 | <0.0001 | 16 |
| Output CAR+ CD4/CD8 ratio | 1.22 | .80 | | | |

The analysis indicated that using the exemplary protocol described in Example 1, the CAR+ CD4/CD8 ratio positively correlated with the CD45RA+/CCR7+CD4/CD8 T-cell ratio for healthy donors but, in this experiment, not for the one patient sample. The CAR+ CD4/CD8 ratio was shown to correlate positively with CD62L−/CCR7+CD4/CD8 and CD27+/CCR7+CD4/CD8 ratios in both healthy donor and patient sample starting cell compositions. Based on the model fit, it was calculated that a starting CD27+/CCR7+CD4/CD8 ratio of 1.69:1 would be predicted to generate an output cell composition with a CAR+ CD4/CD8 ratio of approximately 1:1. These results were consistent with the finding that the CD27+CCR7+CD4/CD8 ratio can be adjusted in the starting cell composition to control and/or predict the resulting CAR+CD4/CD8 ratio of the engineered cell composition.

Example 3: Process to Produce CAR+ T Cell Composition Based on Phenotype of Starting Composition Ten CAR+ T cell compositions containing autologous T cells expressing a CAR were generated from apheresis collected from 3 separate donors, including two healthy donors and one multiple myeloma patient. CD4+ and CD8+ T cells were selected from apheresis samples as described in Example 1. The apheresis samples and the selected CD4+ and CD8+ T cells were assessed by flow cytometry for viability and surface markers including CD27, CCR7, CD4, and CD8. The frequency of CD27+/CCR7+ cells among the selected CD4+ and CD8+ T cells was determined, with each donor exhibiting a different ratio of CD27+/CCR7+CD4+ cells to CD27+/CCR7+CD8+ cells in apheresis samples. For example, the patient sample exhibited a ratio of CD27+/ CCR7+CD4+ cells to CD27+/CCR7+CD8+ cells of approximately 12.2:1, whereas the two healthy donor samples exhibited ratios of CD27+/CCR7+CD4+ cells to CD27+/CCR7+CD8+ cells of 3.56:1 and 2.15:1. Input cell compositions were generated by either (1) combining selected CD4+ and CD8+ cells at a 1:1 viable CD4+ to CD8+ ratio (viable CD4/CD8) or (2) combining CD4+ and CD8+ cells at a 1.69:1 ratio of CD27+/CCR7+CD4+ cells and CD27+/CCR7+CD8+ cells (CD27+/CCR7+CD4/CD8) before activation. A total of either 300×10$^6$ cells or 100×10$^6$ cells from the input compositions were activated, transduced, and expanded to generate output cell compositions substantially as described in Example 1.

The total number of cells in the activation step was not observed to impact the CAR+CD4/CD8 ratio. The output cell compositions generated from starting compositions containing CD27+/CCR7+CD4/CD8 cells mixed at about a 1.69:1 ratio, including from the patient sample, exhibited CAR+ CD4/CD8 ratios that were close to of the desired target ratio of 1:1 (e.g. between approximately 1.86:1 to 1:1.86). Output cell compositions generated from input compositions containing viable CD4/CD8 cells mixed at a 1:1 ratio showed grater variation in CAR+ CD4/CAR+CD8 ratios, compared with compositions generated from input compositions containing CD4+ and CD8+ cells at a 1.69:1 ratio of CD27+/CCR7+CD4+ cells and CD27+/CCR7+CD8+ cells. In this experiment, output compositions generated using patient material in an exemplary process exhibited CAR+ CD4/CAR+CD8 ratios of approximately 7.6 and 8.6 when 100×10$^6$ cells or 300×10$^6$ cells were activated, respectively. When mixed based on the phenotype in a similar process, for example a 1.69:1 ratio of CD27+CCR7+CD4+:CD27+CCR7+CD8+ T cells, the final CAR+ CD4/CAR+CD8 ratio was 1.6 and 1.3 when 100×10$^6$ cells or 300×10$^6$ cells were activated, respectively. These results are consistent with a finding that particular phenotypes, e.g. CD27+/CCR7+ cells, may correlate with the resulting CAR+ CD4/CAR+CD8 ratios in output compositions generated from both healthy donor and patient samples.

Example 4: Assessment of Samples from Diseased Subjects of Correlation Between Phenotype of Starting Composition and the Ratio of CD4+ to CD8+ CAR Expressing Cells in a CAR+ T Cell Composition CAR+ T cell compositions containing autologous T cells expressing a chimeric antigen receptor (CAR) were generated from apheresis collected from 7 separate donors with multiple myeloma.

CD4+ and CD8+ T cells were selected from apheresis samples by immuno-affinity-based selection. CD4+ T cells and CD8+ T cells were combined at a 1:1 ratio of viable CD4+ to CD8+ cells. A sample of the combined cells was assessed for surface expression of markers that included CD4, CD8, CD27, CD45RA, CCR7 and CD62L. In the mixture of selected CD4 and CD8 cells, the ratio of the following cell phenotypes were determined (1) CD27+/CCR7+CD4+ cells to CD27+/CCR7+CD8+ cells (CD27+/CCR7+CD4/CD8 ratio), (2) CD45RA+/CCR7+CD4+ cells to CD45RA+/CCR7+CD8+ cells (CD45RA+/CCR7+CD4/CD8 ratio), and (3) CD62L−/CCR7+CD4+ cells to CD62L−/CCR7+CD8+ cells (CD62L−/CCR7+CD4/CD8 ratio).

A CAR+ T cell composition expressing an anti-BCMA CAR was generated using the process substantially as described in Example 1, including activation, transduction, expansion and cryopreservation of generated cells. The cells in the frozen composition were thawed and assessed by flow cytometry for viability, surface expression of CD4 and CD8, and CAR expression using a BCMA-Fc reagent. The ratio of viable CAR+ cells that were CD4+ to viable CAR+ cells that were CD8+ was determined (CAR+ CD4/CD8 ratio).

Figure 3A:
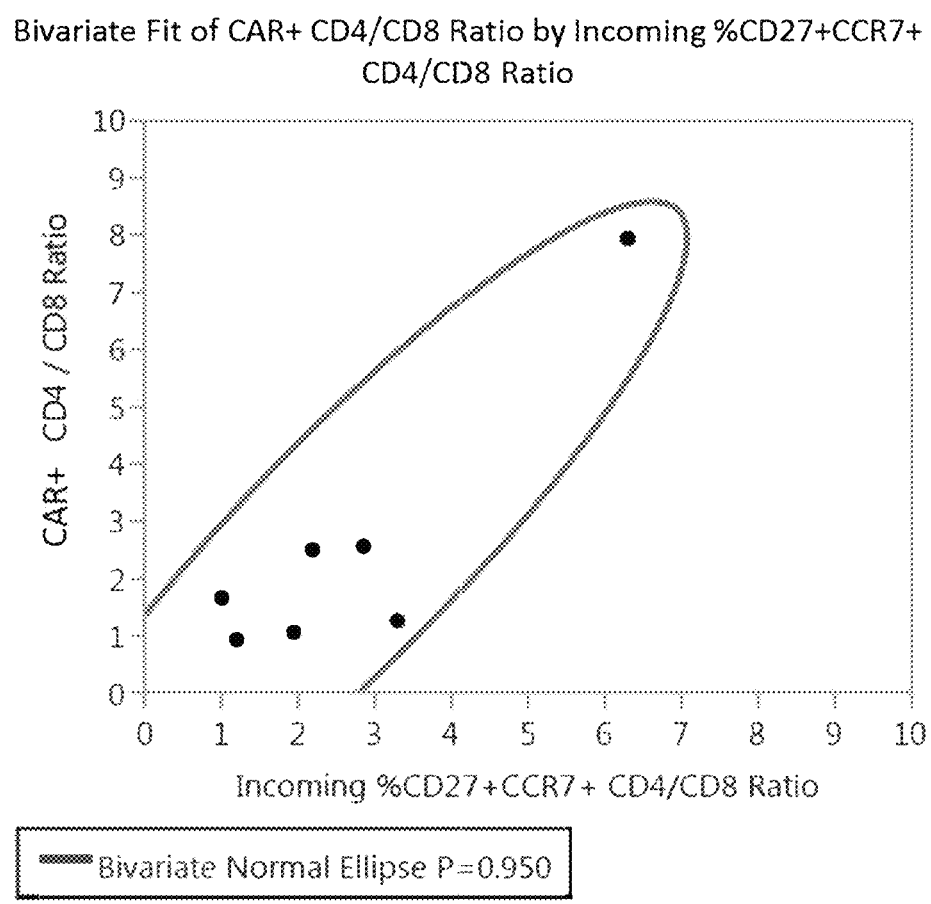
FIGS. 3A-3C show plots of bivariate fit analysis of the ratio of the different phenotypes cells of in a starting mixture of selected CD4 and CD8 cells from seven donors with multiple myeloma compared to the CAR+ CD4+/CD8+ ratio in the generated engineered CAR+ T cell composition.
Figure 3B:
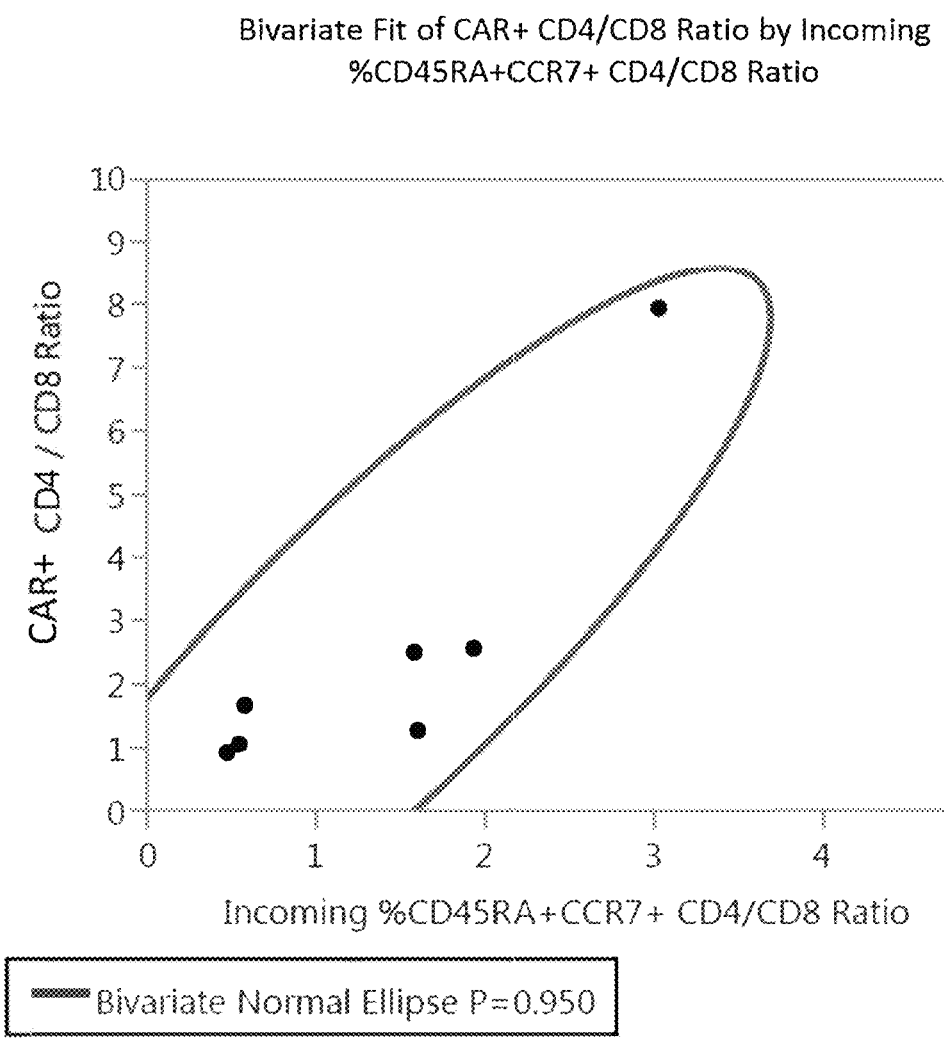
Figure 3C:
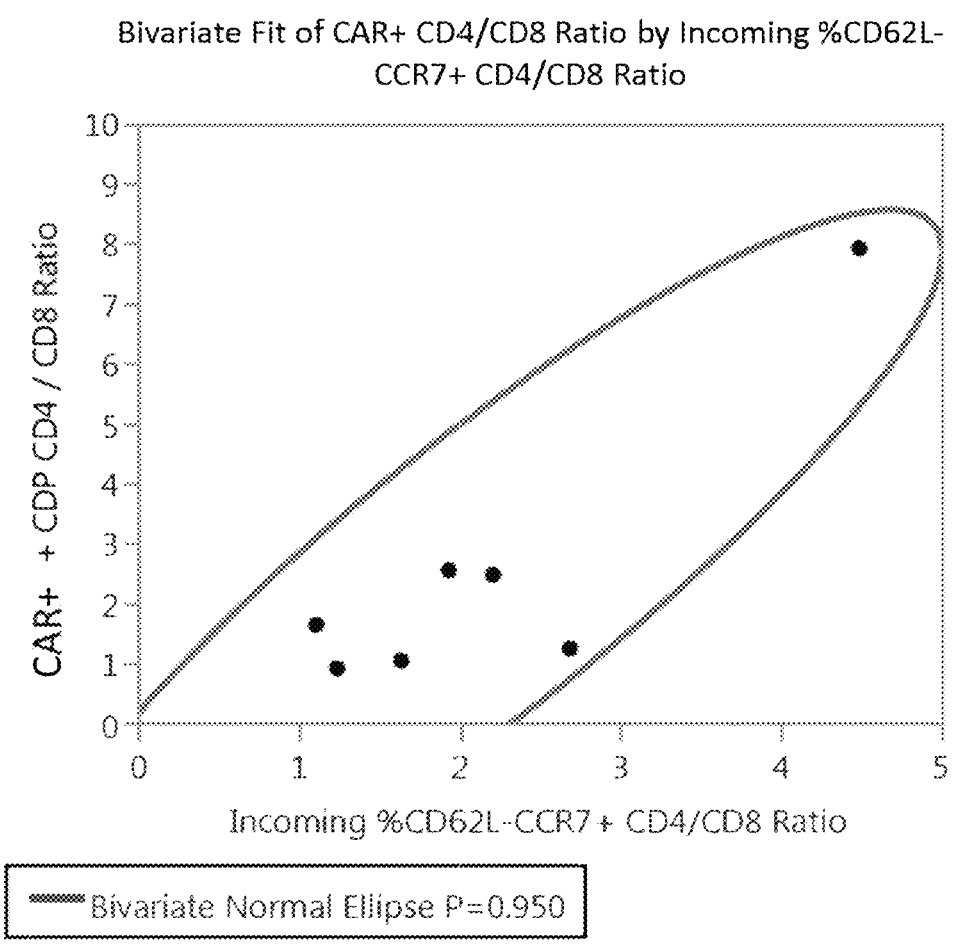

The CD27+/CCR7+CD4/CD8 ratio, CD45RA+/CCR7+ CD4/CD8 ratio, or CD62L-/CCR7+CD4/CD8 ratio in the mixture of selected CD4 and CD8 cells, was compared, post facto, to the CAR+ CD4/CD8 ratio in the engineered CAR-T cell composition. The degree of correlation of the mean ratios from each subject was assessed by bivariate normal ellipse representing the 0.950 probability region for the plotted data are shown in in FIGS. 3A-3C. As shown, a correlation between the CD27+/CCR7+CD4/CD8 ratio, CD45RA+/CCR7+CD4/CD8 ratio, or CD62L-/CCR7+ CD4/CD8 ratio in the starting sample to the CAR+ CD4/ CD8 ratio in the T cell composition was significant based on Pearson correlation analysis. Tables 3A-3C display the results of correlation analysis carried out with respect to the data plotted in FIGS. 3A-3C. Significance <0.05 is noted by *.

TABLE 3A

Bivariate Normal Ellipse P = 0.950; CD4/CD8 ratios in starting sample and output cell composition

| Variable | Mean | Std. Dev. | Correlation | Signif. Prob. |
|---|---|---|---|---|
| Starting % CD27+CCR7+ CD4/CD8 Ratio | 2.689438 | 1.788478 | 0.895786 | 0.0064* |
| CAR+ CD4/CD8 ratio | 2.560108 | 2.459516 | | |

TABLE 3B

Bivariate Normal Ellipse P = 0.950; CD4/CD8 ratios in starting sample and output cell composition

| Variable | Mean | Std. Dev. | Correlation | Signif. Prob. |
|---|---|---|---|---|
| Starting % CD45RA+CCR7+ CD4/CD8 Ratio | 1.394018 | 0.937173 | 0.86723 | 0.0115* |
| CAR+ CD4/CD8 ratio | 2.560108 | 2.459516 | | |

TABLE 3C

Bivariate Normal Ellipse P = 0.950; CD4/CD8 ratios in starting sample and output cell

| Variable | Mean | Std. Dev. | Correlation | Signif. Prob. |
|---|---|---|---|---|
| Starting % CD62L-CCR7+ CD4/CD8 Ratio | 2.179702 | 1.153181 | 0.88584 | 0.0079* |
| CAR+ CD4/CD8 ratio | 2.560108 | 2.456516 | | |

The present invention is not intended to be limited in scope to the particular disclosed embodiments, which are provided, for example, to illustrate various aspects of the invention. Various modifications to the compositions and methods described will become apparent from the description and teachings herein. Such variations may be practiced without departing from the true scope and spirit of the disclosure and are intended to fall within the scope of the present disclosure.

SEQUENCES

| # | SEQUENCE | ANNOTATION |
|---|---|---|
| 1 | ESKYGPPCPPCP | spacer (IgG4hinge) (aa) Homo sapiens |
| 2 | GAATCTAAGTACGGACCGCCCTGCCCCCCTTGCCCT | spacer (IgG4hinge) (nt) Homo sapiens |
| 3 | ESKYGPPCPPCPGQPREPQVYTLPPSQEEMTKNQVSLTCLVKGFYPS DIAVEWESNGQPENNYKTTPPVLDSDGSFFLYSRLTVDKSRWQEGN VFSCSVMHEALHNHYTQKSLSLSLGK | Hinge-CH3 spacer Homo sapiens |
| 4 | ESKYGPPCPPCPAPEFLGGPSVFLFPPKPKDTLMISRTPEVTCVVVDV SQEDPEVQFNWYVDGVEVHNAKTKPREEQFNSTYRVVSVLTVLHQ DWLNGKEYKCKVSNKGLPSSIEKTISKAKGQPREPQVYTLPPSQEE MTKNQVSLTCLVKGFYPSDIAVEWESNGQPENNYKTTPPVLDSDGS FFLYSRLTVDKSRWQEGNVFSCSVMHEALHNHYTQKSLSLSLGK | Hinge-CH2-CH3 spacer Homo sapiens |
| 5 | RWPESPKAQASSVPTAQPQAEGSLAKATTAPATTRNTGRGGEEKKK EKEKEEQEERETKTPECPSHTQPLGVYLLTPAVQDLWLRDKATFTC FVVGSDLKDAHLTWEVAGKVPTGGVEEGLLERHSNGSQSQHSRLT LPRSLWNAGTSVTCTLNHPSLPPQRLMALREPAAQAPVKLSLNLLA SSDPPEAASWLLCEVSGFSPPNILLMWLEDQREVNTSGFAPARPPPQ PGSTTFWAWSVLRVPAPPSPQPATYTCVVSHEDSRTLLNASRSLEVS YVTDH | IgD-hinge-Fc Homo sapiens |
| 6 | LEGGGEGRGSLLTCGDVEENPGPR | T2A artificial |
| 7 | MLLLVTSLLLCELPHPAFLLIPRKVCNGIGIGEFKDSLSINATNIKHFK NCTSISGDLHILPVAFRGDSFTHTPPLDPQELDILKTVKEITGFLLIQA WPENRTDLHAFENLEIIRGRTKQHGQFSLAVVSLNITSLGLRSLKEIS DGDVIISGNKNLCYANTINWKKLFGTSGQKTKIISNRGENSCKATGQ | tEGFR artificial |

| # | SEQUENCE | ANNOTATION |
|---|---|---|
|   | VCHALCSPEGCWGPEPRDCVSCRNVSRGRECVDKCNLLEGEPREFV<br>ENSECIQCHPECLPQAMNITCTGRGPDNCIQCAHYIDGPHCVKTCPA<br>GVMGENNTLVWKYADAGHVCHLCHPNCTYGCTGPGLEGCPTNGP<br>KIPSIATGMVGALLLLLVVALGIGLFM |   |
| 8 | FWVLVVVGGVLACYSLLVTVAFIIFWV | CD28 (amino acids 153-179 of Accession No. P10747) *Homo sapiens* |
| 9 | IEVMYPPPYLDNEKSNGTIIHVKGKHLCPSPLFPGPSKP<br>FWVLVVVGGVLACYSLLVTVAFIIFWV | CD28 (amino acids 114-179 of Accession No. P10747) *Homo sapiens* |
| 10 | RSKRSRLLHSDYMNMTPRRPGPTRKHYQPYAPPRDFAAYRS | CD28 (amino acids 180-220 of P10747) *Homo sapiens* |
| 11 | RSKRSRGGHSDYMNMTPRRPGPTRKHYQPYAPPRDFAAYRS | CD28 (LL to GG) *Homo sapiens* |
| 12 | KRGRKKLLYIFKQPFMRPVQTTQEEDGCSCRFPEEEEGGCEL | 4-1BB (amino acids 214-255 of Q07011.1) *Homo sapiens* |
| 13 | RVKFSRSADAPAYQQGQNQLYNELNLGRREEYDVLDKRRGRDPEM<br>GGKPRRKNPQEGLYNELQKDKMAEAYSEIGMKGERRRGKGHDGL<br>YQGLSTATKDTYDALHMQALPPR | CD3 zeta *Homo sapiens* |
| 14 | RVKFSRSAEPPAYQQGQNQLYNELNLGRREEYDVLDKRRGRDPEM<br>GGKPRRKNPQEGLYNELQKDKMAEAYSEIGMKGERRRGKGHDGL<br>YQGLSTATKDTYDALHMQALPPR | CD3 zeta *Homo sapiens* |
| 15 | RVKFSRSADAPAYKQGQNQLYNELNLGRREEYDVLDKRRGRDPEM<br>GGKPRRKNPQEGLYNELQKDKMAEAYSEIGMKGERRRGKGHDGL<br>YQGLSTATKDTYDALHMQALPPR | CD3 zeta *Homo sapiens* |
| 16 | RKVCNGIGIGEFKDSLSINATNIKHFKNCTSISGDLHILPVAFRGDSFT<br>HTPPLDPQELDILKTVKEITGFLLIQAWPENRTDLHAFENLEIIRGRTK<br>QHGQFSLAVVSLNITSLGLRSLKEISDGDVIISGNKNLCYANTINWK<br>KLFGTSGQKTKIISNRGENSCKATGQVCHALCSPEGCWGPEPRDCVS<br>CRNVSRGRECVDKCNLLEGEPREFVENSECIQCHPECLPQAMNITCT<br>GRGPDNCIQCAHYIDGPHCVKTCPAGVMGENNTLVWKYADAGHV<br>CHLCHPNCTYGCTGPGLEGCPTNGPKIPSIATGMVGALLLLLVVALG<br>IGLFM | tEGFR artificial |
| 17 | EGRGSLLTCGDVEENPGP | T2A artificial |
| 18 | PLGLWA | MMP cleavable linker |
| 19 | GSGATNFSLLKQAGDVEENPGP | P2A |
| 20 | ATNFSLLKQAGDVEENPGP | P2A |
| 21 | QCTNYALLKLAGDVESNPGP | E2A |
| 22 | VKQTLNFDLLKLAGDVESNPGP | F2A |
| 23 | X1PPX2P<br>X1 is glycine, cysteine or arginine<br>X2 is cysteine or threonine | Hinge |
| 24 | Glu Pro Lys Ser Cys Asp Lys Thr His Thr Cys Pro Pro Cys Pro | Hinge |
| 25 | Glu Arg Lys Cys Cys Val Glu Cys Pro Pro Cys Pro | Hinge |
| 26 | ELKTPLGDTHTCPRCPEPKSCDTPPPCPRCPEPKSCDTPPPCPRCPEPK<br>SCDTPPPCPRCP | Hinge |

-continued

| # | SEQUENCE | ANNOTATION |
|---|---|---|
| 27 | Glu Ser Lys Tyr Gly Pro Pro Cys Pro Ser Cys Pro | Hinge |
| 28 | Glu Ser Lys Tyr Gly Pro Pro Cys Pro Pro Cys Pro | Hinge |
| 29 | Tyr Gly Pro Pro Cys Pro Pro Cys Pro | Hinge |
| 30 | Lys Tyr Gly Pro Pro Cys Pro Pro Cys Pro | Hinge |
| 31 | Glu Val Val Val Lys Tyr Gly Pro Pro Cys Pro Pro Cys Pro | Hinge |
| 32 | -PGGG-(SGGGG)5-P- wherein P is proline, G is glycine and S is serine | Exemplary linker sequence |
| 33 | GSADDAKKDAAKKDGKS | Exemplary linker sequence |
| 34 | QQGNTLPYT | FMC63 LC-CDR3 |
| 35 | RASQDISKYLN | FMC63 CDR L1 |
| 36 | SRLHSGV | FMC63 CDR L2 |
| 37 | GNTLPYTFG | FMC63 CDR L3 |
| 38 | DYGVS | FMC63 CDR H1 |
| 39 | VIWGSETTYYNSALKS | FMC63 CDR H2 |
| 40 | YAMDYWG | FMC63 CDR H3 |
| 41 | EVKLQESGPGLVAPSQSLSVTCTVSGVSLPDYGVSWIRQPPRKGLEWLGVIWGSETTYYNSALKSRLTIIKDNSKSQVFLKMNSLQTDDTAIYYCAKHYYYGGSYAMDYWGQGTSVTVSS | FMC63 VH |
| 42 | DIQMTQTTSSLSASLGDRVTISCRASQDISKYLNWYQQKPDGTVKLLIYHTSRLHSGVPSRFSGSGSGTDYSLTISNLEQEDIATYFCQQGNTLPYTFGGGTKLEIT | FMC63 VL |
| 43 | DIQMTQTTSSLSASLGDRVTISCRASQDISKYLNWYQQKPDGTVKLLIYHTSRLHSGVPSRFSGSGSGTDYSLTISNLEQEDIATYFCQQGNTLPYTFGGGTKLEITGSTSGSGKPGSGEGSTKGEVKLQESGPGLVAPSQSLSVTCTVSGVSLPDYGVSWIRQPPRKGLEWLGVIWGSETTYYNSALKSRLTIIKDNSKSQVFLKMNSLQTDDTAIYYCAKHYYYGGSYAMDYWGQGTSVTVSS | FMC63 scFv |
| 44 | KASQNVGTNVA | SJ25C1 CDR L1 |
| 45 | SATYRNS | SJ25C1 CDR L2 |
| 46 | QQYNRYPYT | SJ25C1 CDR L3 |
| 47 | SYWMN | SJ25C1 CDR H1 |
| 48 | QIYPGDGDTNYNGKFKG | SJ25C1 CDR H2 |
| 49 | KTISSVVDFYFDY | SJ25C1 CDR H3 |
| 50 | EVKLQQSGAELVRPGSSVKISCKASGYAFSSYWMNWVKQRPGQGLEWIGQIYPGDGDTNYNGKFKGQATLTADKSSSTAYMQLSGLTSEDSAVYFCARKTISSVVDFYFDYWGQGTTVTVSS | SJ25C1 VH |
| 51 | DIELTQSPKFMSTSVGDRVSVTCKASQNVGTNVAWYQQKPGQSPKPLIYSATYRNSGVPDRFTGSGSGTDFTLTITNVQSKDLADYFCQQYNRYPYTSGGGTKLEIKR | SJ25C1 VL |
| 52 | GGGGSGGGGSGGGGS | Linker |
| 53 | EVKLQQSGAELVRPGSSVKISCKASGYAFSSYWMNWVKQRPGQGLEWIGQIYPGDGDTNYNGKFKGQATLTADKSSSTAYMQLSGLTSEDSAVYFCARKTISSVVDFYFDYWGQGTTVTVSSGGGGSGGGGSGGGGSDIELTQSPKFMSTSVGDRVSVTCKASQNVGTNVAWYQQKPGQSPKPLIYSATYRNSGVPDRFTGSGSGTDFTLTITNVQSKDLADYFCQQYNRYPYTSGGGTKLEIKR | SJ25C1 scFv |
| 54 | HYYYGGSYAMDY | FMC63 HC-CDR3 |

| # | SEQUENCE | ANNOTATION |
|---|---|---|
| 55 | HTSRLHS | FMC63 LC-CDR2 |
| 56 | GSTSGSGKPGSGEGSTKG | Linker |
| 57 | gacatccagatgacccagaccacctccagcctgagcgccagcctgggcgaccgggtgaccatcagctgccgggcca<br>gccaggacatcagcaagtacctgaactggtatcagcagaagcccgacggcaccgtcaagctgctgatctaccacacc<br>agccggctgcacagcggcgtgcccagccggtttagcggcagcggctccggcaccgactacgccctgaccatctcca<br>acctggaacaggaagatatcgccacctactttgccagcagggcaacacactgccctacacctttggggcggaacaa<br>agctggaaatcaccggcagcacctccggcagcggcaagcctggcagcggcgagggcagcaccaagggcgaggtg<br>aagctgcaggaaagcggccctggcctggtggcccccagccagaccctgagcgtgacctgcaccgtgagcggcgtg<br>agcctgcccgactacgcgtgagctggatccggcagcccccaggaagggcctggaatggctgggcgtgatctggg<br>gcagcgagaccacctactacaacagcgccctgaagagccggctgaccatcatcaaggacaacagcaagagccaggt<br>gttcctgaagatgaacagcctgcagaccgacgacaccgccatctactactgcgccaagcactactactacggcggcag<br>ctacgccatggactactggggccagggcaccagcgtgaccgtgagcagc | Sequence<br>encoding scFv |

What is claimed:

1. A method of generating a composition of engineered cells, the method comprising:
  contacting an input cell composition comprising naïve-like CD4+ T cells and naïve-like CD8+ T cells from a biological sample from a subject with an agent comprising a nucleic acid molecule encoding a recombinant receptor under conditions to introduce the nucleic acid encoding the recombinant receptor into cells in the composition;
  wherein the naïve-like CD4+ T cells and the naïve-like CD8+ T cells are surface positive for CD45RA, CD27 and/or CCR7 and are surface negative for CD45RO and/or CD62L;
  wherein the ratio of naïve-like CD4+ T cells to naïve-like CD8+ T cells present in the input cell composition is between 10:1 and 0.05:1, inclusive; and
  wherein the method produces recombinant receptor expressing T cells.

2. The method of claim 1, further comprising stimulating the cells, prior to, during and/or subsequent to said contacting, wherein stimulating comprises incubating the cells in the presence of one or more stimulating agents, wherein stimulating results in activation and/or proliferation of the cells.

3. A method of generating a composition of engineered cells, the method comprising:
  (i) stimulating an input cell composition comprising naïve-like CD4+ T cells and naïve-like CD8+ T cells from a biological sample from a subject in the presence of one or more stimulating agents, wherein the naïve-like CD4+ T cells and the naïve-like CD8+ T cells are surface positive for CD45RA, CD27 and/or CCR7 and are surface negative for CD45RO and/or CD62L, wherein the ratio of naïve-like CD4+ T cells to naïve-like CD8+ T cells present in the input cell composition is between 10:1 and 0.05:1, inclusive; and wherein stimulating results in activation of the cells;
  (ii) contacting the input cell composition with an agent comprising a nucleic acid molecule encoding a recombinant receptor under conditions to introduce the nucleic acid encoding the recombinant receptor into cells in the composition; and
  (iii) stimulating the cells subsequent to said contacting, wherein stimulating comprises incubating the cells in the presence of one or more stimulating agents and wherein stimulating results in proliferation of the cells, wherein the method produces recombinant receptor expressing T cells.

4. The method of claim 1, wherein the naïve-like CD4+ T cells and the naïve-like CD8+ T cells are surface positive for CD45RA and CCR7.

5. The method of claim 1, wherein the naïve-like CD4+ T cells and the naïve-like CD8+ T cells are surface positive for CD27 and CCR7.

6. The method of claim 1, wherein the naïve-like CD4+ T cells and the naïve-like CD8+ T cells are surface positive for CCR7 and surface negative for CD62L.

7. The method of claim 1, wherein the input cell composition comprises a ratio of naïve-like CD4+ T cells to naïve-like CD8+ T cells of between 0.8:1 and 2.2:1, each inclusive.

8. The method of claim 4, wherein the input cell composition comprises a ratio of CCR7+CD45RA+CD4+ cells to CCR7+CD45RA+CD8+ cells of between 0.8:1 and 2.2:1, each inclusive.

9. The method of claim 4, wherein the input cell composition comprises a ratio of CCR7+CD45RA+CD4+ cells to CCR7+CD45RA+CD8+ cells of or about 1.4:1, 1.1:1, or 1.0:1.

10. The method of claim 5, wherein the input cell composition comprises a ratio of CD27+CCR7+CD4+ cells to CD27+CCR7+CD8+ cells of between 1.2:1 and 2.4:1, each inclusive.

11. The method of claim 5, wherein the input cell composition comprises a ratio of CD27+CCR7+CD4+ cells to CD27+CCR7+CD8+ cells of or about 2.7:1.

12. The method of claim 5, wherein the input cell composition comprises a ratio of CD27+CCR7+CD4+ cells to CD27+CCR7+CD8+ cells of or about 1.69:1.

13. The method of claim 6, wherein the input cell composition comprises a ratio of CD62L-CCR7+CD4+ cells to CD62L-CCR7+CD8+ cells of between 0.8:1 and 2.2:1, each inclusive.

14. The method of claim 6, wherein the input cell composition comprises a ratio of CD62L-CCR7+CD4+ cells to CD62L-CCR7+CD8+ cells of or about 2.2:1, 2:1, 1.6:1, or 1.66:1.

15. The method of claim 1, wherein the composition of engineered cells comprises at least 50%, at least 70%, at least 90%, or 100% of cells that express the recombinant receptor.

16. The method of claim 1, wherein the ratio of recombinant receptor expressing CD4+ T cells to recombinant receptor expressing CD8+ T cells is or is about 8.6:1, 7.6:1, 2.6:1, 2.0:1, 1.6:1, 1.4:1, 1.3:1, 1.2:1, 1.1:1, or 1.0:1.

17. The method of claim 1, wherein the ratio of recombinant receptor expressing CD4+ T cells to recombinant receptor expressing CD8+ T cells is or is about 2.6:1 or 2.0:1.

18. The method of claim 1, wherein the ratio of recombinant receptor expressing CD27+CCR7+CD4+ T cells to recombinant receptor expressing CD27+CCR7+CD8+ T cells is or is about 8.6:1, 7.6:1, 2.6:1, 2.0:1, 1.6:1, 1.4:1, 1.3:1, 1.2:1, 1.1:1, or 1.0:1.

19. The method of claim 1, wherein the ratio of recombinant receptor expressing CCR7+CD45RA+CD4+ T cells to recombinant receptor expressing CCR7+CD45RA+CD8+ T cells is or is about 8.6:1, 7.6:1, 2.6:1, 2.0:1, 1.6:1, 1.4:1, 1.3:1, 1.2:1, 1.1:1, or 1.0:1.

20. The method of claim 1, wherein the ratio of recombinant receptor expressing CD62L-CCR7+CD4+ T cells to recombinant receptor expressing CD62L-CCR7+CD8+ T cells is or is about 8.6:1, 7.6:1, 2.6:1, 2.0:1, 1.6:1, 1.4:1, 1.3:1, 1.2:1, 1.1:1, or 1.0:1.

21. The method of claim 1, wherein the recombinant receptor is a chimeric antigen receptor (CAR).

22. The method of claim 1, wherein the biological sample is or comprises a whole blood sample, a buffy coat sample, a peripheral blood mononuclear cells (PBMC) sample, an unfractionated T cell sample, a lymphocyte sample, a white blood cell sample, an apheresis product, or a leukapheresis product.

23. The method of claim 1, wherein the subject is a human subject.

24. The method of claim 1, wherein the input cell composition comprises from or from about $1\times10^7$ to $5\times10^9$ total cells or total T cells, or of viable populations of any of the foregoing.

25. The method of claim 3, wherein the one or more one stimulating agents is selected from the group consisting of CD3-binding molecules; CD28-binding molecules; recombinant IL-2; recombinant IL-15; and recombinant IL-7, a vaccine comprising an antigen specifically recognized by the antigen receptor, and an anti-idiotype antibody that specifically binds the antigen receptor or combinations thereof.

26. The method of claim 25, wherein the one or more one stimulating agents comprises CD3-binding molecules and CD28-binding molecules.

* * * * *

SEQUENCE LISTING

```
Sequence total quantity: 57
SEQ ID NO: 1              moltype = AA  length = 12
FEATURE                   Location/Qualifiers
REGION                    1..12
                          note = spacer (IgG4hinge)
source                    1..12
                          mol_type = protein
                          organism = Homo sapiens
SEQUENCE: 1
ESKYGPPCPP CP                                                                12

SEQ ID NO: 2              moltype = DNA  length = 36
FEATURE                   Location/Qualifiers
misc_feature              1..36
                          note = spacer (IgG4hinge)
source                    1..36
                          mol_type = unassigned DNA
                          organism = Homo sapiens
SEQUENCE: 2
gaatctaagt acggaccgcc ctgccccct tgccct                                       36

SEQ ID NO: 3              moltype = AA  length = 119
FEATURE                   Location/Qualifiers
REGION                    1..119
                          note = Hinge-CH3 spacer
source                    1..119
                          mol_type = protein
                          organism = Homo sapiens
SEQUENCE: 3
ESKYGPPCPP CPGQPREPQV YTLPPSQEEM TKNQVSLTCL VKGFYPSDIA VEWESNGQPE            60
NNYKTTPPVL DSDGSFFLYS RLTVDKSRWQ EGNVFSCSVM HEALHNHYTQ KSLSLSLGK             119

SEQ ID NO: 4              moltype = AA  length = 229
FEATURE                   Location/Qualifiers
REGION                    1..229
                          note = Hinge-CH2-CH3 spacer
source                    1..229
                          mol_type = protein
                          organism = Homo sapiens
SEQUENCE: 4
ESKYGPPCPP CPAPEFLGGP SVFLFPPKPK DTLMISRTPE VTCVVVDVSQ EDPEVQFNWY            60
VDGVEVHNAK TKPREEQFNS TYRVVSVLTV LHQDWLNGKE YKCKVSNKGL PSSIEKTISK            120
AKGQPREPQV YTLPPSQEEM TKNQVSLTCL VKGFYPSDIA VEWESNGQPE NNYKTTPPVL            180
DSDGSFFLYS RLTVDKSRWQ EGNVFSCSVM HEALHNHYTQ KSLSLSLGK                        229

SEQ ID NO: 5              moltype = AA  length = 282
FEATURE                   Location/Qualifiers
REGION                    1..282
                          note = IgD-hinge-Fc
source                    1..282
                          mol_type = protein
                          organism = Homo sapiens
SEQUENCE: 5
```

```
RWPESPKAQA SSVPTAQPQA EGSLAKATTA PATTRNTGRG GEEKKKEKEK EEQEERETKT    60
PECPSHTQPL GVYLLTPAVQ DLWLRDKATF TCFVVGSDLK DAHLTWEVAG KVPTGGVEEG   120
LLERHSNGSQ SQHSRLTLPR SLWNAGTSVT CTLNHPSLPP QRLMALREPA AQAPVKLSLN   180
LLASSDPPEA ASWLLCEVSG FSPPNILLMW LEDQREVNTS GFAPARPPPQ PGSTTFWAWS   240
VLRVPAPPSP QPATYTCVVS HEDSRTLLNA SRSLEVSYVT DH                     282

SEQ ID NO: 6             moltype = AA   length = 24
FEATURE                  Location/Qualifiers
REGION                   1..24
                         note = T2A
source                   1..24
                         mol_type = protein
                         organism = synthetic construct
SEQUENCE: 6
LEGGGEGRGS LLTCGDVEEN PGPR                                          24

SEQ ID NO: 7             moltype = AA   length = 357
FEATURE                  Location/Qualifiers
REGION                   1..357
                         note = tEGFR
source                   1..357
                         mol_type = protein
                         organism = synthetic construct
SEQUENCE: 7
MLLLVTSLLL CELPHPAFLL IPRKVCNGIG IGEFKDSLSI NATNIKHFKN CTSISGDLHI    60
LPVAFRGDSF THTPPLDPQE LDILKTVKEI TGFLLIQAWP ENRTDLHAFE NLEIIRGRTK   120
QHGQFSLAVV SLNITSLGLR SLKEISDGDV IISGNKNLCY ANTINWKKLF GTSGQKTKII   180
SNRGENSCKA TGQVCHALCS PEGCWGPEPR DCVSCRNVSR GRECVDKCNL LEGEPREFVE   240
NSECIQCHPE CLPQAMNITC TGRGPDNCIQ CAHYIDGPHC VKTCPAGVMG ENNTLVWKYA   300
DAGHVCHLCH PNCTYGCTGP GLEGCPTNGP KIPSIATGMV GALLLLLVVA LGIGLFM     357

SEQ ID NO: 8             moltype = AA   length = 27
FEATURE                  Location/Qualifiers
REGION                   1..27
                         note = CD28 (amino acids 153-179 of Accession No. P10747)
source                   1..27
                         mol_type = protein
                         organism = Homo sapiens
SEQUENCE: 8
FWVLVVVGGV LACYSLLVTV AFIIFWV                                       27

SEQ ID NO: 9             moltype = AA   length = 66
FEATURE                  Location/Qualifiers
REGION                   1..66
                         note = CD28 (amino acids 114-179 of Accession No. P10747)
source                   1..66
                         mol_type = protein
                         organism = Homo sapiens
SEQUENCE: 9
IEVMYPPPYL DNEKSNGTII HVKGKHLCPS PLFPGPSKPF WVLVVVGGVL ACYSLLVTVA    60
FIIFWV                                                              66

SEQ ID NO: 10            moltype = AA   length = 41
FEATURE                  Location/Qualifiers
REGION                   1..41
                         note = CD28 (amino acids 180-220 of P10747)
source                   1..41
                         mol_type = protein
                         organism = Homo sapiens
SEQUENCE: 10
RSKRSRLLHS DYMNMTPRRP GPTRKHYQPY APPRDFAAYR S                       41

SEQ ID NO: 11            moltype = AA   length = 41
FEATURE                  Location/Qualifiers
REGION                   1..41
                         note = CD28 (LL to GG)
source                   1..41
                         mol_type = protein
                         organism = Homo sapiens
SEQUENCE: 11
RSKRSRGGHS DYMNMTPRRP GPTRKHYQPY APPRDFAAYR S                       41

SEQ ID NO: 12            moltype = AA   length = 42
FEATURE                  Location/Qualifiers
REGION                   1..42
                         note = 4-1BB (amino acids 214-255 of Q07011.1)
source                   1..42
                         mol_type = protein
                         organism = Homo sapiens
```

```
SEQUENCE: 12
KRGRKKLLYI FKQPFMRPVQ TTQEEDGCSC RFPEEEEGGC EL                          42

SEQ ID NO: 13              moltype = AA   length = 112
FEATURE                    Location/Qualifiers
REGION                     1..112
                           note = CD3 zeta
source                     1..112
                           mol_type = protein
                           organism = Homo sapiens
SEQUENCE: 13
RVKFSRSADA PAYQQGQNQL YNELNLGRRE EYDVLDKRRG RDPEMGGKPR RKNPQEGLYN        60
ELQKDKMAEA YSEIGMKGER RRGKGHDGLY QGLSTATKDT YDALHMQALP PR              112

SEQ ID NO: 14              moltype = AA   length = 112
FEATURE                    Location/Qualifiers
REGION                     1..112
                           note = CD3 zeta
source                     1..112
                           mol_type = protein
                           organism = Homo sapiens
SEQUENCE: 14
RVKFSRSAEP PAYQQGQNQL YNELNLGRRE EYDVLDKRRG RDPEMGGKPR RKNPQEGLYN        60
ELQKDKMAEA YSEIGMKGER RRGKGHDGLY QGLSTATKDT YDALHMQALP PR              112

SEQ ID NO: 15              moltype = AA   length = 112
FEATURE                    Location/Qualifiers
REGION                     1..112
                           note = CD3 zeta
source                     1..112
                           mol_type = protein
                           organism = Homo sapiens
SEQUENCE: 15
RVKFSRSADA PAYKQGQNQL YNELNLGRRE EYDVLDKRRG RDPEMGGKPR RKNPQEGLYN        60
ELQKDKMAEA YSEIGMKGER RRGKGHDGLY QGLSTATKDT YDALHMQALP PR              112

SEQ ID NO: 16              moltype = AA   length = 335
FEATURE                    Location/Qualifiers
REGION                     1..335
                           note = tEGFR
source                     1..335
                           mol_type = protein
                           organism = synthetic construct
SEQUENCE: 16
RKVCNGIGIG EFKDSLSINA TNIKHFKNCT SISGDLHILP VAFRGDSFTH TPPLDPQELD        60
ILKTVKEITG FLLIQAWPEN RTDLHAFENL EIIRGRTKQH GQFSLAVVSL NITSLGLRSL      120
KEISDGDVII SGNKNLCYAN TINWKKLFGT SGQKTKIISN RGENSCKATG QVCHALCSPE      180
GCWGPEPRDC VSCRNVSRGR ECVDKCNLLE GEPREFVENS ECIQCHPECL PQAMNITCTG      240
RGPDNCIQCA HYIDGPHCVK TCPAGVMGEN NTLVWKYADA GHVCHLCHPN CTYGCTGPGL      300
EGCPTNGPKI PSIATGMVGA LLLLLVVALG IGLFM                                 335

SEQ ID NO: 17              moltype = AA   length = 18
FEATURE                    Location/Qualifiers
REGION                     1..18
                           note = T2A
source                     1..18
                           mol_type = protein
                           organism = synthetic construct
SEQUENCE: 17
EGRGSLLTCG DVEENPGP                                                     18

SEQ ID NO: 18              moltype = AA   length = 6
FEATURE                    Location/Qualifiers
REGION                     1..6
                           note = MMP cleavable linker
source                     1..6
                           mol_type = protein
                           organism = synthetic construct
SEQUENCE: 18
PLGLWA                                                                   6

SEQ ID NO: 19              moltype = AA   length = 22
FEATURE                    Location/Qualifiers
REGION                     1..22
                           note = P2A
source                     1..22
                           mol_type = protein
                           organism = synthetic construct
SEQUENCE: 19
```

```
GSGATNFSLL KQAGDVEENP GP                                                    22

SEQ ID NO: 20           moltype = AA   length = 19
FEATURE                 Location/Qualifiers
REGION                  1..19
                        note = P2A
source                  1..19
                        mol_type = protein
                        organism = synthetic construct
SEQUENCE: 20
ATNFSLLKQA GDVEENPGP                                                        19

SEQ ID NO: 21           moltype = AA   length = 20
FEATURE                 Location/Qualifiers
REGION                  1..20
                        note = E2A
source                  1..20
                        mol_type = protein
                        organism = synthetic construct
SEQUENCE: 21
QCTNYALLKL AGDVESNPGP                                                       20

SEQ ID NO: 22           moltype = AA   length = 22
FEATURE                 Location/Qualifiers
REGION                  1..22
                        note = F2A
source                  1..22
                        mol_type = protein
                        organism = synthetic construct
SEQUENCE: 22
VKQTLNFDLL KLAGDVESNP GP                                                    22

SEQ ID NO: 23           moltype =      length =
SEQUENCE: 23
000

SEQ ID NO: 24           moltype = AA   length = 15
FEATURE                 Location/Qualifiers
REGION                  1..15
                        note = Hinge
source                  1..15
                        mol_type = protein
                        organism = synthetic construct
SEQUENCE: 24
EPKSCDKTHT CPPCP                                                            15

SEQ ID NO: 25           moltype = AA   length = 12
FEATURE                 Location/Qualifiers
REGION                  1..12
                        note = Hinge
source                  1..12
                        mol_type = protein
                        organism = synthetic construct
SEQUENCE: 25
ERKCCVECPP CP                                                               12

SEQ ID NO: 26           moltype = AA   length = 61
FEATURE                 Location/Qualifiers
REGION                  1..61
                        note = Hinge
source                  1..61
                        mol_type = protein
                        organism = synthetic construct
SEQUENCE: 26
ELKTPLGDTH TCPRCPEPKS CDTPPPCPRC PEPKSCDTPP PCPRCPEPKS CDTPPPCPRC           60
P                                                                           61

SEQ ID NO: 27           moltype = AA   length = 12
FEATURE                 Location/Qualifiers
REGION                  1..12
                        note = Hinge
source                  1..12
                        mol_type = protein
                        organism = synthetic construct
SEQUENCE: 27
ESKYGPPCPS CP                                                               12

SEQ ID NO: 28           moltype = AA   length = 12
FEATURE                 Location/Qualifiers
```

```
REGION                  1..12
                        note = Hinge
source                  1..12
                        mol_type = protein
                        organism = synthetic construct
SEQUENCE: 28
ESKYGPPCPP CP                                                              12

SEQ ID NO: 29           moltype = AA  length = 9
FEATURE                 Location/Qualifiers
REGION                  1..9
                        note = Hinge
source                  1..9
                        mol_type = protein
                        organism = synthetic construct
SEQUENCE: 29
YGPPCPPCP                                                                   9

SEQ ID NO: 30           moltype = AA  length = 10
FEATURE                 Location/Qualifiers
REGION                  1..10
                        note = Hinge
source                  1..10
                        mol_type = protein
                        organism = synthetic construct
SEQUENCE: 30
KYGPPCPPCP                                                                 10

SEQ ID NO: 31           moltype = AA  length = 14
FEATURE                 Location/Qualifiers
REGION                  1..14
                        note = Hinge
source                  1..14
                        mol_type = protein
                        organism = synthetic construct
SEQUENCE: 31
EVVVKYGPPC PPCP                                                            14

SEQ ID NO: 32           moltype = AA  length = 10
FEATURE                 Location/Qualifiers
REGION                  1..10
                        note = Exemplary linker sequence
REPEAT                  5..9
                        note = SGGGG is repeated 5 times
source                  1..10
                        mol_type = protein
                        organism = synthetic construct
SEQUENCE: 32
PGGGSGGGGP                                                                 10

SEQ ID NO: 33           moltype = AA  length = 17
FEATURE                 Location/Qualifiers
REGION                  1..17
                        note = Exemplary linker sequence
source                  1..17
                        mol_type = protein
                        organism = synthetic construct
SEQUENCE: 33
GSADDAKKDA AKKDGKS                                                         17

SEQ ID NO: 34           moltype = AA  length = 9
FEATURE                 Location/Qualifiers
REGION                  1..9
                        note = FMC63 LC-CDR3
source                  1..9
                        mol_type = protein
                        organism = synthetic construct
SEQUENCE: 34
QQGNTLPYT                                                                   9

SEQ ID NO: 35           moltype = AA  length = 11
FEATURE                 Location/Qualifiers
REGION                  1..11
                        note = FMC63 CDR L1
source                  1..11
                        mol_type = protein
                        organism = synthetic construct
SEQUENCE: 35
RASQDISKYL N                                                               11
```

```
SEQ ID NO: 36           moltype = AA  length = 7
FEATURE                 Location/Qualifiers
REGION                  1..7
                        note = FMC63 CDR L2
source                  1..7
                        mol_type = protein
                        organism = synthetic construct
SEQUENCE: 36
SRLHSGV                                                                    7

SEQ ID NO: 37           moltype = AA  length = 9
FEATURE                 Location/Qualifiers
REGION                  1..9
                        note = FMC63 CDR L3
source                  1..9
                        mol_type = protein
                        organism = synthetic construct
SEQUENCE: 37
GNTLPYTFG                                                                  9

SEQ ID NO: 38           moltype = AA  length = 5
FEATURE                 Location/Qualifiers
REGION                  1..5
                        note = FMC63 CDR H1
source                  1..5
                        mol_type = protein
                        organism = synthetic construct
SEQUENCE: 38
DYGVS                                                                      5

SEQ ID NO: 39           moltype = AA  length = 16
FEATURE                 Location/Qualifiers
REGION                  1..16
                        note = FMC63 CDR H2
source                  1..16
                        mol_type = protein
                        organism = synthetic construct
SEQUENCE: 39
VIWGSETTYY NSALKS                                                         16

SEQ ID NO: 40           moltype = AA  length = 7
FEATURE                 Location/Qualifiers
REGION                  1..7
                        note = FMC63 CDR H3
source                  1..7
                        mol_type = protein
                        organism = synthetic construct
SEQUENCE: 40
YAMDYWG                                                                    7

SEQ ID NO: 41           moltype = AA  length = 120
FEATURE                 Location/Qualifiers
REGION                  1..120
                        note = FMC63 VH
source                  1..120
                        mol_type = protein
                        organism = synthetic construct
SEQUENCE: 41
EVKLQESGPG LVAPSQSLSV TCTVSGVSLP DYGVSWIRQP PRKGLEWLGV IWGSETTYYN          60
SALKSRLTII KDNSKSQVFL KMNSLQTDDT AIYYCAKHYY YGGSYAMDYW GQGTSVTVSS         120

SEQ ID NO: 42           moltype = AA  length = 107
FEATURE                 Location/Qualifiers
REGION                  1..107
                        note = FMC63 VL
source                  1..107
                        mol_type = protein
                        organism = synthetic construct
SEQUENCE: 42
DIQMTQTTSS LSASLGDRVT ISCRASQDIS KYLNWYQQKP DGTVKLLIYH TSRLHSGVPS          60
RFSGSGSGTD YSLTISNLEQ EDIATYFCQQ GNTLPYTFGG GTKLEIT                       107

SEQ ID NO: 43           moltype = AA  length = 245
FEATURE                 Location/Qualifiers
REGION                  1..245
                        note = FMC63 scFv
source                  1..245
                        mol_type = protein
```

```
                               -continued
                        organism = synthetic construct
SEQUENCE: 43
DIQMTQTTSS LSASLGDRVT ISCRASQDIS KYLNWYQQKP DGTVKLLIYH TSRLHSGVPS    60
RFSGSGSGTD YSLTISNLEQ EDIATYFCQQ GNTLPYTFGG GTKLEITGST SGSGKPGSGE   120
GSTKGEVKLQ ESGPGLVAPS QSLSVTCTVS GVSLPDYGVS WIRQPPRKGL EWLGVIWGSE   180
TTYYNSALKS RLTIIKDNSK SQVFLKMNSL QTDDTAIYYC AKHYYYGGSY AMDYWGQGTS   240
VTVSS                                                              245

SEQ ID NO: 44           moltype = AA   length = 11
FEATURE                 Location/Qualifiers
REGION                  1..11
                        note = SJ25C1 CDR L1
source                  1..11
                        mol_type = protein
                        organism = synthetic construct
SEQUENCE: 44
KASQNVGTNV A                                                        11

SEQ ID NO: 45           moltype = AA   length = 7
FEATURE                 Location/Qualifiers
REGION                  1..7
                        note = SJ25C1 CDR L2
source                  1..7
                        mol_type = protein
                        organism = synthetic construct
SEQUENCE: 45
SATYRNS                                                             7

SEQ ID NO: 46           moltype = AA   length = 9
FEATURE                 Location/Qualifiers
REGION                  1..9
                        note = SJ25C1 CDR L3
source                  1..9
                        mol_type = protein
                        organism = synthetic construct
SEQUENCE: 46
QQYNRYPYT                                                           9

SEQ ID NO: 47           moltype = AA   length = 5
FEATURE                 Location/Qualifiers
REGION                  1..5
                        note = SJ25C1 CDR H1
source                  1..5
                        mol_type = protein
                        organism = synthetic construct
SEQUENCE: 47
SYWMN                                                               5

SEQ ID NO: 48           moltype = AA   length = 17
FEATURE                 Location/Qualifiers
REGION                  1..17
                        note = SJ25C1 CDR H2
source                  1..17
                        mol_type = protein
                        organism = synthetic construct
SEQUENCE: 48
QIYPGDGDTN YNGKFKG                                                  17

SEQ ID NO: 49           moltype = AA   length = 13
FEATURE                 Location/Qualifiers
REGION                  1..13
                        note = SJ25C1 CDR H3
source                  1..13
                        mol_type = protein
                        organism = synthetic construct
SEQUENCE: 49
KTISSVVDFY FDY                                                      13

SEQ ID NO: 50           moltype = AA   length = 122
FEATURE                 Location/Qualifiers
REGION                  1..122
                        note = SJ25C1 VH
source                  1..122
                        mol_type = protein
                        organism = synthetic construct
SEQUENCE: 50
EVKLQQSGAE LVRPGSSVKI SCKASGYAFS SYWMNWVKQR PGQGLEWIGQ IYPGDGDTNY    60
NGKFKGQATL TADKSSSTAY MQLSGLTSED SAVYFCARKT ISSVVDFYFD YWGQGTTVTV   120
SS                                                                 122
```

```
SEQ ID NO: 51           moltype = AA   length = 108
FEATURE                 Location/Qualifiers
REGION                  1..108
                        note = SJ25C1 VL
source                  1..108
                        mol_type = protein
                        organism = synthetic construct
SEQUENCE: 51
DIELTQSPKF MSTSVGDRVS VTCKASQNVG TNVAWYQQKP GQSPKPLIYS ATYRNSGVPD    60
RFTGSGSGTD FTLTITNVQS KDLADYFCQQ YNRYPYTSGG GTKLEIKR                108

SEQ ID NO: 52           moltype = AA   length = 15
FEATURE                 Location/Qualifiers
REGION                  1..15
                        note = Linker
source                  1..15
                        mol_type = protein
                        organism = synthetic construct
SEQUENCE: 52
GGGGSGGGGS GGGGS                                                     15

SEQ ID NO: 53           moltype = AA   length = 245
FEATURE                 Location/Qualifiers
REGION                  1..245
                        note = SJ25C1 scFv
source                  1..245
                        mol_type = protein
                        organism = synthetic construct
SEQUENCE: 53
EVKLQQSGAE LVRPGSSVKI SCKASGYAFS SYWMNWVKQR PGQGLEWIGQ IYPGDGDTNY    60
NGKFKGQATL TADKSSSTAY MQLSGLTSED SAVYFCARKT ISSVVDFYFD YWGQGTTVTV   120
SSGGGGSGGG GSGGGGSDIE LTQSPKFMST SVGDRVSVTC KASQNVGTNV AWYQQKPGQS   180
PKPLIYSATY RNSGVPDRFT GSGSGTDFTL TITNVQSKDL ADYFCQQYNR YPYTSGGGTK   240
LEIKR                                                               245

SEQ ID NO: 54           moltype = AA   length = 12
FEATURE                 Location/Qualifiers
REGION                  1..12
                        note = FMC63 HC-CDR3
source                  1..12
                        mol_type = protein
                        organism = synthetic construct
SEQUENCE: 54
HYYYGGSYAM DY                                                        12

SEQ ID NO: 55           moltype = AA   length = 7
FEATURE                 Location/Qualifiers
REGION                  1..7
                        note = FMC63 LC-CDR2
source                  1..7
                        mol_type = protein
                        organism = synthetic construct
SEQUENCE: 55
HTSRLHS                                                               7

SEQ ID NO: 56           moltype = AA   length = 18
FEATURE                 Location/Qualifiers
REGION                  1..18
                        note = Linker
source                  1..18
                        mol_type = protein
                        organism = synthetic construct
SEQUENCE: 56
GSTSGSGKPG SGEGSTKG                                                  18

SEQ ID NO: 57           moltype = DNA   length = 735
FEATURE                 Location/Qualifiers
misc_feature            1..735
                        note = Sequence encoding scFv
source                  1..735
                        mol_type = other DNA
                        organism = synthetic construct
SEQUENCE: 57
gacatccaga tgacccagac cacctccagc ctgagcgcca gcctgggcga ccgggtgacc    60
atcagctgcc gggccagcca ggacatcagc aagtacctga actggtatca gcagaagccc   120
gacggcaccg tcaagctgct gatctaccac accagccggc tgcacagcgg cgtgcccagc   180
cggtttagcg gcagcggctc cggcaccgac tacagcctga ccatctccaa cctggaacag   240
gaagatatcg ccacctactt ttgccagcag ggcaacacac tgccctacac ctttggcggc   300
```

-continued

```
ggaacaaagc tggaaatcac cggcagcacc tccggcagcg gcaagcctgg cagcggcgag    360
ggcagcacca agggcgaggt gaagctgcag gaaagcggcc ctggcctggt ggcccccagc    420
cagagcctga gcgtgacctg caccgtgagc ggcgtgagcc tgcccgacta cggcgtgagc    480
tggatccggc agcccccag gaagggcctg gaatggctgg gcgtgatctg gggcagcgag    540
accacctact acaacagcgc cctgaagagc cggctgacca tcatcaagga caacagcaag    600
agccaggtgt tcctgaagat gaacagcctg cagaccgacg acaccgccat ctactactgc    660
gccaagcact actactacgg cggcagctac gccatggact actggggcca gggcaccagc    720
gtgaccgtga gcagc                                                     735
```

UNITED STATES PATENT AND TRADEMARK OFFICE
CERTIFICATE OF CORRECTION

PATENT NO. : 12,215,348 B2
APPLICATION NO. : 18/506851
DATED : February 4, 2025
INVENTOR(S) : Mirna Mujacic and Ayu Rahardjo Page 1 of 1

It is certified that error appears in the above-identified patent and that said Letters Patent is hereby corrected as shown below:

In the Claims

At Column 135, Claim number 25, Lines 20-21, please replace "one or more one stimulating agents" with -- one or more stimulating agents --.

At Column 135, Claim number 26, Lines 27-28, please replace "one or more one stimulating agents" with -- one or more stimulating agents --.

Signed and Sealed this
Twentieth Day of May, 2025

Coke Morgan Stewart
*Acting Director of the United States Patent and Trademark Office*